(12) United States Patent
Shang et al.

(10) Patent No.: US 8,758,301 B2
(45) Date of Patent: Jun. 24, 2014

(54) FIRING BUTTON FOR AUTOMATIC INJECTION DEVICE

(75) Inventors: Sherwin S. Shang, Vernon Hills, IL (US); Esra Ozdaryal, Deerfield, IL (US); David A. Post, Kenosha, WI (US); Eduard N. Tsvirko, Arlington Heights, IL (US)

(73) Assignee: AbbVie Biotechnology Ltd, Hamilton (BM)

( * ) Notice: Subject to any disclaimer, the term of this patent is extended or adjusted under 35 U.S.C. 154(b) by 368 days.

(21) Appl. No.: 12/968,744

(22) Filed: Dec. 15, 2010

(65) Prior Publication Data

US 2011/0178500 A1 Jul. 21, 2011

Related U.S. Application Data

(60) Provisional application No. 61/286,760, filed on Dec. 15, 2009, provisional application No. 61/286,771, filed on Dec. 15, 2009.

(51) Int. Cl.
*A61M 5/20* (2006.01)

(52) U.S. Cl.
USPC ............................................. 604/135

(58) Field of Classification Search
USPC ................ 604/131, 134–136, 182, 187
See application file for complete search history.

(56) References Cited

U.S. PATENT DOCUMENTS

| | | | |
|---|---|---|---|
| 2,398,544 A | 4/1946 | Lockhart | |
| 2,459,875 A | 1/1949 | Folkman | |
| 2,565,081 A | 8/1951 | Maynes | |
| 2,591,457 A | 4/1952 | Maynes | |
| 2,701,566 A | 2/1955 | Krug | |
| 2,752,918 A | 7/1956 | Uytenbogaart | |
| 2,832,339 A | 4/1958 | Sarnoff et al. | |
| 2,888,924 A | 6/1959 | Dunmire | |
| 2,960,087 A | 11/1960 | Uytenbogaart | |
| 3,051,173 A | 8/1962 | Johnson et al. | |
| 3,055,362 A | 9/1962 | Uytenbogaart | |

(Continued)

FOREIGN PATENT DOCUMENTS

| | | |
|---|---|---|
| DE | 2019296 | 11/1971 |
| DE | 19821933 | 11/1999 |

(Continued)

OTHER PUBLICATIONS

Office Action issued in Canadian Application No. 2,571,571, dated Oct. 24, 2011.

(Continued)

*Primary Examiner* — Aarti Bhatia Berdichevsky
*Assistant Examiner* — Bradley Osinski
(74) *Attorney, Agent, or Firm* — McCarter & English, LLP; David R. Burns

(57) ABSTRACT

Exemplary embodiments provide firing mechanism assemblies that minimize or eliminate a misfire of an automatic injection device that causes a delay in the delivery of an injection. Exemplary embodiments provide automatic injection devices including firing mechanism assemblies that minimize or eliminate a misfire that causes a delay in the delivery of an injection. Exemplary embodiments provide methods for minimizing or eliminating misfire that causes a delay in delivery of an injection in automatic injection devices. Exemplary embodiments provide methods for using automatic injection devices that are free of a misfire that causes delay in delivery of a therapeutic substance into a patient's body.

35 Claims, 77 Drawing Sheets

(56) References Cited

U.S. PATENT DOCUMENTS

| | | | |
|---|---|---|---|
| 3,066,670 A | 12/1962 | Stauffer | |
| 3,136,313 A | 6/1964 | Enstrom et al. | |
| 3,314,428 A | 4/1967 | Johnson et al. | |
| 3,330,279 A | 7/1967 | Sarnoff et al. | |
| 3,403,680 A | 10/1968 | Sinclair et al. | |
| 3,543,603 A | 12/1970 | Gley | |
| 3,605,743 A | 9/1971 | Arce | |
| 3,618,603 A | 11/1971 | Levenson | |
| 3,702,609 A | 11/1972 | Steiner | |
| 3,712,301 A | 1/1973 | Sarnoff | |
| 3,742,948 A | 7/1973 | Post | |
| 3,797,488 A | 3/1974 | Hurschman et al. | |
| 3,797,489 A | 3/1974 | Sarnoff | |
| 3,882,863 A | 5/1975 | Sarnoff et al. | |
| 3,892,237 A | 7/1975 | Steiner | |
| 3,910,260 A | 10/1975 | Sarnoff et al. | |
| 3,941,130 A | 3/1976 | Tibbs | |
| 4,031,893 A | 6/1977 | Kaplan et al. | |
| 4,106,770 A | 8/1978 | Gray | |
| 4,178,928 A | 12/1979 | Tischlinger | |
| 4,202,314 A | 5/1980 | Smirnov et al. | |
| 4,214,584 A | 7/1980 | Smirnov et al. | |
| 4,226,235 A | 10/1980 | Sarnoff et al. | |
| 4,258,713 A | 3/1981 | Wardlow | |
| 4,261,358 A | 4/1981 | Vargas et al. | |
| 4,275,729 A | 6/1981 | Silver et al. | |
| 4,394,863 A | 7/1983 | Bartner | |
| 4,399,216 A | 8/1983 | Axel et al. | |
| 4,425,120 A | 1/1984 | Sampson et al. | |
| 4,437,859 A | 3/1984 | Whitehouse et al. | |
| 4,447,231 A | 5/1984 | Bekkering | |
| 4,510,245 A | 4/1985 | Cousens et al. | |
| 4,530,695 A | 7/1985 | Phillips et al. | |
| 4,565,543 A | 1/1986 | Bekkering et al. | |
| 4,573,976 A | 3/1986 | Sampson et al. | |
| 4,578,064 A | 3/1986 | Sarnoff et al. | |
| 4,624,660 A | 11/1986 | Mijers et al. | |
| 4,634,665 A | 1/1987 | Axel et al. | |
| 4,637,403 A | 1/1987 | Garcia et al. | |
| 4,664,653 A | 5/1987 | Sagstetter et al. | |
| 4,678,461 A | 7/1987 | Mesa | |
| 4,689,042 A | 8/1987 | Sarnoff et al. | |
| 4,723,937 A | 2/1988 | Sarnoff et al. | |
| 4,755,169 A | 7/1988 | Sarnoff et al. | |
| 4,795,432 A | 1/1989 | Karczmer | |
| 4,795,433 A | 1/1989 | Sarnoff | |
| 4,816,397 A | 3/1989 | Boss et al. | |
| 4,816,567 A | 3/1989 | Cabilly et al. | |
| 4,820,286 A | 4/1989 | van der Wal | |
| 4,822,340 A | 4/1989 | Kamstra | |
| 4,850,994 A | 7/1989 | Zerbst et al. | |
| 4,852,768 A | 8/1989 | Bartsch | |
| 4,902,279 A | 2/1990 | Schmidtz et al. | |
| 4,923,447 A | 5/1990 | Morgan | |
| 4,927,416 A | 5/1990 | Tomkiel | |
| 4,929,237 A | 5/1990 | Medway | |
| 4,955,868 A | 9/1990 | Klein | |
| 4,966,592 A | 10/1990 | Burns et al. | |
| 4,968,615 A | 11/1990 | Koszinowski et al. | |
| 4,994,034 A | 2/1991 | Botich et al. | |
| 5,041,088 A | 8/1991 | Ritson et al. | |
| 5,042,977 A | 8/1991 | Bechtold et al. | |
| 5,049,133 A | 9/1991 | Villen Pascual | |
| D322,479 S | 12/1991 | Miyaguchi | |
| 5,085,641 A | 2/1992 | Sarnoff et al. | |
| 5,085,642 A | 2/1992 | Sarnoff et al. | |
| 5,092,842 A | 3/1992 | Bechtold et al. | |
| 5,092,843 A | 3/1992 | Monroe et al. | |
| 5,102,393 A | 4/1992 | Sarnoff et al. | |
| 5,104,380 A | 4/1992 | Holman et al. | |
| 5,114,406 A | 5/1992 | Gabriel et al. | |
| 5,114,410 A | 5/1992 | Caralt Batlle | |
| 5,137,516 A | 8/1992 | Rand et al. | |
| 5,163,918 A | 11/1992 | Righi et al. | |
| 5,168,062 A | 12/1992 | Stinski | |
| 5,179,017 A | 1/1993 | Axel et al. | |
| 5,201,708 A | 4/1993 | Martin | |
| 5,223,409 A | 6/1993 | Ladner et al. | |
| 5,224,936 A | 7/1993 | Gallagher | |
| 5,225,539 A | 7/1993 | Winter | |
| 5,231,024 A | 7/1993 | Moeller et al. | |
| 5,242,240 A | 9/1993 | Gorham | |
| 5,244,465 A | 9/1993 | Michel | |
| 5,259,840 A | 11/1993 | Boris | |
| 5,263,934 A | 11/1993 | Haak | |
| 5,267,963 A | 12/1993 | Bachynsky | |
| 5,267,972 A | 12/1993 | Anderson | |
| 5,267,976 A | 12/1993 | Guerineau et al. | |
| 5,273,544 A | 12/1993 | van der Wal | |
| D343,897 S | 2/1994 | Rand et al. | |
| 5,295,965 A | 3/1994 | Wilmot | |
| 5,295,975 A | 3/1994 | Lockwood | |
| 5,298,024 A | 3/1994 | Richmond | |
| D346,219 S | 4/1994 | Fardigh | |
| 5,300,030 A * | 4/1994 | Crossman et al. | 604/136 |
| 5,318,538 A | 6/1994 | Martin | |
| 5,320,609 A | 6/1994 | Haber et al. | |
| 5,334,144 A | 8/1994 | Alchas et al. | |
| 5,342,308 A | 8/1994 | Boschetti | |
| 5,346,480 A | 9/1994 | Hess et al. | |
| 5,358,489 A * | 10/1994 | Wyrick | 604/136 |
| 5,376,080 A | 12/1994 | Petrussa | |
| 5,378,233 A | 1/1995 | Haber et al. | |
| 5,383,865 A | 1/1995 | Michel | |
| 5,391,151 A | 2/1995 | Wilmot | |
| 5,425,715 A | 6/1995 | Dalling et al. | |
| 5,433,712 A | 7/1995 | Stiles et al. | |
| 5,478,316 A | 12/1995 | Bitdinger et al. | |
| 5,480,387 A | 1/1996 | Gabriel et al. | |
| 5,530,101 A | 6/1996 | Queen et al. | |
| 5,531,705 A | 7/1996 | Alter et al. | |
| 5,569,192 A | 10/1996 | van der Wal | |
| 5,585,089 A | 12/1996 | Queen et al. | |
| 5,591,138 A | 1/1997 | Vaillancourt | |
| 5,599,309 A | 2/1997 | Marshall et al. | |
| 5,616,128 A | 4/1997 | Meyer | |
| 5,620,421 A | 4/1997 | Schmitz | |
| 5,634,906 A | 6/1997 | Haber et al. | |
| 5,637,094 A | 6/1997 | Stewart, Jr. et al. | |
| 5,645,534 A | 7/1997 | Chanoch | |
| 5,656,272 A | 8/1997 | Le et al. | |
| 5,658,259 A | 8/1997 | Pearson et al. | |
| 5,681,291 A | 10/1997 | Galli | |
| 5,693,761 A | 12/1997 | Queen et al. | |
| 5,693,762 A | 12/1997 | Queen et al. | |
| 5,744,360 A | 4/1998 | Hu et al. | |
| 5,779,677 A | 7/1998 | Frezza | |
| 5,807,335 A | 9/1998 | Kriesel et al. | |
| 5,807,346 A | 9/1998 | Frezza | |
| 5,817,111 A | 10/1998 | Riza | |
| 5,843,036 A | 12/1998 | Olive et al. | |
| 5,885,250 A | 3/1999 | Kriesel et al. | |
| 5,931,817 A | 8/1999 | Nguyen et al. | |
| 5,957,886 A | 9/1999 | Weston | |
| 5,957,897 A | 9/1999 | Jeffrey | |
| 5,984,900 A | 11/1999 | Mikkelsen | |
| 5,993,421 A | 11/1999 | Kriesel | |
| 6,048,336 A | 4/2000 | Gabriel | |
| 6,056,728 A | 5/2000 | von Schuckmann | |
| 6,077,247 A | 6/2000 | Marshall et al. | |
| 6,090,070 A | 7/2000 | Hager et al. | |
| 6,090,080 A | 7/2000 | Jost et al. | |
| 6,090,382 A | 7/2000 | Salfeld et al. | |
| 6,099,503 A | 8/2000 | Stradella | |
| 6,102,896 A | 8/2000 | Roser | |
| 6,110,147 A | 8/2000 | Perouse | |
| 6,149,626 A | 11/2000 | Bachynsky et al. | |
| 6,159,181 A | 12/2000 | Crossman et al. | |
| 6,171,285 B1 | 1/2001 | Johnson | |
| 6,203,530 B1 | 3/2001 | Stewart, Sr. | |
| 6,210,369 B1 | 4/2001 | Wilmot et al. | |
| 6,213,987 B1 | 4/2001 | Hirsch | |
| 6,221,044 B1 | 4/2001 | Greco | |
| 6,241,709 B1 | 6/2001 | Bechtold et al. | |

(56) References Cited

U.S. PATENT DOCUMENTS

| | | |
|---|---|---|
| 6,258,068 B1 | 7/2001 | Kirchofer et al. |
| 6,258,562 B1 | 7/2001 | Salfeld et al. |
| 6,270,479 B1 | 8/2001 | Bergens et al. |
| 6,277,097 B1 | 8/2001 | Mikkelsen et al. |
| 6,277,098 B1 | 8/2001 | Klitmose et al. |
| 6,277,099 B1 | 8/2001 | Strowe et al. |
| 6,280,421 B1 | 8/2001 | Kirchofer et al. |
| 6,312,412 B1 | 11/2001 | Saied et al. |
| 6,319,233 B1 | 11/2001 | Jansen et al. |
| 6,319,234 B1 | 11/2001 | Restelli et al. |
| 6,322,540 B1 | 11/2001 | Grabis et al. |
| 6,371,939 B2 | 4/2002 | Bergens et al. |
| 6,387,074 B1 | 5/2002 | Horppu et al. |
| 6,387,078 B1 * | 5/2002 | Gillespie, III ............... 604/181 |
| 6,413,237 B1 | 7/2002 | Caizza et al. |
| 6,419,658 B1 | 7/2002 | Restelli et al. |
| D461,555 S | 8/2002 | Binet et al. |
| 6,448,380 B2 | 9/2002 | Rathjen et al. |
| 6,451,983 B2 | 9/2002 | Rathjen et al. |
| 6,475,194 B2 | 11/2002 | Domici |
| 6,498,237 B2 | 12/2002 | Rathjen et al. |
| 6,509,015 B1 | 1/2003 | Salfeld et al. |
| 6,517,517 B1 | 2/2003 | Farrugia et al. |
| 6,544,234 B1 | 4/2003 | Gabriel |
| 6,575,939 B1 | 6/2003 | Brunel |
| 6,589,210 B1 | 7/2003 | Rolfe |
| 6,593,458 B1 | 7/2003 | Rathjen et al. |
| 6,656,163 B1 | 12/2003 | Marshall et al. |
| 6,656,164 B1 | 12/2003 | Smith |
| 6,673,035 B1 | 1/2004 | Rice et al. |
| 6,692,469 B1 | 2/2004 | Weekes et al. |
| 6,712,788 B2 | 3/2004 | Righi |
| 6,743,203 B1 | 6/2004 | Pickhard |
| 6,752,798 B2 | 6/2004 | McWethy |
| 6,767,336 B1 | 7/2004 | Kaplan |
| D494,270 S | 8/2004 | Reschke |
| 6,773,415 B2 | 8/2004 | Heiniger |
| 6,796,967 B2 | 9/2004 | Jensen |
| 6,802,827 B2 | 10/2004 | Andersson |
| 6,805,686 B1 | 10/2004 | Fathallah et al. |
| 6,808,507 B2 | 10/2004 | Roser |
| 6,817,989 B2 | 11/2004 | Svendsen |
| 6,872,194 B2 | 3/2005 | Doyle et al. |
| 6,926,697 B2 | 8/2005 | Malenchek |
| 6,932,793 B1 | 8/2005 | Marshall et al. |
| 6,945,960 B2 | 9/2005 | Barker |
| 6,976,976 B2 | 12/2005 | Doyle |
| 6,986,760 B2 | 1/2006 | Giambattista |
| 7,004,929 B2 | 2/2006 | McWethy |
| D518,175 S | 3/2006 | Hardin et al. |
| 7,056,306 B1 | 6/2006 | Halseth |
| 7,223,394 B2 | 5/2007 | Salfeld et al. |
| 7,320,682 B2 | 1/2008 | Cocker |
| 7,361,160 B2 | 4/2008 | Hommann et al. |
| 7,497,847 B2 | 3/2009 | Crawford et al. |
| 7,541,031 B2 | 6/2009 | Salfeld et al. |
| 7,588,761 B2 | 9/2009 | Salfeld et al. |
| 7,694,828 B2 | 4/2010 | Swift et al. |
| D622,374 S | 8/2010 | Julian et al. |
| D629,509 S | 12/2010 | Julian et al. |
| 7,863,426 B2 | 1/2011 | Wan et al. |
| 7,919,264 B2 | 4/2011 | Maksymowych et al. |
| 7,938,802 B2 | 5/2011 | Bicknell et al. |
| 8,162,887 B2 | 4/2012 | Bicknell et al. |
| D677,380 S | 3/2013 | Julian et al. |
| 2001/0005781 A1 | 6/2001 | Bergens |
| 2001/0053894 A1 | 12/2001 | Steenfeldt-Jensen |
| 2002/0002344 A1 | 1/2002 | Douglas et al. |
| 2002/0016563 A1 | 2/2002 | Hill et al. |
| 2002/0042592 A1 | 4/2002 | Wilmot et al. |
| 2002/0095120 A1 | 7/2002 | Larsen et al. |
| 2002/0111587 A1 | 8/2002 | Hommann et al. |
| 2002/0161337 A1 | 10/2002 | Shaw et al. |
| 2002/0169408 A1 | 11/2002 | Beretta et al. |
| 2002/0183690 A1 | 12/2002 | Arnisolle |
| 2003/0004466 A1 | 1/2003 | Bitdinger et al. |
| 2003/0004467 A1 | 1/2003 | Musick et al. |
| 2003/0012786 A1 | 1/2003 | Teoh et al. |
| 2003/0023203 A1 | 1/2003 | Lavi et al. |
| 2003/0023205 A1 | 1/2003 | Botich et al. |
| 2003/0050606 A1 | 3/2003 | Brand et al. |
| 2003/0093036 A1 | 5/2003 | Crossman et al. |
| 2003/0105430 A1 | 6/2003 | Lavi et al. |
| 2003/0161828 A1 | 8/2003 | Abdelghany et al. |
| 2003/0187401 A1 | 10/2003 | Doyle |
| 2003/0206898 A1 | 11/2003 | Fischkoff et al. |
| 2003/0212362 A1 | 11/2003 | Roser |
| 2003/0219438 A1 | 11/2003 | Salfeld et al. |
| 2003/0229308 A1 | 12/2003 | Tsals et al. |
| 2003/0235585 A1 | 12/2003 | Fischkoff et al. |
| 2003/0236502 A1 | 12/2003 | De La Serna et al. |
| 2004/0009172 A1 | 1/2004 | Fischkoff et al. |
| 2004/0019326 A1 | 1/2004 | Gilbert et al. |
| 2004/0024367 A1 | 2/2004 | Gilbert |
| 2004/0033228 A1 | 2/2004 | Krause et al. |
| 2004/0039336 A1 | 2/2004 | Amark et al. |
| 2004/0039337 A1 | 2/2004 | Letzing |
| 2004/0054327 A1 | 3/2004 | Gillespie |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0147875 A1 | 7/2004 | Wallace et al. |
| 2004/0151722 A1 | 8/2004 | Banerjee et al. |
| 2004/0166111 A1 | 8/2004 | Kaymakcalan et al. |
| 2004/0199117 A1 | 10/2004 | Giambattista et al. |
| 2004/0215151 A1 | 10/2004 | Marshall et al. |
| 2004/0219142 A1 | 11/2004 | Banerjee et al. |
| 2004/0225262 A1 | 11/2004 | Fathallah et al. |
| 2004/0229854 A1 | 11/2004 | Haan De |
| 2005/0020979 A1 | 1/2005 | Westbye et al. |
| 2005/0020984 A1 | 1/2005 | Lesch, Jr. |
| 2005/0027255 A1 | 2/2005 | Lavi et al. |
| 2005/0049550 A1 | 3/2005 | Kirchofer et al. |
| 2005/0049561 A1 | 3/2005 | Hommann et al. |
| 2005/0085776 A1 | 4/2005 | Hommann et al. |
| 2005/0090647 A1 | 4/2005 | Gatanaga et al. |
| 2005/0095208 A1 | 5/2005 | Battaglia et al. |
| 2005/0096597 A1 | 5/2005 | Crawford et al. |
| 2005/0101919 A1 | 5/2005 | Brunnberg |
| 2005/0124940 A1 | 6/2005 | Martin et al. |
| 2005/0137196 A1 | 6/2005 | Timmer et al. |
| 2005/0137534 A1 | 6/2005 | Hommann |
| 2005/0137571 A1 | 6/2005 | Hommann |
| 2005/0165360 A1 | 7/2005 | Stamp |
| 2005/0165361 A1 | 7/2005 | Marshall et al. |
| 2005/0165362 A1 | 7/2005 | Slawson |
| 2005/0165363 A1 | 7/2005 | Judson et al. |
| 2005/0171476 A1 | 8/2005 | Judson et al. |
| 2005/0171477 A1 | 8/2005 | Rubin et al. |
| 2005/0209569 A1 | 9/2005 | Ishikawa et al. |
| 2005/0222539 A1 | 10/2005 | Gonzales et al. |
| 2005/0222540 A1 | 10/2005 | Kirchofer et al. |
| 2005/0261634 A1 | 11/2005 | Karlsson |
| 2005/0273054 A1 | 12/2005 | Asch |
| 2005/0273055 A1 | 12/2005 | Harrison et al. |
| 2005/0273061 A1 | 12/2005 | Hommann et al. |
| 2005/0277885 A1 | 12/2005 | Scherer |
| 2005/0277886 A1 | 12/2005 | Hommann et al. |
| 2005/0277893 A1 | 12/2005 | Liversidge |
| 2005/0288633 A1 | 12/2005 | Jeffrey |
| 2006/0009385 A1 | 1/2006 | Hoffman et al. |
| 2006/0030819 A1 | 2/2006 | Young et al. |
| 2006/0036216 A1 | 2/2006 | Rimlinger et al. |
| 2006/0047250 A1 | 3/2006 | Hickinbotham et al. |
| 2006/0069350 A1 | 3/2006 | Buenger et al. |
| 2006/0069354 A1 | 3/2006 | Buenger et al. |
| 2006/0083741 A1 | 4/2006 | Hoffman et al. |
| 2006/0100588 A1 | 5/2006 | Brunnberg et al. |
| 2006/0111666 A1 | 5/2006 | Hommann et al. |
| 2006/0111674 A1 | 5/2006 | Vedrine |
| 2006/0129122 A1 | 6/2006 | Wyrick |

(56) References Cited

U.S. PATENT DOCUMENTS

| | | |
|---|---|---|
| 2006/0140907 A1 | 6/2006 | Blumberg et al. |
| 2006/0153846 A1 | 7/2006 | Krause et al. |
| 2006/0167413 A1 | 7/2006 | Marshall et al. |
| 2006/0189933 A1 | 8/2006 | Alheidt |
| 2006/0253083 A1 | 11/2006 | Liu |
| 2007/0041905 A1 | 2/2007 | Hoffman et al. |
| 2007/0049865 A1 | 3/2007 | Radmer et al. |
| 2007/0071747 A1 | 3/2007 | Hoffman et al. |
| 2007/0081996 A1 | 4/2007 | Hoffman et al. |
| 2007/0129674 A1 | 6/2007 | Liversidge |
| 2007/0142776 A9 | 6/2007 | Kovelman et al. |
| 2007/0161960 A1 | 7/2007 | Chen et al. |
| 2007/0202104 A1 | 8/2007 | Banerjee et al. |
| 2007/0239117 A1 | 10/2007 | Chelak |
| 2008/0019969 A1* | 1/2008 | Gorman ................. 424/141.1 |
| 2008/0097337 A1 | 4/2008 | Judd |
| 2008/0118496 A1 | 5/2008 | Medich et al. |
| 2008/0131374 A1 | 6/2008 | Medich |
| 2008/0166348 A1 | 7/2008 | Kupper et al. |
| 2008/0193466 A1 | 8/2008 | Banerjee et al. |
| 2008/0208125 A1 | 8/2008 | Bicknell et al. |
| 2008/0208140 A1 | 8/2008 | Barrelle |
| 2008/0227136 A1 | 9/2008 | Pla et al. |
| 2008/0269692 A1 | 10/2008 | James |
| 2008/0300549 A1 | 12/2008 | Verespej |
| 2008/0311043 A1 | 12/2008 | Hoffman et al. |
| 2009/0017472 A1 | 1/2009 | Stuhlmuller et al. |
| 2009/0024076 A1 | 1/2009 | Babaev |
| 2009/0024093 A1 | 1/2009 | Carrel |
| 2009/0028794 A1 | 1/2009 | Medich et al. |
| 2009/0036870 A1 | 2/2009 | Mounce et al. |
| 2009/0110679 A1 | 4/2009 | Li et al. |
| 2009/0123378 A1 | 5/2009 | Wong et al. |
| 2009/0148513 A1 | 6/2009 | Fraunhofer et al. |
| 2009/0155205 A1 | 6/2009 | Salfeld et al. |
| 2009/0157012 A1 | 6/2009 | Magne |
| 2009/0226530 A1 | 9/2009 | Lassner et al. |
| 2009/0239259 A1 | 9/2009 | Hsieh et al. |
| 2009/0240210 A1 | 9/2009 | Walton |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0299328 A1* | 12/2009 | Mudd et al. ................. 604/506 |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0160869 A1 | 6/2010 | Liversidge |
| 2010/0160894 A1 | 6/2010 | Julian et al. |
| 2010/0278822 A1 | 11/2010 | Fraunhofer et al. |
| 2011/0002935 A1 | 1/2011 | Wan et al. |
| 2011/0054414 A1 | 3/2011 | Shang et al. |
| 2011/0178500 A1 | 7/2011 | Shang et al. |
| 2012/0022499 A1 | 1/2012 | Anderson et al. |
| 2012/0197209 A1 | 8/2012 | Bicknell et al. |
| 2012/0233834 A1 | 9/2012 | Szechinski et al. |
| 2012/0238961 A1 | 9/2012 | Julian et al. |
| 2012/0289905 A1 | 11/2012 | Julian et al. |

FOREIGN PATENT DOCUMENTS

| | | |
|---|---|---|
| DE | 60207576 | 6/2006 |
| EP | 0068864 | 1/1983 |
| EP | 0173494 | 3/1986 |
| EP | 0184187 | 6/1986 |
| EP | 0260610 | 3/1988 |
| EP | 0154316 | 9/1989 |
| EP | 0171496 | 5/1993 |
| EP | 0401384 | 3/1996 |
| EP | 0125023 | 3/2002 |
| EP | 1334740 | 8/2003 |
| EP | 1364667 | 11/2003 |
| EP | 1523360 | 4/2005 |
| EP | 2067496 | 6/2009 |
| EP | 2085104 | 8/2009 |
| GB | 2243552 | 11/1991 |
| GB | 2388033 | 11/2003 |
| JP | 50-14835 | 5/1975 |
| JP | 5-161712 | 6/1993 |
| JP | 2001-512038 | 8/2001 |
| RU | 2004256 | 12/1993 |
| RU | 2069584 | 11/1996 |
| RU | 2131748 | 6/1999 |
| RU | 2169584 | 6/2001 |
| WO | WO 86/01533 | 3/1986 |
| WO | WO 87/02671 | 5/1987 |
| WO | WO 90/01047 | 2/1990 |
| WO | WO 90/07861 | 7/1990 |
| WO | WO 91/03553 | 3/1991 |
| WO | WO 91/17271 | 11/1991 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 93/06213 | 4/1993 |
| WO | WO 93/13819 A1 | 7/1993 |
| WO | WO 93/19751 | 10/1993 |
| WO | WO 94/06476 | 3/1994 |
| WO | WO 94/08609 | 4/1994 |
| WO | WO 94/09839 A1 | 5/1994 |
| WO | WO 94/13342 A1 | 6/1994 |
| WO | WO 94/26333 A1 | 11/1994 |
| WO | WO 97/29131 | 8/1997 |
| WO | WO 99/22789 A1 | 5/1999 |
| WO | WO 99/22792 A1 | 5/1999 |
| WO | WO 01/37908 A1 | 5/2001 |
| WO | WO 01/62319 A2 | 8/2001 |
| WO | WO 02/12502 | 2/2002 |
| WO | WO 02/072636 | 9/2002 |
| WO | WO 03/039633 A2 | 5/2003 |
| WO | WO 03/077968 A2 | 9/2003 |
| WO | WO 03/097133 A1 | 11/2003 |
| WO | WO 03/099358 | 12/2003 |
| WO | WO 04/000397 | 12/2003 |
| WO | WO 2004/016286 | 2/2004 |
| WO | WO 2004/060451 A1 | 7/2004 |
| WO | WO 2004/067068 A1 | 8/2004 |
| WO | WO 2005/002653 | 1/2005 |
| WO | WO 2005/046765 A2 | 5/2005 |
| WO | WO 2005/079889 A1 | 9/2005 |
| WO | WO 2005/090836 | 9/2005 |
| WO | WO 2005/113039 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115511 A1 | 12/2005 |
| WO | WO 2005/115512 A1 | 12/2005 |
| WO | WO 2005/115513 A1 | 12/2005 |
| WO | WO 2005/115516 A1 | 12/2005 |
| WO | WO 2006/000785 | 1/2006 |
| WO | WO 2006/058061 A1 | 6/2006 |
| WO | WO 2008/005315 | 1/2008 |

OTHER PUBLICATIONS

Office Action issued in Chinese Application No. 201010576413.6, dated Nov. 2, 2011.

International Preliminary Report on Patentability issued in International Application No. PCT/US2010/033012, dated Nov. 1, 2011.

Communication pursuant to Article 94(3) EPC issued by the European Patent Office in European Application No. 05758156.3-2320, dated Jan. 18, 2011.

Communication of a Notice of Opposition issued in European Application No. 04822031.3-1526, dated Jan. 6, 2010.

Communication pursuant to Article 96(2) EPC issued in European Application No. 04822031.3-1526, dated May 31, 2007.

(56) References Cited

OTHER PUBLICATIONS

Communication under Rule 112 EPC issued in European Application No. 04822031.3, dated Mar. 13, 2007.
International Search Report issued in International Application No. PCT/GB2005/002487, dated Aug. 19, 2005.
Written Opinion issued in International Application No. PCT/GB2005/002487, dated Dec. 23, 2006.
International Preliminary Report on Patentability issued in International Application No. PCT/GB2005/002487, dated Sep. 7, 2006.
International Search Report issued in International Application No. PCT/US2011/033504, dated Jul. 8, 2011.
Written Opinion issued in International Application No. PCT/US2011/033504, dated Jul. 8, 2011.
International Search Report issued in International Application No. PCT/US2007/015095, dated Sep. 11, 2008.
Written Opinion issued in International Application No. PCT/US2007/015095, dated Sep. 11, 2008.
International Preliminary Report on Patentability issued in International Application No. PCT/US2007/015095, dated Jun. 19, 2009.
International Search Report issued in International Application No. PCT/US2010/033012, dated Jul. 2, 2010.
Written Opinion issued in International Application No. PCT/US2010/033012, dated Jul. 2, 2010.
International Search Report issued in International Application No. PCT/US2010/060496, dated Feb. 16, 2011.
Written Opinion issued in International Application No. PCT/US2010/060496, dated Feb. 16, 2011.
International Search Report issued in International Application No. PCT/US2004/013278, dated May 30, 2005.
Written Opinion issued in International Application No. PCT/US2004/013278, dated Oct. 29, 2006.
International Preliminary Report on Patentability issued in International Application No. PCT/US2004/013278, dated Nov. 1, 2006.
Office Action issued in Russian Application No. 2006145501/14(049694), dated May 21, 2009.
Decision on Grant issued in Russian Application No. 2006145501/14(049694), dated Nov. 2, 2009.
Decision on Grant issued in Russian Application No. 2009102986/14(003862), dated Jun. 30, 2011.
Notice of Reasons for Rejection issued in Japanese Application No. 2007-517459, dated Aug. 24, 2010.
Notice of Reasons for Rejection issued in Japanese Application No. 2007-517459, dated Mar. 8, 2011.
Office Action issued in Mexican Application No. PA/a/2006/015056, dated Jul. 28, 2010.
Office Action issued in Mexican Application No. PA/a/2006/015056, dated Apr. 1, 2011.
Reexamination Decision issued in Chinese Application No. 200580020958.6, dated Jun. 13, 2011.
Notification of Reexamination issued in Chinese Application No. 200580020958.6, dated Aug. 17, 2010.
Rejection Decision issued in Chinese Application No. 200580020958.6, dated Jun. 5, 2009.
Office Action issued in Chinese Application No. 200580020958.6, dated Sep. 5, 2008.
Office Action issued in Australian Application No. 2005256832, dated Apr. 18, 2011.
Office Action issued in Australian Application No. 2005256832, dated Feb. 22, 2010.
Examination Report issued in New Zealand Application No. 552340, dated Apr. 27, 2009.
Examination Report issued in New Zealand Application No. 552340, dated Aug. 12, 2010.
BD Preventis, Shielding System for Prefilled Syringes, http://www.bd.com/pharmaceuticals/products/safety-engineered.asp, last accessed Aug. 26, 2010.
"Abbott Receives FDA Approval for New Humira Delivery Device," Press Release, dated Jun. 26, 2006 (color).
Notification of Provisional Rejection issued in Korean Application No. 10-2006-7026814, dated Jul. 19, 2011.
Correspondence from Dept. of Health & Human Services, Food and Drug Administration, to Robert Shaw/Owen Mumford, Inc. regarding Section 501(k) notification to market device, dated Nov. 10, 1999.
Correspondence from Dept. of Health & Human Services, Food and Drug Administration, to Robert Shaw/Owen Mumford, Inc. regarding Section 501(k) notification to market device, dated Mar. 6, 2000.
Owen Mumford drawing/schematic of the Abbott-Plunger AUTOject Mini, dated Mar. 25, 2002, Drawing No. P02 207.
Owen Mumford drawing/schematic of the Plunger-Miniject dated Mar. 30, 1993, Drawing No. P93.022.
Owen Mumford drawing/schematic of the Plunger-Miniject dated Mar. 30, 1993, Drawing No. AJ 358.
Owen Mumford drawing/schematic A of the Plunger-Miniject dated Sep. 5, 1997, Drawing No. AJ 654.
Owen Mumford drawing/schematic B of the Plunger-Miniject dated Sep. 5, 1997, Drawing No. AJ 654.
International Preliminary Report on Patentability issued in PCT/US2010/060496, mailed Jun. 19, 2012.
Examination Report issued in Australian Application No. 2010331936, dated Nov. 12, 2012.
Examination Report issued in New Zealand Application No. 600069, dated Mar. 28, 2013.
Decision of Final Rejection issued in Japanese Application No. 2007-517459, dated Jan. 10, 2012.

\* cited by examiner

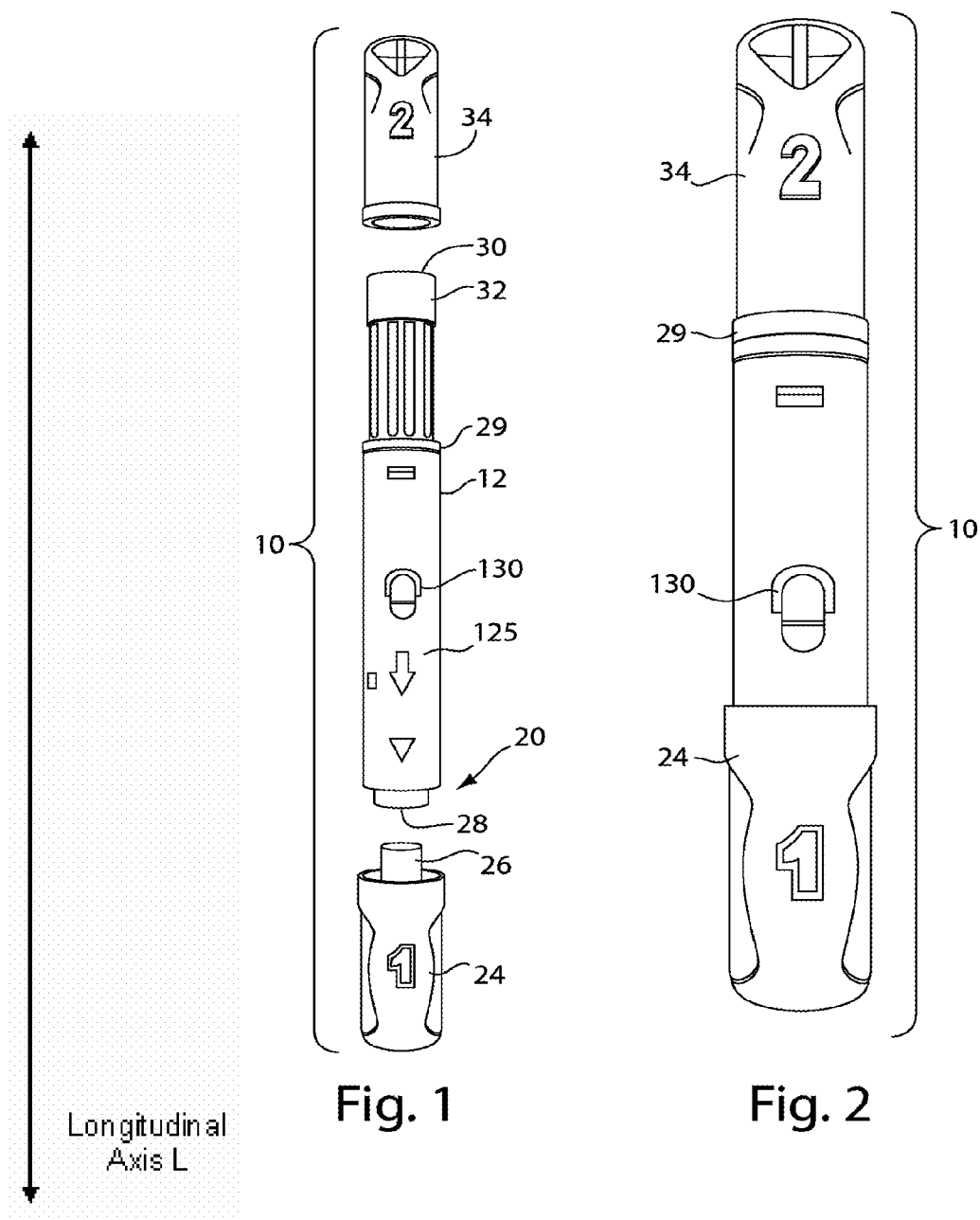

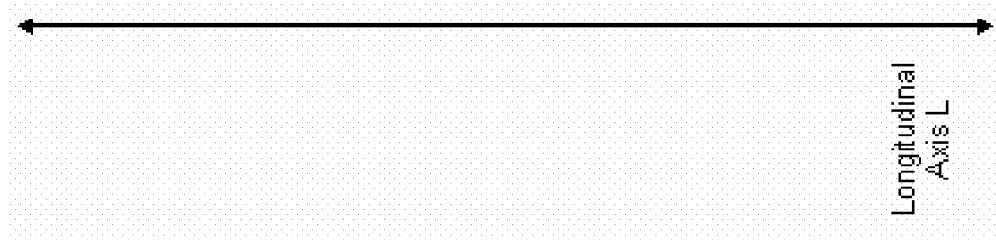
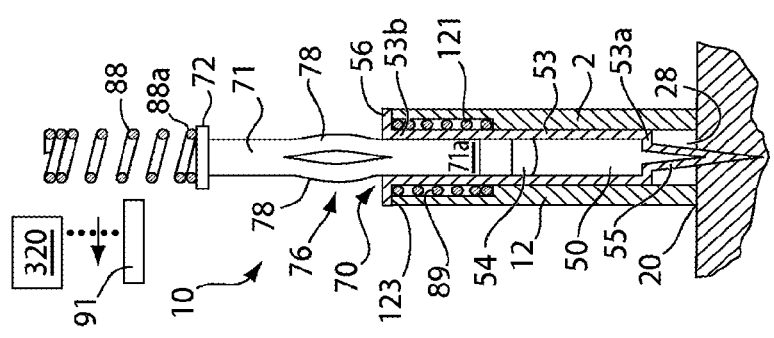
Fig. 4
PRIOR ART
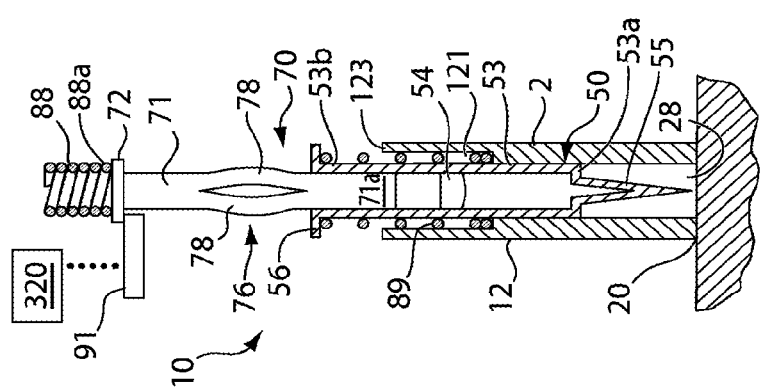
Fig. 3
PRIOR ART

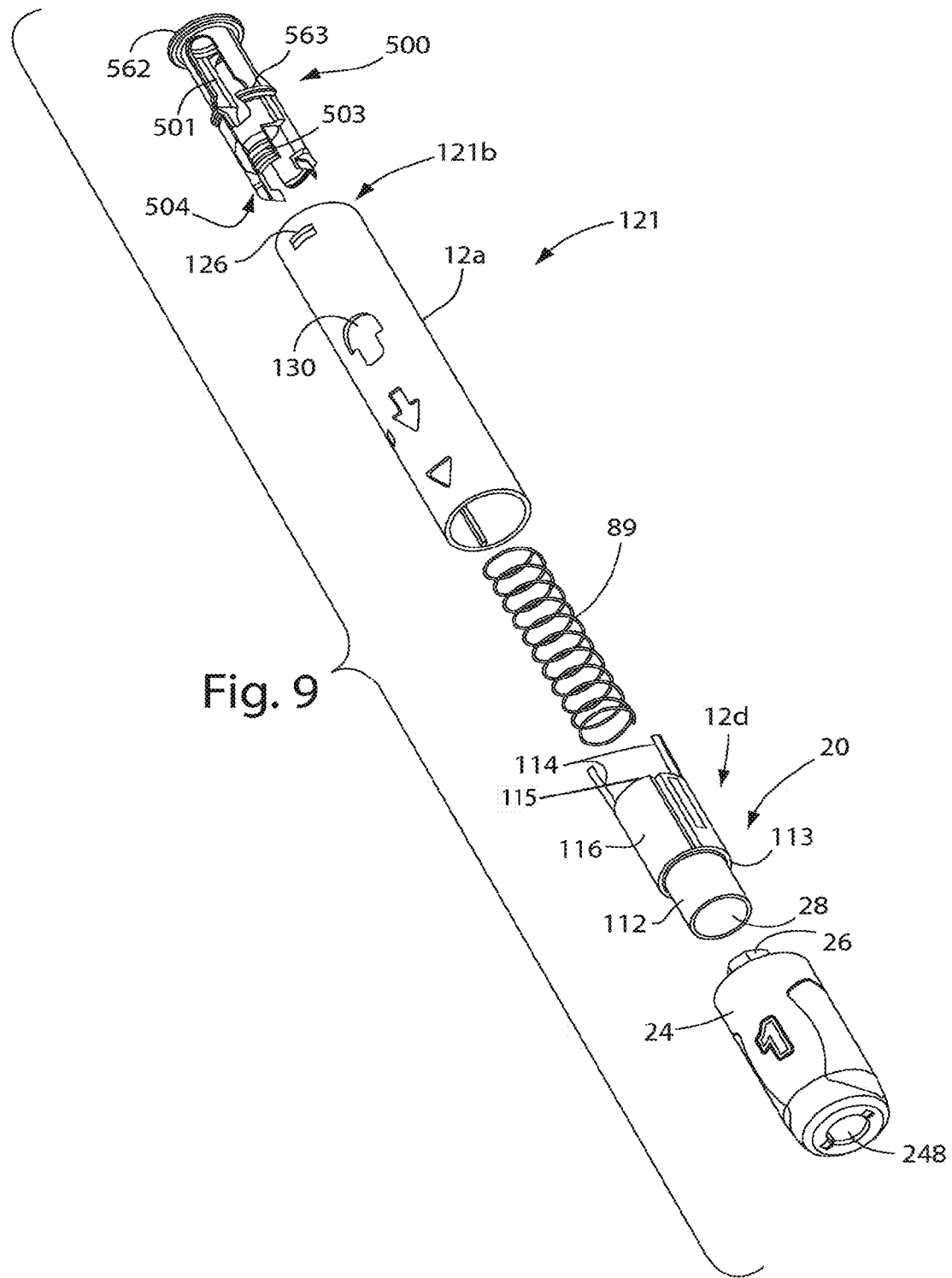

FIRING BUTTON FOR AUTOMATIC INJECTION DEVICE

RELATED APPLICATIONS

This application is related to and claims priority to U.S. Provisional Application Ser. No. 61/286,760, filed Dec. 15, 2009 and to U.S. Provisional Application Ser. No. 61/286,771 filed Dec. 15, 2009, and is related to U.S. patent application Ser. No. 12/770,557, filed Apr. 29, 2010. The entire contents of the aforementioned applications are expressly incorporated herein by reference in their entirety.

BACKGROUND

Automatic injection devices offer an alternative to manually-operated syringes for delivering therapeutic agents into patients' bodies and allowing patients to self-administer injections. Automatic injection devices have been used to deliver medications under emergency conditions, for example, to administer epinephrine to counteract the effects of a severe allergic reaction. Automatic injection devices have also been described for use in administering anti-arrhythmic medications and selective thrombolytic agents during a heart attack (See, e.g., U.S. Pat. Nos. 3,910,260; 4,004,577; 4,689, 042; 4,755,169; and 4,795,433). Various types of automatic injection devices are also described in, for example, U.S. Pat. Nos. 3,941,130; 4,261,358; 5,085,642; 5,092,843; 5,102,393; 5,267,963; 6,149,626; 6,270,479; and 6,371,939; and International Patent Publication No. WO/2008/005315.

Conventionally, an automatic injection device houses a syringe and, when operated, causes the syringe to move forwardly and a needle to project from the housing so that a therapeutic agent contained in the syringe is ejected into a patient's body. An automatic injection device typically includes a plunger with a distal end that is seated on a firing body before firing. In order to fire the device, a patient depresses a firing button which disengages the distal end of the plunger from the firing body and that allows the plunger to move the syringe forwardly.

Certain conventional devices may fail to fire or may fire after a delay if the firing button is not depressed with sufficient force, for example in the case of a rheumatic patient who is unable to exert high forces on the firing button. Even when a sufficient force is applied to the firing button, certain conventional devices may fail to fire or may fire after a delay due to conventional configurations of one or more structural components of the devices. These problematic firing patterns or misfires, i.e., failing to fire or firing with a delay, may be referred to as delayed delivery of an injection.

SUMMARY

In accordance with one exemplary embodiment, a firing button is provided for use in an automatic injection device that prevents or eliminates a misfiring of the automatic injection device that causes a delay in the delivery of an injection to the user. The firing button avoids a misfiring of the automatic injection device, the misfiring causing a delayed delivery of an injection. The unacceptable delay in the delivery of the injection can range from one second to several hours. The firing button includes an outer portion configured for contact by a user of the automatic injection device to allow the user to depress the outer portion toward a distal end of the automatic injection device. The firing button also includes an inner ring coupled to the outer portion and provided in proximity to a bifurcated end of a plunger in the automatic injection device. The inner ring is configured to engage the bifurcated end of the plunger when the outer portion is depressed by the user. The inner ring has an inner diameter of between 6.0 mm and 6.7 mm.

In accordance with another exemplary embodiment, an automatic injection device free of delayed delivery of an injection is provided. The automatic injection device avoids a misfiring, the misfiring causing a delayed delivery of an injection. A proximal end of the device is configured to deliver a dose, and a distal end of the device may be configured to be controllable by a user. The automatic injection device includes a firing body provided at the distal end of the automatic injection device. The firing body includes a hollow tubular member having a bore, and a radial surface extending from a distal portion of the hollow tubular member. The automatic injection device includes a plunger having a longitudinally extending plunger arm and a radially extending plunger foot, the plunger arm extending through the bore of the hollow tubular member of the firing body, and the plunger foot seated on the radial surface of the firing body. The automatic injection device includes a firing button provided at the distal end of the automatic injection device. The firing button has an inner ring having an inner diameter of between 6.0 mm and 6.7 mm provided in proximity to the plunger foot. The inner ring is configured to contact the plunger foot and to disengage the plunger foot from the radial surface of the firing body to allow the plunger to move through the bore of the hollow tubular member of the firing body, when the firing button is activated by the user.

In accordance with another exemplary embodiment, a firing button is provided for use in an automatic injection device free of delayed delivery of an injection. The firing button avoids a misfiring of the automatic injection device, the misfiring causing a delayed delivery of an injection. The firing button includes an outer portion configured for contact by a user of the automatic injection device to allow the user to depress the outer portion toward a distal end of the automatic injection device. The firing button includes an inner ring coupled to the outer portion and provided in proximity to a bifurcated end of a plunger in the automatic injection device. The inner ring is configured to engage the bifurcated end of the plunger when the outer portion is depressed by the user. The inner ring has a minimum wall thickness configured to reduce deformation of the inner ring when the inner ring engages with the bifurcated end of the plunger.

In accordance with another exemplary embodiment, a method for forming a firing button for use in an automatic injection device free of delayed delivery of an injection. The firing button avoids a misfiring of the automatic injection device, the misfiring causing a delayed delivery of an injection. The method includes forming an outer portion for contact by a user of the automatic injection device to allow the user to depress the outer portion toward a distal end of the automatic injection device. The method includes forming an inner ring having an inner diameter of between 6.0 mm and 6.7 mm. The inner ring is configured to engage the bifurcated end of the plunger when the outer portion is depressed by the user. The method includes coupling the inner ring to the outer portion in proximity to a bifurcated end of a plunger in the automatic injection device.

In accordance with another exemplary embodiment, a method is provided for forming an automatic injection device free of delayed delivery of an injection. The automatic injection device avoids a misfiring, the misfiring causing a delayed delivery of an injection. The method includes providing a firing body at the distal end of the automatic injection device. The firing body includes a hollow tubular member having a bore and a radial surface extending from a distal portion of the hollow tubular member. The method includes extending a longitudinally extending plunger arm of a plunger through the bore of the hollow tubular member of the firing body, and seating a plunger foot provided at a distal end of the plunger on the radial surface of the firing body. The method includes providing a firing button at the distal end of the automatic injection device in proximity to the plunger foot, the firing button comprising an inner ring having an inner diameter of between 6.0 mm and 6.7 mm, the inner ring of the firing button configured to contact the plunger foot and to disengage the plunger foot from the radial surface of the firing body to allow the plunger to move through the bore of the hollow tubular member of the firing body, when the firing button is activated by the user.

In accordance with another exemplary embodiment, a method is provided for using an automatic injection device free of delayed delivery of an injection to deliver a dose. The automatic injection device avoids a misfiring, the misfiring causing a delayed delivery of an injection. The method includes depressing a firing button provided at a distal end of the automatic injection device, and engaging an inner ring of the firing button with a plunger foot to disengage the plunger foot from a surface of a firing body. The inner ring has an inner diameter ranging between 6.0 mm and 6.7 mm. The method includes moving the plunger through a bore of a hollow tubular member of the firing body when the plunger foot is disengaged from the firing body, transmitting an expulsion force to a bung using the moving plunger, and expelling the dose from a syringe using the expulsion force applied to the bung.

BRIEF DESCRIPTION OF THE DRAWINGS

The foregoing and other objects, aspects, features and advantages of exemplary embodiments will be more fully understood from the following description when read together with the accompanying drawings, in which:

FIG. 1 illustrates a perspective view of an exemplary automatic injection device in which caps that cover proximal and distal ends of the housing are removed.

FIG. 2 illustrates a perspective view of the exemplary automatic injection device of FIG. 1 in which the housing is capped.

FIG. 3 (prior art) illustrates a cross-sectional schematic view of an exemplary automatic injection device prior to use.

FIG. 4 (prior art) illustrates a cross-sectional schematic view of the exemplary automatic injection device of FIG. 3 during a subsequent stage of operation.

FIG. 5 (prior art) illustrates a cross-sectional schematic view of the exemplary automatic injection device of FIGS. 3 and 4 during an additional stage of operation.

FIG. 9 illustrates a perspective view of the syringe housing assembly of the exemplary automatic injection device of FIG. 6.

DETAILED DESCRIPTION

Figure 6:
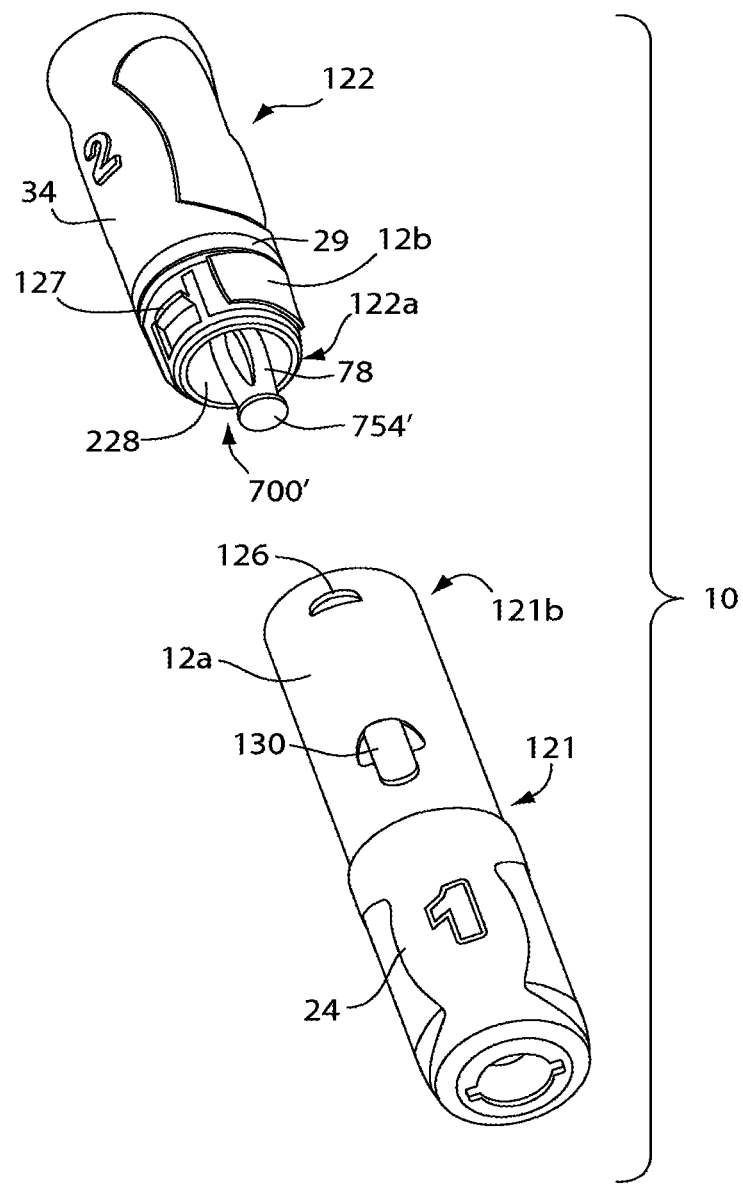
FIG. 6 illustrates a perspective view of an exemplary automatic injection device with a syringe housing assembly and a firing mechanism assembly.

Exemplary embodiments minimize or eliminate a misfire of an automatic injection device that causes a delay in the delivery of an injection to a user. Exemplary automatic injection devices ensure consistent successful firing of the automatic injection devices. Exemplary embodiments provide, in part, firing mechanism assemblies that minimize or eliminate a misfire that causes a delay in delivery of an injection. In some cases, the unacceptable delay in delivery can range from four seconds to several hours. Exemplary embodiments provide, automatic injection devices including firing mechanism assemblies that minimize or eliminate the delayed delivery of an injection once the firing button is depressed, methods for minimizing or eliminating the delayed delivery of an injection in automatic injection devices once the firing button is depressed, and methods for using automatic injection devices that minimize or eliminate delayed delivery of an injection to deliver a substance into a patient's body. Automatic injection devices provided in accordance with exemplary embodiments may be used for administering any type of substance into a patient's body including, but not limited to, liquid therapeutic agents, e.g., adalimumab (HUMIRA®), golimumab, etc.

The delayed delivery of an injection once the firing button is depressed exhibited by a misfired automatic injection device may be affected by one or more factors associated with the device, the patient activating the device, the manufacturing process of the device, the environment in which the device is stored, etc. Exemplary factors associated with the misfire of the device may include the structure, configuration and/or material of one or more of the following components: the inner ring of a firing button ring, the length of a firing button ring, the diameter of a firing body tunnel, the angle of a firing body conical surface, the height of a plunger foot, the width of a plunger foot, etc.

Exemplary factors of the misfire of the device associated with the patient activating the device may include, but are not limited to, the force applied by the patient on the firing button of the device, the distance from a starting position over which the patient depresses the firing button of the device, etc. Exemplary factors of the misfire of the device associated with the manufacturing process of the device may include, but are not limited to, the mold temperature used in molding one or more components (e.g., the plunger) of the device, the cooling time used in molding one or more components (e.g., the plunger) of the device, etc. Exemplary factors of the misfire of the device associated with the environment in which the device is stored may include, but are not limited to, the age of the device or the components of the device, the post-assembly time of the device, the temperature of the environment, the humidity of the environment, etc.

Exemplary embodiments may configure one or more of the above factors and optionally additional factors to minimize or eliminate misfiring or the delay in delivery of an injection to a user of an exemplary automatic injection device. For example, in a surprising result, the inner diameter of the firing button ring may be decreased to minimize or eliminate the delay in delivery of an injection in exemplary automatic injection devices. In another surprising result, the length of the firing button ring may be increased to minimize or eliminate the delay in delivery of an injection in exemplary automatic injection devices.

I. DEFINITIONS

Certain terms are defined in this section to facilitate understanding of exemplary embodiments.

The automatic injection device, e.g., autoinjector pen, of exemplary embodiments may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the patient, and the ability of the antibody, antibody portion, or other TNFα inhibitor to elicit a desired response in the patient. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in patients prior to or at an earlier stage of disease, the prophylactically effective amount will be less than the therapeutically effective amount.

The term "substance" refers to any type of drug, biologically active agent, biological substance, chemical substance or biochemical substance that is capable of being administered in a therapeutically effective amount to a patient employing exemplary automatic injection devices. Exemplary substances include, but are not limited to, agents in a liquid state. Such agents may include, but are not limited to, adalimumab (HUMIRA®) and proteins that are in a liquid solution, e.g., fusion proteins and enzymes. Examples of proteins in solution include, but are not limited to, Pulmozyme (Dornase alfa), Regranex (Becaplermin), Activase (Alteplase), Aldurazyme (Laronidase), Amevive (Alefacept), Aranesp (Darbepoetin alfa), Becaplermin Concentrate, Betaseron (Interferon beta-1b), BOTOX (Botulinum Toxin Type A), Elitek (Rasburicase), Elspar (Asparaginase), Epogen (Epoetin alfa), Enbrel (Etanercept), Fabrazyme (Agalsidase beta), Infergen (Interferon alfacon-1), Intron A (Interferon alfa-2a), Kineret (Anakinra), MYOBLOC (Botulinum Toxin Type B), Neulasta (Pegfilgrastim), Neumega (Oprelvekin), Neupogen (Filgrastim), Ontak (Denileukin diftitox), PEGASYS (Peginterferon alfa-2a), Proleukin (Aldesleukin), Pulmozyme (Dornase alfa), Rebif (Interferon beta-1a), Regranex (Becaplermin), Retavase (Reteplase), Roferon-A (Interferon alfa-2), TNKase (Tenecteplase), and Xigris (Drotrecogin alfa), Arcalyst (Rilonacept), NPlate (Romiplostim), Mircera (methoxypolyethylene glycol-epoetin beta), Cinryze (C1 esterase inhibitor), Elaprase (idursulfase), Myozyme (alglucosidase alfa), Orencia (abatacept), Naglazyme (galsulfase), Kepivance (palifermin) and Actimmune (interferon gamma-1b).

A protein in solution may also be an immunoglobulin or antigen-binding fragment thereof, such as an antibody or antigen-binding portion thereof. Examples of antibodies that may be used in an exemplary automatic injection device include, but are not limited to, chimeric antibodies, non-human antibodies, human antibodies, humanized antibodies, and domain antibodies (dAbs). In an exemplary embodiment, the immunoglobulin or antigen-binding fragment thereof, is an anti-TNF and/or an anti-IL-12 antibody (e.g., it may be a dual variable domain immunoglobulin (DVD) Ig™). Other examples of immunoglobulins or antigen-binding fragments thereof that may be used in the methods and compositions of exemplary embodiments include, but are not limited to, 1D4.7 (anti-IL-12/IL-23 antibody; Abbott Laboratories); 2.5 (E)mg1 (anti-IL-18; Abbott Laboratories); 13C5.5 (anti-IL-13 antibody; Abbott Laboratories); J695 (anti-IL-12; Abbott Laboratories); Afelimomab (Fab 2 anti-TNF; Abbott Laboratories); HUMIRA (adalimumab) Abbott Laboratories; Campath (Alemtuzumab); CEA-Scan Arcitumomab (fab fragment); Erbitux (Cetuximab); Herceptin (Trastuzumab); Myoscint (Imciromab Pentetate); ProstaScint (Capromab Pendetide); Remicade (Infliximab); ReoPro (Abciximab); Rituxan (Rituximab); Simulect (Basiliximab); Synagis (Palivizumab); Verluma (Nofetumomab); Xolair (Omalizumab); Zenapax (Daclizumab); Zevalin (Ibritumomab Tiuxetan); Orthoclone OKT3 (Muromonab-CD3); Panorex (Edrecolomab); Mylotarg (Gemtuzumab ozogamicin); golimumab (Centocor); Cimzia (Certolizumab pegol); Soliris (Eculizumab); CNTO 1275 (ustekinumab); Vectibix (panitumumab); Bexxar (tositumomab and $I^{131}$ tositumomab); and Avastin (bevacizumab).

Additional examples of immunoglobulins, or antigen-binding fragments thereof, that may be used in the methods and compositions of exemplary embodiments include, but are not limited to, proteins comprising one or more of the following: the D2E7 light chain variable region (SEQ ID NO: 1), the D2E7 heavy chain variable region (SEQ ID NO: 2), the D2E7 light chain variable region CDR3 (SEQ ID NO: 3), the D2E7 heavy chain variable region CDR3 (SEQ ID NO:4), the D2E& light chain variable region CDR2 (SEQ ID NO: 5), the D2E7 heavy chain variable region CDR2 (SEQ ID NO: 6), the D2E7 light chain variable region CDR1 (SEQ ID NO: 7), the D2E7 heavy chain variable region CDR1 (SEQ ID NO: 8), the 2SD4 light chain variable region (SEQ ID NO: 9), the 2SD4 heavy chain variable region (SEQ ID NO: 10), the 2SD4 light chain variable CDR3 (SEQ ID NO: 11), the EP B12 light chain variable CDR3 (SEQ ID NO: 12), the VL10E4 light chain variable CDR3 (SEQ ID NO: 13), the VL100A9 light chain variable CDR3 (SEQ ID NO: 14), the VLL100D2 light chain variable CDR3 (SEQ ID NO: 15), the VLL0F4 light chain variable CDR3 (SEQ ID NO: 16), the LOE5 light chain variable CDR3 (SEQ ID NO: 17), the VLLOG7 light chain variable CDR3 (SEQ ID NO: 18), the VLLOG9 light chain variable CDR3 (SEQ ID NO: 19), the VLLOH1 light chain variable CDR3 (SEQ ID NO: 20), the VLLOH10 light chain variable CDR3 (SEQ ID NO: 21), the VL1B7 light chain variable CDR3 (SEQ ID NO: 22), the VL1C1 light chain variable CDR3 (SEQ ID NO: 23), the VL0.1F4 light chain variable CDR3 (SEQ ID NO: 24), the VL0.1H8 light chain variable CDR3 (SEQ ID NO: 25), the LOE7. A light chain variable CDR3 (SEQ ID NO: 26), the 2SD4 heavy chain variable region CDR (SEQ ID NO: 27), the VH1B11 heavy chain variable region CDR (SEQ ID NO: 28), the VH1D8 heavy chain variable region CDR (SEQ ID NO: 29), the VH1A11 heavy chain variable region CDR (SEQ ID NO: 30), the VH1B12 heavy chain variable region CDR (SEQ ID NO: 31), the VH1E4 heavy chain variable region CDR (SEQ ID NO: 32), the VH1F6 heavy chain variable region CDR (SEQ ID NO: 33), the 3C-H2 heavy chain variable region CDR (SEQ ID NO: 34), and the VH1-D2.N heavy chain variable region CDR (SEQ ID NO: 35).

The term "human TNFα" (abbreviated herein as hTNFα, or simply hTNF) refers to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) Biochem. 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" refers to an agent that interferes with TNFα activity. The term also includes each of the anti-TNFα human antibodies (used interchangeably herein with TNFα antibodies) and antibody portions described herein as well as those described in U.S. Pat. Nos. 6,090,382; 6,258,562; 6,509,015; 7,223,394; and 6,509,015. In one embodiment, the TNFα inhibitor used in the invention is an anti-TNFα antibody, or a fragment thereof, including infliximab (Remicade®, Johnson and Johnson; described in U.S. Pat. No. 5,656,272); CDP571 (a humanized monoclonal anti-TNF-alpha IgG4 antibody); CDP 870 (a humanized monoclonal anti-TNF-alpha antibody fragment); an anti-TNF dAb (Peptech); CNTO 148 (golimumab; Centocor, see WO 02/12502 and U.S. Pat. No. 7,521,206 and U.S. Pat. No. 7,250,165); and adalimumab (HUMIRA® Abbott Laboratories, a human anti-TNF mAb, described in U.S. Pat. No. 6,090,382 as D2E7). Additional TNF antibodies that may be used in the invention are described in U.S. Pat. Nos. 6,593,458; 6,498,237; 6,451,983; and 6,448,380. In another embodiment, the TNFα inhibitor is a TNF fusion protein, e.g., etanercept (Enbrel®, Amgen; described in WO 91/03553 and WO 09/406,476). In another embodiment, the TNFα inhibitor is a recombinant TNF binding protein (r-TBP-I) (Serono).

In one embodiment, the term "TNFα inhibitor" excludes infliximab. In one embodiment, the term "TNFα inhibitor" excludes adalimumab. In another embodiment, the term "TNFα inhibitor" excludes adalimumab and infliximab.

In one embodiment, the term "TNFα inhibitor" excludes etanercept, and, optionally, adalimumab, infliximab, and adalimumab and infliximab.

In one embodiment, the term "TNFα antibody" excludes infliximab. In one embodiment, the term "TNFα antibody" excludes adalimumab. In another embodiment, the term "TNFα antibody" excludes adalimumab and infliximab.

The term "antibody" refers to immunoglobulin molecules generally comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015.

The term "antigen-binding portion" of an antibody (or simply "antibody portion") refers to one or more fragments of an antibody that retain the ability to specifically bind to an antigen (e.g., hTNFα). Fragments of a full-length antibody can perform the antigen-binding function of an antibody. Examples of binding fragments encompassed within the term "antigen-binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989)*Nature* 341:544-546), which consists of a VH or VL domain; (vi) an isolated complementarity determining region (CDR); and (vii) a dual variable domain immunoglobulin (DVD-Ig). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123). The antibody portions of the invention are described in further detail in U.S. Pat. Nos. 6,090,382; 6,258,562; and 6,509,015.

The term "recombinant human antibody" refers to all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germ line immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germ line VH and VL sequences, may not naturally exist within the human antibody germ line repertoire in vivo.

Such chimeric, humanized, human, and dual specific antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc.

Natl. Acad. Sci. USA 84:214-218; Nishimura et al. (1987) Cancer Res. 47:999-1005; Wood et al. (1985) Nature 314: 446-449; Shaw et al. (1988) J. Natl. Cancer Inst. 80:1553-1559; Morrison (1985) Science 229:1202-1207; Oi et al. (1986) BioTechniques 4:214; U.S. Pat. No. 5,225,539; Jones et al. (1986) Nature 321:552-525; Verhoeyan et al. (1988) Science 239:1534; and Beidler et al. (1988) J. Immunol. 141:4053-4060, Queen et al. (1989) Proc. Natl. Acad. Sci. USA 86:10029-10033 (1989); U.S. Pat. No. 5,530,101; U.S. Pat. No. 5,585,089; U.S. Pat. No. 5,693,761; U.S. Pat. No. 5,693,762; WO 90/07861; and U.S. Pat. No. 5,225,539.

The term "isolated antibody" refers to an antibody that is substantially free of other antibodies having different antigenic specificities (e.g., an isolated antibody that specifically binds hTNFα and is substantially free of antibodies that specifically bind antigens other than hTNFα). An isolated antibody that specifically binds hTNFα may have cross-reactivity to other antigens, such as TNFα molecules from other species. Moreover, an isolated antibody may be substantially free of other cellular material and/or chemicals.

The term "neutralizing antibody" (or an "antibody that neutralized hTNFα activity") refers to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFαbiological activity can be assessed by one or more of several standard in vitro or in vivo assays known in the art (see U.S. Pat. No. 6,090,382). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance" refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) *Ann. Biol. Clin.* 51:19; Jönsson et al. (1991) *Biotechniques* 11:620-627; Johnsson et al. (1995) *J. Mol. Recognit.* 8:125; and Johnnson et al. (1991) *Anal. Biochem.* 198:268.

The term "$K_{off}$" refers to the off rate constant for dissociation of an antibody from the antibody/antigen complex.

The term "$K_d$" refers to the dissociation constant of a particular antibody-antigen interaction.

The term "$IC_{50}$" refers to the concentration of the inhibitor required to inhibit the biological endpoint of interest, e.g., neutralize cytotoxicity activity.

The term "dose" or "dosage" refers to an amount of a substance, such as a TNFαinhibitor, which is administered to a patient preferably using the automatic injection device of the invention. In one embodiment, the dose comprises an effective amount, for example, including 20 mg, 30 mg, 40 mg, 50 mg, 60 mg, 70 mg, 80 mg, 90 mg, 100 mg, 110 mg, 120 mg, 130 mg, 140 mg, 150 mg, and 160 mg, of the TNFα inhibitor adalimumab.

The term "dosing" refers to the administration of a substance (e.g., an anti-TNFα antibody) to achieve a therapeutic objective (e.g., treatment of rheumatoid arthritis).

The term "dosing regimen" describes a treatment schedule for a substance, such as a TNFα inhibitor, e.g., a treatment schedule over a prolonged period of time and/or throughout the course of treatment, e.g. administering a first dose of a TNFα inhibitor at week 0 followed by a second dose of a TNFα inhibitor on a biweekly dosing regimen.

The term "biweekly dosing regimen", "biweekly dosing", and "biweekly administration" refer to the time course of administering a substance (e.g., an anti-TNFα antibody) to a patient to achieve a therapeutic objective, e.g., throughout the course of treatment. The biweekly dosing regimen is not intended to include a weekly dosing regimen. Preferably, the substance is administered every 9 to 19 days, more preferably, every 11 to 17 days, even more preferably, every 13 to 15 days, and most preferably, every 14 days. In one embodiment, the biweekly dosing regimen is initiated in a patient at week 0 of treatment. In another embodiment, a maintenance dose is administered on a biweekly dosing regimen. In one embodiment, both the loading and maintenance doses are administered according to a biweekly dosing regimen. In one embodiment, biweekly dosing includes a dosing regimen wherein doses of a TNFα inhibitor are administered to a patient every other week beginning at week 0. In one embodiment, biweekly dosing includes a dosing regimen where doses of a TNFα inhibitor are administered to a patient every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc. Biweekly dosing methods are also described in U.S. 2003/0235585.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent.

The term "concomitant" as in the phrase "concomitant therapeutic treatment" includes administering an agent in the presence of a second agent. A concomitant therapeutic treatment method includes methods in which the first, second, third, or additional substances are co-administered. A concomitant therapeutic treatment method also includes methods in which the first or additional agents are administered in the presence of a second substance or additional substances, wherein the second or additional agents, for example, may have been previously administered. A concomitant therapeutic treatment method may be executed step-wise by different patients. For example, one subject may administer to a patient a first agent and a second subject may to administered to the patient a second substance, and the administering steps may be executed at the same time, or nearly the same time, or at distant times, so long as the first substance (and additional substances) are after administration in the presence of the second substance (and additional substances). The actor and the patient may be the same entity (e.g., human).

The term "combination therapy" refers to the administration of two or more therapeutic substances, e.g., an anti-TNFα antibody and another drug. The other drug(s) may be administered concomitant with, prior to, or following the administration of an anti-TNFα antibody.

The term "treatment" refers to therapeutic treatment, as well as prophylactic or suppressive measures, for the treatment of a disorder, such as a disorder in which TNFα is detrimental, e.g., rheumatoid arthritis.

The term "patient" or "user" refers to any type of animal, human or non-human, that may be injected a substance using exemplary automatic injection devices.

The term "automatic injection device" or "autoinjector" refers to a device that enables a patient to self-administer a dose of a substance, such as a liquid medication, wherein the automatic injection device differs from a standard syringe by the inclusion of a firing mechanism assembly for automatically delivering the substance into the patient's body by injection when the firing mechanism assembly is engaged. In an exemplary embodiment, the automatic injection device may be wearable on the patient's body.

The term "firing mechanism" refers to a mechanism that, when engaged by a firing engagement mechanism, automatically delivers a substance contained in an automatic injection device into a patient's body. A firing engagement mechanism may be any type of mechanism that engages and triggers the firing mechanism including, but not limited to, a firing button that may be pushed by a patient to trigger the firing mechanism.

The term "force to fire" (or "FtF") refers to the minimum force that must be delivered to a firing engagement mechanism of an automatic injection device in order to trigger the firing mechanism so that it expels the substance contained in the device. Delivery of a force equal to or greater than the required FtF to a firing engagement mechanism causes the firing engagement mechanism to trigger the firing mechanism so that it expels the substance from the device. The FtF may be delivered to the firing engagement mechanism manually by a patient or automatically by an actuation mechanism. An exemplary FtF for an automatic injection device may range between about 5 N and about 25 N. Another exemplary FtF for an automatic injection device may range between about 10 N and about 15 N. Another exemplary FtF for an automatic injection device may range between about 8 N and about 12 N. Another exemplary FtF for an automatic injection device has a minimum value of about 25 N. Another exemplary FtF for an automatic injection device has a maximum value of about 25 N.

The term "flexural modulus" (or "flex modulus" or "flexural modulus of elasticity") refers to the ratio of maximum stress to maximum strain of a material within the elastic limit of the material, as determined from a stress-strain diagram obtained in a flexure test. The flex modulus of a material is a measure of the material's elasticity, or the ability of the material to be deformed and to subsequently return to its original shape.

The term "tabbed foot" or "tab foot" refers to a material attached to or radially projecting from one or both arms of a bifurcated end of a syringe plunger, and is configured to contact and engage a firing engagement mechanism.

The term "initial contact surface" (or "ICS") refers to a portion of the outer surface of a tabbed foot formed at the bifurcated end of a syringe plunger. The ICS is formed between a top surface of the tabbed foot and a secondary contact surface (SCS) of the tabbed foot, and is configured to contact a firing engagement mechanism, e.g., a firing button.

The term "secondary contact surface" (or "SCS") refers to a portion of the outer surface of a tabbed foot formed at the bifurcated end of a syringe plunger. The SCS is formed between the ICS of the tabbed foot and a bottom surface of the tabbed foot.

The term "initial contact surface angle" or "ICS angle" refers to the angle formed by the ICS relative to the longitudinal axis of the plunger arm.

The term "initial contact surface length" or "ICS length" refers to the length of the tabbed foot at a transition point between the ICS and the SCS as measured along an axis transverse to the longitudinal axis.

The term "plunger arm width" refers to the distance between the arms of a bifurcated end of a syringe plunger.

The term "plunger base bridge angle" or "PBB angle" refers to the angle formed between the arms of a bifurcated end of a syringe plunger. For example, a PBB angle of 0° means that the plunger arms are parallel to each other. There is a direct relationship between the PBB angle and the plunger arm width in that increasing the PBB angle increases the plunger arm width and decreasing the PBB angle decreases the plunger arm width.

The term "pre-filled syringe/device" refers to a syringe/device that is filled with a substance immediately prior to administration of the substance to a patient, or a syringe/device that is filled with a substance and stored in this pre-filled form for a period of time before administration of the substance to a patient.

The term "thermoplastic material" refers to a material that has the property of softening or fusing when heated and of hardening and becoming rigid when cooled. A thermoplastic material is a polymer that turns into a liquid state or a molten state when heated sufficiently, and that freezes into a very glassy state when cooled sufficiently. Thermoplastic materials can be re-melted and cooled repeatedly without the materials undergoing any appreciable chemical change.

Most thermoplastics are high-molecular-weight polymers whose chains associate through weak Van der Waals forces (polyethylene), stronger dipole-dipole interactions and hydrogen bonding (nylon), or even stacking of aromatic rings (polystyrene). Thermoplastic polymers differ from thermosetting polymers (vulcanized rubber) as they, unlike thermosetting polymers, can be re-melted and re-molded.

Many thermoplastic materials are formed by addition polymers or by condensation polymers. An addition polymer is a polymer formed by an addition reaction in which many monomers bond together via rearrangement of bonds without the loss of any atoms or molecules. Exemplary addition polymers include, but are not limited to, vinyl chain-growth polymers such as polyethylene and polypropylene. An condensation polymer is a polymer formed by a condensation reaction in which a molecule, usually water, is lost during formation of the polymer.

The term "thermosetting material" refers to a polymeric material that softens when initially heated and then condenses (often cross-linking) into a hard permanent form. A thermosetting material cannot be softened or reprocessed through the subsequent application of heat.

Thermosetting materials are polymer materials that cure irreversibly. Curing may be performed by applying heat (generally above 200° C.) by a chemical reaction (two-part epoxy, for example), or by irradiation (electron beam processing, for example). Thermosetting materials are made of long-chain polymers that cross-link with each other after they have been cured by thermal radiation, ultraviolet (UV) radiation and/or visible radiation and/or after they have been heated. The curing process renders the material permanently hard. Thermosetting plastics are polymer materials that are usually liquid or malleable prior to curing and designed to be molded into their final form or used as adhesives. Some thermosetting plastics are solids, like the molding compounds typically used in semiconductors and integrated circuits.

The term "delayed delivery" of an injection refers to a misfire or misfiring that causes delay of the injection, beyond an acceptable range, in the delivery of a therapeutic agent or a failure to deliver the therapeutic agent from an automatic injection device after activation of the firing engagement mechanism, e.g., the firing button, of the device. In an exemplary embodiment, an acceptable delay may range from about zero to about three seconds. Delay greater than three seconds is a misfiring of the automatic injection device.

The term "strain" or "actual strain" refers to the force with which the firing engagement mechanism, e.g., the firing button, of an automatic injection device is depressed or the distance relative to a starting position over which the firing engagement mechanism is depressed for firing the device.

The term "threshold strain" refers to the minimum strain applied to depress a firing engagement mechanism, e.g., the firing button, during firing at or above which no delayed delivery of an injection is observed. In an exemplary embodiment, the threshold strain may be provided as the distance relative to a starting position over which the firing button must be depressed to cause the automatic injection device to fire. In exemplary embodiments, if the firing button of an automatic injection device is compressed over a distance equal to or greater than the threshold strain value, the automatic injection device does not experience any delayed delivery of an injection. In exemplary embodiments, if the firing button of an automatic injection device is compressed over a distance less than the threshold strain value, the automatic injection device may experience delayed delivery of an injection.

The term "distal" refers to a portion or end or component of an exemplary automatic injection device that is farthest from an injection site on the patient's body when the device is held against the patient for an injection or for mimicking an injection.

The term "proximal" refers to a portion or end or component of an exemplary automatic injection device that is closest to an injection site on a patient's body when the device is held against the patient for an injection or for mimicking an injection.

II. EXEMPLARY AUTOMATIC INJECTION DEVICES

Exemplary embodiments will be described below with reference to certain illustrative embodiments. While exemplary embodiments are described with respect to using an automatic injection device to provide an injection of a dose of a liquid medication, one of ordinary skill in the art will recognize that exemplary embodiments are not limited to the illustrative embodiments and that exemplary automatic injection devices may be used to inject any suitable substance into a patient. In addition, components of exemplary automatic injection devices and methods of making and using exemplary automatic injection devices are not limited to the illustrative embodiments described below.

FIGS. 1 and 2 illustrate an exemplary automatic injection device 10 suitable for injecting a dose of a substance, such as a liquid drug, into a patient.

FIG. 1 illustrates a perspective view of the exemplary automatic injection device 10 in which caps that cover proximal and distal ends of the housing are removed.

FIG. 2 illustrates a perspective view of the exemplary automatic injection device 10 of FIG. 1 in which the proximal and distal ends of the housing are capped.

Referring to FIG. 1, the automatic injection device 10 includes a housing 12 for housing a container, such as a syringe, which may contain a dose of a substance to be injected into a patient's body. The housing 12 preferably has a tubular configuration, although one of ordinary skill in the art will recognize that the housing 12 may have any suitable size, shape and configuration for housing a syringe or other container. While exemplary embodiments will be described with respect to a syringe mounted in the housing 12, one of ordinary skill in the art will recognize that the automatic injection device 10 may employ any suitable container for storing and dispensing a substance.

The exemplary syringe is preferably slidably mounted in the housing 12, as described in detail below. When the device is in an inactivated position, the syringe is sheathed and retracted within the housing 12. When the device 10 is actuated, a needle of the syringe projects from a first proximal end 20 of the housing 12 to allow ejection of the substance from the syringe into the patient's body. As shown, the first proximal end 20 of the housing 12 includes an opening 28 through which the needle of the syringe projects during actuation of the device 10.

Referring still to FIG. 1, a second distal end 30 of the housing 12 includes a firing engagement mechanism, e.g., a firing button 32, for actuating a firing mechanism. The housing 12 also houses the firing mechanism, e.g., one or more actuators or one or more bias/biasing members, that moves the syringe from a sheathed position with the housing 12 to a projecting position and subsequently expels the substance from the syringe into the patient's body.

The exemplary automatic injection device 10 may also include a first removable cap 24 (or needle cap) for covering the first end 20 of the housing 12 to prevent exposure of the needle prior to an injection. In the illustrative embodiment, the first cap 24 may include a boss 26 for locking and/or joining the cap 24 of the device 10 until the patient is ready to activate the device 10. Alternatively, the first cap 24 may include a threaded screw portion, and the internal surface of the housing 12 at opening 28 may include a screw thread. Any suitable mating mechanism may be used in accordance with the teachings of exemplary embodiments.

The housing 12 and caps 24, 34 may further include graphics, symbols and/or numbers to facilitate use of the automatic injection device 10. For example, the housing 12 includes an arrow 125 on an outer surface pointing towards the first end 20 of the device 10 to indicate how the device 10 should be held relative to the patient (i.e., with the first end 20 adjacent to the injection site), as shown in FIG. 2. In addition, the first cap 24 is labeled with a "1" to indicate that a patient should remove the first cap 24 of the device first, and the second cap is labeled with a "2" to indicate that the second cap 34 should be removed after the first cap 24 is removed during preparation for and subsequent injection using the illustrative automatic injection device 10. One of ordinary skill in the art will recognize that the automatic injection device 10 may have any suitable graphics, symbols and/or numbers to facilitate patient instruction, or the automatic injection device may omit such graphics, symbols and/or numbers.

As shown in FIG. 2, the first end 20 of the housing 12 may have a wider diameter than the second end 30. A step 29 may be formed at the transition between the two diameters to accommodate the second cap 34 and to facilitate seating of the second cap 34 on the second end 30 of the housing.

The housing 12 may also preferably include a display window 130 to allow a patient to view the contents of the syringe housed within the housing 12. The window 130 may include an opening in the sidewall of the housing 12, or may include a translucent material in the housing 12 to allow viewing of the interior of the device 10.

The housing 12 may be formed of any suitable surgical material including, but not limited to, plastic and other known materials.

FIGS. 3-5 (prior art) are schematic views of interior components of an exemplary automatic injection device 10.

FIG. 3 (prior art) illustrates a cross-sectional schematic view of an exemplary automatic injection device prior to use.

FIG. 4 (prior art) illustrates a cross-sectional schematic view of the exemplary automatic injection device of FIG. 3 during an intermediate stage of operation.

FIG. 5 (prior art) illustrates a cross-sectional schematic view of the exemplary automatic injection device of FIGS. 3 and 4 during a post-injection stage of operation.

Still referring to FIGS. 3-5, a syringe 50 or other suitable container for a substance is disposed within the interior of the housing 12. An exemplary syringe 50 may include a hollow barrel portion 53 for holding a dose of a liquid substance to be injected into a patient's body. An exemplary barrel portion 53 is substantially cylindrical in shape, although one of ordinary skill in the art will recognize that the barrel portion 53 may have any suitable shape or configuration. A seal, illustrated as a bung 54, seals the dose within the barrel portion 53. The syringe 50 may also include a hollow needle 55 connected to and in fluid communication with the barrel portion 53, through which the dose can be ejected by applying pressure to the bung 54. The hollow needle 55 extends from a first proximal end 53a of the barrel portion 53. The second distal end 53b of the barrel portion 53 includes a flange 56, or other suitable mechanism, for abutting a stop (represented schematically as 123) in the housing 12 to limit the movement of the syringe 50 within the housing 12, as described below. One of ordinary skill in the art will recognize that exemplary embodiments are not limited to the illustrative embodiment of the syringe 50 and that any suitable container for containing a dose of a substance to be injected may be used in accordance with the teachings of exemplary embodiments.

In an exemplary embodiment, the needle 55 may be a fixed twenty-seven gauge one-half inch needle. The tip of an exemplary hollow needle 55 may include a number of bevels, e.g., five bevels, to facilitate insertion. However, the needle 55 may have any suitable size, shape and configuration suitable for piercing a patient's skin to deliver a substance to the patient's body, and is not limited to the illustrative embodiment. Suitable types of needles are well-known in the art.

The automatic injection device 10 shown in FIGS. 3-5 may include an exemplary syringe actuator 70, illustrated as a plunger, for selectively moving and actuating the syringe 50 to inject the dose contained in the syringe 50 into a patient's body. In an exemplary embodiment, the plunger 70 may weigh more than about 1.93 grams. In another exemplary embodiment, the plunger 70 may weigh between about 1.93 grams and about 2.02 grams.

The exemplary plunger 70 may include a rod portion 71 having a first end 71a integral with, e.g., connected to and/or in fluid communication with, the bung 54 for selectively applying pressure to the bung 54 to expel the dose from the needle 55. The plunger 70 may include a flanged second end 72. In an exemplary embodiment, the plunger 70 may include multiple components than those illustrated in FIGS. 3-5. In an exemplary embodiment, the device 10 may include more or fewer actuators than those illustrated in FIGS. 3-5.

The plunger 70 may be biased forward towards the first end 20 of the device 10 by a first biasing mechanism, illustrated as a coil spring 88, disposed about or above the flanged second end 72 of the plunger 70. A proximal end 88a of the coiled spring 88 may abuts the flanged second end 72 of the plunger 70 to selectively apply pressure to the plunger 70 and to move the plunger 70 proximally. Alternatively, the plunger 70 may extend through the center of the spring 88.

As illustrated in FIG. 3, prior to use of the device 10, the coil spring 88 (or another suitable mechanism) may be compressed between the plunger 70 and the housing 12, thus storing energy. A trigger 91, which may be activated by any suitable actuation means such as the firing button 32, may retain the plunger 70 and the first biasing mechanism 88 in a retracted, latched position before the firing button 32 is activated. The trigger 91 may latch the flanged second end 72 of the plunger 70. When the firing button 32 or other actuation means is activated, the trigger 91 may release the flanged second end 72 of the plunger 70, allowing the coil spring 88 to propel the plunger 70 towards the first end of the device 10.

A second biasing mechanism, illustrated as an exemplary coil spring 89, may hold the syringe 50 in a retracted position within the housing 12 prior to use, as shown in FIG. 3. In the retracted position, the needle 55 may be preferably sheathed entirely within the housing 12. The exemplary syringe coil spring 89 may be disposed about the proximal portion of the barrel portion 53 and may be seated in a shelf 121 formed within the housing interior. The top end of the coil spring 89 may abut the flanged second end 56 of the syringe 50. The spring force of the second biasing mechanism 89 may push the flanged second end 56 of the syringe 50 away from the first end 20 of the housing 12, thereby holding the syringe 50 in the retracted position until activated. Other components of the device 10 may also position the syringe 50 relative to the housing 12.

The first biasing mechanism 88 and the second biasing mechanism 89 may have any suitable configuration and tension suitable for use in biasing certain components of the device. For example, the first biasing mechanism 88 may have any suitable size, shape, energy and properties suitable for moving the plunger 70 and the syringe 50 forward when released. The second biasing mechanism 89 may have any suitable size, shape, energy and properties suitable for retracting the syringe 50 prior to activation. Other suitable means for facilitating movement of the plunger 70 and/or syringe 50 may also be used.

Referring still to the illustrative embodiment of FIGS. 3-5, the plunger 70 may include an exemplary radially compressible expanded portion 76, e.g., in the center of the plunger 70. In an illustrative embodiment, the rod 71 may be split, e.g., in a central portion and expanded to form a pair of projecting elbows 78 that define the radially compressible expanded portion 76. The projecting elbows 78 may be pre-formed as part of the molded plunger 70 or, alternatively, may be attached to the plunger 70 separately. The projecting elbows 78 may be compressible so that they can be moved radially inwardly to cause that portion of the rod 71 to adopt a circumference similar to the rest of the rod 71. The compressible expanded portion 76 facilitates movement of the syringe 50, followed by expulsion of the dose in two substantially separate stages, as described below.

Referring to FIG. 4, when an activation means 320 activates the trigger 91 to release the plunger 70, the spring force of the coil spring 88 propels the plunger 70 forward (proximally). During a first operational stage, the moving plunger 70 pushes the syringe 50 forward such that the tip of the needle 55 projects from the first end 20 of the housing 12. The initial biasing force provided by the first coil spring 88 is sufficient to overcome the biasing force of the second coil spring 89 to allow movement of the syringe 50 against the backward biasing force of the second coil spring 89. In the first operational stage, the expanded region 76 of the plunger 70, formed by the projecting elbows 78, rests against the second end 56 of the barrel portion 53. This prevents the plunger 70 from traveling within the syringe barrel portion 53. In this manner, all biasing force from the first coil spring 88 is applied to move the syringe 50 forward towards the first end 20 of the device 10.

The activation means 320 may have any suitable size, shape, configuration and location suitable for releasing the plunger 70 or otherwise activating the device 10. For example, the activation means 320 may include a firing button 32 formed on a distal end 30 of the housing 12, and/or may include another suitable device, such as a latch, twist-activated switch and other devices known in the art. While the illustrative activation means 320 is located towards a distal end 30 of the device 10, one of ordinary skill in the art will recognize that the activation means 320 may be positioned in any suitable location on the device 10.

The forward motion of the syringe 50 towards the proximal end 20 of the device 10 may continue against the biasing force of the coil spring 89 until the flanged end 56 of the barrel portion 53 abuts the stop 123, such as a protrusion or flange, on the housing 12, as shown in FIG. 4, thereby forming a stopping mechanism 56, 123. One of ordinary skill in the art will recognize that alternate stopping mechanisms may be employed and that exemplary embodiments are not limited to the illustrative stopping mechanism.

As further shown in FIG. 4, the first operational stage may propel the tip of the needle 55 through the opening 28 at the first end 20 of the device 10, so that the needle 55 may pierce the patient's skin. During this stage, the syringe barrel portion 53 may preferably remain sealed without expelling the substance through the needle 55. The interference caused by the stopping mechanism 56, 123 may maintain the needle 55 in a selected position extending from the proximal open end 28 of the device 10 during subsequent steps. Until the stopping mechanism 56, 123 stops the movement of the syringe 50, the compressible expanded portion 76 of the plunger 70 may prevent movement of the plunger 70 relative to the barrel portion 53. The stopping mechanism 56, 123 may be positioned at any suitable location relative to the open first end 20 to allow the syringe 50 to penetrate the skin by any suitable depth suitable for an injection.

The second operational stage commences after the stop 123 of the housing 12 catches the flanged portion 56, stopping further movement of the barrel portion 53. During this stage, the continued biasing force of the coil spring 88 may continue to push the plunger 70 relative to the housing 12, as shown in FIG. 5. The biasing force may cause the elbows 78 of the plunger 70 to compress radially inward and slide into the interior of the barrel portion 53. While the interference between components 123 and 56 may retain the barrel portion 53 in a selected position (with the needle 55 exposed) and with the elbows 78 in a collapsed stage, the coil spring 88 may push the plunger 70 within the barrel portion 53. After the plunger 70 overcomes the necessary force to allow the elbows 78 to compress and extend into the barrel portion 53, the plunger 70 may apply pressure to the bung 54, causing ejection of the substance contained in the syringe 50 through the projecting needle 55. Because the needle 55 was made to penetrate the patient's skin in the first operational stage, the substance contained in the barrel portion 53 of the syringe 50 is injected directly into a portion of the patient's body.

FIG. 6 illustrates a perspective view of an exemplary automatic injection device 10 including a syringe housing assembly and a firing mechanism assembly. In an exemplary embodiment, the automatic injection device 10 may include two interlocking components: a syringe housing assembly 121 containing the proximal components of the device 10 (e.g., the syringe barrel 53, coil spring 89, needle 55 and other proximal components), and a firing mechanism assembly 122 containing the distal components of the device 10 (e.g., the means for actuating the syringe 50). The syringe housing assembly 121 and the firing mechanism assembly 122 may be coupled through any suitable means. In an exemplary embodiment, a proximal end 122a of the firing mechanism assembly 122 may be sized and configured to be inserted into a distal end 121b of the syringe housing assembly 121. In addition, one or more tabs 127 on the proximal end 122a of the firing mechanism assembly 122 may snap-fit into corresponding openings 126 on the distal end 121b of the syringe housing assembly 122 to ensure alignment and coupling of the two assemblies 121, 122 and the components housed therein.

Figure 7:
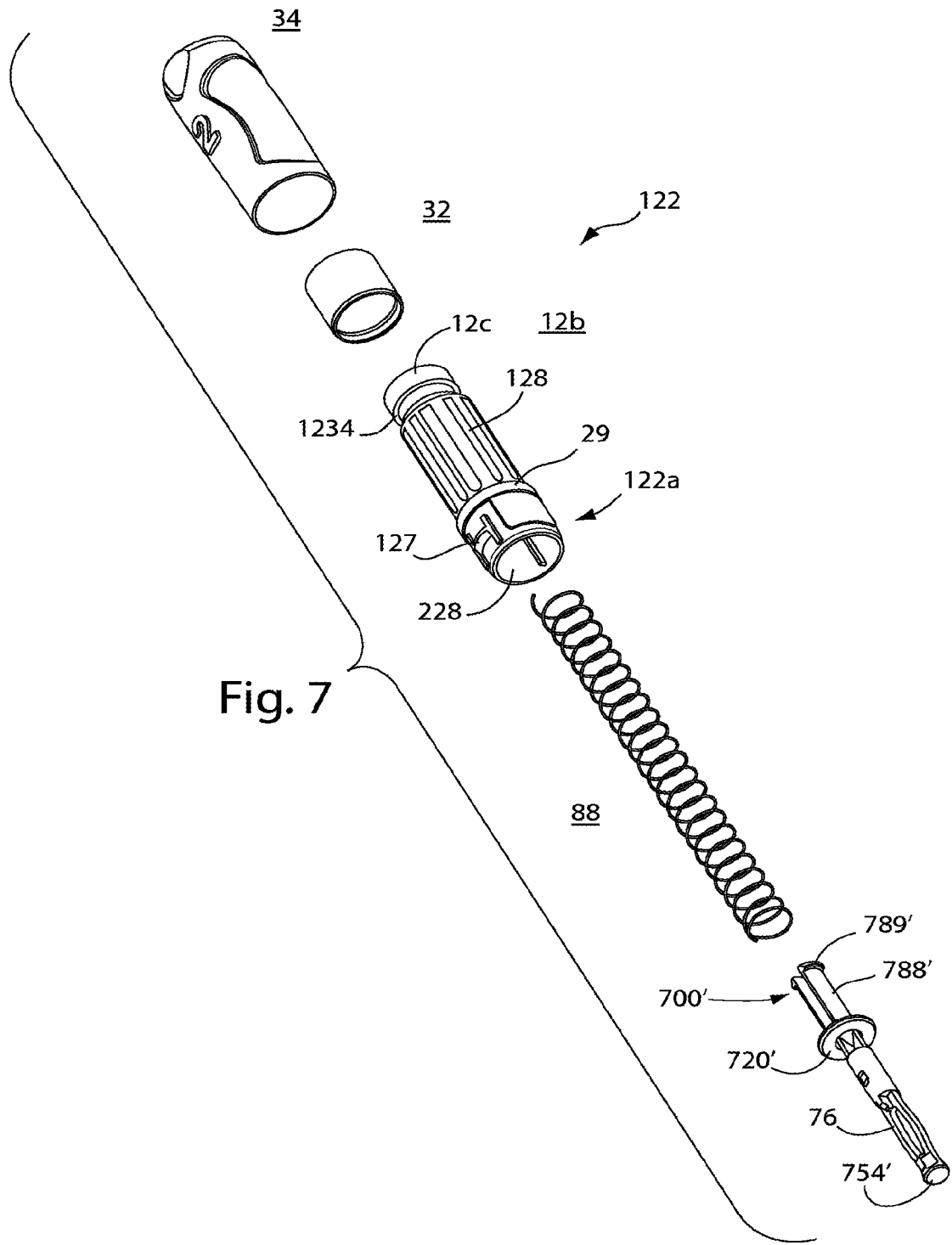
FIG. 7 illustrates a perspective view of the firing mechanism assembly of the exemplary automatic injection device of FIG. 6.

FIG. 7 illustrates a perspective view of the firing mechanism assembly of the exemplary automatic injection device of FIG. 6. The firing mechanism assembly 122 may include the exemplary firing button 32, the exemplary actuator cap 34, the exemplary distal housing component 12b (firing body), and the exemplary coil spring 88 or other biasing mechanism. The firing mechanism assembly 122 may also include a syringe actuator, illustrated as a syringe actuation component 700', which extends from the proximal end 122a of the distal housing component 12b for moving the syringe 50 forward within the housing 12 in a first stage, and for actuating the syringe 50 to expel its contents in a second stage.

Figure 8:
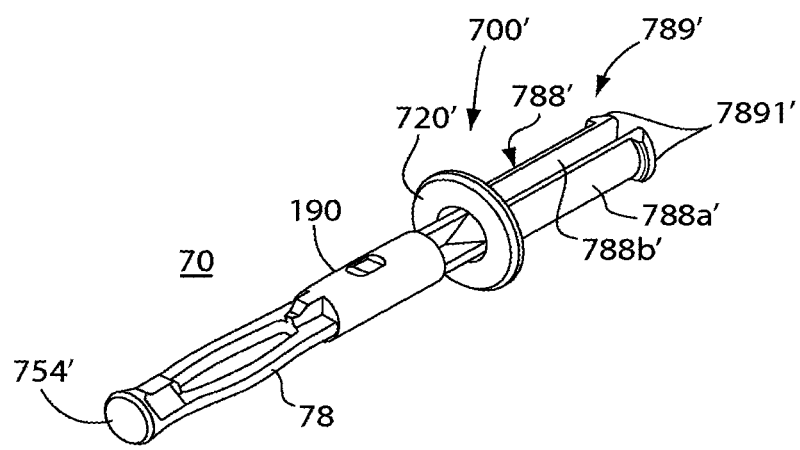
FIG. 8 illustrates a perspective view of a syringe actuation component of the exemplary firing mechanism assembly of FIG. 7.

The syringe actuation component 700' of FIGS. 2 and 8 further may include an indicator 190 in a solid rod portion 70 distal from the elbows 78. During operation of the device 10 and after completion of an injection, the indicator 190 is configured to align with the window 130 on the housing 12 to indicate at least partial completion of the injection. The indicator 190 preferably has a distinctive color or design to represent completion of an injection.

As shown in FIG. 8, the illustrative syringe actuation component 700' further includes a retaining flange 720' for holding the actuating coil spring 88 in a compressed position until actuation. The retaining flange 720' is sized, dimensioned and formed of a material that preferably allows the syringe actuation component 700' to slidably and easily move within the housing 12 when the device 10 is actuated. Extending distally from the retaining flange 720', the syringe actuation component 700' forms a base 788', for the actuating coil spring 88. The base 788' terminates in a trigger anchoring portion 789'. The illustrative base 788' may comprise flexible arms 788a', 788b' around which the spring 88 coils. The trigger anchoring portion 789' may comprise tabbed feet 7891' extending from the base 788' and configured to selectively engage the anchoring cap 12c and/or distal housing component 12b. The firing button 32 coupled to the distal end of the distal housing component 12b is configured to hold the trigger anchoring portion 789' until activation. When activated, the firing button 32 releases the trigger anchoring portion 789', allowing the coil spring 88 to propel the syringe actuation component 700' towards the proximal end 20 of the device 10 in an operation described above.

In a retracted, anchored position shown FIGS. 7 and 8 (corresponding to the schematic of FIG. 3), the trigger anchoring portion 789' interacts with the housing 12, which holds the tabbed feet 7891' in a latched position, against the biasing force of the coil spring 88, to maintain the syringe actuation component 700' in a retracted position. In this position, the flange 720' retracts the spring 88 against the back, distal wall 712' of the distal housing component 12b. An opening 713' in the anchoring cap 12c allows the firing button 32 access to the anchoring portion 789'. In the retracted position, the pressurizer 754' of the syringe actuation component 700' extends out of an opening 228 on the proximal end 122a of the distal housing component 12b.

Also referring to FIG. 9, when the distal housing component 12b couples to a corresponding syringe actuation mechanism 121, the pressurizer 754' extends into the barrel portion of a syringe housed therein. The pressurizer 754' may be integral with, the same as, connected to, or otherwise in communication with the bung 54 of a syringe 50 housed in the device 10 and may have any suitable size, shape and configuration suitable for applying pressure to the bung 54. In one embodiment, the pressurizer 754' has a cross-section corresponding to the shape of the barrel portion 53 of a corresponding syringe 50 so as to substantially seal the barrel portion 53, and the pressurizer 754' is configured to slidably move within the barrel portion 53 to apply pressure to the bung 54 and actuate the syringe 50.

In the illustrative embodiment of FIGS. 7 and 8, the syringe actuation component 700' constitutes a single, integrated mechanism for anchoring a corresponding syringe 50, spring 88 and other components, actuating and moving the syringe 50 to a protracted position, and separately expelling the contents of the syringe 50.

FIG. 9 is an exploded view of the syringe housing assembly 121 of an illustrative embodiment of the invention, which is configured to couple to and interact with the FM assembly 122 of FIGS. 7 and 8. The illustrative syringe housing assembly 121 includes a proximal housing component 12a, the proximal cap 24, a proximal, second biasing mechanism 89, a syringe carrier 500 and a stepped shroud 12d forming a proximal portion 20 of the housing 12 when assembled and includes the proximal opening 28, as also shown in FIG. 2. The components 12a, 12d, 89, 500 and 24 cooperate to house a syringe 50 containing a substance to be injected and facilitate operation of the device 10 in the two different operational stages as described above.

Referring now to FIGS. 1, 2, and 9, the syringe carrier 500 of the illustrative embodiment envelopes the distal half of a syringe 50 used in the device 10. The syringe 50 rests in the carrier 500 and both are contained in the housing 12. During operation, the syringe 50 and the carrier 500 move forward (e.g., proximally) within the housing 12. The housing 12 stops and limits the movement of the carrier 500, and the carrier 500 in turn stops and limits the movement of the syringe 50. The illustrative syringe carrier 500 has a substantially tubular structure including window cutouts 501 preferably aligned with the window 130 on the housing 12a to allow a patient to view the contents of the syringe 50 prior to operation. The syringe carrier 500 may include a flanged distal end 562 configured to interface with a flanged distal end 56 (shown in FIG. 3) of the syringe 50.

Referring to FIG. 9, the flanged distal end 562 may serve as a damper for the syringe 50. The syringe carrier 500 may further include an intermediate flange 563, which in the illustrative embodiment forms a stop for the syringe 50 that interacts with an interior stop 256 (shown in FIGS. 10A and 10B) on the proximal housing component 12a to limit forward motion of the syringe 50. Referring again to FIG. 9, the illustrative syringe carrier 500 may further include a proximal anchor portion 503 that limits movement of the syringe 50 in a distal, rearward direction. In the illustrative embodiment, the proximal anchor portion 503 includes a radial groove configured to engage the interior stop 256. A syringe carrier coupler 504 extends forward past the proximal anchor portion 503 to facilitate coupling of the syringe carrier 500 with the distal end of the spring 89 and the stepped shroud 12d. In one embodiment, the syringe carrier 500 is stationary within the housing 12 and the syringe 50 selectively and controllably slides within and relative to the syringe carrier 500. Alternatively, the syringe carrier 500 is slidably disposed within the housing 12 and selectively carries the syringe 50 within the housing 12. The syringe carrier 500 may have any suitable configuration and size suitable for carrying or guiding the syringe 50 within the housing 12.

Referring again to FIG. 9, the illustrative stepped shroud 12d forms a proximal end 20 of the housing 12. The illustrative stepped shroud 12d has a substantially tubular body, including a proximal boss 112 defining the proximal opening 28 of the device 10, through which the syringe needle 55 projects during operation of the device 10. A step 113 from the main tubular body portion 116 forms the proximal boss 112 of smaller diameter than the main tubular body portion 116 of the stepped shroud 12d.

Figure 10A:
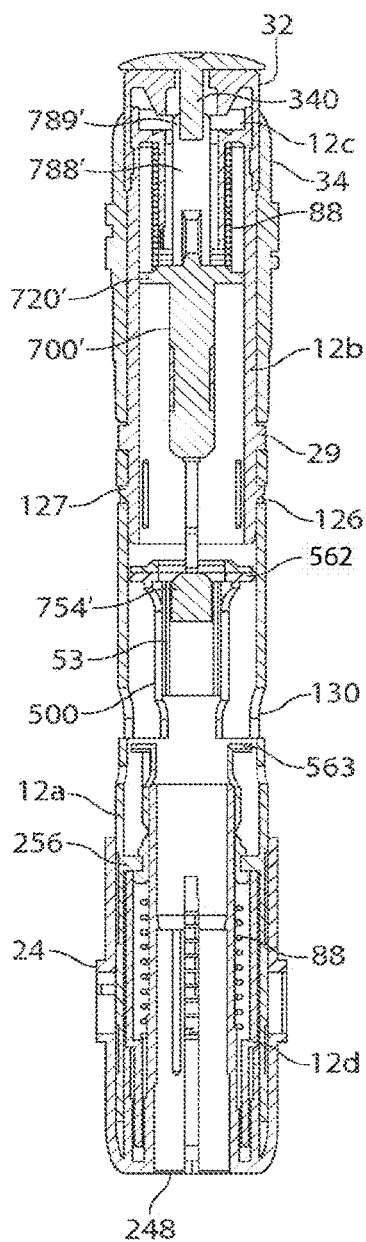
FIGS. 10A and 10B illustrate cross-sectional views of an exemplary assembled automatic injection device at 90° offset angles from each other, in which the syringe housing assembly and the firing mechanism assembly are coupled together, provided in accordance with exemplary embodiments.

As shown in FIG. 10A, the step 113 forms a forward stop for the spring 89 to confine the spring 89 and prevent forward movement of the spring 89 towards the proximal end 20 of the device 10. In the illustrative embodiment, shown in FIG. 10A, the distal rim 115 of the stepped shroud 12d abuts the proximal side of the stop 256 of the proximal housing component 12a. Referring now to FIG. 9, distal arms 114 extend from the stepped shroud 12d to lock in the stepped shroud 12d to prevent accidental needle sticks.

Figure 10B:
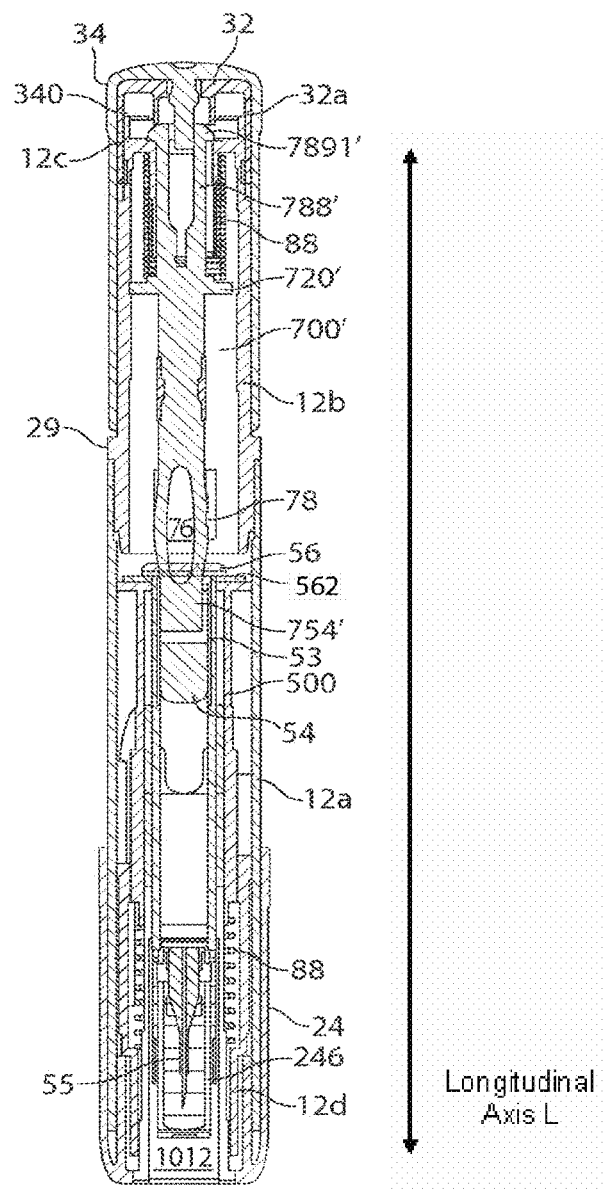

FIGS. 10A and 10B are cross-sectional views at 90° offset angles from each other, illustrating an assembled automatic injection device 10, wherein the syringe housing assembly 121 and a FM assembly 122 of FIG. 6 are coupled together, such that the pressurizer 754' of the syringe actuation component 700' extends into the barrel portion 53 of a syringe 50 housed in the syringe housing assembly 121 and in communication with a bung 54 of the syringe 50.

Referring again to FIGS. 8 and 10B, the syringe actuation component 700' includes, at its proximal end, a pressurizing end 754' for applying pressure to the bung 54, a plunger rod portion 70 with a compressible expanded portion 76 (illustrated as the plunger elbows 78), as well as other components, such as components for anchoring the coil spring 88 to the syringe actuation component 700', as described below. The compressible expanded portion 76 facilitates movement of a corresponding syringe 50 into a protracted position and expulsion of the contents of the syringe 50 in two separate steps, as described herein. Alternatively, the syringe actuation component 700' may comprise multiple actuators for moving and/or promoting expulsion of the syringe 50.

As shown, in FIG. 10B, the trigger anchoring portion 789' of the syringe actuation component 700' is anchored towards the distal end of the housing 12 by the firing button 32. When a patient depresses the firing button 32, an internal ring 32a connected to the firing button 32 compresses the tabbed feet 7891' of the trigger anchoring portion 789' inwards, thereby decreasing the distance (plunger arm width) between the tabbed feet of the plunger arms 788a', 788b', releasing the syringe actuation mechanism 700' and releasing the spring 88. Prior to operation, the compressible expanded portion 76, illustrated as elbows 78, of the syringe actuation component 700' rests above the flange 56 of the syringe 50 to allow the compressible expanded portion 76, when pushed by a released coil spring 88, to apply pressure to the syringe barrel portion 53, thereby moving the syringe 50 forward within the housing 12 when actuated.

As described above, once a stop, such as a stop 256 on the proximal housing component 12a shown in FIG. 10B, catches the syringe 50 and halts additional forward motion of the projecting syringe 50, the continued biasing force on the spring 88 will continue to move the syringe actuation component 700' forward, causing the compressible expanded portion 76 to compress and move into the barrel portion 53 of the syringe 50. The forward motion of the syringe actuation component 700' within the barrel portion 53 causes the pressurizer 754' to apply pressure to the bung 54, causing expulsion of the syringe contents into an injection site.

As also shown in FIGS. 10A and 10B, the actuator cap 34 may include a stabilizing protrusion 340 that extends through the activator button 32 and between the feet tabbed 7891' of the syringe actuation component 700' to stabilize the components of the device prior to activation.

Figure 11A:
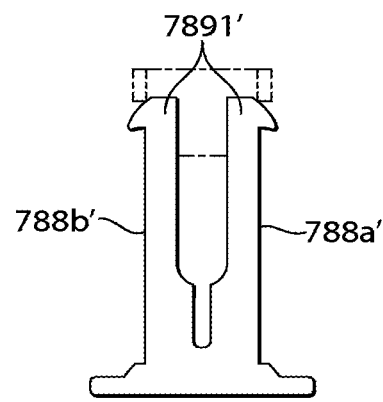
FIGS. 11A-11C illustrate cross-sectional views of the syringe actuation component of the firing mechanism assembly of FIG. 7, provided in accordance with exemplary embodiments, showing the position of the plunger arms at various stages of actuation.
Figure 11B:
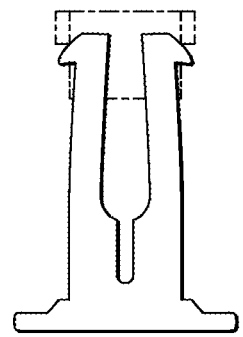
Figure 11C:
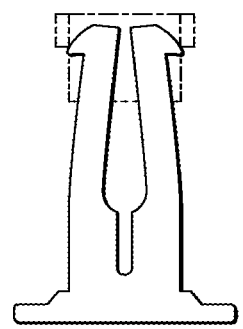

FIGS. 11A-11C illustrate cross-sectional views of the syringe actuation component of the firing mechanism assembly of FIG. 7, provided in accordance with exemplary embodiments, showing the position of the plunger arms at various stages of actuation.

In FIG. 11A, the syringe actuation component 700' is preloaded by the first biasing mechanism 88 before actuation of the firing button. The plunger arms are spread apart with the plunger arm width being a first, larger width.

In FIG. 11B, the plunger arms are pushed together at the start of actuation of the firing button.

In FIG. 11C, the plunger is released during actuation of the firing button. The plunger arms are disposed closer to each other with the plunger arm width being a second, smaller width.

Figure 12:
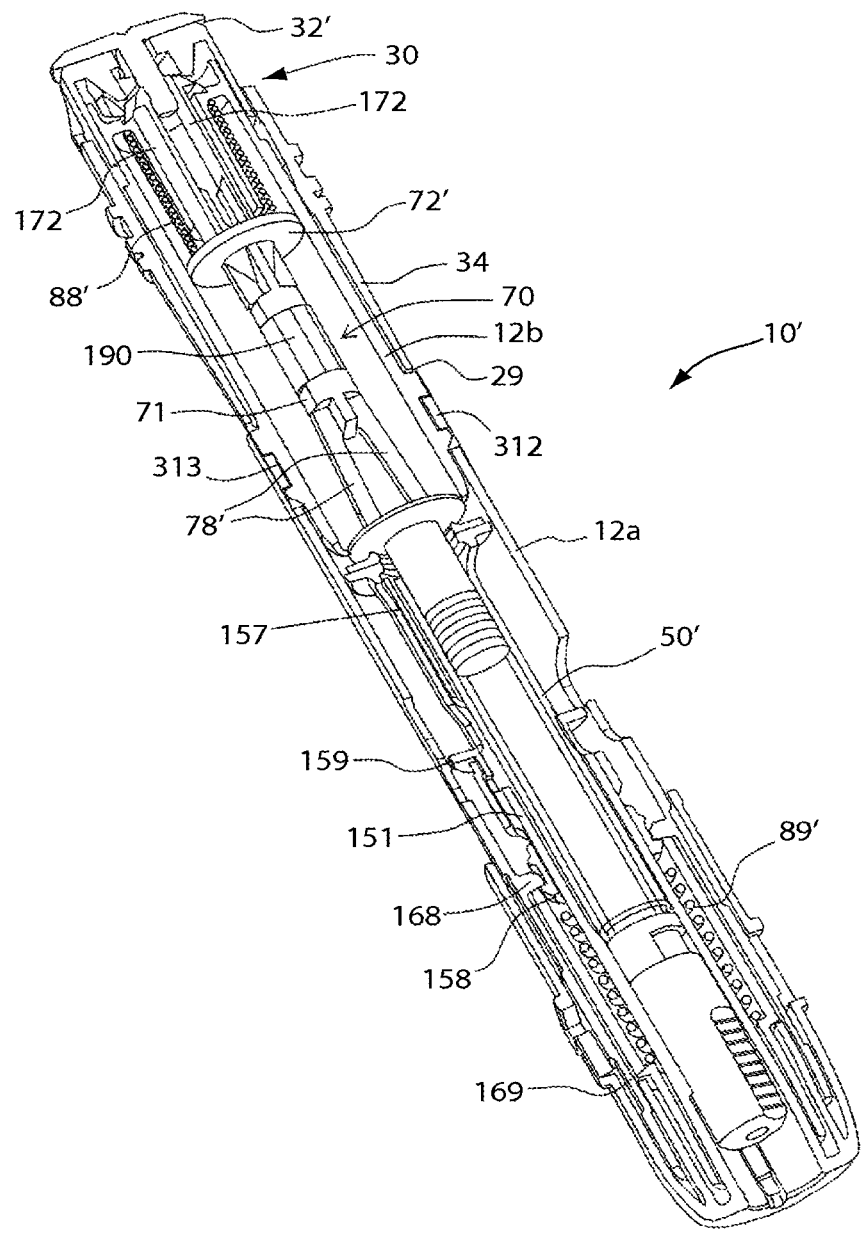
FIG. 12 illustrates a cross-sectional view of an exemplary automatic injection device, provided in accordance with exemplary embodiments.

FIG. 12 is a cross-sectional view of an assembled automatic injection device 10' according to an illustrative embodiment of the invention. The illustrative embodiment of the automatic injection device 10' includes two mating proximal and distal housing components 12a, 12b. The proximal and distal housing components 12a, 12b mate to form a complete housing 12. As shown, a proximal housing component 12a, forming a proximal end of the housing 12, receives a proximal end of the distal housing components 12b. A cooperating projection 312 and groove 313, or a plurality of cooperating projections 312 and grooves 313, facilitate mating of the proximal and distal housing components 12a, 12b in the illustrative embodiment. Other suitable mating mechanisms may alternatively be employed. A shelf 29 formed on an outer surface of the distal housing component 12b may form a stop for the second removable cap 34.

As shown, the firing button 32' may be a cap covering the distal end of the distal housing component 12b. The illustrative firing button 32' slides relative to the distal housing component 12b to actuate a syringe actuator, such as the plunger 70. The illustrative firing button 32' releasably retains flexible anchoring arms 172 of the plunger 70'. When depressed, the firing button 32' releases the flexible anchoring arms 172 to allow a first biasing mechanism, illustrated as spring 88' to propel the plunger 70' towards the proximal end of the device 10'.

In the embodiment of FIG. 12, the plunger 70' further includes a flange 72' located between the compressible expanded portion 78' and the distal end of the plunger rod 71'. A first biasing mechanism 88' is seated between an interior distal end of the housing 12 and the flange 72' to bias the plunger 70 towards the proximal end of the housing 12'. As described above, when the firing button 34' releases the anchoring arms 172, the coil spring 88', or other suitable biasing mechanism propels the plunger 70' towards the proximal end 20 of the device 10.

The illustrative embodiment 10' further includes an indicator 190 formed at an intermediate portion of the plunger rod 71' between the flange 72' and the compressible expanded portion 76, illustrated as flexible elbows 78'.

The syringe 50' of FIG. 12 may include protrusions or other suitable component to facilitate controlled movement of the syringe within the housing 12'. For example, with reference to FIG. 12, the syringe 50' includes a sleeve 157 forming a proximal protrusion 158 for abutting a proximal side of a first protrusion 168 formed on an inner surface of the housing 12' for limited movement of the syringe 50' in the distal direction within the housing 12'. The sleeve 157 may also form a flange 159 that may abut the distal side of the first protrusion 168 to limit movement of the syringe 50' in the proximal direction during an injection.

In the embodiment of FIG. 12, the second biasing mechanism, illustrated as coil spring 89' is disposed about a proximal portion of the syringe 50'. A shelf 169 formed at a proximal inner surface of the housing 12' receives a proximal end of the coil spring 89'. The proximal protrusion 158 of the syringe sleeve 157, or another suitably disposed mechanism, receives the distal end of the coil spring 89'. As described above, the second biasing mechanism 89' biases the syringe 50' in a retracted position within the housing 12' until activation of the device 10.

As shown in FIGS. 10A, 10B and 12, the automatic injection device 10'incorporates an indicator 190 to indicate to the patient of the device 10' when the dose from the syringe 50 has been fully or substantially fully ejected. In the illustrative embodiment, the indicator 190 is formed on a portion of the plunger rod 71' between the compressible expanded central portion 76 and the flange 72'. As the plunger rod 71 moves during operation, the indicator 190 advances towards and aligns with window 130 as the dose empties from the syringe. The indicator 190, which is preferably a different color or pattern from the substance being injected, fills the window 130 entirely to indicate that the dosage has been ejected. Any suitable indicator may be used.

After injection of the dose from the device 10' via the needle 55, a needle sheath 112, which may be formed by the proximal end 20 of the shroud 12d may automatically advance over the exposed needle 55 extending from the housing proximal end 20 to prevent accidental needle sticks.

The syringe actuation component 700', or distal portion thereof, may be composed at least partially of any suitable material, such as an acetal-based plastic, though other suitable materials may also be used. In exemplary embodiments, the syringe actuation component 700' may be made at least partially of a thermoplastic material or a thermosetting material.

Thermoplastic materials include polyacetal, polycarbonate, polyacrylate, polyamide, acryonitrile-butadiene-styrene (ABS), polyvinyl chloride (PVC) and their copolymers, terpolymers, and filled composites thereof. Polyacetal materials include acetal homopolymers, copolymers, and filled materials thereof. Hostaform™ C is an exemplary acetal polyoxymethylene (POM) copolymer. Acetal copolymers, e.g., Hostaform™ C copolymer, may be filled materials and may be glass sphere filled and glass fiber filled materials thereof.

Thermosetting materials include epoxy, acrylic, urethane, ester, vinyl ester, epoxy-polyester, acrylic-urethane, and fluorovinyl. In exemplary embodiments, acrylic materials may include a reactive functionality such as an acid and a hydroxyl. In an embodiment, the epoxy material includes a reactive functionality that can be cured by a method selected from the group consisting of visible, UV and thermal crosslinking. Exemplary thermosetting materials include, but are not limited to, different kinds of stereolithography resins that may be photopolymers (e.g., the Somos® 9420 photopolymer, the Somos® ProtoGen™ O-XT 18420 photopolymer, the Somos® WaterShed™ 11120 resin, the Somos® DMX-SL™ 100 resin, the Somos®ProtoTherm™ 12120 resin, the Somos® Nanoform™ 15120 plastic material, the Waterclear® Ultra 10122 resin, and the Somos® ProtoCast™ AF 19120 resin). In an embodiment, the thermosetting material is an epoxy homopolymer, copolymer or filled composite thereof.

In an exemplary embodiment, the material composing the syringe actuation component 700' may have a flex modulus of between about 1000 MPa and about 6000 MPa. In another exemplary embodiment, the material may have a flex modulus of between about 2000 MPa and about 5500 MPa. In another exemplary embodiment, the material may have a flex modulus of between about 3000 MPa and about 5000 MPa. In another exemplary embodiment, the material may have a flex modulus of about 3800 MPa.

Figure 13:
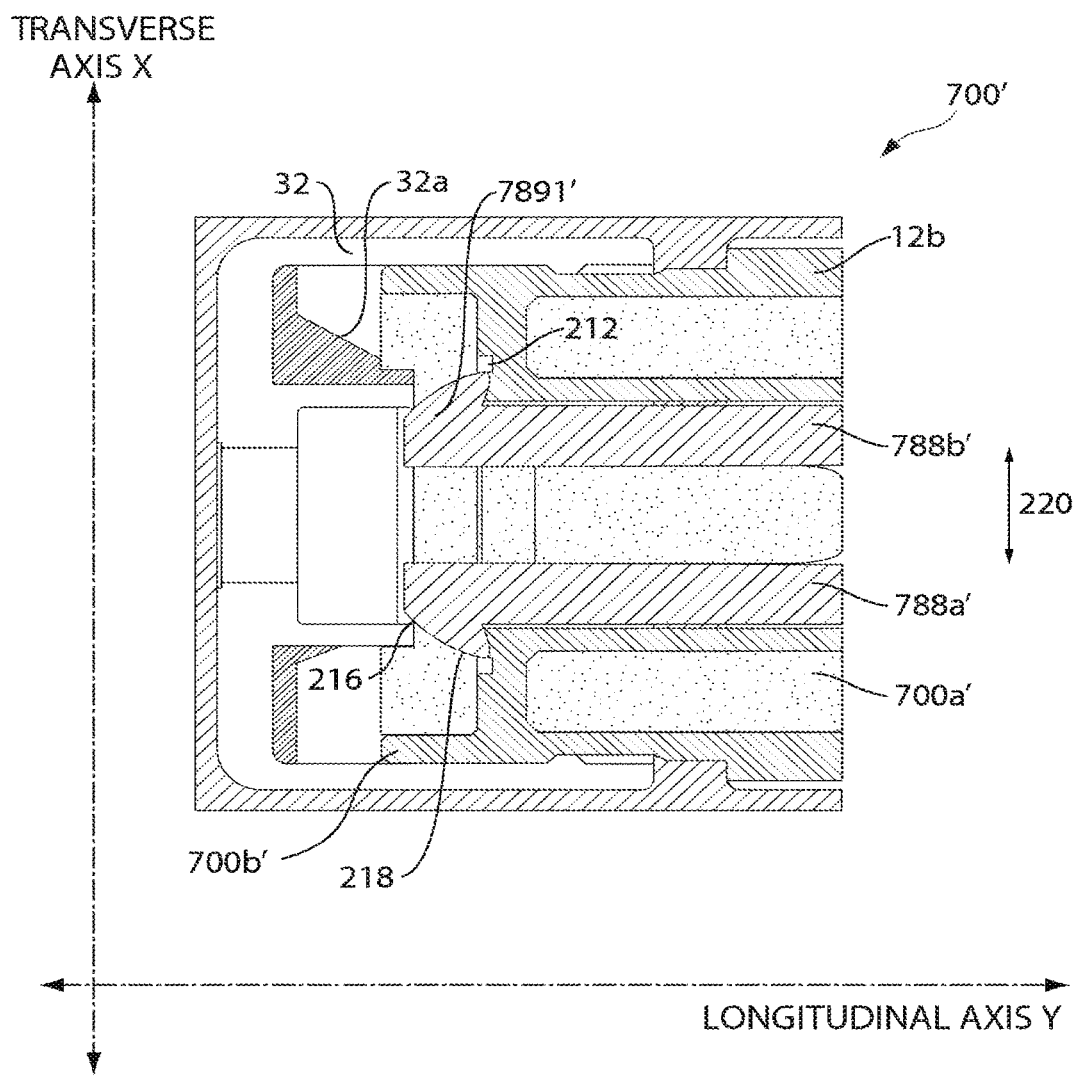
FIG. 13 illustrates a cross-sectional schematic view of the distal end of the firing mechanism assembly of FIG. 7, provided in accordance with exemplary embodiments.

FIG. 13 illustrates a cross-sectional schematic view of a distal end 700b' of the syringe actuation component 700', i.e., the end disposed farther away from the bung 54. The distal end 700b' of the syringe actuation component 700' may be bifurcated into a pair of plunger arms 788a' and 788b'. Each plunger arm 788a', 788b' may have a tabbed foot 7891' at a distal end closest to the firing button 32.

Figure 14:
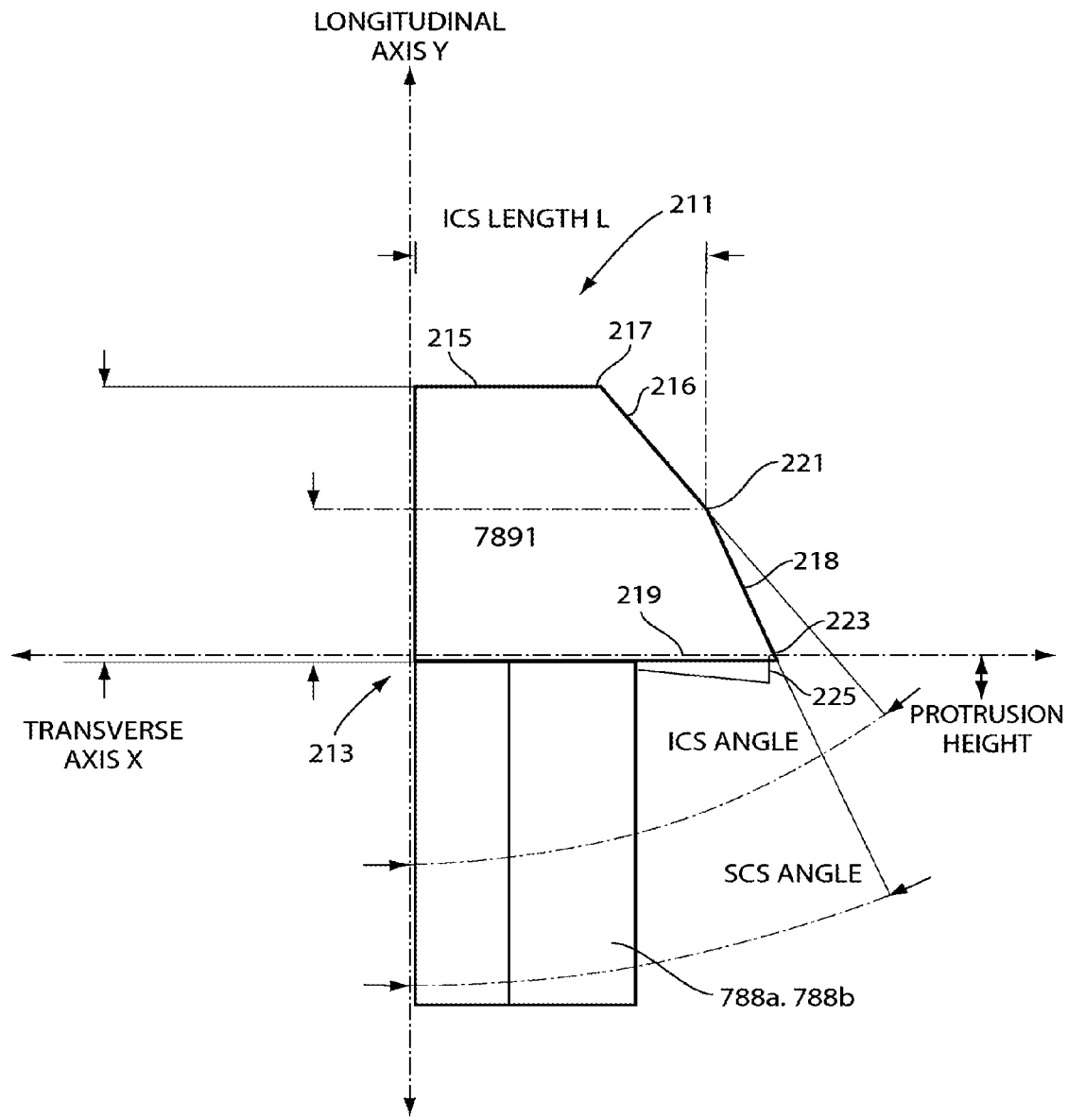
FIG. 14 illustrates a cross-sectional schematic outline of a plunger arm at the distal end of the firing mechanism assembly of FIG. 13, provided in accordance with exemplary embodiments.

FIG. 14 illustrates a cross-sectional schematic outline of a plunger arm 788a'/788b' disposed at the distal end 700b' of the syringe actuation component 700'. FIG. 14 also pictorially indicates the ICS angle, the SCS angle, and the ICS length L which is the length of the tabbed foot 7891' along the transverse axis X at its second transition edge 221 (ICS-SCS transition edge).

Along the longitudinal axis Y of the syringe actuation component 700', each tabbed foot 7891' may have a distal end 211 closest to the firing button 32 and a proximal end 213 farthest from the firing button 32. Each tabbed foot 7891' may have a top surface 215 disposed at the distal end 211 that is substantially flat along the transverse axis X of the syringe actuation component 700', and a bottom surface 219 disposed at the proximal end 213 that is substantially flat along the transverse axis X.

Each tabbed foot 7891' may have a first outer conical surface—initial contact surface (ICS) 216—formed between the top surface 215 and the secondary contact surface (SCS) 218 of the tabbed foot 7891' that is configured to initially contact the firing button 32. The ICS may form an angle—the ICS angle—relative to the longitudinal axis Y of the syringe actuation component 700'. In an exemplary embodiment, the ICS angle is between about 0° and about 90°. In another exemplary embodiment, the ICS angle is between about 40° and about 80°. In another exemplary embodiment, the ICS angle is about 28°. In another exemplary embodiment, the ICS angle is about 38°. In still another exemplary embodiment, the ICS angle is about 48°. The tabbed foot 7891' may have a first transition edge 217 formed between the top surface 215 and the ICS 216.

The tabbed foot 7891' may have a second outer conical surface—SCS 218—disposed between the ICS 216 and the bottom surface 219 of the tabbed foot 7891' that is configured to subsequently contact the firing button 32 after the firing button 32 has contacted the ICS 216. The SCS 218 may form an angle—the SCS angle—relative to the longitudinal axis Y. In an exemplary embodiment, the SCS angle is between about 0° and about 90°. In another exemplary embodiment, the SCS angle is between about 6° and about 38°. In another exemplary embodiment, the SCS angle is between about 8° and about 25°. The tabbed foot 7891' may have a second transition edge 221 disposed between the ICS 216 and the SCS 218, and a third transition edge 223 disposed between the SCS 218 and the bottom surface 219.

In an exemplary embodiment, a first contact surface is formed by the first outer conical surfaces ICS 216 of the two tabbed feet 7891' of the two plunger arms 788a' and 788b'. The first contact surface includes at least one open segment between the two plunger arms 788a' and 788b', such that the two ICS 216 are non-contiguous. A conical contact surface is formed by the second outer conical surfaces SCS 218 of the two tabbed feet 7891' of the two plunger arms 788a' and 788b'. The second contact surface includes at least one open segment between the two plunger arms 788a' and 788b', such that the two SCS 218 are non-contiguous. The first and second contact surfaces are configured to contact the firing button 32. The first contact surface makes initial contact with the firing button 32, and the second contact surface makes subsequent contact with the firing button 32 after the first contact surface has made initial contact with the firing button 32.

In an exemplary embodiment, the ICS and SCS angles may be different. In another exemplary embodiment, the ICS and SCS angles may be the same.

In an exemplary embodiment, the tabbed foot 7891' may have a third outer surface 225 that protrudes from the bottom surface 219 in the proximal direction along the longitudinal axis L, which may or may not be conical. In exemplary embodiments including third outer surface 225, the SCS 218 is disposed between the ICS 216 and the third surface 225, and the third surface is disposed between the SCS 218 and the bottom surface 29 of the tabbed foot 7891'. The third surface 225 may be configured to contact the firing body 12b. The third surface 225 may form an angle—the protrusion angle—relative to the longitudinal axis Y. In an exemplary embodiment, the protrusion angle may range between about 0° and about 90°. In another exemplary embodiment, the protrusion angle may range between about 62° and about 82°. In another exemplary embodiment, the protrusion angle may range between about 65° and about 79°. In another exemplary embodiment, the protrusion angle may range between about 68° and about 76°.

The third surface 225 may project from and extend beyond the SCS 218 to a particular height—the protrusion height—as measured along the longitudinal axis Y. In an exemplary embodiment, the protrusion height ranges between about 0.17 mm and about 0.47 mm. In another exemplary embodiment, the protrusion height ranges between about 0.20 mm and about 0.42 mm. In another exemplary embodiment, the protrusion height ranges between about 0.23 mm and about 0.37 mm.

The firing body 12b may include a firing body conical surface (FBCS) 212 that is configured to contact the third outer surface 225. When the firing button 32 is pushed down, the contact between the third outer surface 225 and the FBCS 212 causes the plunger to move up slightly.

During activation of the firing mechanism assembly 122, the spring 88 which holds the plunger 70 in place does not move when the button 32 is depressed. The angle of the firing body 12b and the underside of the plunger 70 interact, while the firing button 32 and ICS 216 interact. The firing button 32 moves down along the longitudinal axis Y of the firing mechanism assembly, and the tabbed foot 7891' bends inward. When the tabbed foot 7891' enters the firing button 32, the plunger 70 collapses in a bending motion.

An exemplary tabbed foot 7891' of a plunger arm 788a'/788b' may be configured in mid point fixed (MPF) configuration or a top point fixed (TPF) configuration. In the MPF configuration, the transition point between the ICS 216 and the SCS 218 is kept fixed as the ICS angle is varied. In the TPF configuration, the transition point between the top flat surface 215 and the ICS 216 is kept fixed as the ICS angle is varied. The distance traveled by the firing button along the ICS 216 during firing of the automatic injection device is higher in the TPF configuration than in the MPF configuration. This distance is the distance from the initial contact point between the firing button and the ICS 216 to the ICS-SCS transition point 221.

Figure 15A:
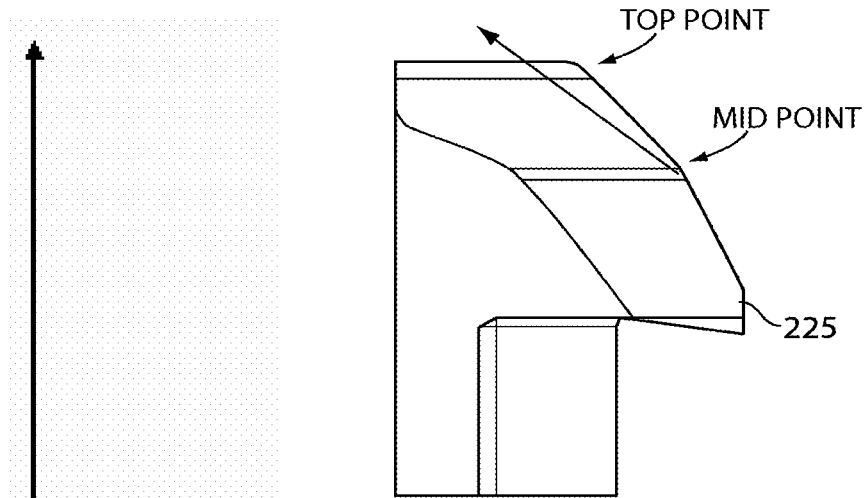
FIG. 15A provides a perspective view of a control plunger with an initial contact surface (ICS) angle of about 38°.

FIG. 15A provides a perspective view of a control plunger with an ICS angle of about 38°.

Figure 15B:
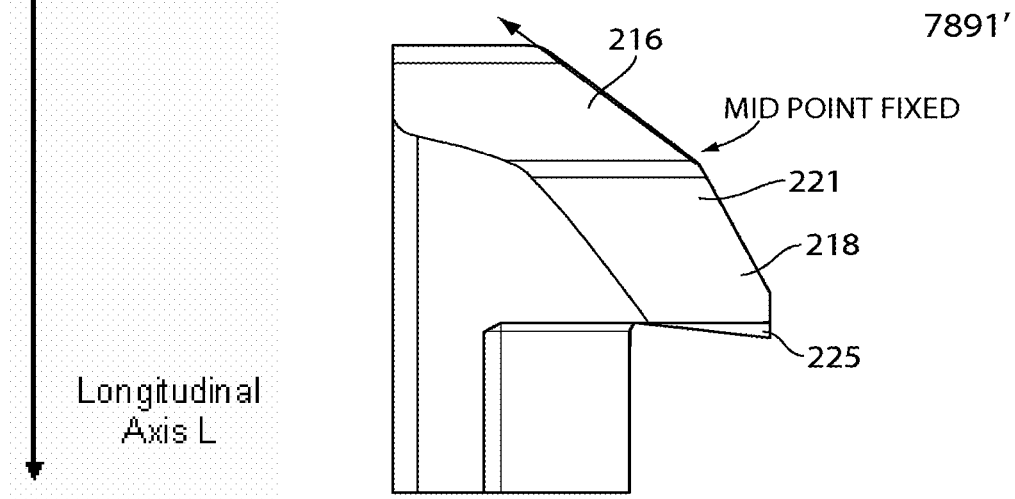
FIG. 15B provides a perspective view of an exemplary plunger with a mid point fixed (MPF) configuration and an ICS angle of about 48°.

FIG. 15B provides a perspective view of an exemplary plunger with an MPF configuration and an ICS angle of about 48°.

Figure 16A:
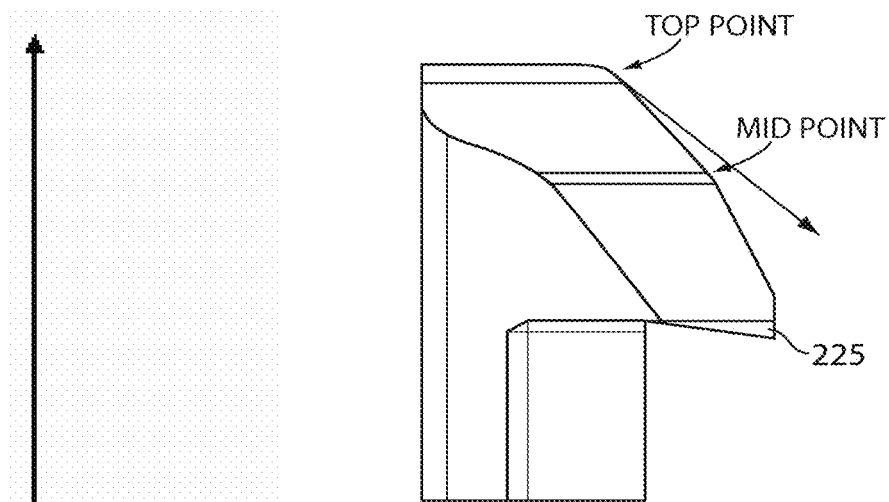
FIG. 16A provides a perspective view of a control plunger with an ICS angle of about 38°.

FIG. 16A provides a perspective view of a control plunger with an ICS angle of about 38°.

Figure 16B:
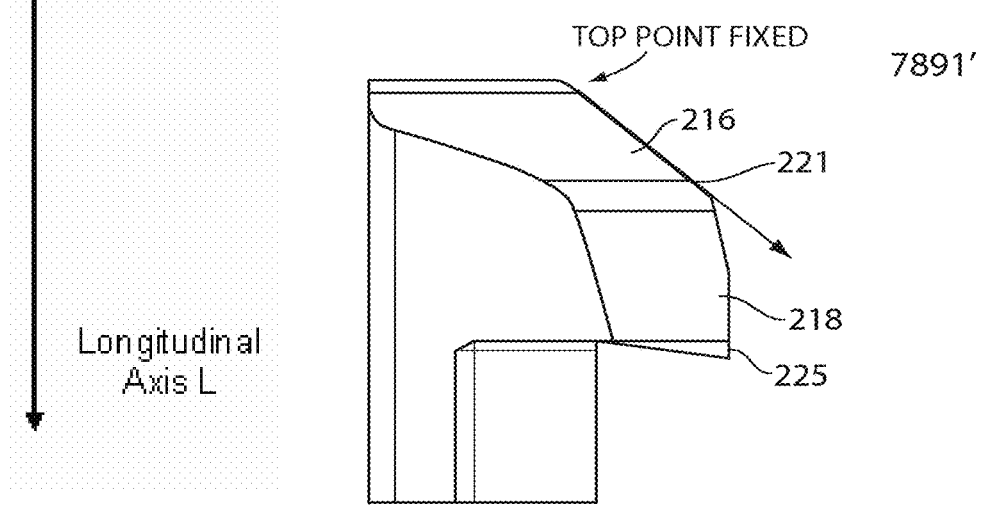
FIG. 16B provides a perspective view of an exemplary plunger with a top point fixed (TPF) configuration and an ICS angle of about 48°.

FIG. 16B provides a perspective view of an exemplary plunger with a TPF configuration and an ICS angle of about 48°.

Figure 17A:
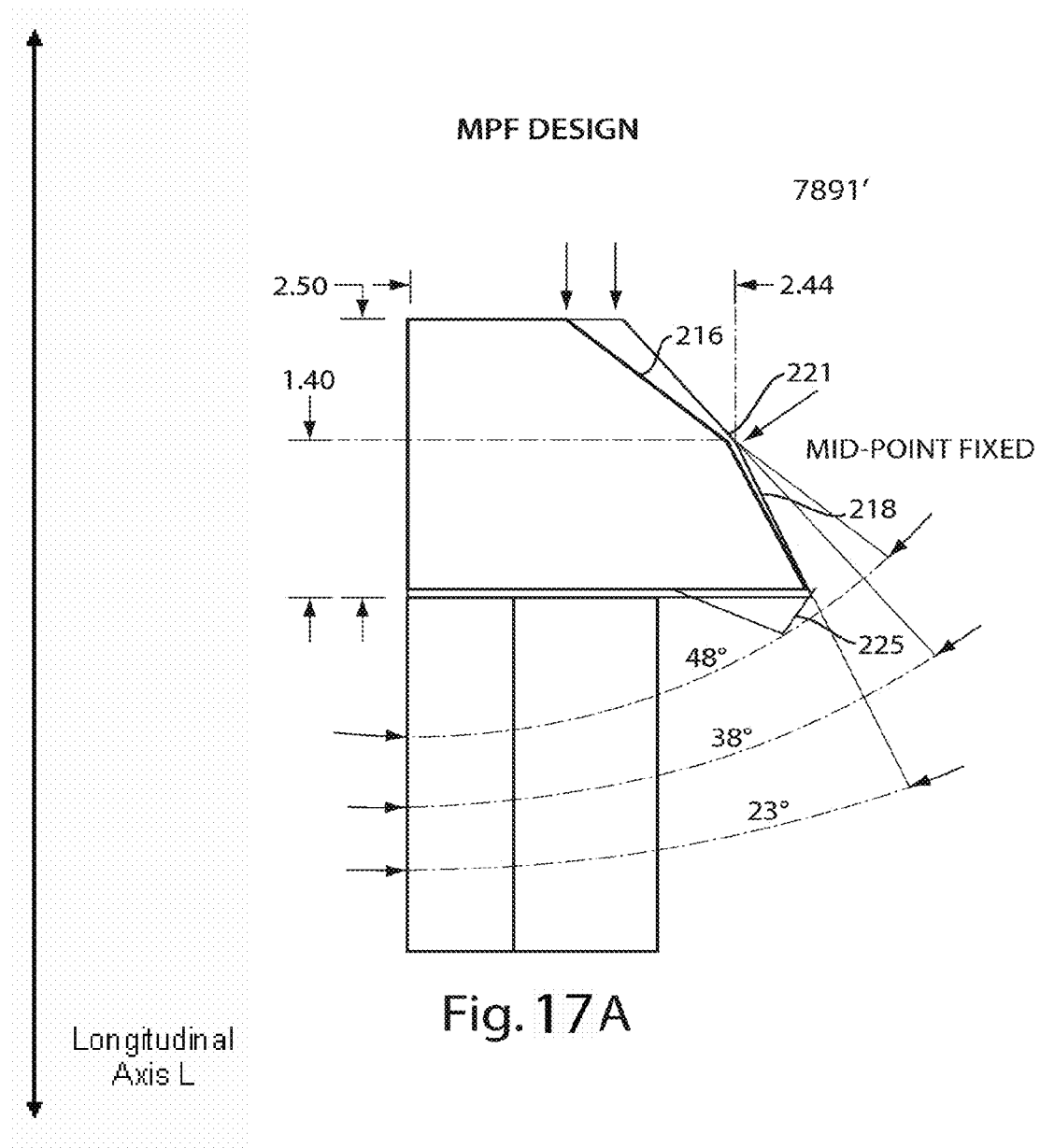
FIG. 17A illustrates a schematic diagram of an exemplary plunger arm having an MPF configuration and an ICS angle of about 48°. In this example, the plunger arm has a secondary contact surface (SCS) angle of about 23°.

FIG. 17A illustrates a schematic diagram of an exemplary plunger arm having an MPF configuration and an ICS angle of about 48°. In this example, the plunger arm had an SCS angle was about 23°.

Figure 17B:
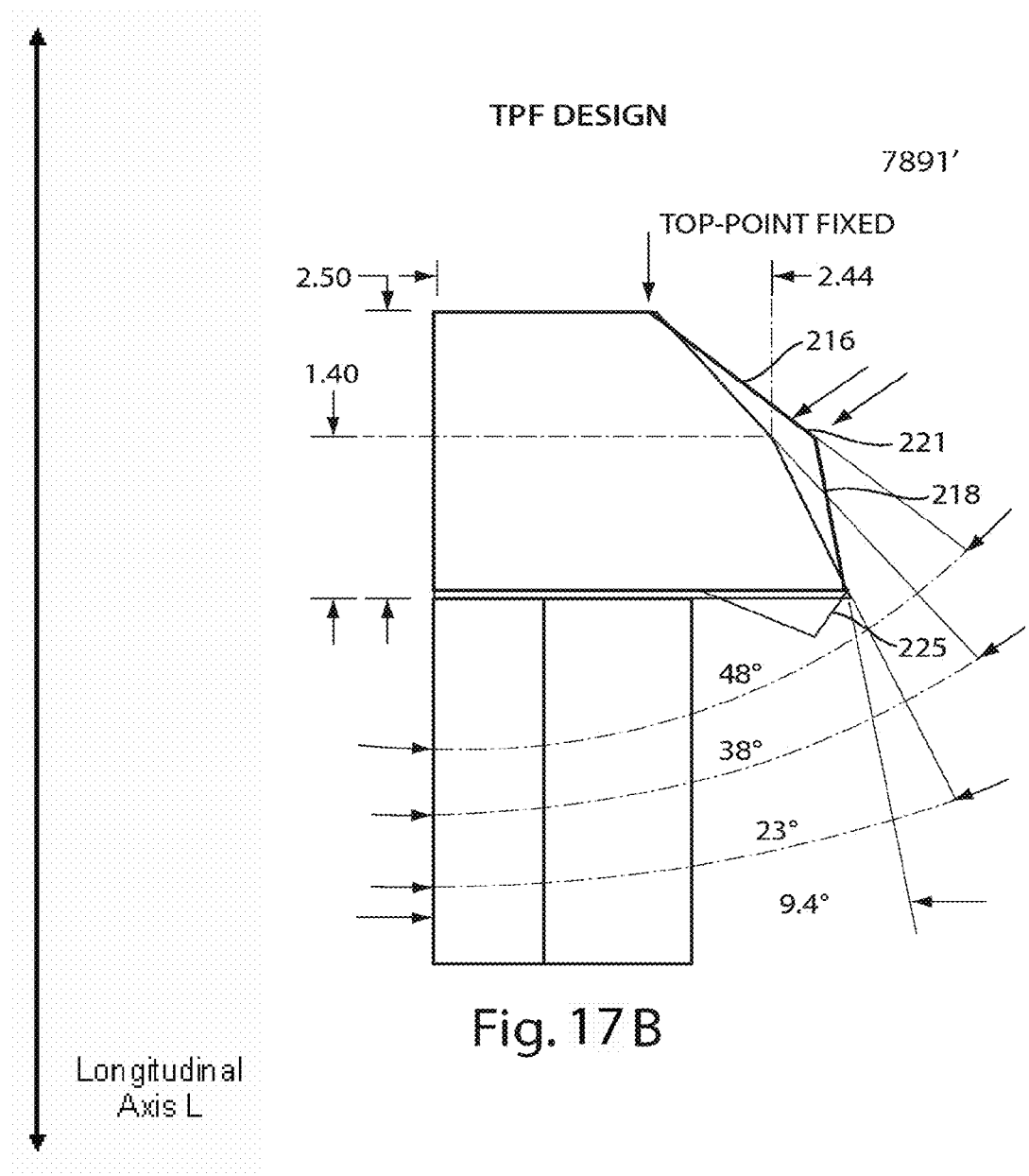
FIG. 17B illustrates a schematic diagram of an exemplary plunger arm having a TPF configuration and an ICS angle of about 48°. In this example, the plunger arm has an SCS angle of about 9.4°.

FIG. 17B illustrates a schematic diagram of an exemplary plunger arm having a TPF configuration and an ICS angle of about 48°. In this example, the plunger arm had an SCS angle of about 9.4° because the diameter of the plunger arm was kept constant between the MPF and TPF configurations. An exemplary diameter of the plunger arm was about 8.9 mm.

FIGS. 18A-18D illustrate an exemplary firing button 32 provided in accordance with exemplary embodiments. An exemplary firing button 32 provided in accordance with exemplary embodiments may serve as an external cap with a contact surface configured for contact by a patient in order to depress the firing button 32. An exemplary firing button 32 provided in accordance with exemplary embodiments may also include an inner ring or internal driving portion 32a configured to contact the tabbed feet of the plunger arms in order to activate or fire the device when the firing button 32 is depressed by a patient.

Figure 18A:
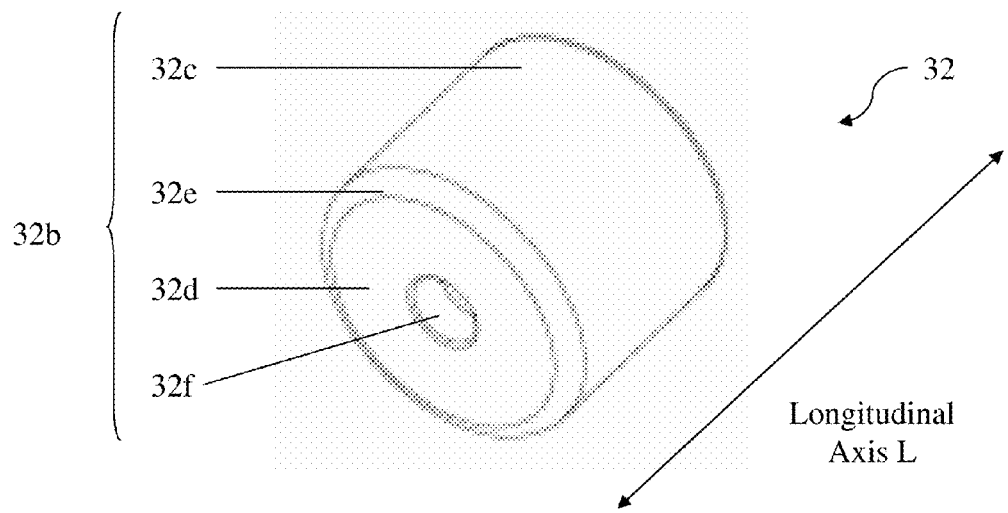
FIG. 18A illustrates an external perspective view of an exemplary firing button.

FIG. 18A illustrates an external perspective view of the firing button 32, showing an end wall 32d of the firing button configured as a contact surface that, when assembled with the automatic injection device, protrudes from the distal end of the distal housing component 12b (not shown). In an exemplary embodiment, an external cap portion 32b, when assembled with the automatic injection device, covers part or the entirety of the distal end of the distal housing component 12b.

Figure 18B:
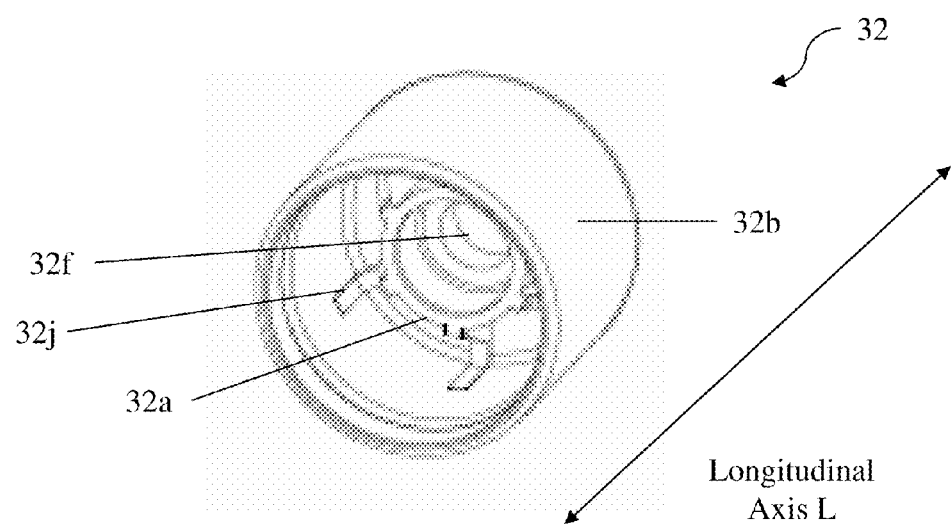
FIG. 18B illustrates an internal perspective view of an exemplary firing button.

The firing button 32 may take any suitable shape or form including, but not limited to, a substantially cylindrical shape with a circular cross-section, a substantially box shape with a rectangular or square cross-section, etc. In an exemplary embodiment in which the firing button 32 has a substantially cylindrical shape with a circular cross-section, as illustrated in FIGS. 18A and 18B, the firing button 32 includes a tubular or substantially cylindrical outer wall 32c having a substantially circular cross-section. The tubular outer wall 32c extends substantially along the longitudinal axis L.

A terminal end the tubular outer wall 32c is coupled to the end wall 32d that forms the contact surface. The end wall may partly or entirely cover the terminal end of the outer wall 32c. The end wall 32d extends substantially along the transverse axis T. The end wall may take any suitable shape or form. In an exemplary embodiment, as illustrated in FIG. 18A, the end wall 32d may be flat and planar. In another exemplary embodiment, the end wall 32d may have an upward or downward arcing surface as opposed to a planar surface. In an exemplary embodiment, the end wall 32d may have a regular or irregular textured surface to allow for a more secure and dexterous handling of the firing button by a patient during activation or firing of the device. In an exemplary embodiment, as illustrated in FIG. 18A, the end wall 32d may include a through hole 32f for accommodating a safety mechanism that prevents accidental firing of the device before intended use.

In an exemplary embodiment, the terminal end of the tubular outer wall 32c may be directly coupled to the end wall 32d.

In another exemplary embodiment, the terminal end of the tubular outer wall 32c, the end wall 32d or both may include a beveled surface 32e. The beveled surface 32e may lie between and couple the end wall 32d to the tubular outer wall 32c, and may be oriented at an angle less than 90° in relation to the upper wall 32d and also in relation to the longitudinal axis L. The beveled surface 32e may take any suitable shape or form. In an exemplary embodiment, as illustrated in FIG. 18A, the beveled surface 32e may be flat and planar. In another exemplary embodiment, the beveled surface 32e may have an upward or downward arcing surface as opposed to a planar surface.

FIG. 18B illustrates an internal perspective view of the exemplary firing button 32 of FIG. 18A, showing the inner ring or internal driving portion 32a. The internal driving portion 32a may be coupled to the inner surface of the end wall 32d of the firing button 32. The internal driving portion 32a may protrude in the proximal direction along the longitudinal axis L from the inner surface of the end wall 32d. When assembled in the automatic injection device, the internal driving portion 32a may be disposed in close proximity to or in contact with the distal end of the plunger arms 788a', 788b' so that depressing the firing button 32 causes the internal driving portion 32a to engage one or more surfaces of the distal end of the plunger arms 788a', 788b', e.g., the initial contact surface (ICS) and the secondary contact surface (SCS), etc.

The internal driving portion 32a may take any suitable shape or form including, but not limited to, a substantially cylindrical shape with a circular cross-section, a substantially box shape with a rectangular or square cross-section, etc. The internal driving portion 32a may be formed from any suitable thermoplastic material and/or any suitable thermosetting material.

In exemplary embodiments, one or more mechanical support structures 32j, e.g., buttresses, are formed against and project from the outer surface of the internal driving portion 32a, and are coupled to the inner surface of the external cap portion 32b. The support structures 32j support and reinforce the internal driving portion 32a on the inner surface of the external cap portion 32b.

Figure 18C:
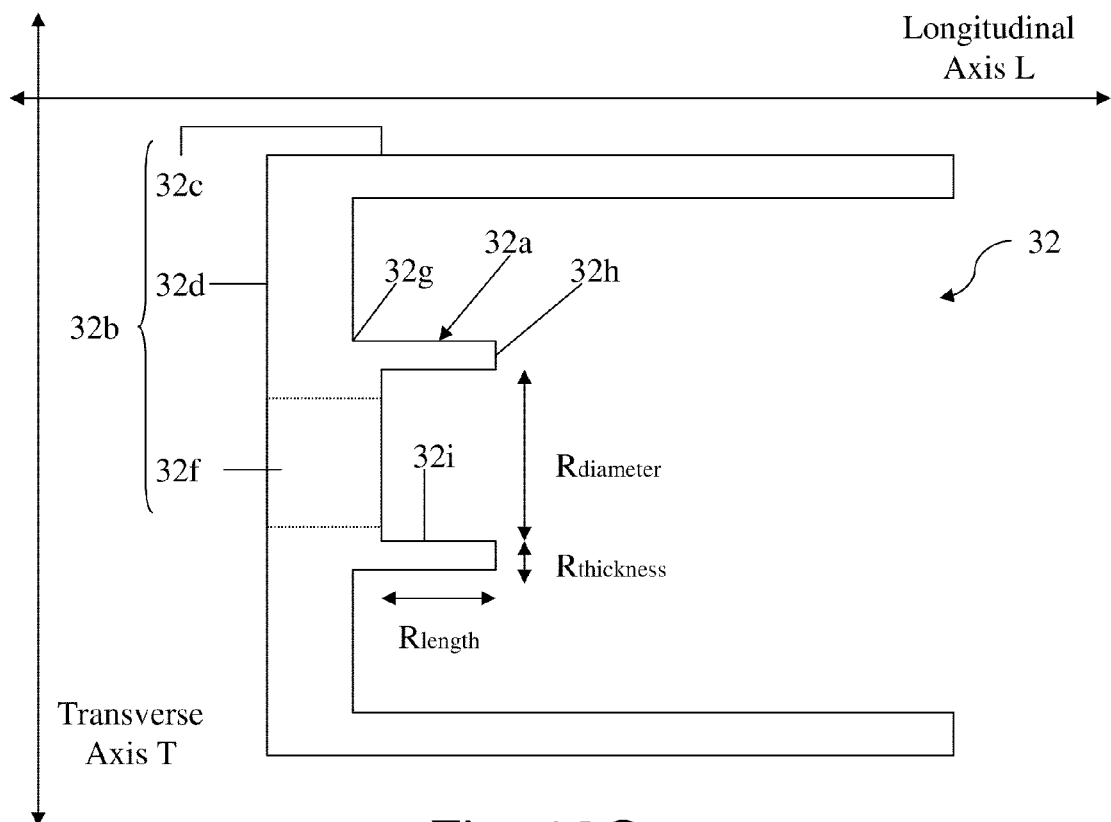
FIG. 18C illustrates a cross-sectional view of an exemplary firing button taken along the longitudinal axis.
Figure 18D:
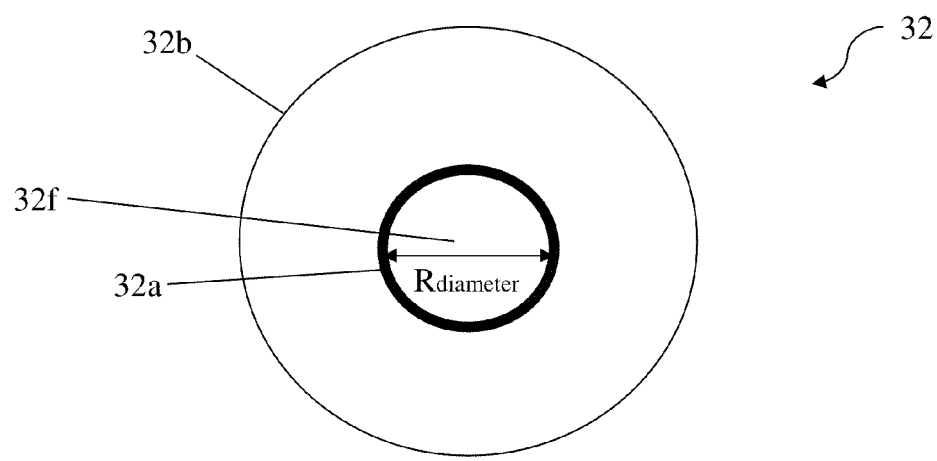
FIG. 18D illustrates a frontal view of an exemplary firing button.

FIG. 18C illustrates a cross-sectional view of the exemplary firing button 32 taken along the longitudinal axis L. FIG. 18D illustrates a frontal view of the inner surface of the exemplary firing button 32.

In an exemplary embodiment, as illustrated in FIGS. 18C and 18D, the exemplary internal driving portion 32a of the firing button 32 is configured as a tubular or substantially cylindrical ring with a circular cross-section.

The ring has an inner diameter, $R_{diameter}$, measured relative to the inner edge 32i of the ring. Exemplary inner diameters, $R_{diameter}$, include, but are not limited to, about 6.0, 6.1, 6.2, 6.3, 6.4, 6.5, 6.6, 6.7, 6.8, 6.9, 7.0 mm, etc. In an exemplary embodiment, the inner diameter, $R_{diameter}$, ranges from about 6.4 mm to about 6.8 mm. In an exemplary embodiment, the inner diameter, $R_{diameter}$, ranges below about 6.7 mm. In an exemplary embodiment, the inner diameter, $R_{diameter}$, is about 6.4 mm. In an exemplary embodiment, the inner diameter, $R_{diameter}$, is about 6.5 mm. In an exemplary embodiment, the inner diameter, $R_{diameter}$, is about 6.6 mm. In an exemplary embodiment, the inner diameter, $R_{diameter}$, is about 6.7 mm. In an exemplary embodiment, the inner diameter, $R_{diameter}$, is about 6.75 mm.

In an exemplary embodiment, a maximum ring inner diameter, $R_{diameter}$, is about 6.30 mm. In an exemplary embodiment, a maximum ring inner diameter, $R_{diameter}$, is about 6.35 mm. In an exemplary embodiment, a maximum ring inner diameter, $R_{diameter}$, is about 6.40 mm. In an exemplary embodiment, a maximum ring inner diameter, $R_{diameter}$, is about 6.45 mm. In an exemplary embodiment, a maximum ring inner diameter, $R_{diameter}$, is about 6.50 mm. In an exemplary embodiment, a maximum ring inner diameter, $R_{diameter}$, is about 6.55 mm. In an exemplary embodiment, a maximum ring inner diameter, $R_{diameter}$, is about 6.60 mm. In an exemplary embodiment, a maximum ring inner diameter, $R_{diameter}$, is about 6.65 mm. In an exemplary embodiment, a maximum ring inner diameter, $R_{diameter}$, is about 6.70 mm. In an exemplary embodiment, a maximum ring inner diameter, $R_{diameter}$, is about 6.75 mm.

The ring has a wall thickness, $R_{thickness}$, measured as half of the difference between the outer diameter of the ring and the inner diameter, $R_{diameter}$, of the ring. Exemplary wall thicknesses, $R_{thickness}$, include, but are not limited to, about 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.0 mm, etc. An exemplary wall thickness, $R_{thickness}$, may range from about 0.60 mm to about 2.00 mm. An exemplary wall thickness, $R_{thickness}$, may range from about 0.80 mm to about 2.00 mm. An exemplary wall thickness, $R_{thickness}$, may be about 0.90 mm.

The ring has a length, $R_{length}$, measured from the distal end 32g of the internal driving portion 32a to the proximal end 32h of the internal driving portion 32a. Exemplary ring lengths, $R_{length}$, include, but are not limited to, about 6.70, 6.71, 6.72, 6.73, 6.74, 6.75, 6.76, 6.77, 6.78, 6.79, 6.80, 6.81, 6.82, 6.83, 6.84, 6.85, 6.86, 6.87, 6.88, 6.89, 6.90 mm, etc. In an exemplary embodiment, the ring length, $R_{length}$, ranges from about 6.73 mm to about 6.83 mm. In an exemplary embodiment, the ring length, $R_{length}$, ranges from about 6.75 mm to about 6.90 mm. In an exemplary embodiment, a minimum ring length, $R_{length}$, is about 6.60 mm. In an exemplary embodiment, a minimum ring length, $R_{length}$, is about 6.65 mm. In an exemplary embodiment, a minimum ring length, $R_{length}$, is about 6.70 mm. In an exemplary embodiment, a minimum ring length, $R_{length}$, is about 6.75 mm. In an exemplary embodiment, a minimum ring length, $R_{length}$, is about 6.80 mm.

In operation, a patient depresses the firing button 32 by contacting and depressing the end wall 32d of the firing button 32. As a result, the firing button 32 slides in a proximal direction along the longitudinal axis L relative to the distal housing component 12b. This causes the internal driving portion 32a of the firing button 32 to engage with and compress the tabbed feet 7891' of the plunger arms 788a', 788b'. Compression of the tabbed feet 7891' of the plunger arms 788a', 788b' decreases the distance between the tabbed feet, i.e., the plunger arm width, which results in a release of the syringe actuation mechanism 700' and a release of the spring 88. Release of the syringe actuation mechanism 700' and of the spring 88 culminates in the successful activation or firing of the automatic injection device.

Figure 19A:
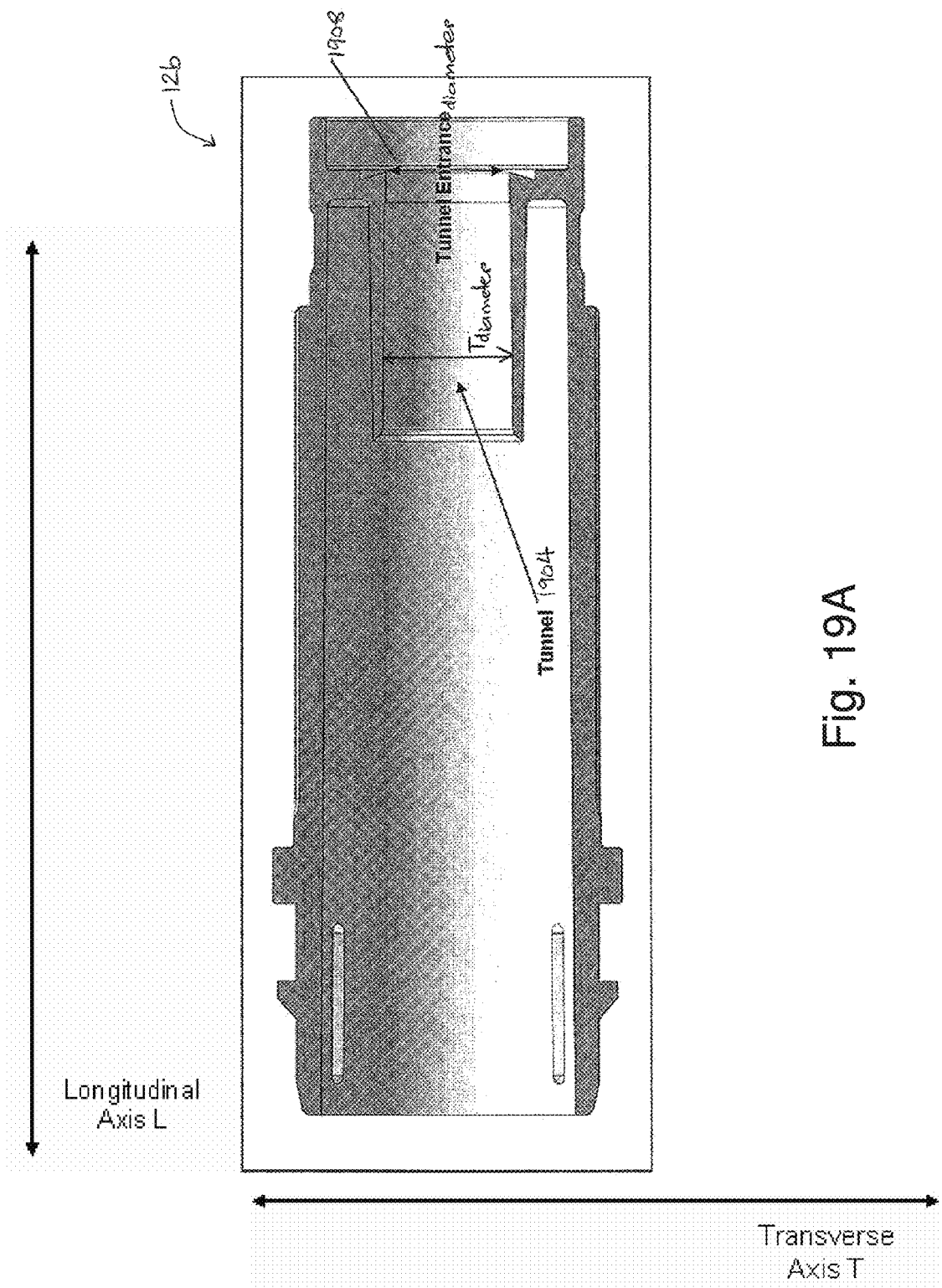
FIG. 19A illustrates a cross-sectional view of an exemplary firing body taken along the longitudinal axis.

FIG. 19A illustrates a cross-sectional view of an exemplary firing body 12b taken along the longitudinal axis. In an exemplary embodiment, a proximal portion of the firing body 12b is configured as a tunnel 1904 that forms a hollow bore extending substantially along the longitudinal axis. The hollow bore of the tunnel 1904 is configured to allow the plunger arms 788a', 788b' to move downward along the longitudinal axis through the hollow bore when the device is fired. In an exemplary embodiment, the tunnel 1904 is substantially cylindrical with a circular cross-section. The tunnel 1904 has an inner diameter, $T_{diameter}$, which is the inner diameter of the circular cross-section. Exemplary inner diameters, $T_{diameter}$, include, but are not limited to, about 6.00, 6.10, 6.20, 6.30, 6.40, 6.50, 6.60, 6.70, 6.80, 6.90, 7.00, 7.10, 7.20, 7.30, 7.40, 7.50, 7.60, 7.70, 7.80, 7.90, 8.00 mm, etc.

The tunnel 1904 forms an entrance region or aperture 1908 at its distal end, which has an inner diameter, $TunnelEntrance_{diameter}$. In an exemplary embodiment, the entrance region 1908 has the same inner diameter as the inner diameter of the tunnel 1904. In another exemplary embodiment, the entrance region 1908 has a different inner diameter, smaller or larger, than the inner diameter of the tunnel 1904.

Exemplary entrance inner diameters, $TunnelEntrance_{diameter}$, include, but are not limited to, about 6.00, 6.10, 6.20, 6.30, 6.40, 6.50, 6.60, 6.70, 6.80, 6.90, 7.00, 7.10, 7.20, 7.30, 7.40, 7.50, 7.60, 7.70, 7.80, 7.90, 8.00 mm, etc. In an exemplary embodiment, the minimum exemplary entrance inner diameter, $TunnelEntrance_{diameter}$, is about 6.70 mm. In an exemplary embodiment, the minimum exemplary entrance inner diameter, $TunnelEntrance_{diameter}$, is about 6.60 mm. In an exemplary embodiment, the minimum exemplary entrance inner diameter, $TunnelEntrance_{diameter}$, is about 6.50 mm. In an exemplary embodiment, the minimum exemplary entrance inner diameter, $TunnelEntrance_{diameter}$, is about 6.40 mm.

Figure 19B:
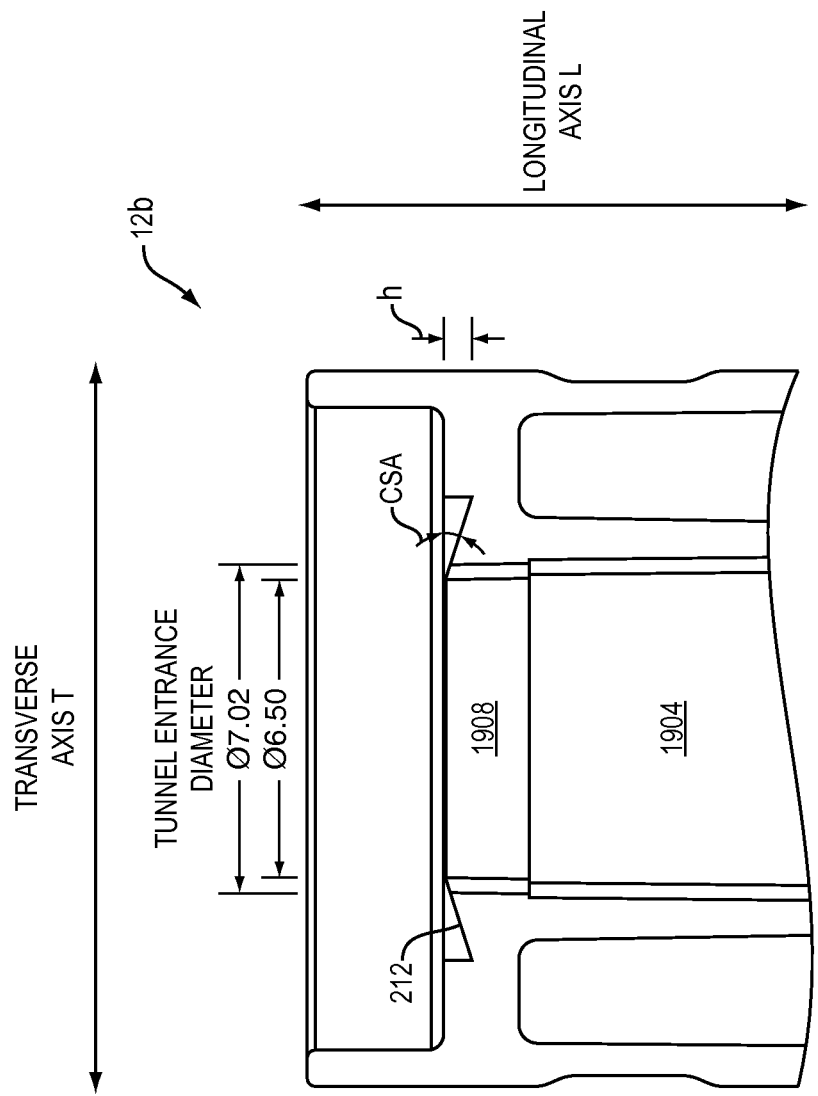
FIG. 19B illustrates a cross-sectional view of an exemplary distal end of the firing body of FIG. 19A.

FIG. 19B illustrates a cross-sectional view of the entrance region 1908 of the tunnel 1904 of FIG. 19A. In an exemplary embodiment, the entrance region 1908 of the tunnel 1904 closest to the firing button 32 may be configured as a conical flange that forms a conical surface 212 on which a plunger foot may rest before the device is fired. The conical surface 212 may extend radially outwardly from the distal end of the tunnel 1904. The conical surface 212 is configured to seat the bottom surface 219 and/or the third surface 225 of the tabbed feet of plunger arms 788a', 788b' (not shown). In operation, when the tabbed feet of the plunger arms are disengaged from the conical surface 212, the plunger arms move downward through the tunnel 1904 of the firing body 12b.

The conical surface 212 may form an angle, the conical surface angle (CSA), relative to the transverse axis T. In an exemplary embodiment, the conical surface 212 may be substantially flat along the transverse axis T, i.e., the CSA is about 0 degrees. In other exemplary embodiments, the conical surface 212 may form an angle from the transverse axis T, i.e., the CSA is greater than 0 degrees. Exemplary CSA values include, but are not limited to, about 1, 2, 3, 4, 5, 6, 7, 8, 9, 10, 11, 12, 13, 14, 15, 16, 17, 18, 19, 20 degrees, etc. In an exemplary embodiment, the CSA is configured to range from about 12 degrees to about 18 degrees. Exemplary CSA values include, but are not limited to, about 12, 13, 14, 15, 16, 17, 18, 19, 20 degrees, etc.

The conical surface 212 may have a height, h, measured along the longitudinal axis L. Exemplary conical surface heights may include, but are not limited to, about 0.10, 0.15, 0.20, 0.25, 0.30, 0.35, 0.40, 0.45, 0.50, 0.55, 0.60, 0.65, 0.70 mm, etc. In an exemplary embodiment, the conical surface height is about 0.50 mm. In an exemplary embodiment, the conical surface height ranges from about 0.24 mm to about 0.28 mm. In one exemplary embodiment, the minimum conical surface height is about 0.20 mm. In another exemplary embodiment, the minimum conical surface height is about 0.3 mm. In another exemplary embodiment, the minimum conical surface height is about 0.4 mm. In another exemplary embodiment, the minimum conical surface height is about 0.5 mm.

III. CONFIGURING MOLDING PARAMETERS TO INCREASE FORCE TO FIRE (FtF)

Certain conventional automatic injection devices can prematurely activate or fire if the Force to Fire (FtF) is below a first optimal level. Certain conventional automatic injection devices may require too much force to fire when the FtF is above a second optimal level. Exemplary systems, devices and methods overcome these problems by providing automatic injection devices with improved FtF and methods of making and using the same, as described herein.

An exemplary FtF for an automatic injection device may range between about 5 N and about 25 N. Another exemplary FtF for an automatic injection device may range between about 10 N and about 15 N. Another exemplary FtF for an automatic injection device may range between about 10 N and about 20 N. Another exemplary FtF for an automatic injection device may range between about 8 N and about 12 N. Another exemplary FtF for an automatic injection device may range above about 5 N. Another exemplary FtF for an automatic injection device may range above about 25 N. Exemplary FtF values include, but are not limited to, about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 N, etc.

Exemplary embodiments may configure one or more molding parameters used to mold one or more components of an automatic injection device firing assembly, e.g., the plunger. Molding parameters may affect the physical properties of the molded plunger, and may, in turn, affect the minimum force required to activate the firing mechanism so that a substance is expelled from the syringe into the patient's body. As such, molding parameters may have an effect on the FtF of a firing mechanism assembly. Exemplary molding parameters configurable by exemplary embodiments include, but are not limited to, the mold temperature, the cooling time, the shot/plunger weight, the injection pressure, the injection speed, etc.

In an exemplary embodiment, an exemplary plunger may be molded using a one-stage injection molding process. In another exemplary embodiment, an exemplary plunger may be molded using a two-stage injection molding process. In an exemplary embodiment, the injection pressure used during the first stage of the injection molding process may range from about $750 \times 10^3$ psi to about $900 \times 10^3$ psi. In another exemplary embodiment, the injection pressure used during the first stage of the injection molding process may range from about $1600 \times 10^3$ psi to about $1800 \times 10^3$ psi. In an exemplary embodiment, the injection pressure used during the second stage of the injection molding process may range from about $500 \times 10^3$ psi to about $750 \times 10^3$ psi. In another exemplary embodiment, the injection pressure used during the second stage of the injection molding process may range from about $800 \times 10^3$ psi to about $900 \times 10^3$ psi.

In an exemplary embodiment, the mold temperature used in the molding process may be reduced in order to increase the plunger width which, in turn, increases the FtF. In an exemplary embodiment, the cooling time used in the molding process may be increased in order to increase the plunger width which, in turn, increases the FtF. In an exemplary embodiment, the mold temperature may be reduced and the cooling time may be increased to increase the FtF. That is, a lower mold temperature and/or a longer cooling time may be used to increase the FtF.

In an exemplary embodiment, the mold temperature may range from about 100 F to about 200 F. In an exemplary embodiment, the mold temperature may be below about 200 F. In another exemplary embodiment, the mold temperature may be below about 100 F.

In an exemplary embodiment, the cooling time may range from about 10 seconds to about 25 seconds. In an exemplary embodiment, the cooling time may be above about 10 seconds. In another exemplary embodiment, the cooling time may be above about 20 seconds. In another exemplary embodiment, the cooling time may be above about 25 seconds. Exemplary cooling times include, but are not limited to, about 10, 11, 12, 13, 14, 15, 16, 17, 18, 19, 20, 21, 22, 23, 24, 25, 26, 27, 28, 29, 30, 31, 32, 33, 34, 35 seconds, etc.

In an exemplary embodiment, the flexural modulus of the material forming the plunger may be increased to increase the FtF. Exemplary plungers discussed herein are formed at least partly of acetal polyoxymethylene (POM) copolymers, e.g., from Ticona, the Hostaform™ C 13031 acetal (POM) copolymer plastic material, unless otherwise stated. Exemplary plungers may also be formed of other thermoplastic and thermosetting materials.

In an exemplary embodiment, the weight of the plunger may be increased to increase the FtF. Exemplary plunger weights may include, but are not limited to, about 1.90, 1.91, 1.92, 1.93, 1.94, 1.95, 1.96, 1.97, 1.98, 1.99, 2.00, 2.01, 2.02, 2.03, 2.04, 2.05, 2.06, 2.07, 2.08, 2.09, 2.10 grams, etc. Exemplary plunger weights may range from about 1.92 grams to about 2.04 grams, but are not limited to this exemplary range. In an exemplary embodiment, the plunger weight may be above about 2 grams. In an exemplary embodiment, the plunger weight may be above about 1.93 grams.

IV. CONFIGURING EXEMPLARY AUTOMATIC INJECTION DEVICES TO MINIMIZE OR ELIMINATE DELAYED DELIVERY OF AN INJECTION

Exemplary embodiments may configure one or more structural features of automatic injection devices including, but not limited to, the firing button, the firing body, the plunger, etc., in order to minimize or eliminate delayed delivery of an injection.

Figure 20:
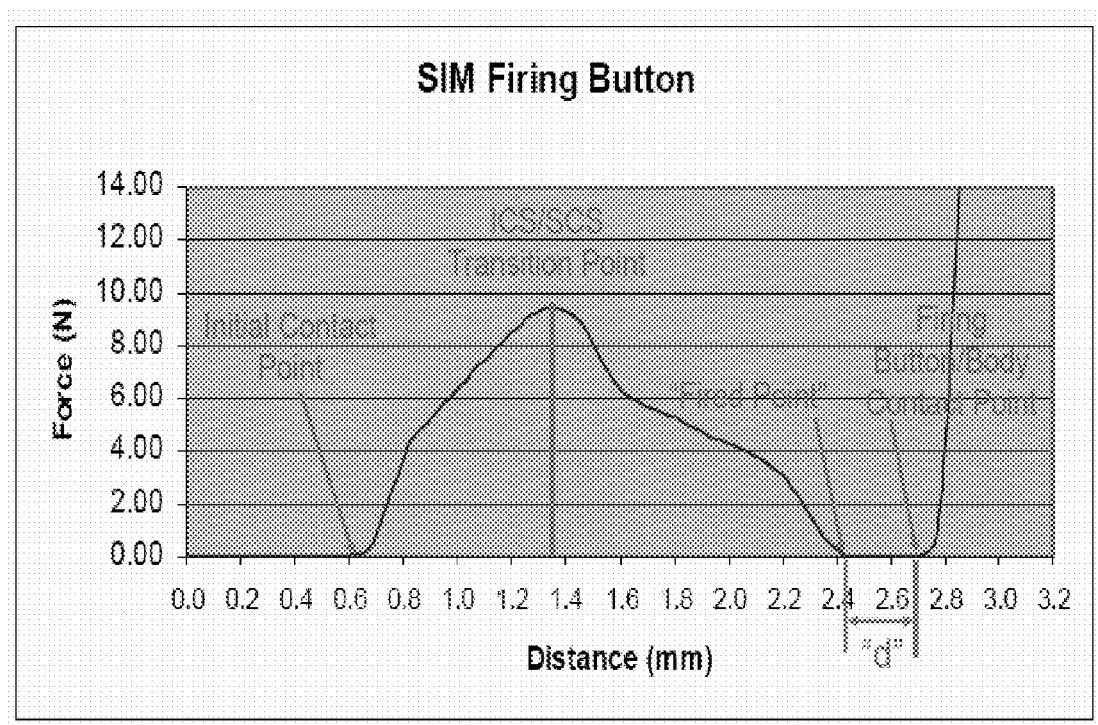
FIG. 20 illustrates an exemplary force profile illustrating forces in N (y-axis) against the distance in mm (x-axis).

Certain terms are defined in this section to facilitate understanding of exemplary embodiments with reference to FIG. 20.

The term "force profile" refers to a graph of the force applied during the automatic injection device firing process against the distance moved by the firing button during the firing process.

FIG. 20 illustrates an exemplary force profile illustrating forces in N (y-axis) against the distance in mm (x-axis).

The term "initial contact point" refers to a point on a force profile at which a force is first experienced during the automatic injection device firing process. This corresponds to the point at which the internal driving portion 32a of the firing button 32 contacts the tabbed foot 7891' of the plunger arms 788a', 788b'.

The term "ICS/SCS transition point" refers to a subsequent point on a force profile at which the force reaches a peak. This corresponds to the point at which the internal driving portion 32a of the firing button 32 passes from the initial contact surface (ICS) 216 to the secondary contact surface (SCS) 218 of the tabbed foot 7891' of the plunger arms 788a', 788b'.

The term "fired point" refers to a subsequent point on a force profile at which the force returns to substantially zero. This corresponds to the point at which the plunger 70 is disengaged and is no longer in contact with the internal driving portion 32a of the firing button 32.

The term "firing button/body contact point" refers to a subsequent point on a force profile at which the force increases, i.e., spikes. This corresponds to the point at which the internal driving portion 32a of the firing button 32 contacts the conical surface 212 of the firing body 12b, as illustrated in FIG. 13.

The term "d" refers to the difference in distance along the x-axis between the fired point and the firing button/body contact point.

A. Inner Diameter, $R_{diameter}$, of Internal Driving Portion of Firing Button

In exemplary automatic injection devices, delayed delivery of an injection tends to decrease with a decreasing inner diameter, $R_{diameter}$, of the internal driving portion 32a of the firing button 32. In an exemplary embodiment, the inner diameter, $R_{diameter}$, of the internal driving portion 32a of the firing button 32 is reduced to minimize or eliminate delayed delivery of an injection.

Figure 21:
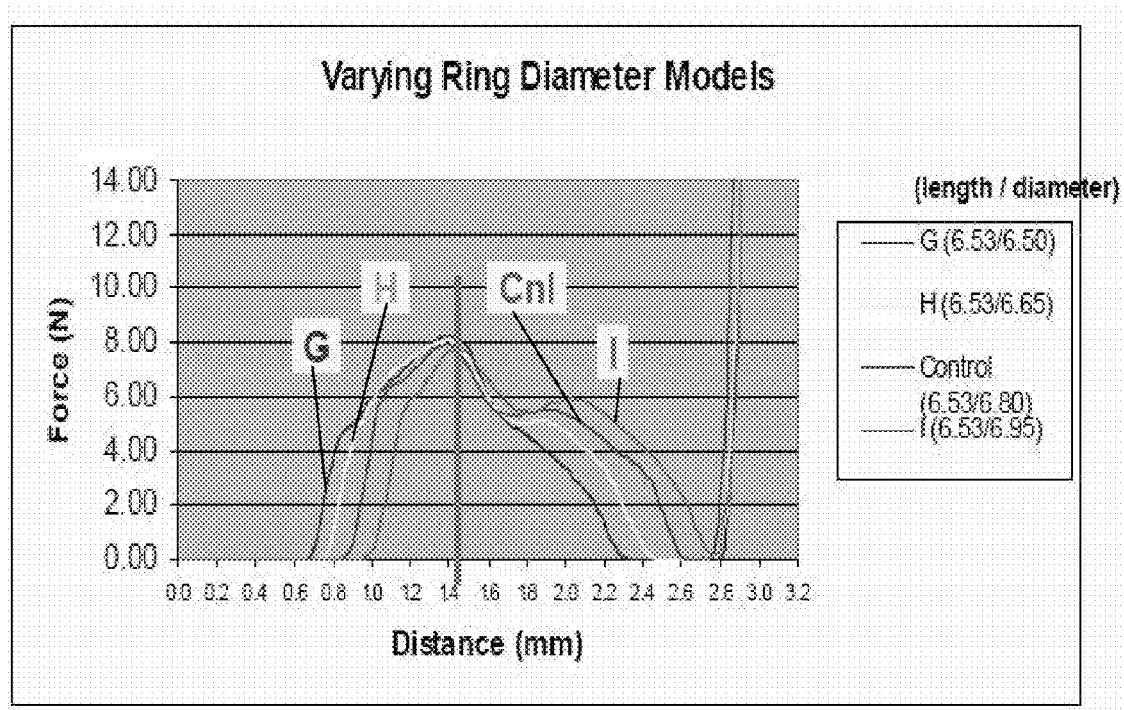
FIG. 21 illustrates four exemplary force profiles illustrating forces in N (y-axis) against the distance in mm (x-axis).

The relationship between a decreasing inner diameter, $R_{diameter}$, of the internal driving portion 32a of a firing button 32 and delayed delivery of an injection is described in this section with reference to FIG. 21.

FIG. 21 illustrates four exemplary force profiles—"G," "H," "Cnl" and "I"—illustrating forces in N (y-axis) against the distance in mm (x-axis) for internal driving portions 32a of firing buttons 32 having a length, $R_{length}$, of about 6.53 mm.

Force profile "G" corresponds to an internal driving portion 32a of a firing button 32 with an inner diameter, $R_{diameter}$, of about 6.50 mm. Force profile "H" corresponds to an internal driving portion 32a of a firing button 32 with an inner diameter, $R_{diameter}$, of about 6.65 mm. Force profile "Cnl" corresponds to an internal driving portion 32a of a firing button 32 with an inner diameter, $R_{diameter}$, of about 6.80 mm. Force profile "I" corresponds to an internal driving portion 32a of a firing button 32 with an inner diameter, $R_{diameter}$, of about 6.95 mm.

An internal driving portion 32a of a firing button 32 with a smaller inner diameter sits higher above the tabbed foot 7891' of the plunger arms 788a', 788b' and makes an earlier contact with the tabbed foot 7891' of the plunger arms 788a', 788b', as compared to an internal driving portion 32a of a firing button 32 with a larger diameter. Since the internal driving portion 32a of a firing button 32 makes an earlier contact with the tabbed foot 7891' of the plunger arms 788a', 788b', the force profile is initiated earlier, i.e., after a shorter distance of depression of the firing button. As a result, for a decreasing inner diameter, the initial contact point on the force profile occurs earlier, i.e., at shorter distances on the x-axis. Decreasing the inner diameter, $R_{diameter}$, of the internal driving portion 32a of a firing button 32 therefore reduces the strain required to achieve adequate collapse in the plunger for a successful firing of the automatic injection device.

In some exemplary embodiments, the ICS/SCS transition point is unchanged and occurs at substantially the same distance on the x-axis.

In some exemplary embodiments, the firing button/body contact point is unchanged and occurs at substantially the same distance on the x-axis. This is because, in the exemplary embodiments, the length, $R_{length}$, of the internal driving portion 32a of a firing button 32 is held constant over the different force profiles. In other exemplary embodiments, the length of the internal driving portion 32a of the firing button 32 may be varied.

Because of the structural configuration of the different components in exemplary automatic injection devices, the distance "d" on the x-axis of the force profile increases with a decreasing inner diameter, $R_{diameter}$, of the internal driving portion 32a of a firing button 32. The distance "d" corresponds to a farther distance over which the internal driving portion 32a of a firing button 32 may be pushed even after the plunger has disengaged from the internal driving portion 32a, until the internal driving portion 32a contacts the firing body conical surface 212 of the firing body 12b and is stopped from moving farther. If the pressing of the firing button fails to fire the automatic injection device until the fired point, the firing button may be depressed farther over the distance "d" in order to fire the automatic injection device. As such, an increasing distance "d" reduces delayed delivery of an injection and increases the probability of a successful firing. Decreasing the inner diameter, $R_{diameter}$, of the internal driving portion 32a of a firing button 32 therefore reduces delayed delivery of an injection.

In summary, decreasing the inner diameter, $R_{diameter}$, of the internal driving portion 32a of a firing button 32 reduces delayed delivery of an injection, increases the probability of successful firing, and reduces the strain required to achieve adequate collapse in the plunger for a successful firing of the automatic injection device. Exemplary embodiments may decrease the inner diameter, $R_{diameter}$, of the internal driving portion 32a of a firing button 32, alone or in combination with one or more additional factors, to minimize or eliminate delayed delivery of an injection, increase the probability of successful firing, and reduce the strain required to achieve adequate collapse in the plunger for a successful firing of the automatic injection device.

In an exemplary embodiment, the inner diameter, $R_{diameter}$, may be decreased while also decreasing the outer diameter of the internal driving portion 32a of the firing button 32. This exemplary embodiment may leave the wall thickness (i.e., the difference between the outer diameter and the inner diameter) of the internal driving portion 32a of the firing button 32 unchanged.

In another exemplary embodiment, the inner diameter, $R_{diameter}$, may be decreased while leaving unchanged the outer diameter of the internal driving portion 32a of the firing button 32. This exemplary embodiment may increase the wall thickness (i.e., the difference between the outer diameter and the inner diameter) of the internal driving portion 32a of the firing button 32. The increased wall thickness tends to reduce the extent of deformation of the internal driving portion 32a of the firing button 32 when the firing button 32 is depressed. The reduction in deformation of the internal driving portion 32a of the firing button 32 advantageously minimizes delayed delivery of an injection.

In exemplary embodiments, the length of exemplary automatic injection device along the longitudinal axis L may be kept constant or limited to within a certain range. In these exemplary embodiments, the inner diameter, $R_{diameter}$, of the internal driving portion 32a of the firing button 32 may not be reduced beyond a certain minimum inner diameter. This is because reducing the inner diameter beyond the minimum inner diameter may result in the firing button sitting too high in the device, which increases the difficulty in assembling the components of the device. In certain exemplary embodiments, the minimum inner diameter beyond which the inner diameter is not reduced may range from about 5.0 mm to about 5.9 mm.

In an exemplary embodiment, the inner diameter, $R_{diameter}$, of the internal driving portion 32a of the firing button 32 is configured to be below about 6.80 mm. In an exemplary embodiment, the inner diameter, $R_{diameter}$, of the internal driving portion 32a of the firing button 32 is configured to be below about 6.70 mm. In an exemplary embodiment, the inner diameter, $R_{diameter}$, of the internal driving portion 32a of the firing button 32 is configured to be below about 6.60 mm. In an exemplary embodiment, the inner diameter, $R_{diameter}$, of the internal driving portion 32a of the firing button 32 is configured to be below about 6.50 mm. In an exemplary embodiment, the inner diameter, $R_{diameter}$, of the inner driving portion 32a of the firing button 32 is configured to be about 6.50 mm. In an exemplary embodiment, the inner diameter, $R_{diameter}$, of the internal driving portion 32a of the firing button 32 is configured to be about 6.40 mm. In exemplary embodiments, the inner diameter, $R_{diameter}$, of the internal driving portion 32a of the firing button 32 is configured to be, but is not limited to, about 6.0, 6.1, 6.2, 6.3, 6.4, 6.5, 6.6, 6.7, 6.8, 6.9, 7.0 mm, etc.

B. Length, $R_{length}$, of Internal Driving Portion of Firing Button

In exemplary automatic injection devices, delayed delivery of an injection tends to decrease with an increasing length, $R_{length}$, of the internal driving portion 32a of the firing button 32. In an exemplary embodiment, the length, $R_{length}$, of the internal driving portion 32a of the firing button 32 is increased to minimize or eliminate delayed delivery of an injection.

Figure 22:
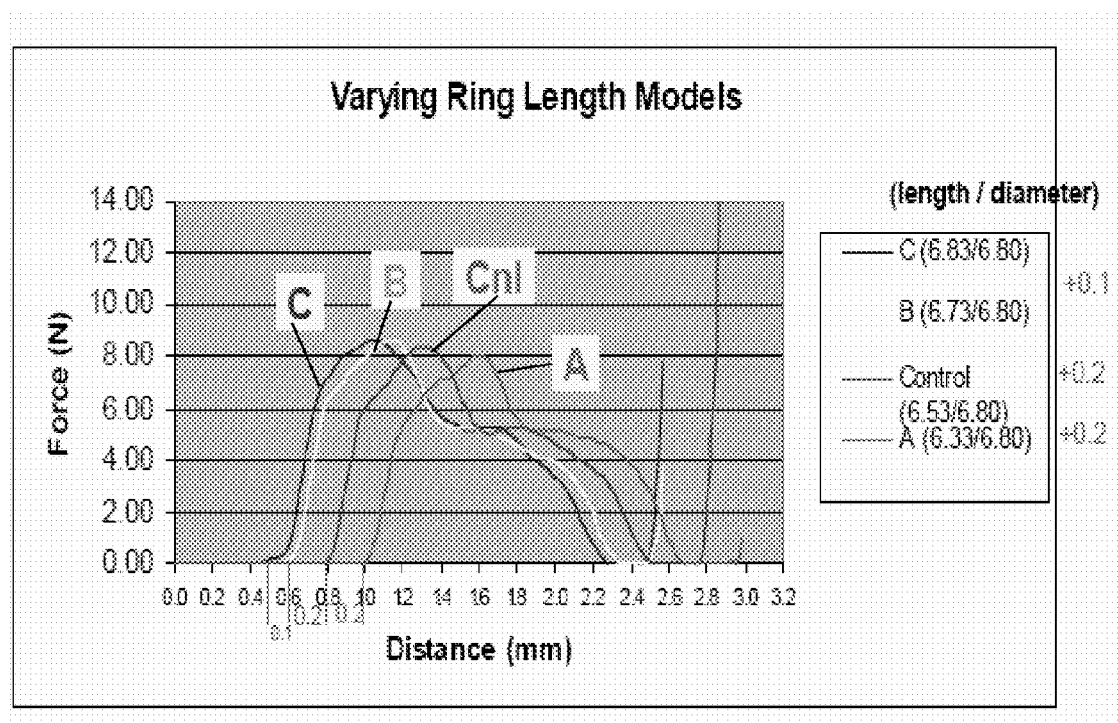
FIG. 22 illustrates four exemplary force profiles illustrating forces in N (y-axis) against the distance in mm (x-axis).

The relationship between an increasing length, $R_{length}$, of the internal driving portion 32a of a firing button 32 and delayed delivery of an injection is described in this section with reference to FIG. 22.

FIG. 22 illustrates four exemplary force profiles—"C," "B," "Cnl" and "A"—illustrating forces in N (y-axis) against the distance in mm (x-axis) for internal driving portions 32a of firing buttons 32 having an inner diameter, $R_{diameter}$, of about 6.80 mm.

Force profile "C" corresponds to an internal driving portion 32a of a firing button 32 with a length, $R_{length}$, of about 6.83 mm. Force profile "B" corresponds to an internal driving portion 32a of a firing button 32 with a length, $R_{length}$, of about 6.73 mm. Force profile "Cnl" corresponds to an internal driving portion 32a of a firing button 32 with a length, $R_{length}$, of about 6.53 mm. Force profile "A" corresponds to an internal driving portion 32a of a firing button 32 with a length, $R_{length}$, of about 6.33 mm.

An internal driving portion 32a of a firing button 32 with a longer length makes an earlier contact with the tabbed foot 7891' of the plunger arms 788a', 788b', as compared to an internal driving portion 32a of a firing button 32 with a shorter length. Since the internal driving portion 32a of a firing button 32 makes an earlier contact with the tabbed foot 7891' of the plunger arms 788a', 788b', the force profile is initiated earlier, i.e., after a shorter distance of depression of the firing button. The forces profiles shift to the left with an increasing length, $R_{length}$, of the internal driving portion 32a of a firing button 32. As a result, the initial contact point on the force profile occurs earlier, i.e., at shorter distances on the x-axis, for an increasing length. Increasing the length, $R_{length}$, of the internal driving portion 32a of a firing button 32 therefore reduces the strain required to achieve adequate collapse in the plunger for a successful firing of the automatic injection device.

The distance "d" on the x-axis of the force profile is unchanged.

In summary, increasing the length, $R_{length}$, of the internal driving portion 32a of a firing button 32 reduces delayed delivery of an injection, increases the probability of successful firing, and reduces the strain required to achieve adequate collapse in the plunger for a successful firing of the automatic injection device. Exemplary embodiments may increase the length, $R_{length}$, of the internal driving portion 32a of a firing button 32, alone or in combination with one or more additional factors, to minimize or eliminate delayed delivery of an injection, increase the probability of successful firing, and reduce the strain required to achieve adequate collapse in the plunger for a successful firing of the automatic injection device.

In an exemplary embodiment, the length, $R_{length}$, of the internal driving portion 32a of a firing button 32 is configured to be above about 6.75 mm. In an exemplary embodiment, the length, $R_{length}$, of the internal driving portion 32a of a firing button 32 is configured to range from about 6.73 mm to about 6.83 mm. In exemplary embodiments, the length, $R_{length}$, of the internal driving portion 32a of a firing button 32 is configured to be, but is not limited to, about 6.70, 6.71, 6.72, 6.73, 6.74, 6.75, 6.76, 6.77, 6.78, 6.79, 6.80, 6.81, 6.82, 6.83, 6.84, 6.85, 6.86, 6.87, 6.88, 6.89, 6.90 mm, etc.

C. Conical Surface Angle, CSA, of Conical Surface of Firing Body

In exemplary automatic injection devices, delayed delivery of an injection tends to decrease with an increasing Conical Surface Angle (CSA) value of the conical surface 212 of the firing body 12b. In an exemplary embodiment, the CSA is increased to minimize or eliminate delayed delivery of an injection.

The tabbed foot 7891' of the plunger arms 788a', 788b' sits higher on a conical surface 212 of a firing body 12b that has a larger CSA. This allows the internal driving portion 32a of a firing button 32 to collapse the plunger 70 at an earlier time when the firing button 32 is depressed. Increasing the CSA of the conical surface 212 of the firing body 12b therefore reduces delayed delivery of an injection.

Exemplary embodiments may increase the CSA of the conical surface 212 of the firing body 12b, alone or in combination with one or more additional factors, to minimize or eliminate delayed delivery of an injection, increase the probability of successful firing, and reduce the strain required to achieve adequate collapse in the plunger for a successful firing of the automatic injection device.

In an exemplary embodiment, the CSA is configured to be range from about 12 degrees to about 18 degrees. Exemplary CSA values include, but are not limited to, about 10, 11, 12, 13, 14, 15, 16, 17, 18, 19, 20 degrees, etc.

D. Height of Conical Surface of Firing Body

In exemplary automatic injection devices, delayed delivery of an injection tends to decrease with an increasing height of the conical surface 212 of the firing body 12b. In an exemplary embodiment, the height of the conical surface 212 of the firing body 12b is increased to minimize or eliminate delayed delivery of an injection. The conical surface height may be reduced over time due to deformation of the conical surface 212 caused by engagement of the conical surface 212 of the firing body 12b with the plunger feet. In an exemplary embodiment, the extent of deformation of the conical surface 212 of the firing body 12b may be reduced to minimize or eliminate delayed delivery of an injection.

A decreasing height and/or greater deformation of the conical surface 212 corresponds to a decrease in the Conical Surface Angle (CSA) of the conical surface 212 of the firing body 12b. The tabbed foot 7891' of the plunger arms 788a', 788b' sits lower on a conical surface 212 of a firing body 12b that has a smaller CSA. This causes the internal driving portion 32a of a firing button 32 to collapse the plunger 70 at a later time when the firing button 32 is depressed. Decreasing the conical surface height and/or decreasing deformation of the conical surface 212 of the firing body 12b therefore increases delayed delivery of an injection.

Exemplary embodiments may decrease the extent of deformation of the conical surface 212 of the firing body 12b, alone or in combination with one or more additional factors, to minimize or eliminate delayed delivery of an injection, increase the probability of successful firing, and reduce the strain required to achieve adequate collapse in the plunger for a successful firing of the automatic injection device. Deformation of the conical surface 212 may result from engagement of the conical surface 212 (formed of a soft material like polypropylene in an exemplary embodiment) of the firing body 12b with the plunger feet (formed of a polyacetal material in an exemplary embodiment). In an exemplary embodiment, the firing body 12b is formed of a relatively high rigidity material to reduce the extent of deformation of the conical surface.

Exemplary embodiments may increase the height of the conical surface 212 of the firing body 12b, alone or in combination with one or more additional factors, to minimize or eliminate delayed delivery of an injection, increase the probability of successful firing, and reduce the strain required to achieve adequate collapse in the plunger for a successful firing of the automatic injection device.

Exemplary conical surface heights may include, but are not limited to, about 0.10, 0.15, 0.20, 0.25, 0.30, 0.35, 0.40, 0.45, 0.50, 0.55, 0.60, 0.65, 0.70 mm, etc. In an exemplary embodiment, the conical surface height is about 0.50 mm. In an exemplary embodiment, the conical surface height ranges from about 0.24 mm to about 0.28 mm. In one exemplary embodiment, the minimum conical surface height is about 0.20 mm. In another exemplary embodiment, the minimum conical surface height is about 0.3 mm. In another exemplary embodiment, the minimum conical surface height is about 0.4 mm. In another exemplary embodiment, the minimum conical surface height is about 0.5 mm.

E. Tunnel Entrance Inner Diameter, $TEntrance_{diameter}$, of Firing Body

In exemplary automatic injection devices, delayed delivery of an injection may be observed when the tunnel entrance inner diameter, $TEntrance_{diameter}$, of the firing body 12b falls below a certain minimum diameter. In an exemplary embodiment, the tunnel entrance inner diameter, $TEntrance_{diameter}$, of the firing body 12b is configured to range above a minimum tunnel entrance inner diameter to minimize or eliminate delayed delivery of an injection.

For a tunnel entrance inner diameter, $TEntrance_{diameter}$, that is too narrow, the plunger 70 may not move all the way down the tunnel of the firing body. The narrow tunnel may cause greater dragging of the plunger feet against the tunnel walls as the plunger travels down the tunnel. Decreasing the tunnel entrance inner diameter, $TEntrance_{diameter}$, below a certain minimum inner diameter may therefore increase delayed delivery of an injection.

Exemplary embodiments may maintain the tunnel entrance inner diameter, $TEntrance_{diameter}$, of the firing body 12b above a minimum inner diameter, alone or in combination with one or more additional factors, to minimize or eliminate delayed delivery of an injection, increase the probability of successful firing, and reduce the strain required to achieve adequate collapse in the plunger for a successful firing of the automatic injection device.

Exemplary entrance inner diameters, $TEntrance_{diameter}$, include, but are not limited to, about 6.00, 6.10, 6.20, 6.30, 6.40, 6.50, 6.60, 6.70, 6.80, 6.90, 7.00, 7.10, 7.20, 7.30, 7.40, 7.50, 7.60, 7.70, 7.80, 7.90, 8.00 mm, etc. In an exemplary embodiment, the minimum exemplary entrance inner diameter, $TEntrance_{diameter}$, is about 6.70 mm. In an exemplary embodiment, the minimum exemplary entrance inner diameter, $TEntrance_{diameter}$, is about 6.60 mm. In an exemplary embodiment, the minimum exemplary entrance inner diameter, $TEntrance_{diameter}$, is about 6.50 mm. In an exemplary embodiment, the minimum exemplary entrance inner diameter, $TEntrance_{diameter}$, is about 6.40 mm.

F. Mid Point Fixed (MPF) or Top Point Fixed (TPF) Plunger Design

In exemplary automatic injection devices, delayed delivery of an injection may be lower for the top point fixed (TPF) plunger design as compared to the mid point fixed (MPF) plunger design. The TPF plunger design allows the tabbed foot 7891' of the plunger arms 788a', 788b' to sit higher on the conical surface 212 of a firing body 12b. This allows the internal driving portion 32a of a firing button 32 to collapse the plunger 70 at an earlier time when the firing button 32 is depressed. The TPF plunger design may therefore reduce delayed delivery of an injection as compared to the MPF plunger design. This effect is observed as an increased distance "d" on the force profile of the TPF plunger design, as compared to the MPF plunger design.

In an exemplary embodiment, the plunger feet may be configured in accordance to the TPF plunger design, alone or in combination with one or more additional other factors, to minimize or eliminate delayed delivery of an injection, increase the probability of successful firing, and reduce the strain required to achieve adequate collapse in the plunger for a successful firing of the automatic injection device.

In another exemplary embodiment, the plunger feet may be configured in accordance to the MPF plunger design for suitability in assembling the firing mechanism.

V. EXEMPLIFICATION

Exemplary systems, devices and methods for making and using at least exemplary firing buttons and exemplary automatic injection devices are described in more detail below with reference to the following experimental examples.

A. Testing of Exemplary Rapid Prototype Technology (RPT) Firing Buttons and Exemplary Commercial Plungers Exemplary automatic injection devices were produced by assembling exemplary Rapid Prototype Technology (RPT) firing buttons with exemplary commercial plungers and other components. The exemplary RPT firing buttons were formed of one or more thermosetting materials. The exemplary plungers each had an initial contact surface (ICS) angle of about 38 degrees. The assembled automatic injection devices were tested to quantitatively determine the impact of different component features on the delayed delivery of an injection, if any, of the devices.

(i) Relationship Between Inner Diameter of Firing Button Ring and Delayed Delivery of an Injection The impact of the combination of the firing button material and the inner diameter of the firing button ring on delayed delivery times was tested. The different combinations tested included: a WaterShed™ 11120 resin and a firing button ring inner diameter of about 6.60 mm, a WaterShed™ 11120 resin and firing button ring inner diameter of about 6.80 mm (used as the control), a WaterShed™ 11120 resin and a firing button ring inner diameter of about 7.00 mm, a ProtoTherm™ 12120 resin and a firing button ring inner diameter of about 6.60 mm, a ProtoTherm™ 12120 resin and a firing button ring inner diameter of about 6.80 mm (used as the control), and a ProtoTherm™ 12120 resin and a firing button ring inner diameter of about 7.00 mm.

TABLE 1

Summary of the specifications of the exemplary components tested

| Firing Button Ring Inner Diameter | Firing Button Ring Length |
|---|---|
| 11120 Resin - 6.60 mm | 11120 Resin - 6.33 mm |
| 11120 Resin - 6.80 mm | 11120 Resin - 6.53 mm |
| 11120 Resin - 7.00 mm | 11120 Resin - 6.73 mm |
| 12120 Resin - 6.60 mm | 12120 Resin - 6.33 mm |
| 12120 Resin - 6.80 mm | 12120 Resin - 6.53 mm |
| 12120 Resin - 7.00 mm | 12120 Resin - 6.73 mm |

In a first set of tests, the firing button of the devices was depressed by a tester to a Zwick strain of about 2.4 mm. The strain was not sufficient to fully depress the firing button and, therefore, the strain in pressing down the firing button was determined to have contributed to the delayed delivery of an injection of the devices.

Figure 23:
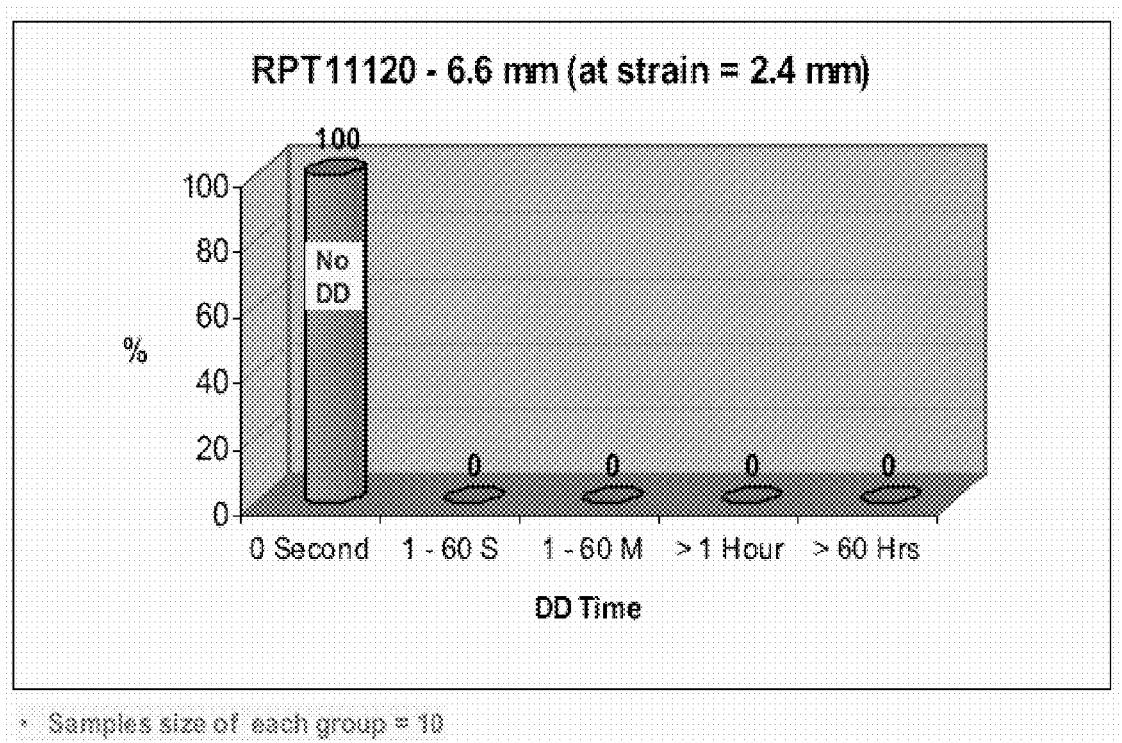
FIG. 23 illustrates a histogram of the percentage of devices that showed delayed delivery (y-axis) against different delayed delivery times (x-axis), for the WaterShed™ 11120 resin plunger and the firing button ring inner diameter of about 6.6 mm.

FIG. 23 illustrates a histogram of the percentage of devices that showed delayed delivery (y-axis) against different delayed delivery times (x-axis), for the WaterShed™ 11120 resin and the firing button ring inner diameter of about 6.6 mm. The histogram shows that none of the devices showed delayed delivery of an injection.

Figure 24:
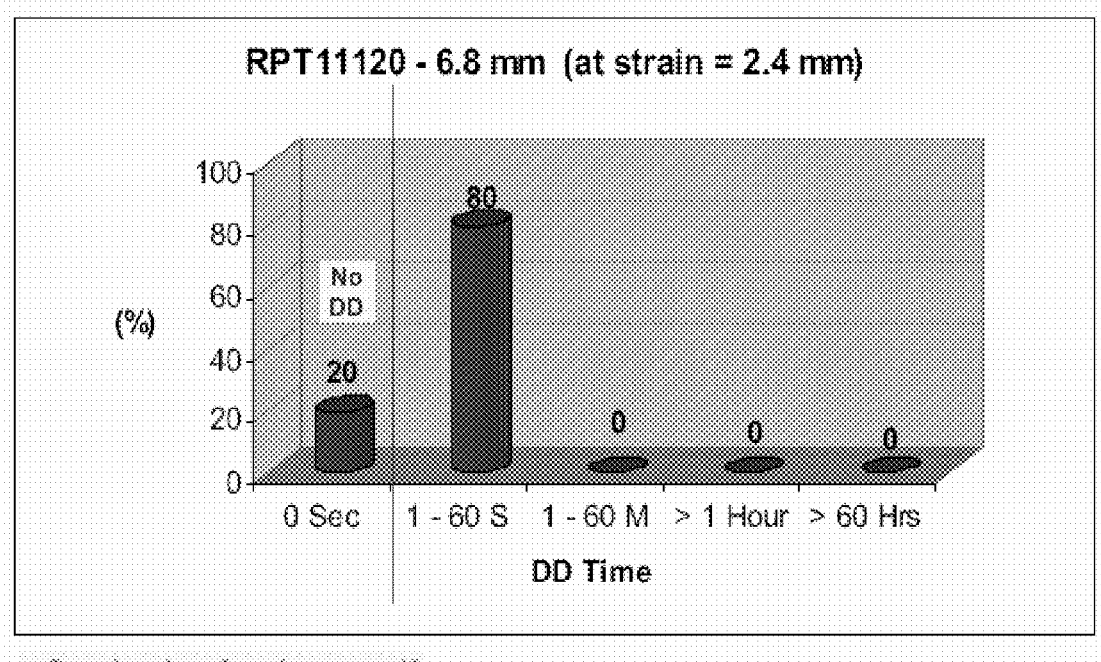
FIG. 24 illustrates a histogram of the percentage of devices that showed delayed delivery (y-axis) against different delayed delivery times (x-axis), for the WaterShed™ 11120 resin plunger and the firing button ring inner diameter of about 6.8 mm.

FIG. 24 illustrates a histogram of the percentage of devices that showed delayed delivery (y-axis) against different delayed delivery times (x-axis), for the WaterShed™ 11120 resin and the firing button ring inner diameter of about 6.8 mm. The histogram shows that about 20% of the devices showed no delayed delivery of an injection, and about 80% of the devices showed a delayed delivery of an injection ranging from about 1 second to about 60 seconds.

Figure 25:
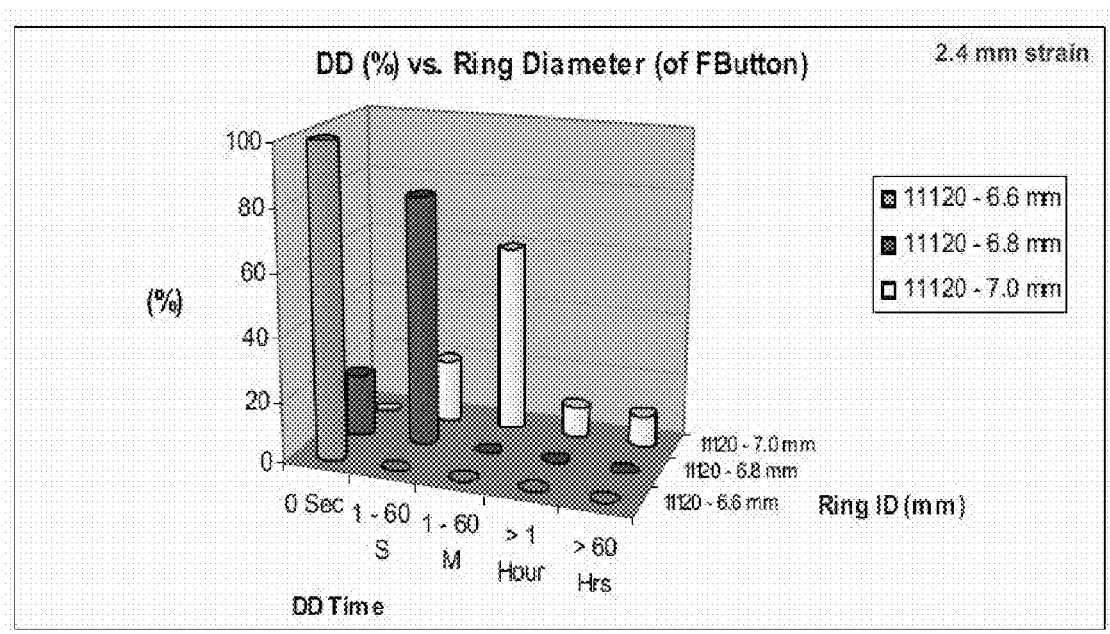
FIG. 25 illustrates a histogram of the percentage of devices that showed delayed delivery (y-axis) against different delayed delivery times and against different firing button ring inner diameters (x-axis) for the WaterShed™ 11120 resin plunger.

FIG. 25 illustrates a histogram of the percentage of devices that showed delayed delivery (z-axis) against different delayed delivery times and against different firing button ring inner diameters for the WaterShed™ 11120 resin. The histogram shows that the percentage of devices that showed no delayed delivery of an injection was highest (100%) for the firing button ring inner diameter of about 6.6 mm, was intermediate (20%) for the firing button ring inner diameter of about 6.8 mm, and was lowest (0%) for the firing button ring inner diameter of about 7.0 mm.

Figure 26:
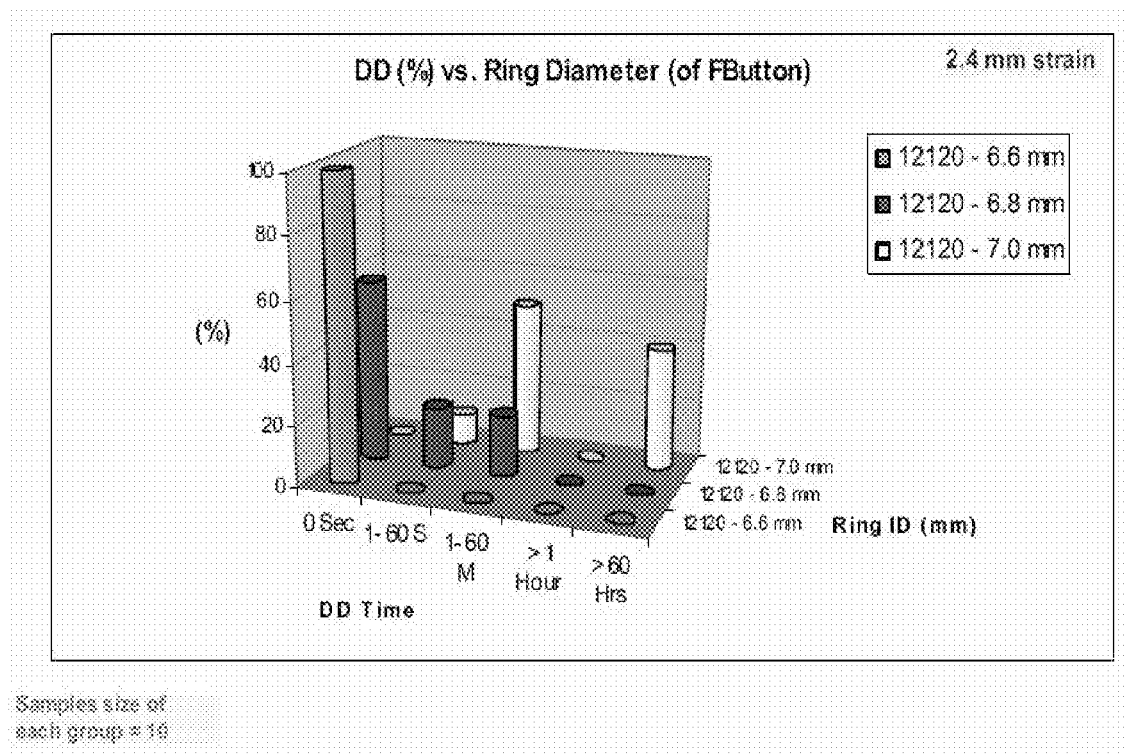
FIG. 26 illustrates a histogram of the percentage of devices that showed delayed delivery (y-axis) against different delayed delivery times and against different firing button ring inner diameters (x-axis) for the ProtoTherm™ 12120 resin plunger.

FIG. 26 illustrates a histogram of the percentage of devices that showed delayed delivery (z-axis) against different delayed delivery times and against different firing button ring inner diameters for the ProtoTherm™ 12120 resin. The histogram shows that the percentage of devices that showed no delayed delivery of an injection was highest (100%) for the firing button ring inner diameter of about 6.6 mm, was intermediate (60%) for the firing button ring inner diameter of about 6.8 mm, and was lowest (0%) for the firing button ring inner diameter of about 7.0 mm.

Figure 27:
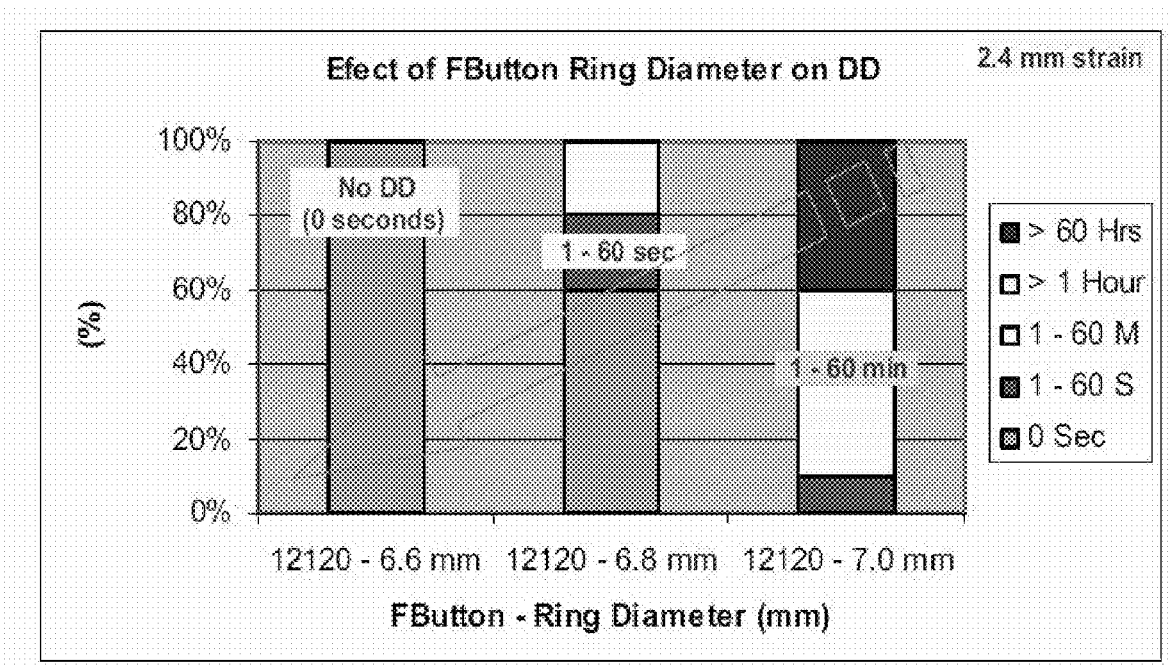
FIG. 27 illustrates a histogram of the percentage of devices that showed different delayed delivery times (y-axis) against different firing button ring inner diameters (x-axis) for the ProtoTherm™ 12120 resin plunger.

FIG. 27 illustrates a histogram of the percentage of devices that showed different delayed delivery times (y-axis) against different firing button ring inner diameters (x-axis) for the ProtoTherm™ 12120 resin. The histogram shows that the percentage of devices that showed no delayed delivery of an injection was highest (100%) for the firing button ring inner diameter of about 6.6 mm, was intermediate (60%) for the firing button ring inner diameter of about 6.8 mm, and was lowest (0%) for the firing button ring inner diameter of about 7.0 mm. The histogram also shows that about 20% of the devices with the 6.8 mm firing button ring inner diameter showed delayed delivery times ranging from about 1 second to about 60 seconds, and about 20% showed delayed delivery times ranging from about 1 minute to about 60 minutes. The histogram further shows that 50% of the devices with the 7.0 mm firing button ring inner diameter showed delayed delivery times ranging from about 1 minute to about 60 minutes, and about 40% showed delayed delivery times above about 60 hours.

Figure 28:
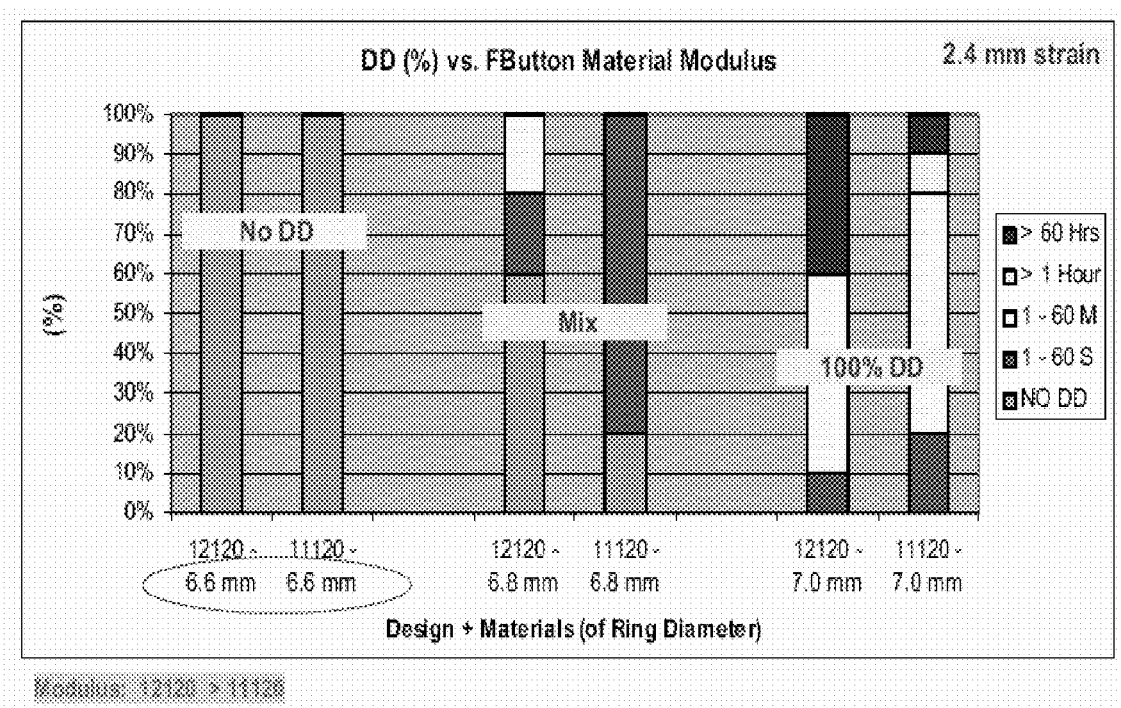
FIG. 28 illustrates a histogram of the percentage of devices that showed different delayed delivery times (y-axis) against different firing button ring inner diameters (x-axis) for the ProtoTherm™ 12120 resin and the WaterShed™ 11120 resin plungers.

FIG. 28 illustrates a histogram of the percentage of devices that showed different delayed delivery times (y-axis) against different firing button ring inner diameters (x-axis) for the ProtoTherm™ 12120 resin and the WaterShed™ 11120 resin. The histogram shows that the percentage of devices that showed no delayed delivery of an injection was highest (100%) for the firing button ring inner diameter of about 6.6 mm (for both resins), was intermediate (60% for the ProtoTherm™ 12120 resin and 20% for the WaterShed™ 11120 resin) for the firing button ring inner diameter of about 6.8 mm, and was lowest (0%) for the firing button ring inner diameter of about 7.0 mm (for both resins).

In a second set of tests, the firing button of the devices was depressed by a tester to a Zwick strain of about 2.6 mm. This strain was sufficient to fully depress the firing button and, therefore, the strain in pressing down the firing button was determined to not have contributed to the delayed delivery of an injection of the devices.

Figure 29:
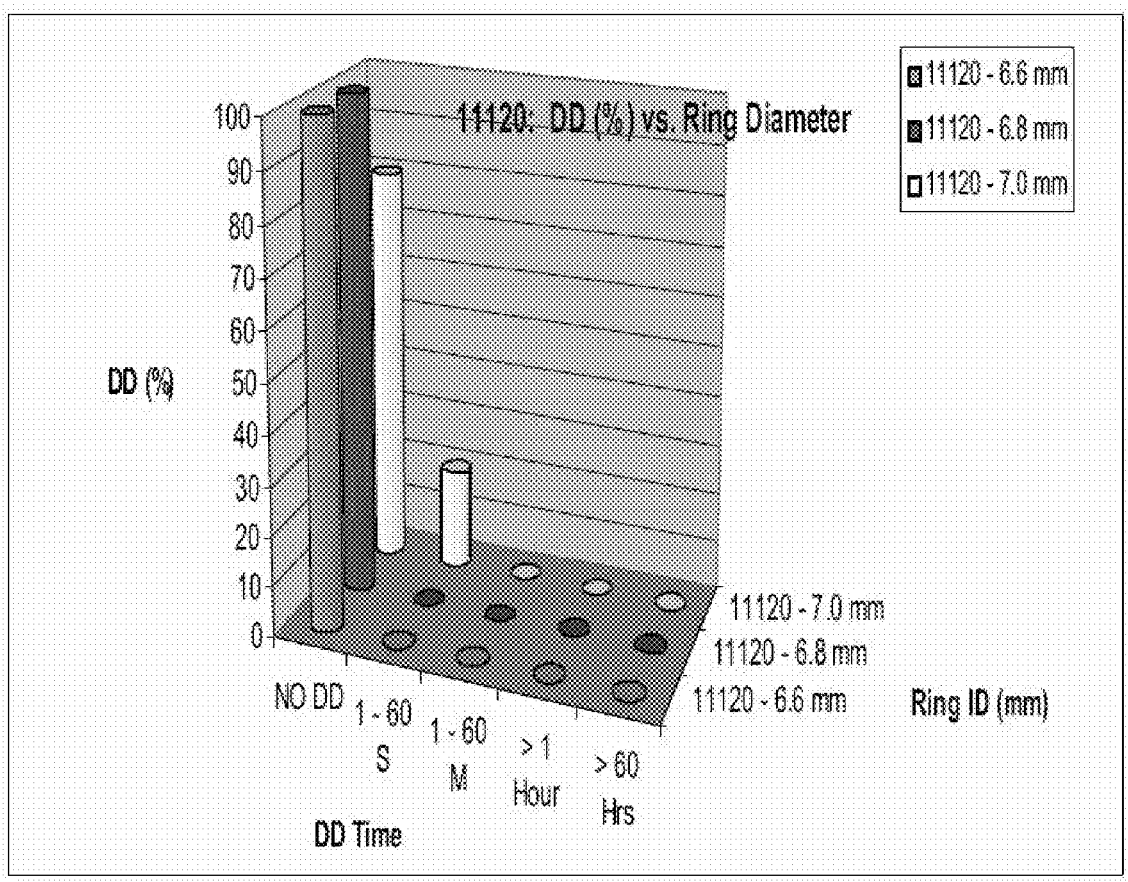
FIG. 29 illustrates a histogram of the percentage of devices that showed delayed delivery (y-axis) against different delayed delivery times and against different firing button ring inner diameters (x-axis) for the WaterShed™ 11120 resin plunger.

FIG. 29 illustrates a histogram of the percentage of devices that showed delayed delivery (z-axis) against different delayed delivery times and against different firing button ring inner diameters for the WaterShed™ 11120 resin. The histogram shows that the percentage of devices that showed no delayed delivery of an injection was high (100%) for the firing button ring inner diameters of about 6.6 mm and about 6.8 mm, and was lower (80%) for the firing button ring inner diameter of about 7.0 mm.

Figure 30:
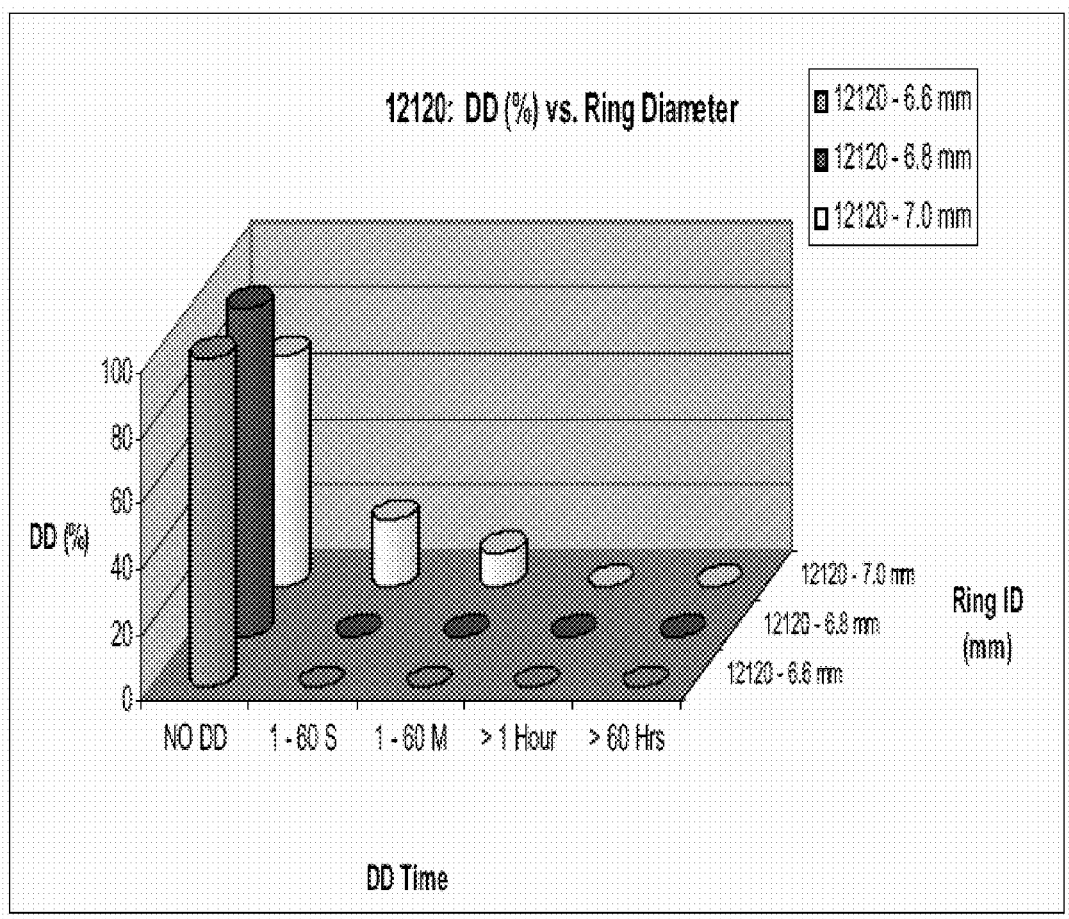
FIG. 30 illustrates a histogram of the percentage of devices that showed delayed delivery (y-axis) against different delayed delivery times and against different firing button ring inner diameters (x-axis) for the ProtoTherm™ 12120 resin plunger.

FIG. 30 illustrates a histogram of the percentage of devices that showed delayed delivery (z-axis) against different delayed delivery times and against different firing button ring inner diameters for the ProtoTherm™ 12120 resin. The histogram shows that the percentage of devices that showed no delayed delivery of an injection was high (100%) for the firing button ring inner diameters of about 6.6 mm and about 6.8 mm, and lower (70%) for the firing button ring inner diameter of about 7.0 mm.

Figure 31:
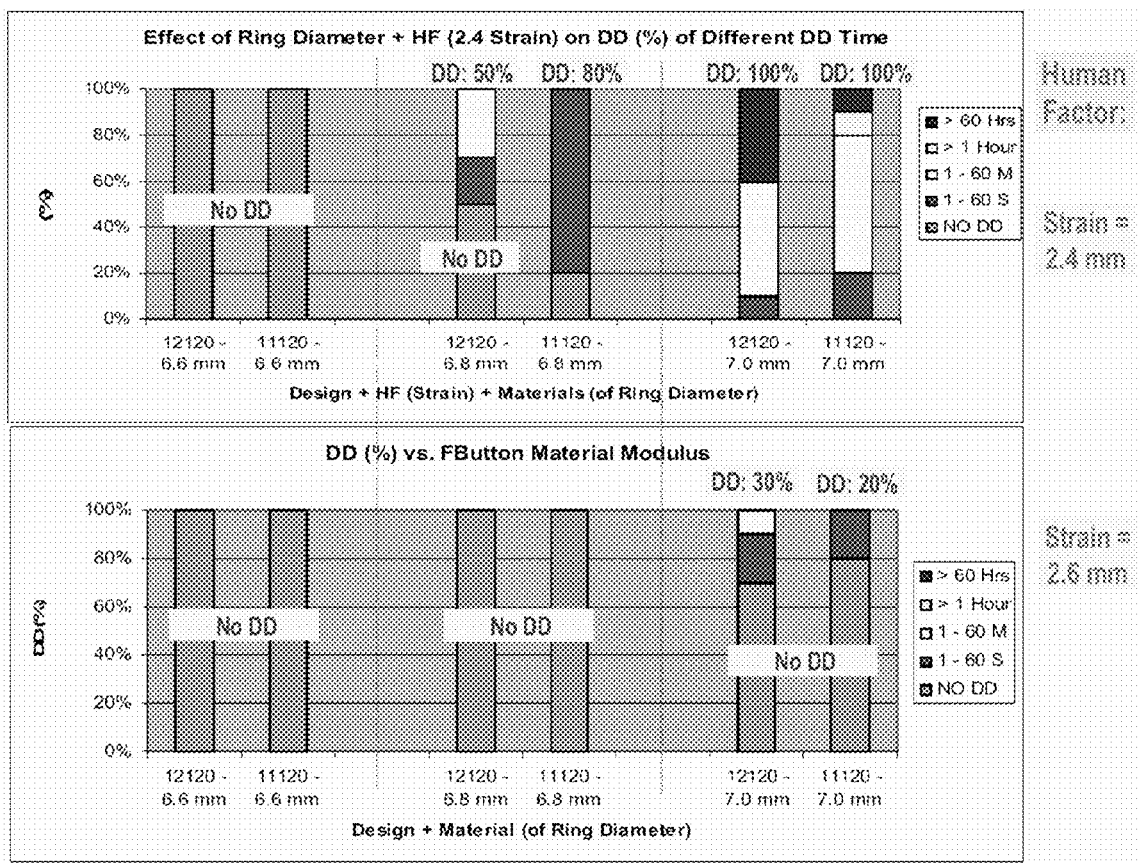
FIG. 31 illustrates a histogram of the percentage of devices that showed different delayed delivery times (y-axis) against different firing button ring inner diameters (x-axis) for the ProtoTherm™ 12120 resin and the WaterShed™ 11120 resin plungers.

FIG. 31 illustrates histograms of the percentage of devices that showed different delayed delivery times (y-axis) against different firing button ring inner diameters (x-axis) for the ProtoTherm™ 12120 resin and the WaterShed™ 11120 resin. The strains used were about 2.4 mm and about 2.6 mm. The histogram shows that the percentage of devices that showed no delayed delivery of an injection was high (100%) for the firing button ring inner diameters of about 6.6 mm and about 6.8 mm (at a strain of 2.6 mm), and lower (70% for the ProtoTherm™ 12120 resin and 80% for the WaterShed™ 11120 resin) for the firing button ring inner diameter of about 7.0 mm (at a strain of 2.6 mm).

In the experimental results shown in FIG. 31, at a sufficient strain of about 2.6 mm, certain exemplary firing buttons formed of the WaterShed™ 11120 resin resulted in reduced delayed delivery of an injection compared to certain exemplary firing buttons formed of the ProtoTherm™ resin at a 7.0 mm firing button ring inner diameter (at a strain of 2.6 mm). The WaterShed™ 11120 resin had a flex modulus ranging from about 2,865 MPa to about 2,880 MPa, and the ProtoTherm™ resin had flex modulus of about 3,520 MPa. In some exemplary embodiments, a decrease in the flex modulus of the material forming the firing button reduces deformation in the firing button ring during firing, and thereby reduces or eliminates delayed delivery of an injection.

In some exemplary embodiments, insufficient strain applied to the firing button contributes to delayed delivery of an injection. In some exemplary embodiments, the percentage of certain exemplary tested devices that showed delayed delivery of an injection increased with decreasing strain on the firing button. In addition, for certain exemplary tested devices that showed delayed delivery of an injection, the delayed delivery times increased with decreasing strain on the firing button. In some exemplary embodiments, a strain of about 2.6 mm was sufficient in pressing down the firing button and did not contribute to delayed delivery of an injection. Thus, in these exemplary embodiments, delayed delivery of an injection tested with a strain of about 2.6 mm did not reflect factors introduced by a patient pressing the firing button.

Based on the experimental results, the percentage of certain exemplary tested devices that showed delayed delivery of an injection increased with increasing firing button ring inner diameters for both firing button materials (the WaterShed™ 11120 resin and the ProtoTherm™ 12120 resin). In some exemplary embodiments, a firing button ring inner diameter of about 6.6 mm resulted in no delayed delivery of an injection in all tested devices, a firing button ring inner diameter of about 6.8 mm resulted in delayed delivery of an injection for a percentage of the tested devices, and a firing button ring inner diameter of about 7.0 mm resulted in delayed delivery of an injection in all of the tested devices. In addition, for certain exemplary devices that showed delayed delivery of an injection, the delayed delivery times increased with increasing firing button ring inner diameters for both firing button materials (the WaterShed™ 11120 resin and the ProtoTherm™ 12120 resin).

(ii) Relationship Between Length of Firing Button Ring and Delayed Delivery of an Injection The relationship between the combination of the firing button material and the length of the firing button ring and delayed delivery times was tested. The different combinations tested included: a WaterShed™ 11120 resin and a firing button ring length of about 6.33 mm, a WaterShed™ 11120 resin and firing button ring length of about 6.53 mm (used as the control), a WaterShed™ 11120 resin and a firing button ring length of about 6.73 mm, a ProtoTherm™ 12120 resin and a firing button ring length of about 6.33 mm, a ProtoTherm™ 12120 resin and a firing button ring length of about 6.53 mm (used as the control), and a ProtoTherm™ 12120 resin and a firing button ring length of about 6.73 mm. Table 1 summarizes the specifications of the exemplary components tested.

In a first set of tests, the firing button of the devices was depressed by a tester to a Zwick strain of about 2.4 mm. This strain was not sufficient to fully depress the firing button and, therefore, the strain in pressing down the firing button was determined to have contributed to the delayed delivery of an injection of the devices.

Figure 32:
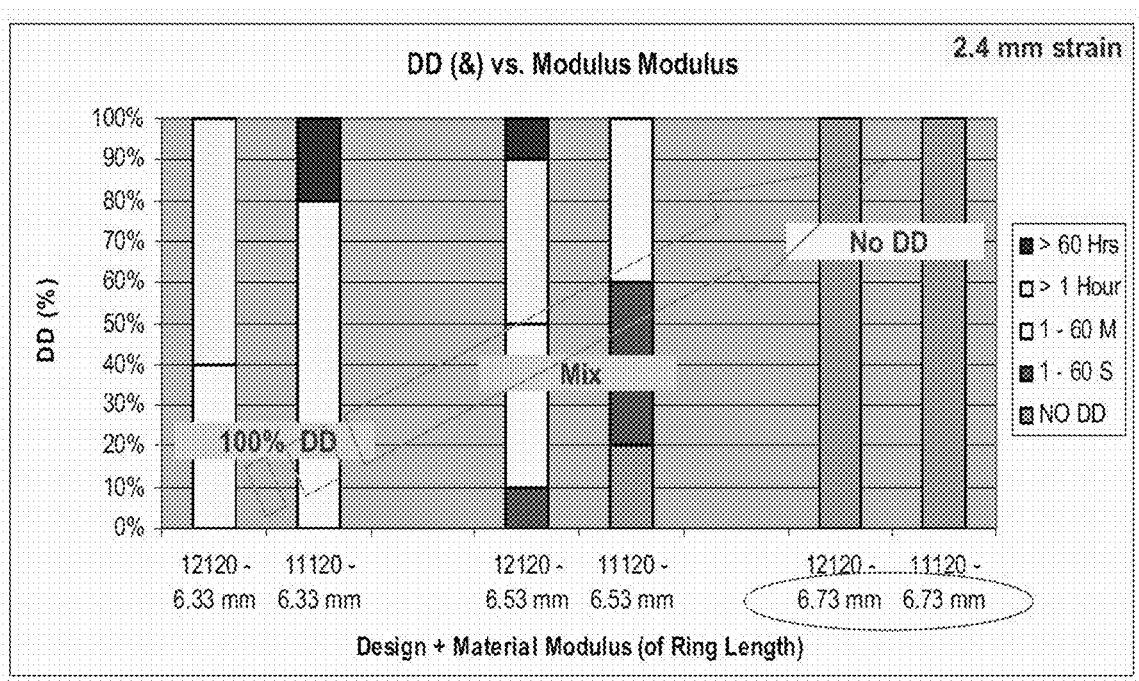
FIG. 32 illustrates a histogram of the percentage of devices that showed different delayed delivery times (y-axis) against different firing button ring lengths (x-axis) for the ProtoTherm™ 12120 resin and the WaterShed™ 11120 resin plungers.

FIG. 32 illustrates a histogram of the percentage of devices that showed different delayed delivery times (y-axis) against different firing button ring lengths (x-axis) for the ProtoTherm™ 12120 resin and the WaterShed™ 11120 resin forming the firing button. The histogram shows that the percentage of devices that showed no delayed delivery of an injection was highest (100%) for the firing button ring length of about 6.73 mm (for both resins), was intermediate (20%) for the WaterShed™ 11120 resin with a firing button ring length of about 6.53 mm, and was lowest (0%) for the firing button ring length of about 6.33 mm (for both resins) and for the ProtoTherm™ 12120 resin with a firing button ring length of about 6.53 mm.

In a second set of tests, the firing button of the devices was depressed by a tester to a Zwick strain of about 2.6 mm. This strain was sufficient to fully depress the firing button and, therefore, the strain in pressing down the firing button was determined to not have contributed to the delayed delivery of an injection of the devices.

Figure 33:
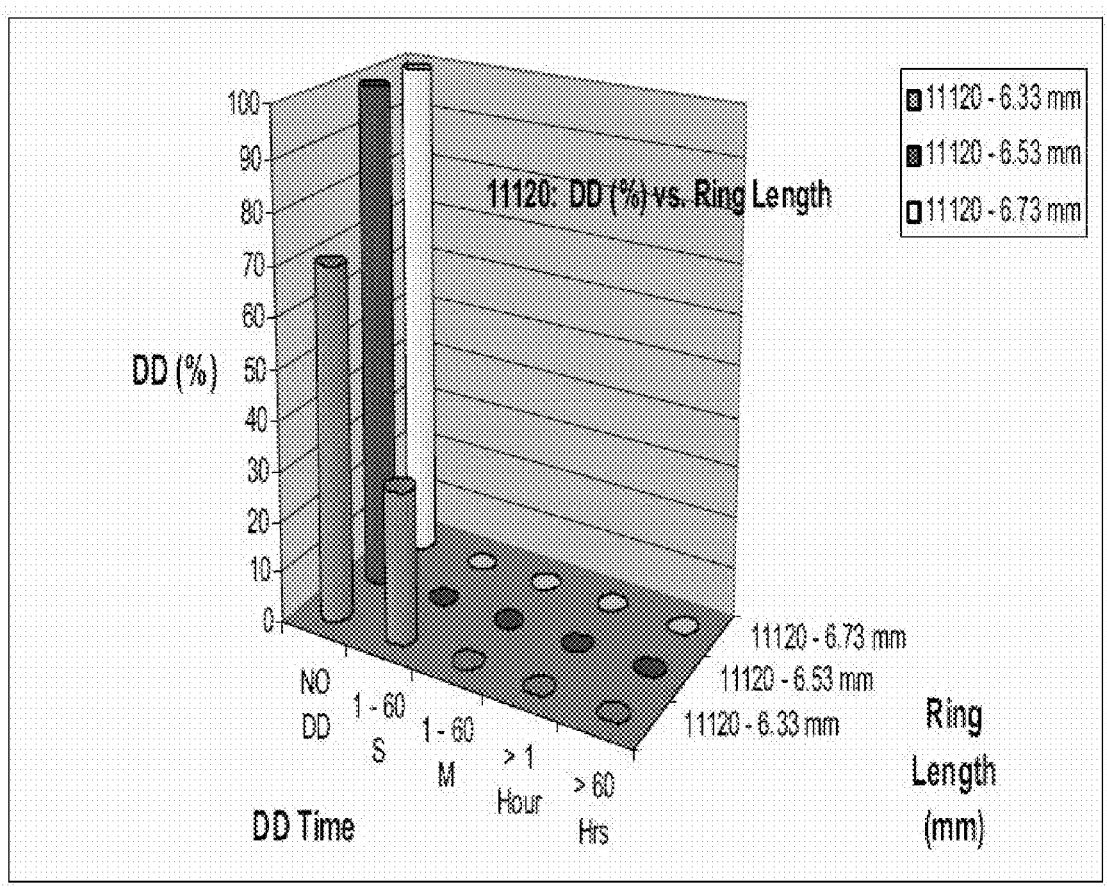
FIG. 33 illustrates a histogram of the percentage of devices that showed delayed delivery (y-axis) against different delayed delivery times and against different firing button ring lengths (x-axis) for the WaterShed™ 11120 resin plunger.

FIG. 33 illustrates a histogram of the percentage of devices that showed delayed delivery (z-axis) against different delayed delivery times and against different firing button ring lengths for the WaterShed™ 11120 resin. The histogram shows that the percentage of devices that showed no delayed delivery of an injection was high (100%) for the firing button ring length of about 6.53 mm and about 6.73 mm, and was lower (70%) for the firing button ring length of about 6.33 mm.

Figure 34:
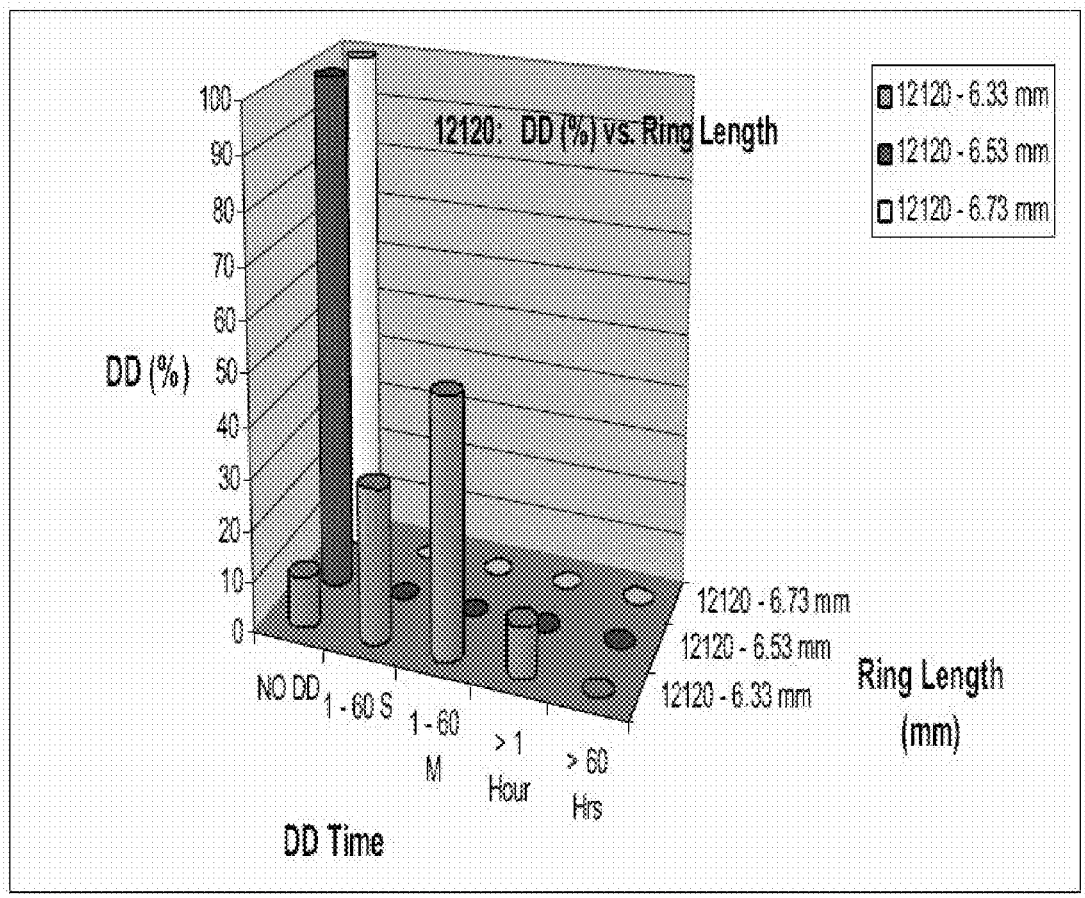
FIG. 34 illustrates a histogram of the percentage of devices that showed delayed delivery (y-axis) against different delayed delivery times and against different firing button ring lengths (x-axis) for the ProtoTherm™ 12120 resin plunger.

FIG. 34 illustrates a histogram of the percentage of devices that showed delayed delivery (z-axis) against different delayed delivery times and against different firing button ring lengths for the ProtoTherm™ 12120 resin. The histogram shows that the percentage of devices that showed no delayed delivery of an injection was high (100%) for the firing button ring lengths of about 6.53 mm and about 6.73 mm, and was lower (10%) for the firing button ring length of about 6.33 mm.

Figure 35:
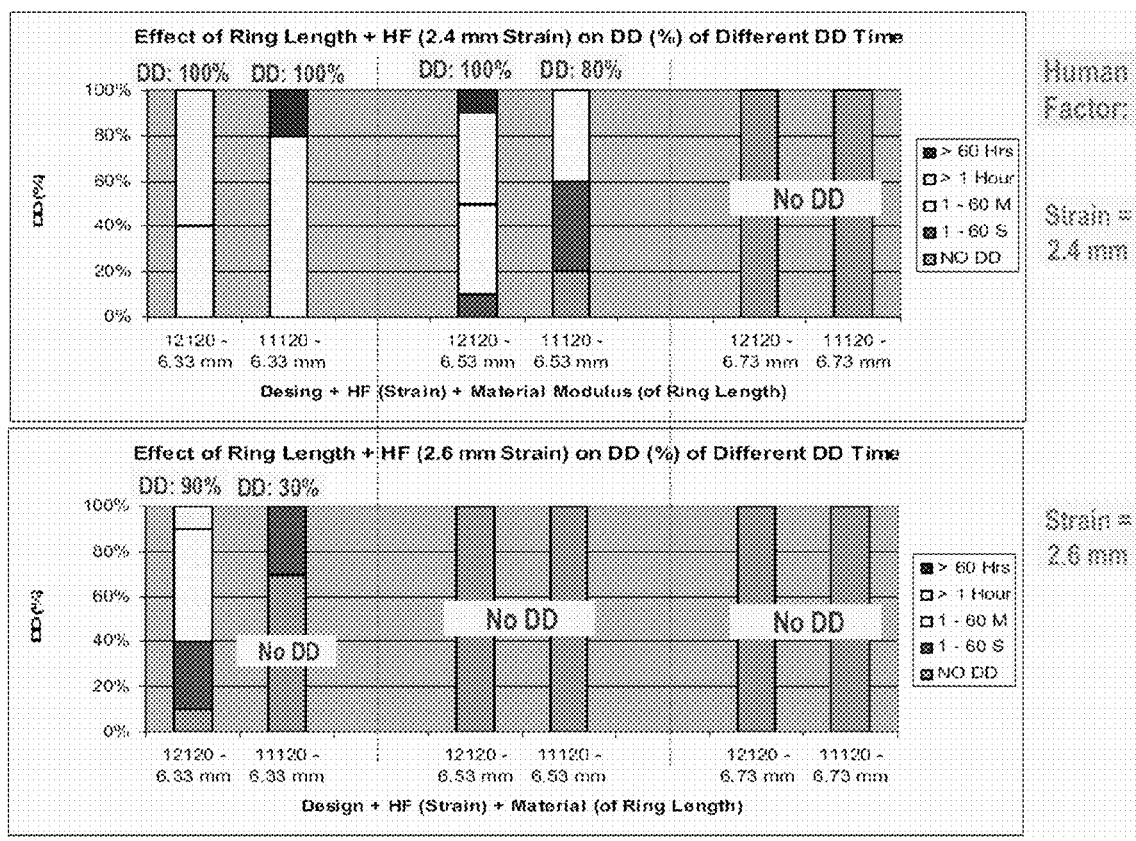
FIG. 35 illustrates a histogram of the percentage of devices that showed different delayed delivery times (y-axis) against different firing button ring lengths (x-axis) for the ProtoTherm™ 12120 resin and the WaterShed™ 11120 resin plungers.

FIG. 35 illustrates histograms of the percentage of devices that showed different delayed delivery times (y-axis) against different firing button ring lengths (x-axis) for the ProtoTherm™ 12120 resin and the WaterShed™ 11120 resin forming the firing button. The strains used were about 2.4 mm and about 2.6 mm. The histogram for the 2.6 mm strain shows that the percentage of devices that showed no delayed delivery of an injection was high (100%) for the firing button ring lengths of about 6.53 mm and about 6.73 mm (for both resins), and lower (10% for the ProtoTherm™ 12120 resin firing button and 70% for the WaterShed™ 11120 resin firing button) for the firing button ring length of about 6.33 mm.

In the experimental results shown in FIG. 35, at a sufficient strain of about 2.6 mm, certain exemplary firing buttons formed of the WaterShed™ 11120 resin resulted in reduced delayed delivery compared to certain exemplary firing buttons formed of the ProtoTherm™ resin at a 6.33 mm firing button ring length. The WaterShed™ 11120 resin had a flex modulus ranging from about 2,865 MPa to about 2,880 MPa, and the ProtoTherm™ resin had flex modulus of about 3,520 MPa. In some exemplary embodiments, a decrease in the flex modulus of the material forming the firing button reduces deformation in the firing button ring during firing, and thereby reduces or eliminates delayed delivery of an injection.

Based on a comparison between FIGS. 32 and 35, insufficient strain on the firing button contributed to delayed delivery of an injection in certain exemplary tested devices. The percentage of certain exemplary tested devices that showed delayed delivery of an injection increased with decreasing strain on the firing button. In addition, for certain exemplary tested devices that showed delayed delivery of an injection, the delayed delivery times increased with decreasing strain on the firing button. In some exemplary embodiments, a strain of about 2.6 mm was sufficient in pressing down the firing button and did not contribute to delayed delivery of an injection. Thus, in some exemplary embodiments, delayed deliveries tested with a strain of about 2.6 mm did not reflect factors introduced by a patient pressing the firing button.

Based on the experimental results, the percentage of certain exemplary tested devices that showed delayed delivery of an injection increased with decreasing firing button ring lengths for both firing button materials (the WaterShed™ 11120 resin and the ProtoTherm™ 12120 resin). More specifically, for some exemplary tested embodiments, a firing button ring length of about 6.73 mm resulted in no delayed delivery of an injection in all tested devices, a firing button ring length of about 6.53 mm resulted in delayed delivery of an injection for a percentage of the tested devices, and a firing button ring length of about 6.33 mm resulted in delayed delivery of an injection in all of the tested devices. In addition, for certain exemplary tested devices that showed delayed delivery of an injection, the delayed delivery times increased with decreasing firing button ring lengths for both firing button materials (the WaterShed™ 11120 resin and the ProtoTherm™ 12120 resin).

(iii) Relationship Between Combination of Firing Button Ring Inner Diameter and Firing Button Ring Length and Delayed Delivery of an Injection The relationship between the combination of the inner diameter of the firing button ring and the length of the firing button ring and delayed delivery times was tested.

The firing button of the devices was depressed by a tester to a Zwick strain of about 2.4 mm. This strain was not sufficient to fully depress the firing button in certain exemplary tested devices and, therefore, the strain in pressing down the firing button was determined to have contributed to the delayed delivery of an injection of the devices.

Figure 36:
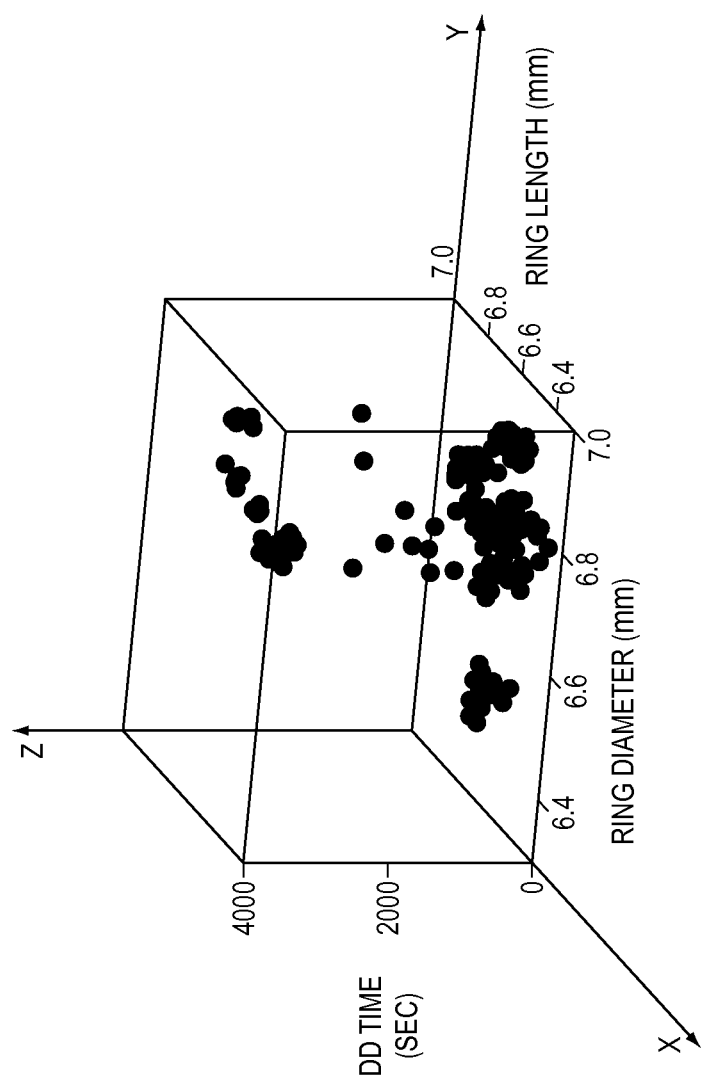
FIG. 36 illustrates a 3D scatterplot of delayed delivery times in seconds (z-axis) against different firing button ring inner diameters in mm (x-axis) and firing button ring lengths in mm (y-axis).

FIG. 36 illustrates a 3D scatterplot of delayed delivery times in seconds (z-axis) against different firing button ring inner diameters in mm (x-axis) and firing button ring lengths in mm (y-axis).

Figure 37:
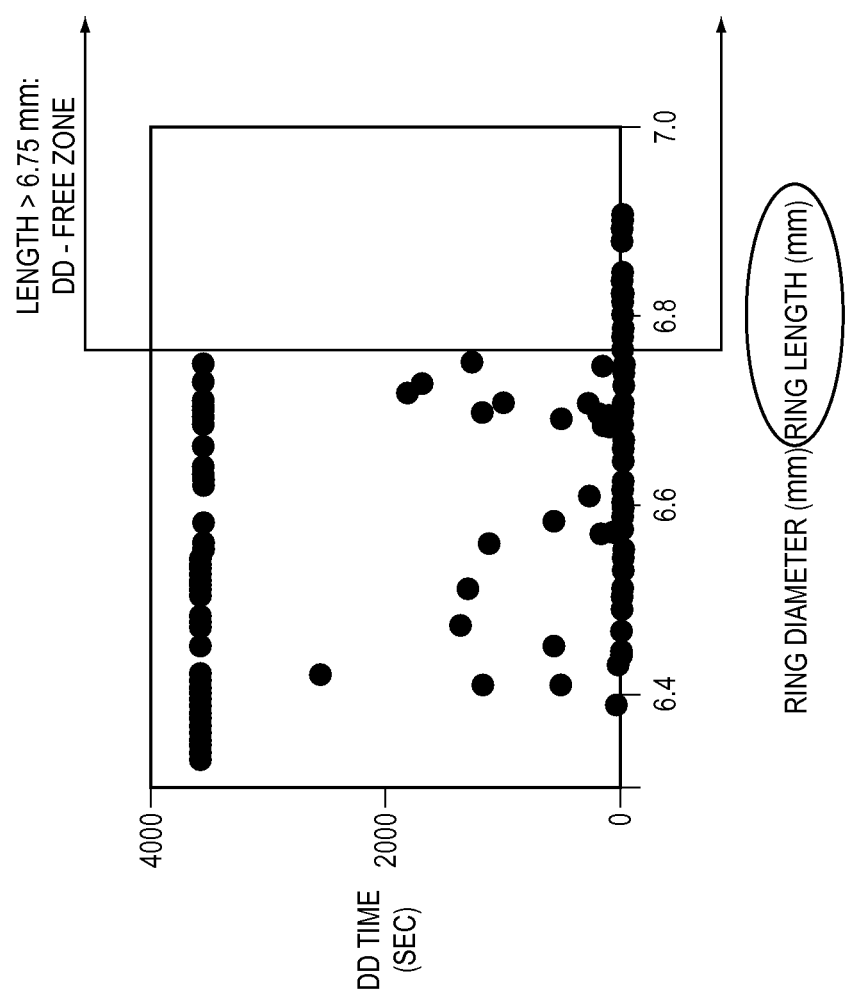
FIG. 37 illustrates a 2D section of FIG. 36 viewed from the x-z plane along the y-axis, which shows that the delayed delivery times decrease with increasing firing button ring lengths.

FIG. 37 illustrates a 2D section of FIG. 36 viewed from the x-z plane along the y-axis, which shows that the delayed delivery times decrease with increasing firing button ring lengths. The delayed delivery of an injection was eliminated at ring lengths at about 6.75 mm and above about 6.75 mm.

Figure 38:
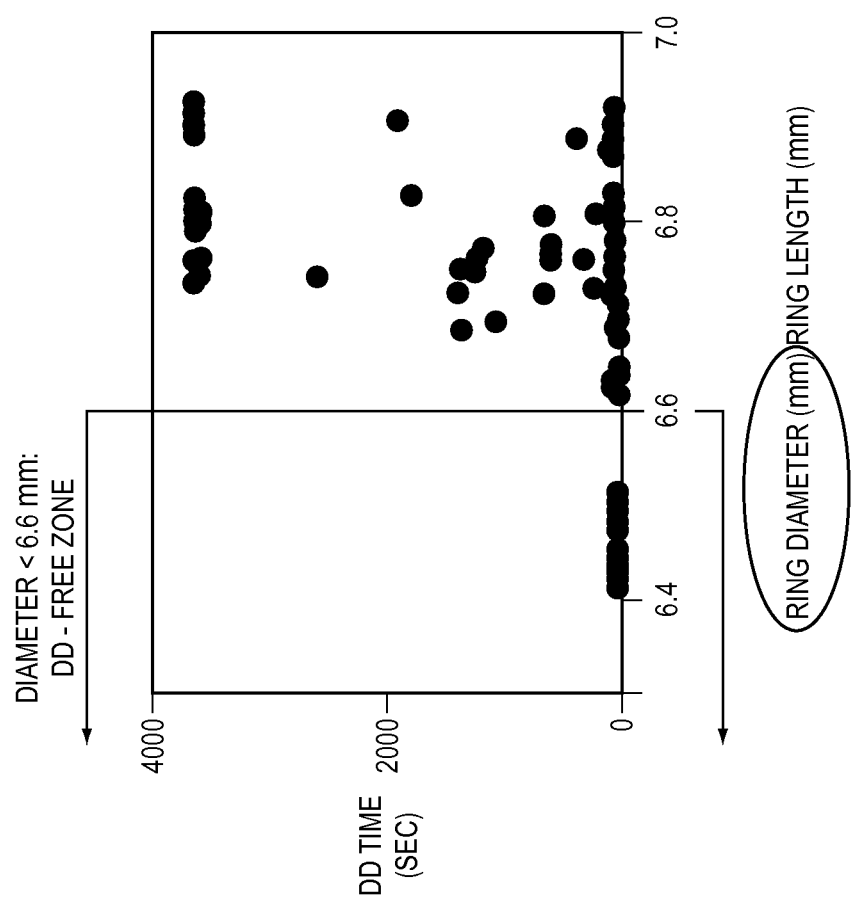
FIG. 38 illustrates a 2D section of FIG. 36 viewed from the y-z plane along the x-axis, which shows that the delayed delivery times decrease with decreasing firing button ring inner diameters.

FIG. 38 illustrates a 2D section of FIG. 36 viewed from the y-z plane along the x-axis, which shows that the delayed delivery times decrease with decreasing firing button ring inner diameters. The delayed delivery of an injection was eliminated at firing button ring inner diameters at about 6.60 mm and below about 6.60 mm.

(iv) Summary of Results

Results for the combination of the RPT firing buttons and the commercial plungers having an ICS angle of about 38 degrees indicate that, for a sufficient strain, delayed delivery of an injection was eliminated for firing button ring inner diameters at or below about 6.60 mm and for firing button ring lengths at or above about 6.75 mm.

B. Testing of Exemplary Rapid Prototype Technology (RPT) Firing Buttons and Exemplary Single Impression Mold (SIM) Plungers Exemplary automatic injection devices were produced by assembling exemplary Rapid Prototype Technology (RPT) firing buttons with exemplary Single Impression Mold (SIM) plungers. The exemplary RPT firing buttons were formed of one or more thermosetting materials, and the exemplary SIM plungers were formed of one or more thermoplastic materials. The exemplary plungers each had an initial contact surface (ICS) angle of about 48 degrees. The assembled automatic injection devices were tested to quantitatively determine the impact of different component features on the delayed delivery of an injection, if any, of the devices.

The firing button of the devices was depressed by a tester to a Zwick strain ranging from about 3.2 mm to about 3.4 mm. This strain was sufficient to fully depress the firing button in certain exemplary tested devices and, therefore, the strain in pressing down the firing button was determined to not have contributed to the delayed delivery of an injection of the devices.

The firing button ring lengths were varied from about 6.30 mm to about 7.40 mm. The firing button ring inner diameters were varied from about 6.40 mm to about 7.10 mm.

(i) Testing of Mid Point Fixed (MPF) Plungers

Figure 39:
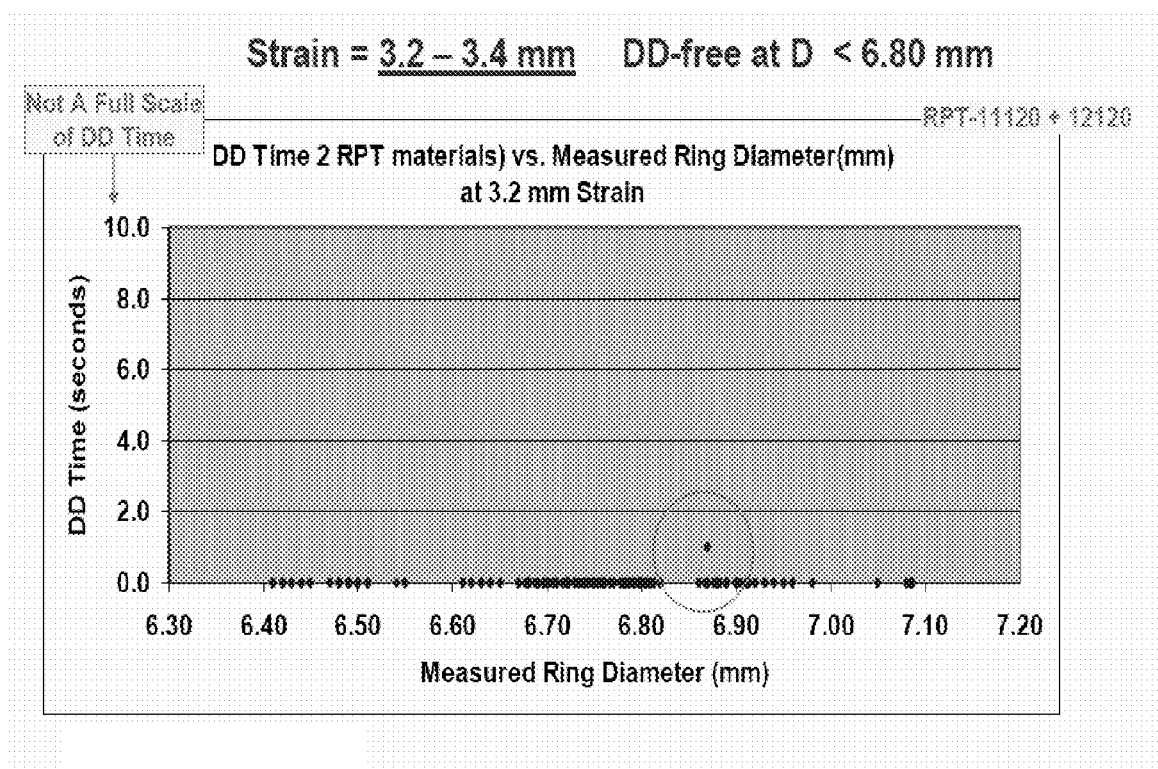
FIG. 39 illustrates a scatterplot of delayed delivery times in seconds (y-axis) against firing button ring inner diameters in mm (x-axis). A delayed delivery of about 1 second occurred at about 6.86 mm inner diameter.

FIG. 39 illustrates a scatterplot of delayed delivery times in seconds (y-axis) against firing button ring inner diameters in mm (x-axis) for strains of about 3.2 mm to about 3.4 mm. The delayed delivery times were about 0 seconds, i.e., there was no delayed delivery of an injection, for all but one of the tested firing buttons. The delayed delivery time was about 1 second for one of the firing buttons having an inner diameter of about 6.86 mm.

Figure 40:
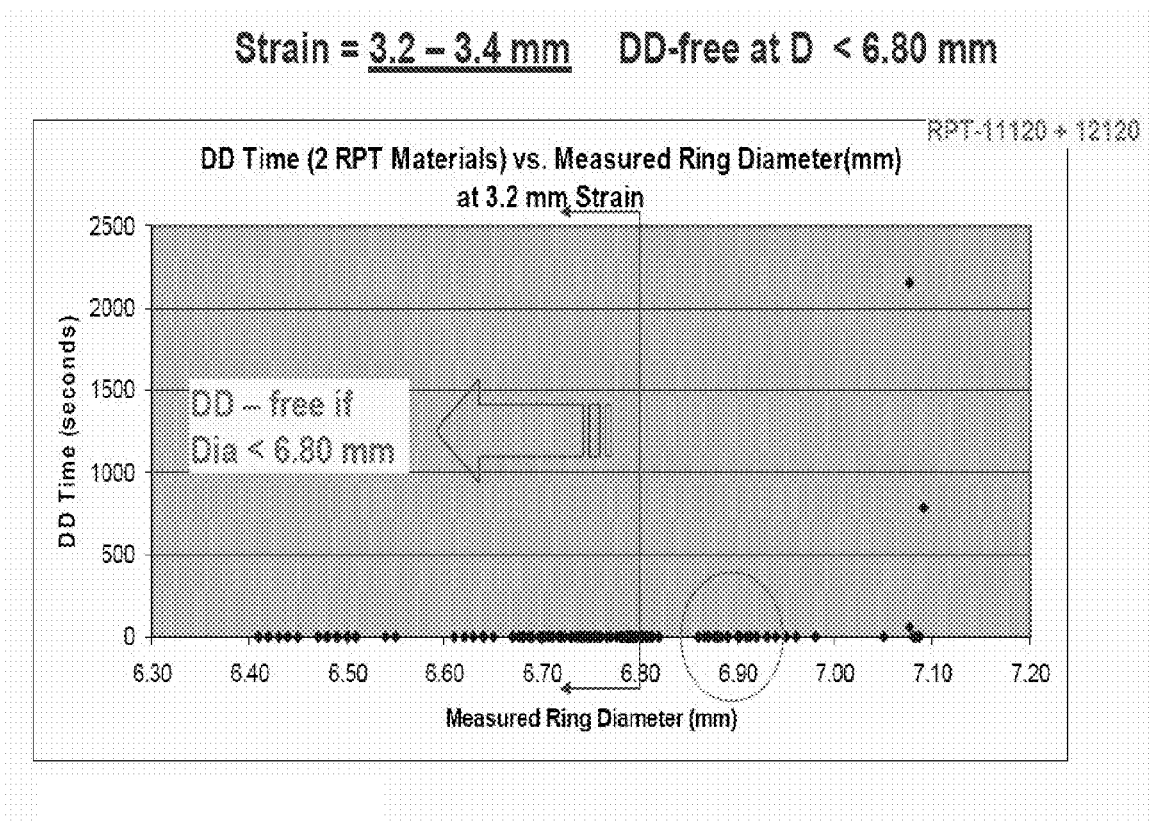
FIG. 40 illustrates a scatterplot of delayed delivery times in seconds (y-axis) against firing button ring inner diameters in mm (x-axis).

FIG. 40 illustrates a scatterplot of delayed delivery times in seconds (y-axis) against firing button ring inner diameters in mm (x-axis) for strains of about 3.2 mm to about 3.4 mm. The delayed delivery times were about 0 seconds, i.e., there was no delayed delivery of an injection, for most of the tested firing buttons. Delayed delivery of an injection was exhibited by about three firing buttons, all having firing button inner diameters of about 7.1 mm.

Based on the experimental results, the firing button inner ring diameter in some exemplary embodiments may be maintained lower than about 6.8 mm at strains of between about 3.2 mm and about 3.4 mm to make exemplary automatic injection devices free of delayed delivery of an injection.

Figure 41:
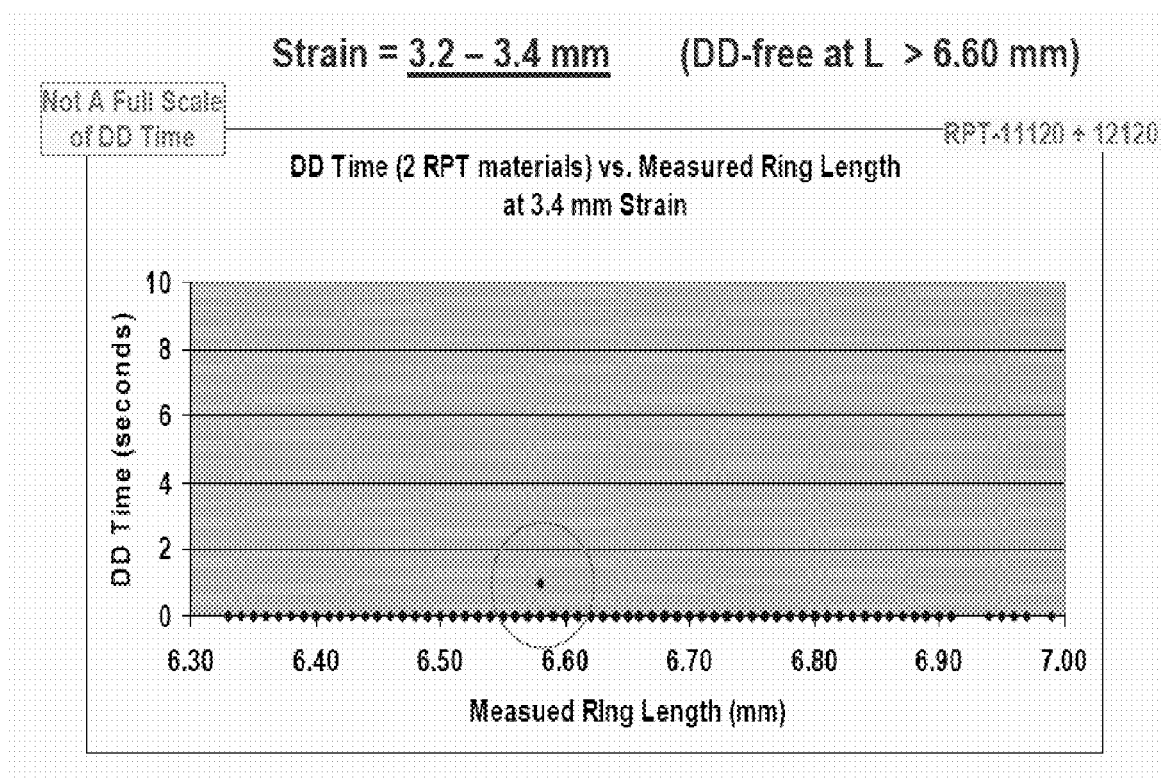
FIG. 41 illustrates a scatterplot of delayed delivery times in seconds (y-axis) against firing button ring lengths in mm (x-axis).

FIG. 41 illustrates a scatterplot of delayed delivery times in seconds (y-axis) against firing button ring lengths in mm (x-axis) for strains of about 3.2 mm to about 3.4 mm. The delayed delivery times were about 0 seconds, i.e., there was no delayed delivery of an injection, for all but one of the tested firing buttons. The delayed delivery time was about 1 second for one of the firing buttons having an inner diameter of about 6.58 mm.

Figure 42:
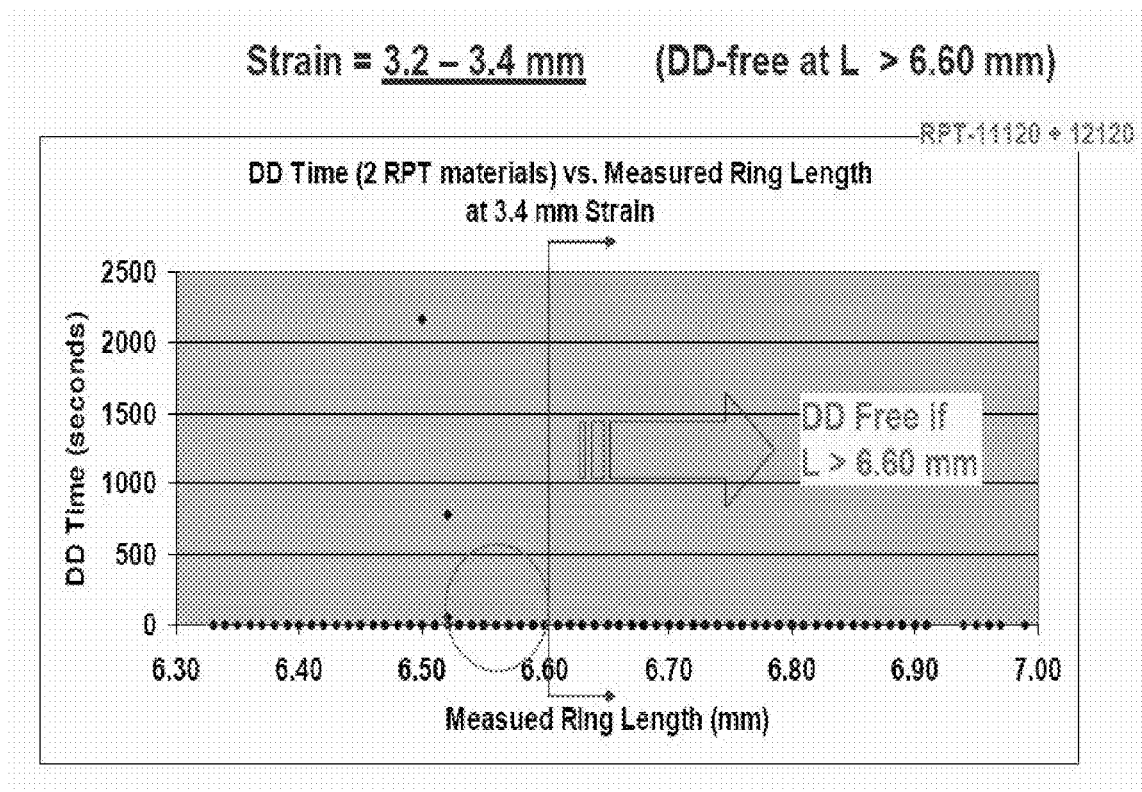
FIG. 42 illustrates a scatterplot of delayed delivery times in seconds (y-axis) against firing button ring lengths in mm (x-axis).

FIG. 42 illustrates a scatterplot of delayed delivery times in seconds (y-axis) against firing button ring lengths in mm (x-axis) for strains of about 3.2 mm to about 3.4 mm. The delayed delivery times were about 0 seconds, i.e., there was no delayed delivery of an injection, for most of the tested firing buttons. Delayed delivery of an injection was exhibited by about three firing buttons, all having firing button lengths of below about 6.55 mm.

Based on the experimental results, the firing button length in some exemplary embodiments is maintained above about 6.60 mm at strains of between about 3.2 mm and about 3.4 mm to make exemplary automatic injection devices free of delayed delivery of an injection.

TABLE 2

Summary of experimental results showing firing button ring lengths and inner diameters that eliminate delayed delivery of an injection in automatic injection devices

| Plunger (SIM) | DD-Free Dimension (mm) | Firing Button Ring Inner Diameter (mm) | Firing Button Ring Length (mm) |
| --- | --- | --- | --- |
| ICS Angle = 38° | 2.4 mm strain | <6.60 mm | >6.75 mm |
| ICS Angle = 38° | 2.6 mm strain | <6.80 mm | >6.60 mm |
| MPF ICS Angle = 48° | 3.2-3.4 mm strain | <6.80 mm | >6.60 mm |
| TPF ICS Angle = 38° | 3.2-3.4 mm strain | | |
| Control | Spec/Study Range | 6.75-6.85 | 6.33-6.73 |

(ii) Testing of Top Point Fixed (TPF) Plungers

Similar results were obtained by testing TPF plungers.

(iii) Summary of Results

Results for the combination of the RPT firing button and the SIM plunger (MPF or TPF) having an ICS angle of about 48 degrees indicate that, for a strain ranging from about 3.2 mm to about 3.4 mm, delayed delivery of an injection was eliminated for firing button ring inner diameters below about 6.80 mm and for firing button ring lengths above about 6.60 mm.

C. Summary of Experimental Results for Rapid Prototype Technology (RPT) Firing Buttons For exemplary Rapid Prototype Technology (RPT) firing buttons, for both commercial and Single Impression Mold (SIM) plungers, delayed delivery of an injection was eliminated at firing button ring inner diameters below about 6.60 mm and for firing button ring lengths above about 6.75 mm.

Exemplary embodiments may configure exemplary firing button ring inner diameters to be below about 6.60 mm and firing button ring lengths to be above about 6.75 mm to reduce or eliminate delayed delivery of an injection in the assembled automatic injection devices.

Figure 43:
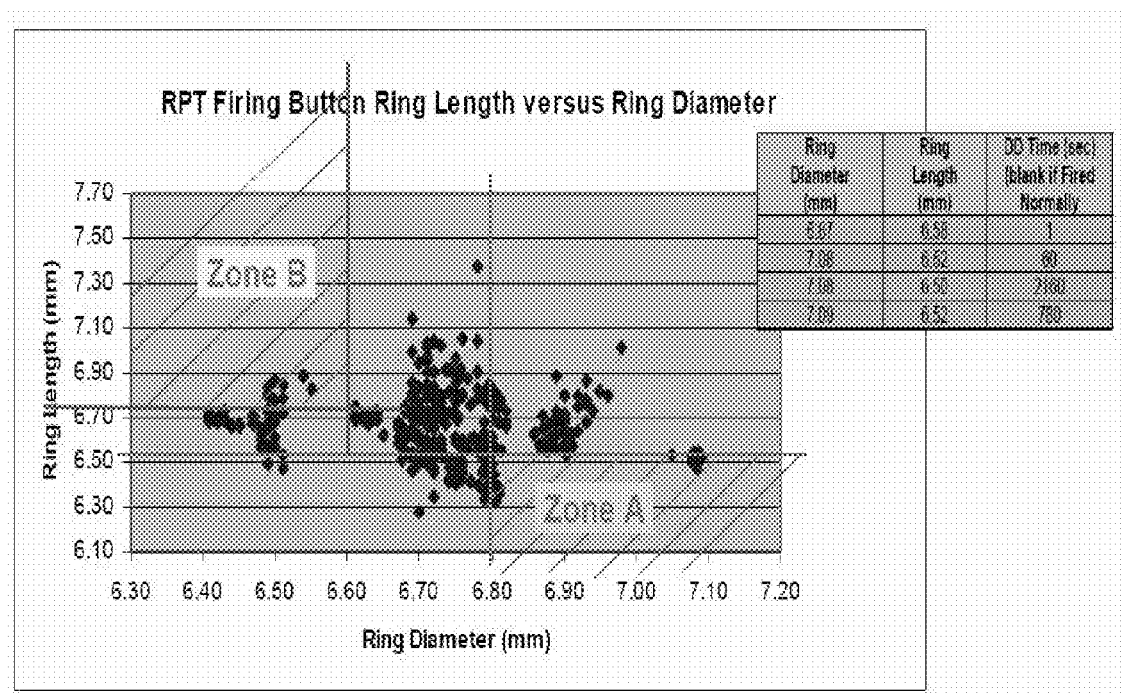
FIG. 43 illustrates a scatterplot of firing button ring lengths in mm (y-axis) against firing button ring inner diameters in mm (x-axis).

FIG. 43 illustrates a scatterplot of firing button ring lengths in mm (y-axis) against firing button ring inner diameters in mm (x-axis). Zone A in FIG. 43 indicates that there is some risk of delayed delivery of an injection for lower ring lengths (below about 6.50 mm) and for higher ring inner diameters (above about 6.80 mm). Exemplary embodiments may avoid selection of ring length and inner diameter combinations in Zone A in order to reduce or eliminate delayed delivery of an injection in the assembled automatic injection devices. Zone B in FIG. 43 indicates that there is very low risk of delayed delivery of an injection for higher ring lengths (above about 6.75 mm) and for lower ring inner diameters (below about 6.60 mm). Exemplary embodiments may select ring length and inner diameter combinations in Zone B in order to reduce or eliminate delayed delivery of an injection in the assembled automatic injection devices.

D. Testing of Exemplary Single Impression Mold (SIM) Firing Buttons and Exemplary Commercial Plungers Having an Exemplary Initial Contact Surface (ICS) Angle of about 38 Degrees Exemplary automatic injection devices were produced by assembling exemplary Single Impression Mold (SIM) firing buttons and commercial plungers. The exemplary firing buttons were formed of one or more thermoplastic materials, e.g., polypropylene. The exemplary plungers each had an initial contact surface (ICS) angle of about 38 degrees. The assembled automatic injection devices were tested to quantitatively determine the impact of different component features on the delayed delivery of an injection, if any, of the devices.

Figure 44:
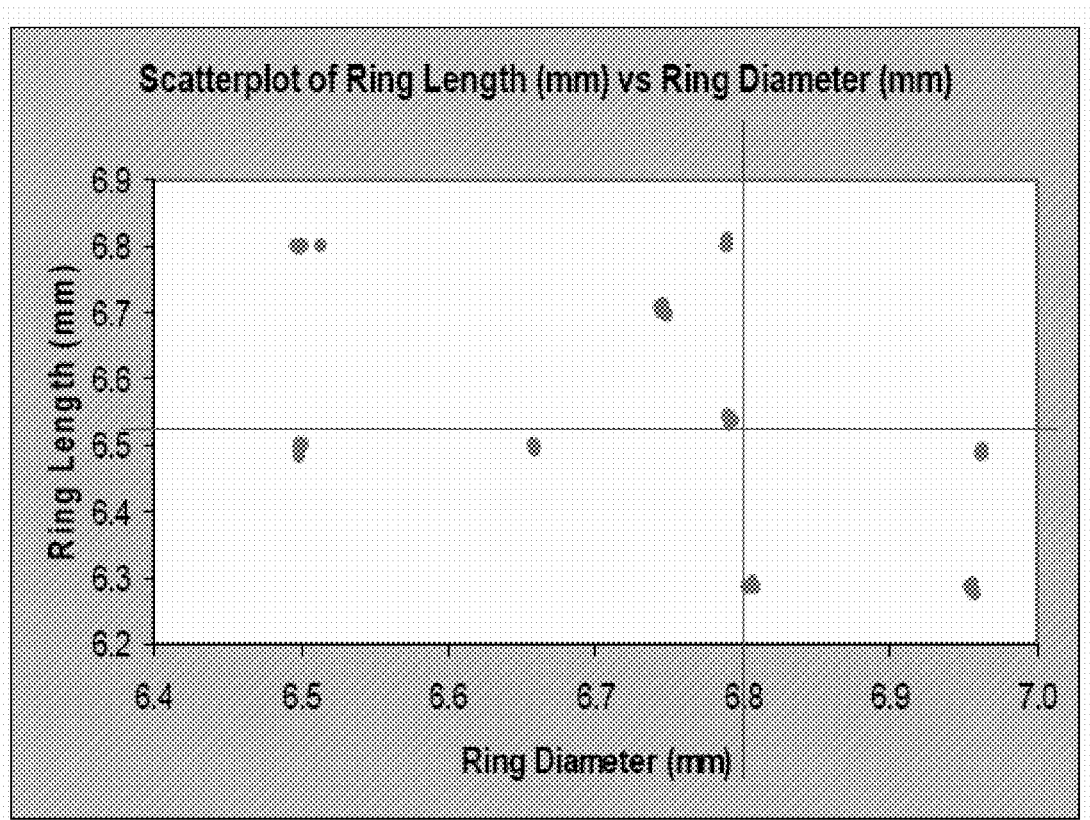
FIG. 44 illustrates a scatterplot of tested devices with different firing button ring lengths in mm (y-axis) and firing button ring inner diameters in mm (x-axis).

FIG. 44 illustrates a scatterplot of tested devices with different firing button ring lengths in mm (y-axis) and firing button ring inner diameters in mm (x-axis).

The strain applied to the firing button was set to about 1.45 mm, 1.55 mm and about 1.65 mm to determine the effect of the varying the strain on the percentage of devices that show delayed delivery of an injection.

Figure 45:
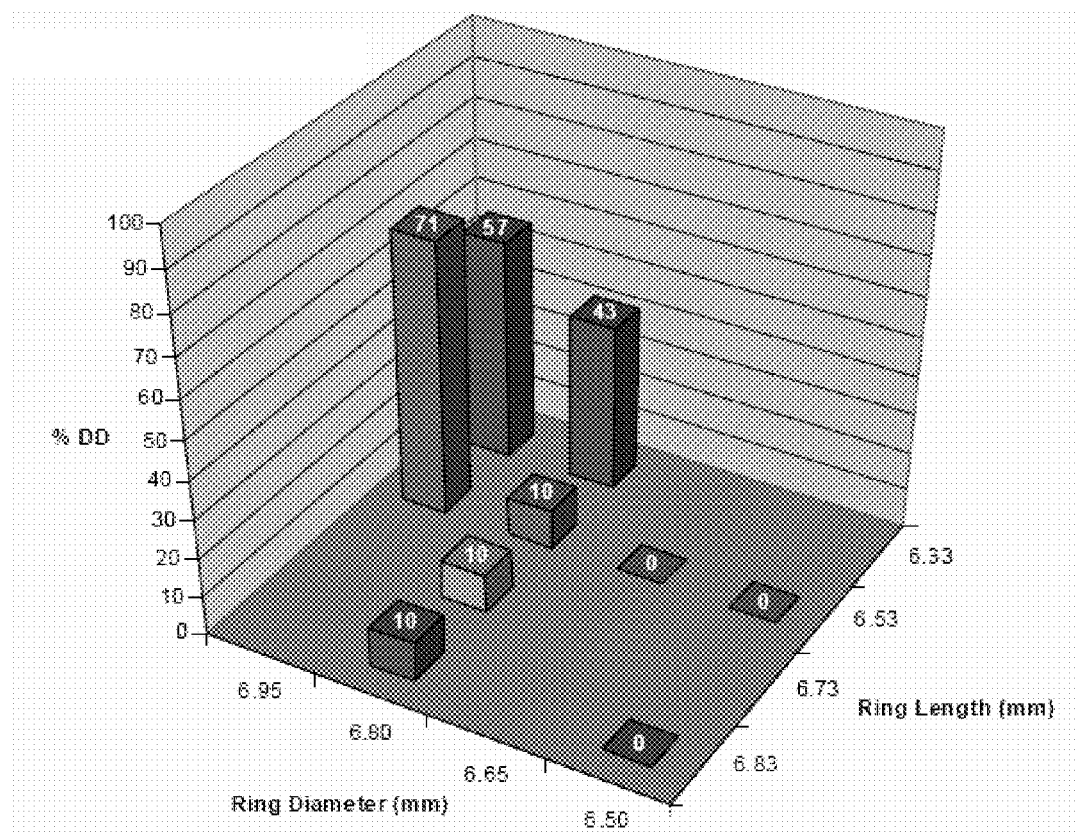
FIG. 45 illustrates a histogram of the percentage of devices that showed delayed delivery (z-axis) for different firing button ring inner diameters in mm (x-axis) and firing button ring lengths in mm (y-axis) for an actual strain of about 1.45 mm.

FIG. 45 illustrates a histogram of the percentage of devices that showed delayed delivery (z-axis) for different firing button ring inner diameters in mm (x-axis) and firing button ring lengths in mm (y-axis) for an actual strain of about 1.45 mm. The actual strain of about 1.45 mm simulates a patient who does not or cannot push the firing button deep enough to activate firing of the device. The percentage of devices that showed delayed delivery of an injection ranged between about 0% and about 70% depending on the firing button ring length and inner diameter.

Figure 46:
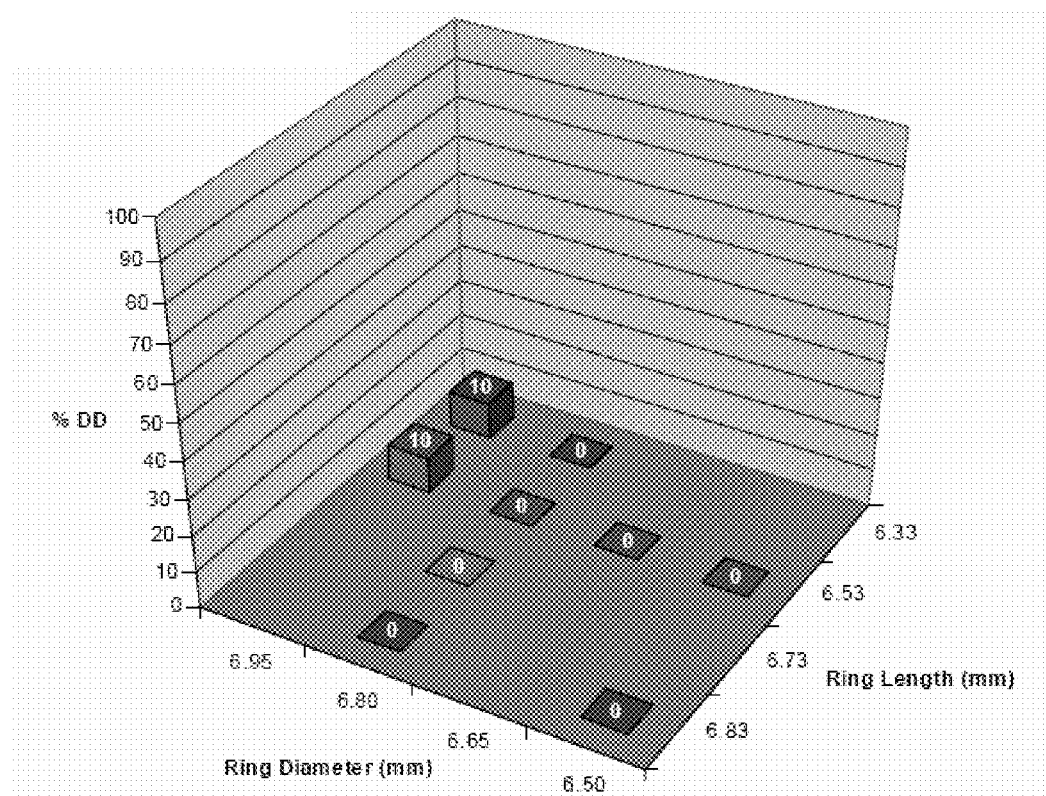
FIG. 46 illustrates a histogram of the percentage of devices that showed delayed delivery (z-axis) for different firing button ring inner diameters in mm (x-axis) and firing button ring lengths in mm (y-axis) for an actual strain of about 1.55 mm.

FIG. 46 illustrates a histogram of the percentage of devices that showed delayed delivery (z-axis) for different firing button ring inner diameters in mm (x-axis) and firing button ring lengths in mm (y-axis) for an actual strain of about 1.55 mm. The actual strain of about 1.55 mm simulates a patient who pushes down the firing button to a greater extent than in the case of an actual strain of about 1.45 mm. The percentage of devices that showed delayed delivery of an injection was reduced and ranged between about 0% and about 10% depending on the firing button ring length and inner diameter.

Figure 47:
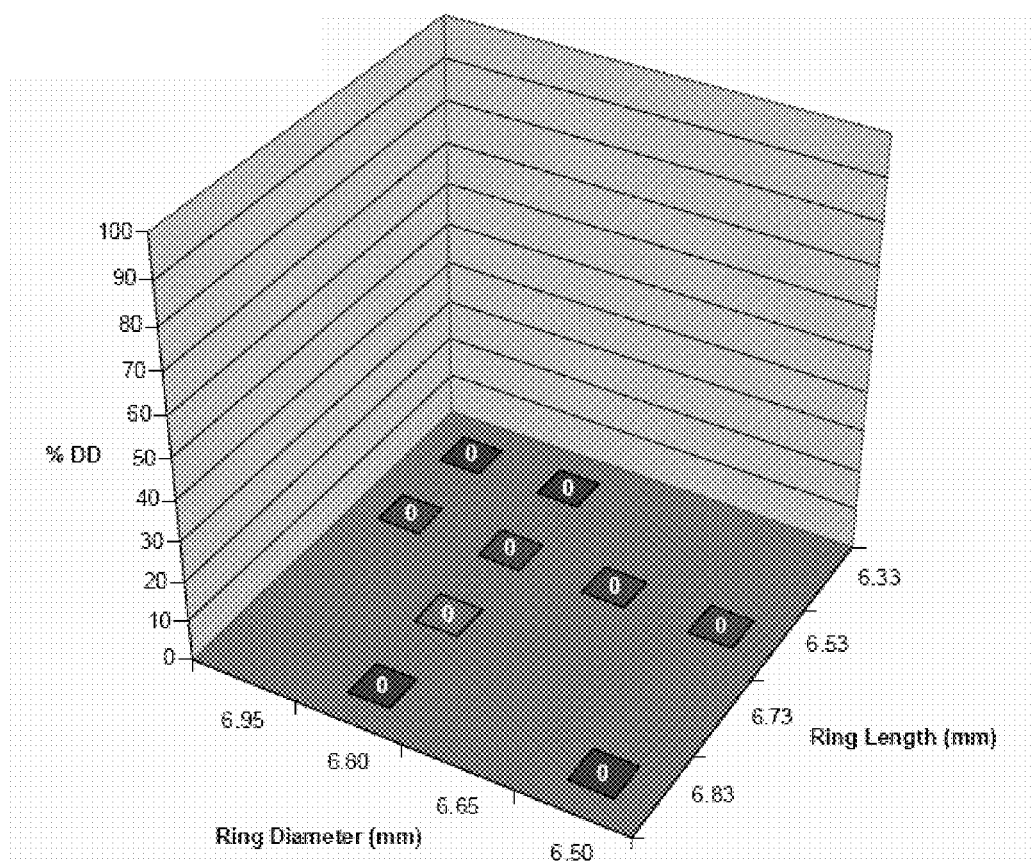
FIG. 47 illustrates a histogram of the percentage of devices that showed delayed delivery (z-axis) for different firing button ring inner diameters in mm (x-axis) and firing button ring lengths in mm (y-axis) for an actual strain of about 1.65 mm.

FIG. 47 illustrates a histogram of the percentage of devices that showed delayed delivery (z-axis) for different firing button ring inner diameters in mm (x-axis) and firing button ring lengths in mm (y-axis) for an actual strain of about 1.65 mm. The actual strain of about 1.65 mm simulates a patient who pushes down the firing button to a greater extent than in the case of an actual strain of about 1.55 mm. The percentage of devices that showed delayed delivery of an injection was reduced and was 0% for all firing button ring lengths and inner diameters.

Based on the experimental results, in some exemplary embodiments, for an actual strain of about 1.65 mm, a firing button ring inner diameter of below about 6.95 mm and a firing button ring length of above about 6.33 mm resulted in automatic injection devices that were free of delayed delivery of an injection. In some exemplary embodiments, for an actual strain of about 1.55 mm, a firing button ring inner diameter of below about 6.80 mm and a firing button ring length of above about 6.53 mm resulted in automatic injection devices that were free of delayed delivery of an injection. In some exemplary embodiments, for an actual strain of about 1.45 mm, a firing button ring inner diameter of below about 6.65 mm and a firing button ring length of above about 6.53 mm resulted in automatic injection devices that were free of delayed delivery of an injection. Based on the actual strains applied, exemplary embodiments may configure the firing button ring lengths and inner diameters based on the experimental results to reduce or eliminate delayed delivery of an injection.

Figure 48:
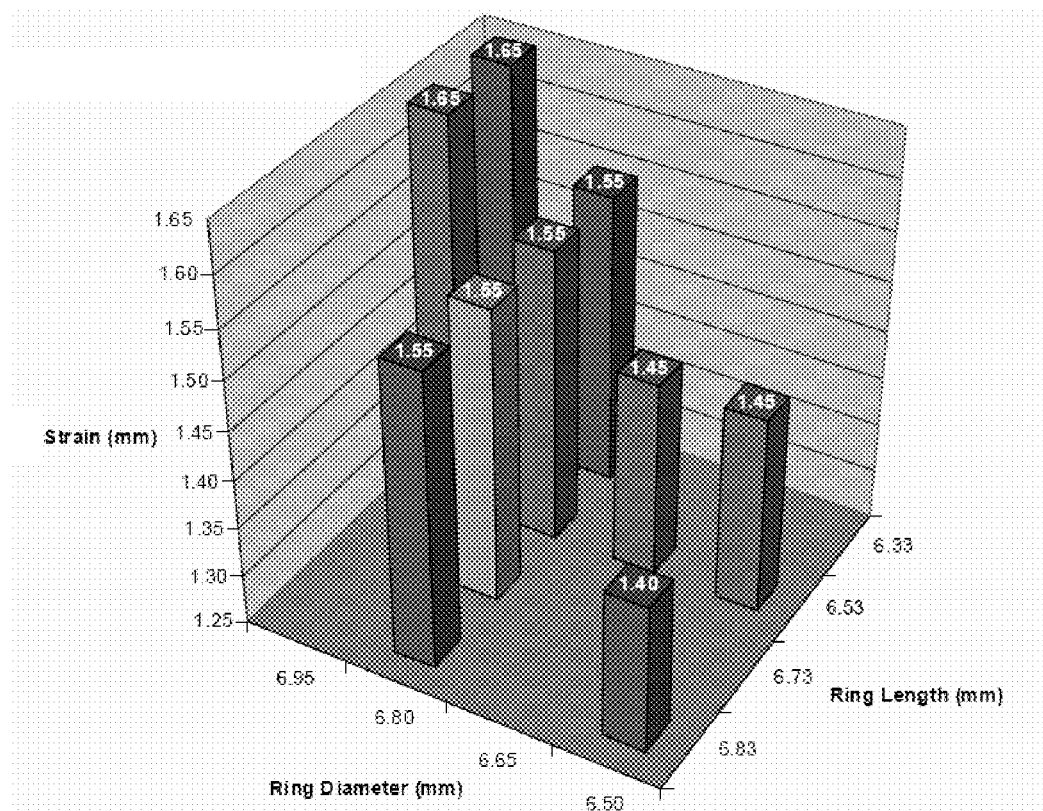
FIG. 48 illustrates a histogram of the threshold strain in mm (z-axis) for different firing button ring inner diameters in mm (x-axis) and firing button ring lengths in mm (y-axis) for SIM firing buttons.

FIG. 48 illustrates a histogram of the threshold strain in mm (z-axis) for different firing button ring inner diameters in mm (x-axis) and firing button ring lengths in mm (y-axis) for the firing buttons. The term "threshold strain" refers to the minimum actual strain applied in pressing down a firing button during firing of an automatic injection device at which no delayed delivery of an injection is observed. Based on the experimental results, in some exemplary embodiments, firing button ring lengths and inner diameters required for elimination of delayed delivery of an injection was affected by the actual strain applied by patients. Patients in high strain groups (i.e., patients who can push the firing button down over a sufficient distance) were able to eliminate delayed delivery of an injection at larger ring inner diameters and shorter ring lengths. However, for patients in lower strain groups (i.e., patients who cannot or do not push the firing button down over a sufficient distance) required smaller ring inner diameters and longer ring lengths for elimination of delayed delivery of an injection.

In an exemplary firing button, the firing button ring length may be set between about 6.73 and about 6.83 mm and the firing button ring inner diameter may be set between about 6.50 mm and about 6.65 mm in order to eliminate delayed delivery of an injection. As illustrated in FIG. 48, the exemplary selected ranges of inner diameters and lengths set the threshold strain at about 1.40 mm. One of ordinary skill in the art will appreciate from at least FIG. 48 that other exemplary ranges of firing button ring inner diameters and lengths may be selected, which may change the associated threshold strain. One of ordinary skill in the art will appreciate that the threshold strain may be configured by configuring the associated firing button ring inner diameter and length.

E. Relationship Between Conical Surface Angle (CSA) of Firing Body and Delayed Delivery of an Injection
(i) Testing of Commercial Firing Bodies Exemplary automatic injection devices were produced by assembling exemplary commercial firing bodies and firing buttons with exemplary plungers. The assembled automatic injection devices were tested to quantitatively determine the impact of the conical surface angle (CSA) of the commercial firing bodies on the delayed delivery of an injection, if any, of the devices.

The CSA value of exemplary firing bodies was varied and the resulting delayed delivery of an injection was measured.

TABLE 3

Summary of different CSA values used to test the effect of the CSA on delayed delivery of an injection

| Commercial Design Specification | Experimental Conical Surface Angle for Commercial Firing Bodies | | | |
|---|---|---|---|---|
| 18° ± 2° | 0° | 6° | 12° | 18° |

Figure 49:
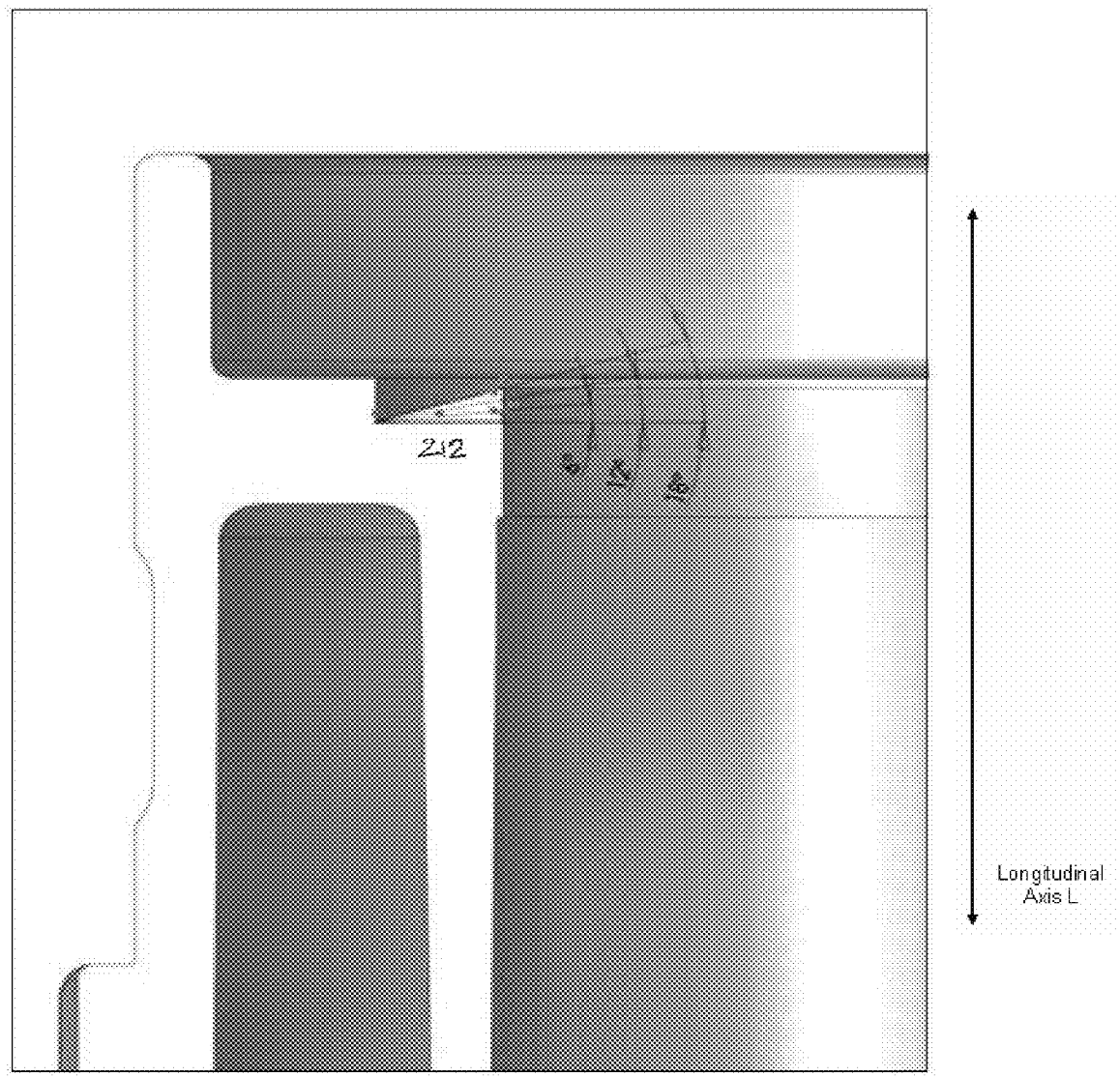
FIG. 49 illustrates a sectional view taken through a firing body along the longitudinal axis, in which exemplary conical surface angles of about 6, about 12 and about 18 degrees are shown.

FIG. 49 illustrates a sectional view taken through a firing body along the longitudinal axis, in which exemplary CSA values of the conical surface 212 of about 6, about 12 and about 18 degrees are shown.

Three exemplary plunger configurations were used in conjunction with the exemplary firing bodies: a commercial plunger with an initial contact surface (ICS) angle of about 38 degrees, a mid point fixed (MPF) single impression mold (SIM) plunger with an ICS angle of about 48 degrees, and a top point fixed (TPF) SIM plunger with an ICS angle of about 48 degrees.

Figures 50A, 50B, 50C:
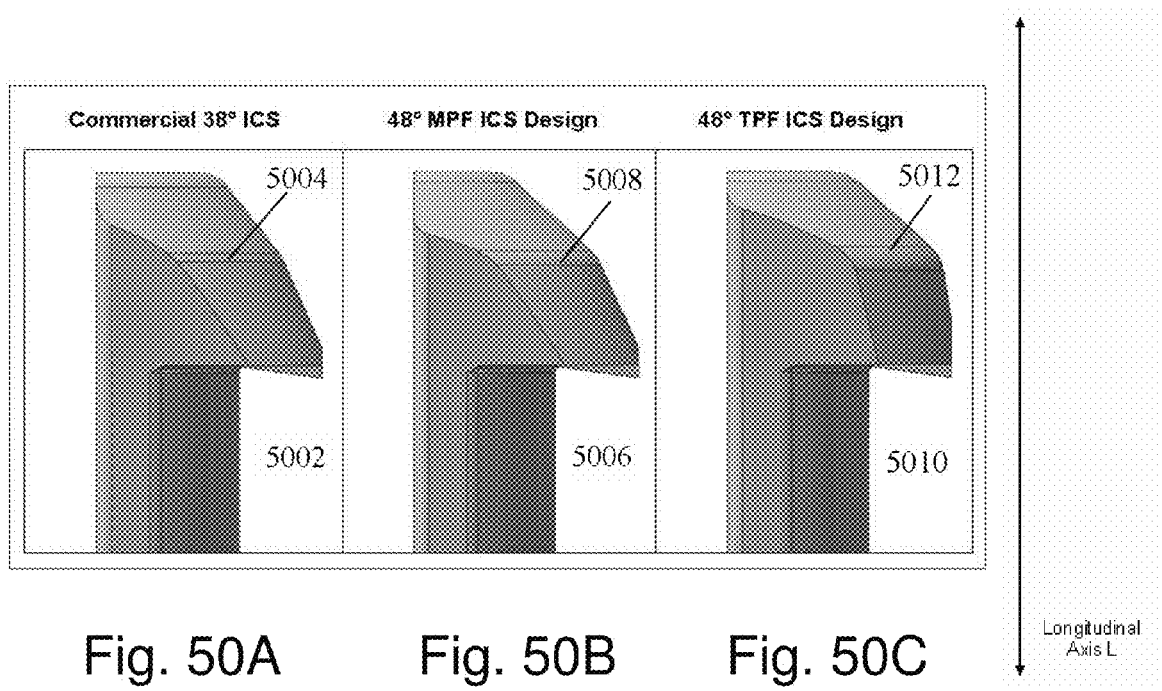
FIG. 50A illustrates a perspective view of the design of a tabbed foot of a commercial plunger with an ICS angle of about 38 degrees.
FIG. 50B illustrates a perspective view of the design of a tabbed foot of a MPF SIM plunger with an ICS angle of about 48 degrees.
FIG. 50C illustrates a perspective view of the design of a tabbed foot of a TPF SIM plunger with an ICS angle of about 48 degrees.

FIGS. 50A-50C illustrate perspective views of the design of a tabbed foot of an exemplary plunger. FIG. 50A illustrates a perspective view of the design of a tabbed foot 5004 of a commercial plunger 5002 with an ICS angle of about 38 degrees. FIG. 50B illustrates a perspective view of the design of a tabbed foot 5008 of an MPF SIM plunger 5006 with an ICS angle of about 48 degrees. FIG. 50C illustrates a perspective view of the design of a tabbed foot 5012 of a TPF SIM plunger 5010 with an ICS angle of about 48 degrees.

In summary, four different exemplary CSA values (i.e., 0, 6, 12 and 18 degrees) for firing bodies were tested with three exemplary plunger types (i.e., commercial, MPF and TPF). Fifteen automatic injection devices were tested for each CSA value studied. The firing button ring inner diameter and firing button ring length were measured before each firing button was assembled with an associated firing body.

During the experiment, each firing body-firing button pairing in the automatic injection devices was fired three times, once with each plunger type. The devices were fired in a Zwick-Roell Force Tester applying high strains to eliminate the effect of strain on delayed delivery of an injection. At high strains, the firing button exerted force on the firing body near the end of firing.

TABLE 4

Summary of experimental results of the impact of different CSA values on delayed delivery of an injection for different plunger types

| Delayed Delivery Rates | Conical Surface Angle | | | |
|---|---|---|---|---|
| Plunger Type | 0° | 6° | 12° | 18° |
| Commercial | 6 | 0 | 0 | 0 |
| Mid Point Fixed (MPF) | 9 | 1 | 0 | 0 |
| Top Point Fixed (TPF) | 3 | 0 | 0 | 0 |

Table 4 shows the number of devices that experienced delayed delivery of an injection.

Figure 51:
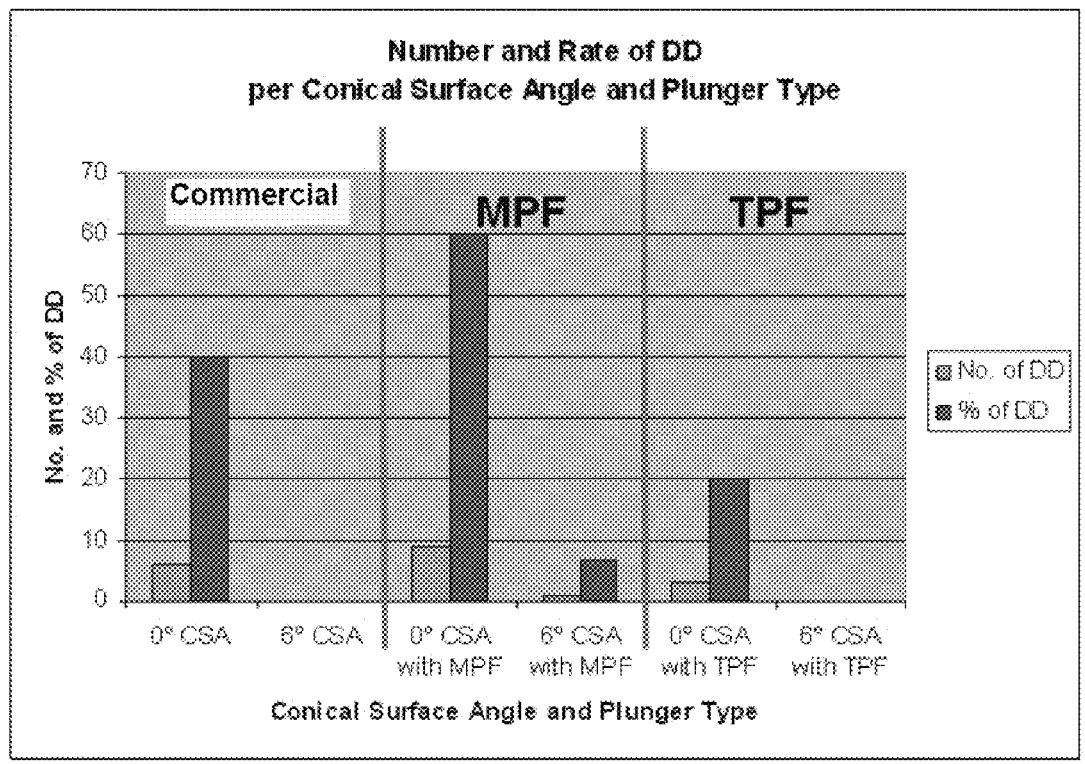
FIG. 51 illustrates a histogram of the number and percentage of devices that experienced delayed delivery (y-axis) over different CSA values and different plunger types (x-axis).

FIG. 51 illustrates a histogram of the number and percentage of devices that experienced delayed delivery (y-axis) over different CSA values and different plunger types (x-axis).

Experimental results for the commercial firing bodies showed that, in some exemplary embodiments, no delayed delivery of an injection was observed at CSA values of about 12 degrees and about 18 degrees for any plunger type. In some exemplary embodiments, at a CSA value of 0 degrees, delayed delivery times were longest for the MPF plungers, intermediate for the commercial plungers, and shortest for the TPF plungers. In some exemplary embodiments, the higher CSA values resulted in elimination of delayed delivery of an injection because the plunger sits higher on the conical surface of the firing body for the higher CSA values. When the plunger sits higher on the conical surface of the firing body, the firing button ring collapses the plunger at an earlier time when the firing button is pushed down.

Exemplary embodiments may increase the CSA values of the firing body, alone or in combination with configuring of the plunger type, to reduce or eliminate delayed delivery of an injection.

(ii) Testing of Rapid Prototype Testing (RPT) Firing Bodies

Exemplary automatic injection devices were produced by assembling exemplary Rapid Prototype Testing (RPT) firing bodies and firing buttons with exemplary plungers. The assembled automatic injection devices were tested to quantitatively determine the impact of the conical surface angle (CSA) of the RPT firing bodies on the delayed delivery of an injection, if any, of the devices.

The CSA value of exemplary firing bodies was varied and the resulting delayed delivery of an injection was measured.

TABLE 5

Summary of different CSA values used to test the effect of the CSA on delayed delivery of an injection

| Commercial Design Specification | Experimental Conical Surface Angle for RPT Firing Bodies | | | | |
|---|---|---|---|---|---|
| 8° ± 12° | 0° | 8° | 18° | 28° | 38° |

Three exemplary plunger configurations were used in conjunction with the exemplary firing bodies: a commercial plunger with an initial contact surface (ICS) angle of about 38 degrees, a mid point fixed (MPF) single impression mold (SIM) plunger with an ICS angle of about 48 degrees, and a top point fixed (TPF) SIM plunger with an ICS angle of about 48 degrees.

FIGS. 50A-50C illustrate perspective views of the design of a tabbed foot of an exemplary plunger. FIG. 50A illustrates a perspective view of the design of a tabbed foot of a commercial plunger with an ICS angle of about 38 degrees. FIG. 50B illustrates a perspective view of the design of a tabbed foot of an MPF SIM plunger with an ICS angle of about 48 degrees. FIG. 50C illustrates a perspective view of the design of a tabbed foot of a TPF SIM plunger with an ICS angle of about 48 degrees.

In summary, five different exemplary CSA values (i.e., 0, 8, 18, 28 and 38 degrees) for firing bodies were tested with three exemplary plunger types (i.e., commercial, MPF and TPF). The firing button ring inner diameter and firing button ring length were measured before each firing button was assembled with an associated firing body.

During the experiment, each firing body-firing button pairing in the automatic injection devices was fired three times, once with each plunger type. The devices were fired in a Zwick-Roell Force Tester applying high strains to eliminate the effect of strain on delayed delivery of an injection. At high strains, near the end of firing, the firing button exerted force on the firing body.

Experiments results for the RPT firing bodies showed that no delayed delivery of an injection was observed for any of the CSA values, even at 0 degrees. The higher CSA values resulted in elimination of delayed delivery of an injection because the plunger sits higher on the conical surface of the firing body for the higher CSA values. When the plunger sits higher on the conical surface of the firing body, the firing button ring collapses the plunger at an earlier time when the firing button is pushed down.

Exemplary embodiments may increase the CSA values of the firing body, alone or in combination with configuring of the plunger type, to reduce or eliminate delayed delivery of an injection.

The exemplary RPT firing bodies showed lower delayed delivery of an injection than the commercial firing bodies (tested in Section (i)). The RPT firing bodies were formed of high rigidity materials, while the commercial firing bodies (tested in Section (i)) were formed of relatively low rigidity materials such as polypropylene (PP). Because of the high rigidity material composition, the conical surface of the RPT firing bodies does not deform as easily as the lower rigidity commercial firing bodies. The lower friction between the plunger and the RPT firing body material also causes the plunger to slide off the conical surface of the RPT firing body more smoothly. These factors resulted in lower delayed delivery of an injection in the RPT firing bodies as compared to the commercial firing bodies.

Exemplary embodiments may configure the firing body material (e.g., use higher rigidity materials) and configuration (e.g., use RPT firing bodies rather than commercial firing bodies), alone or in combination with configuring of the CSA values and/or the plunger type, to reduce or eliminate delayed delivery of an injection.

F. Relationship Between Conical Surface Height of Firing Body and Delayed Delivery of an Injection Exemplary automatic injection devices were produced by assembling exemplary commercial firing bodies and firing buttons with exemplary plungers. The assembled automatic injection devices were tested to quantitatively determine the impact of the conical surface height of the firing bodies on the delayed delivery of an injection, if any, of the devices.

In the experiments described in Sections (i) and (ii), different Conical Surface Angle (CSA) values of the firing body corresponded to different conical surface heights.

TABLE 6

Summary of the correspondence between different exemplary CSA values (in degrees) and their associated conical surface height values (in mm).

| | Conical Surface Angle | | | |
|---|---|---|---|---|
| | 0° | 6° | 12° | 18° |
| Conical Surface Height | 0.000 mm | 0.159 mm | 0.321 mm | 0.491 mm |

Decreasing conical surface heights corresponded with decreasing CSA values. This conical surface height reduction represents an increasing deformation of the conical surface of the firing body.

Deformation in the conical surface may result from engagement of the conical surface (formed of a soft material like polypropylene in an exemplary embodiment) of the firing body with the plunger feet (formed of a polyacetal material in an exemplary embodiment). Different levels of deformation were noted at three stages in the lifetime of an assembled automatic injection device: upon assembly, at the end of a two-year shelf life, and after firing of the device. The deformation was determined to increase with increasing time. Deformation in the conical surface may also be affected by the temperature in which the automatic injection device is stored.

TABLE 7

Summary of exemplary deformation levels (taken to be the peak axial displacement in mm) at the three stages in the lifetime of the devices and for exemplary temperatures of about 23° C. and about 5° C.

| Time | Temperature (° C.) | Peak Axial Displacement (mm) |
|---|---|---|
| Assembly (time zero) | 23 | 0.0865 |
| End of 2-year shelf (creep) | 23 | 0.2098 |
| Post device firing (firing) | 23 | 0.3173 |
| Assembly (time zero) | 5 | 0.0800 |
| End of 2-year shelf (creep) | 5 | 0.2507 |
| Post device firing (firing) | 5 | 0.3167 |

A conical surface height of about 0.491 mm (at a corresponding CSA value of about 18 degrees) was taken as the control.

At the end of the two-year shelf life, the conical surface height becomes about 0.281 mm (=0.491−0.2098) at a temperature of about 25° C. This deformed height corresponds to a CSA angle range of between about 6° C. and about 12° C. At the end of the two-year shelf life, the conical surface height becomes about 0.240 mm (=0.491−0.2507) at a temperature of about 5° C. This deformed height also corresponds to a CSA angle range of between about 6° C. and about 12° C.

Upon firing, the conical surface height becomes about 0.174 mm at temperatures of about 25° C. and about 5° C. This deformed height also corresponds to a CSA angle range of between about 6 degrees and about 12 degrees.

Thus, in some exemplary embodiments, the deformed heights of the conical surface at the end of the two-year shelf life and upon firing correspond to a CSA angle range of between about 6 degrees and about 12 degrees. This indicates that the extent of deformation of the conical surface may affect delayed delivery of an injection in some exemplary embodiments. More specifically, in some exemplary embodiments, greater deformation of the conical surface may result in shorter conical surface heights, which correspond to lower CSA values. This indicates that increasing deformation of the conical surface may lead to increased chances of delayed delivery of an injection and/or increased delayed delivery times in some exemplary embodiments.

Exemplary embodiments may reduce or eliminate delayed delivery of an injection by minimizing deformation of the conical surface of the firing bodies, alone or in combination with one or more additional factors. More specifically, exemplary embodiments may minimize deformation by forming the firing bodies from deformation-resistant materials.

G. Relationship Between Tunnel Entrance Inner Diameter of Firing Body and Delayed Delivery of an Injection Exemplary automatic injection devices were produced by assembling exemplary Rapid Prototype Technology (RPT) firing bodies and firing buttons with exemplary plungers. The assembled automatic injection devices were tested to quantitatively determine the impact of the tunnel entrance inner diameter of the firing bodies on the delayed delivery of an injection, if any, of the devices.

Figure 52:
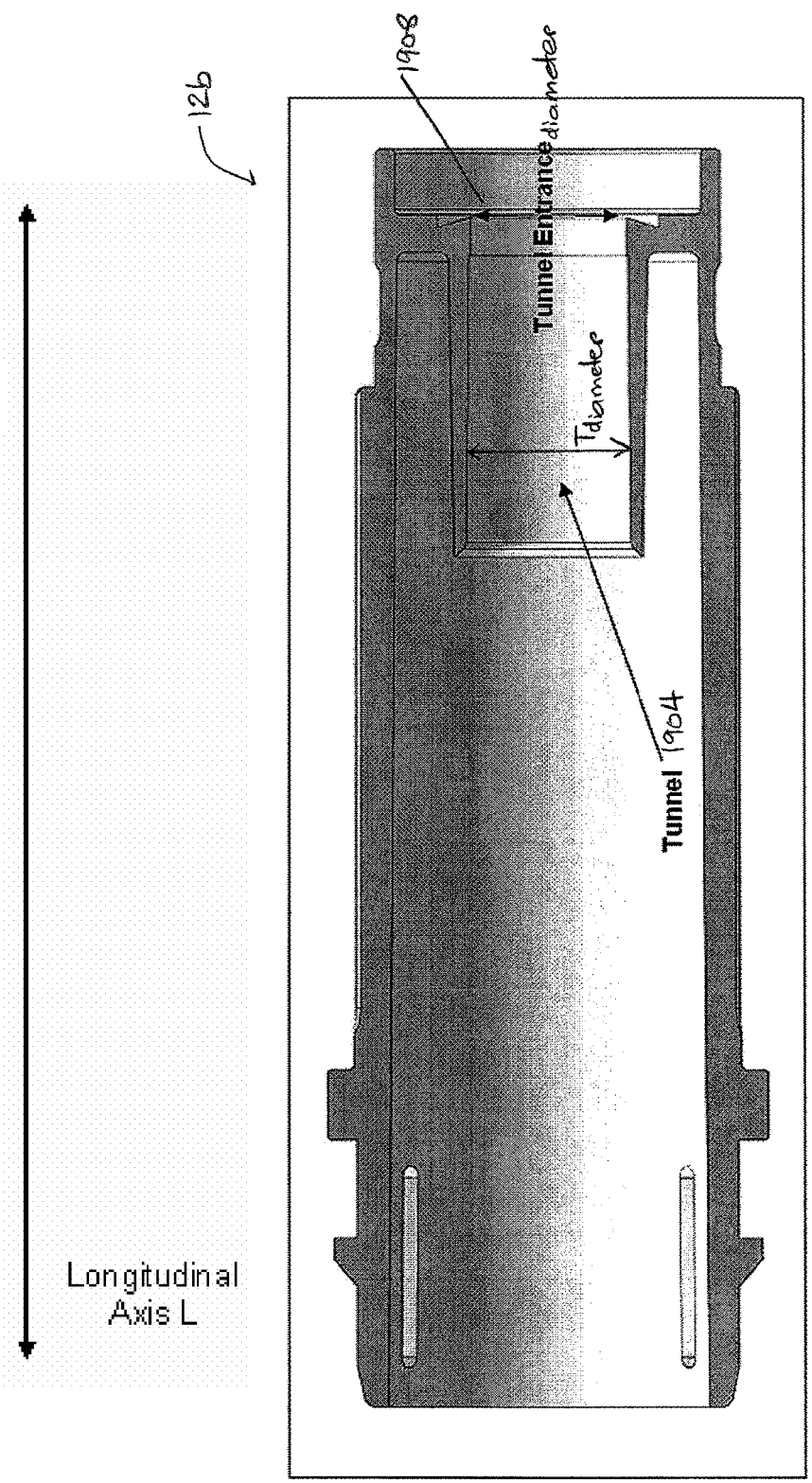
FIG. 52 illustrates a sectional view of an exemplary tunnel of a firing body taken along a longitudinal axis

FIG. 52 illustrates a sectional view of an exemplary tunnel 1904 of a firing body 12b taken along a longitudinal axis L, showing the tunnel 1904 and the tunnel entrance 1908 of the firing body 12b. The inner diameter of the tunnel entrance 1908 of exemplary firing bodies 12b was varied over seventy five automatic injection devices, and the resulting delayed delivery of an injection was measured.

TABLE 8

Summary of design specifications for different tunnel entrance inner diameter values (in mm) used to test the effect of the CSA on delayed delivery of an injection

| Commercial Design Specification | RPT Designed Tunnel Entrance Diameter (mm) | | | | |
|---|---|---|---|---|---|
| 6.90-7.05 mm | 6.70 | 6.80 | 6.90 | 7.02 | 7.12 |

However, the actual tunnel entrance inner diameters varied to some extent from the design specifications.

Figure 53:
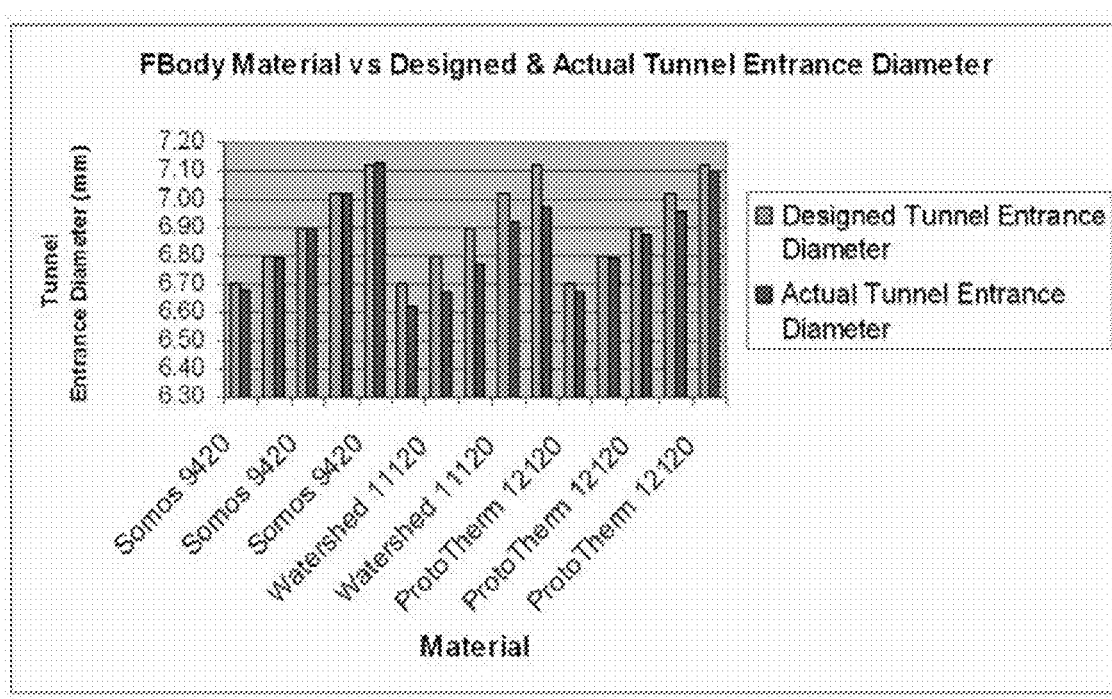
FIG. 53 illustrates a histogram of designed and actual tunnel entrance diameters in mm (y-axis) against different firing body materials (x-axis).

FIG. 53 illustrates a histogram of designed and actual tunnel entrance inner diameters in mm (y-axis) against different firing body materials (x-axis).

Figure 54:
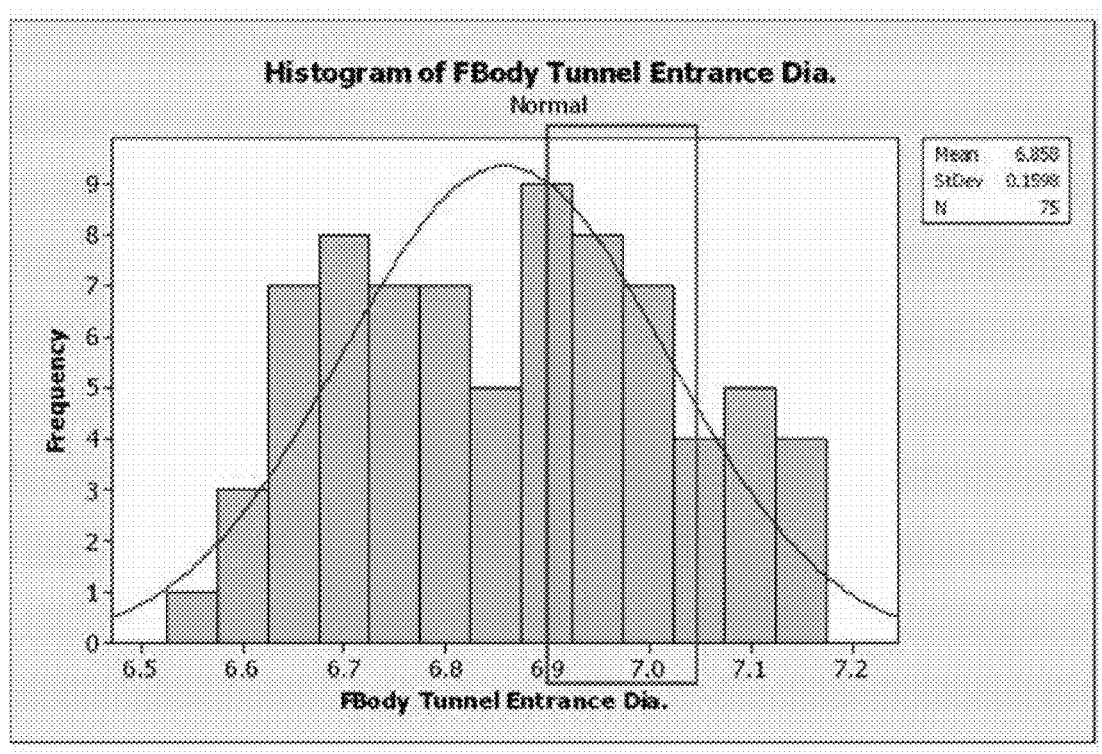
FIG. 54 illustrates a histogram of the number of devices (y-axis) against different actual (measured) tunnel entrance diameters in mm (x-axis) for exemplary firing bodies.

FIG. 54 illustrates a histogram of the number of devices (y-axis) against different actual (measured) tunnel entrance inner diameters in mm (x-axis) for RPT firing bodies.

Figure 55:
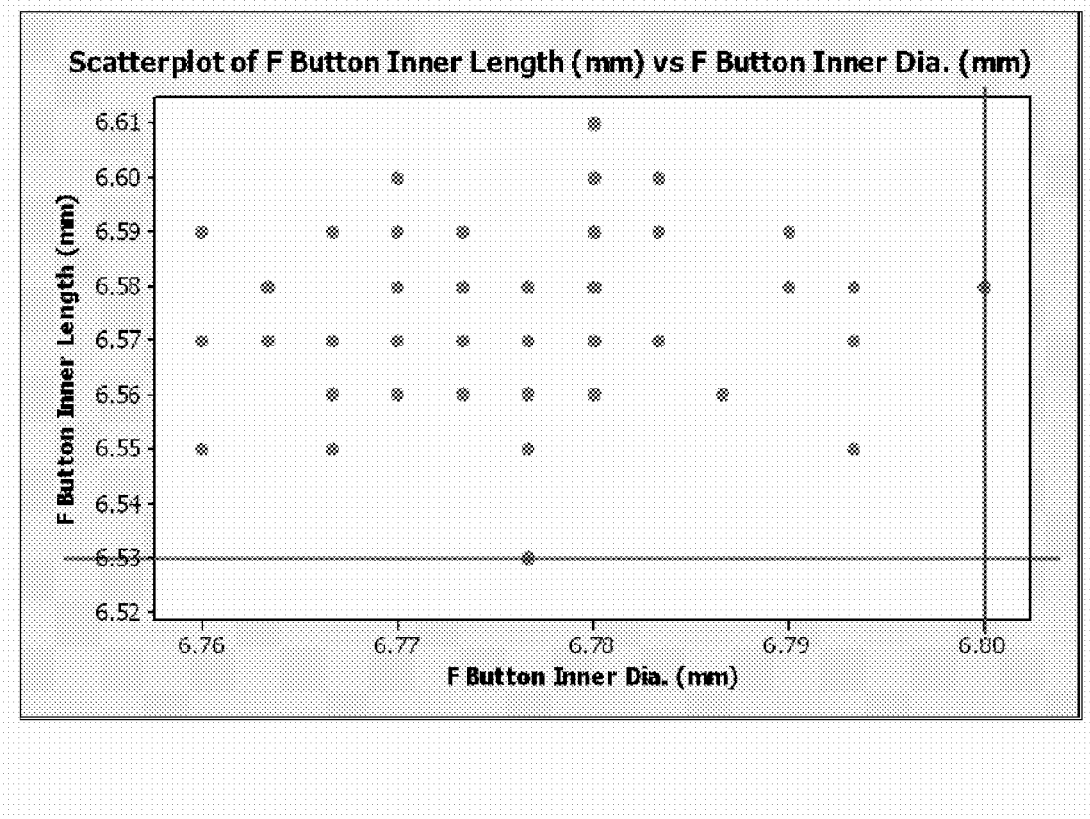
FIG. 55 illustrates a scatterplot of different exemplary firing button ring lengths in mm (y-axis) against different exemplary firing button ring inner diameters in mm (x-axis) for devices tested to determine the effect of the firing body tunnel entrance diameter on delayed delivery.

FIG. 55 illustrates a scatterplot of different exemplary firing button ring lengths in mm (y-axis) against different exemplary firing button ring inner diameters in mm (x-axis) for devices tested to determine the effect of the firing body tunnel entrance inner diameter on delayed delivery of an injection. The dimensions of the firing button ring were within tolerance limits and were configured so that they did not contribute to delayed delivery of an injection, allowing the effect of the firing body tunnel entrance inner diameter to be tested in isolation.

Figure 56:
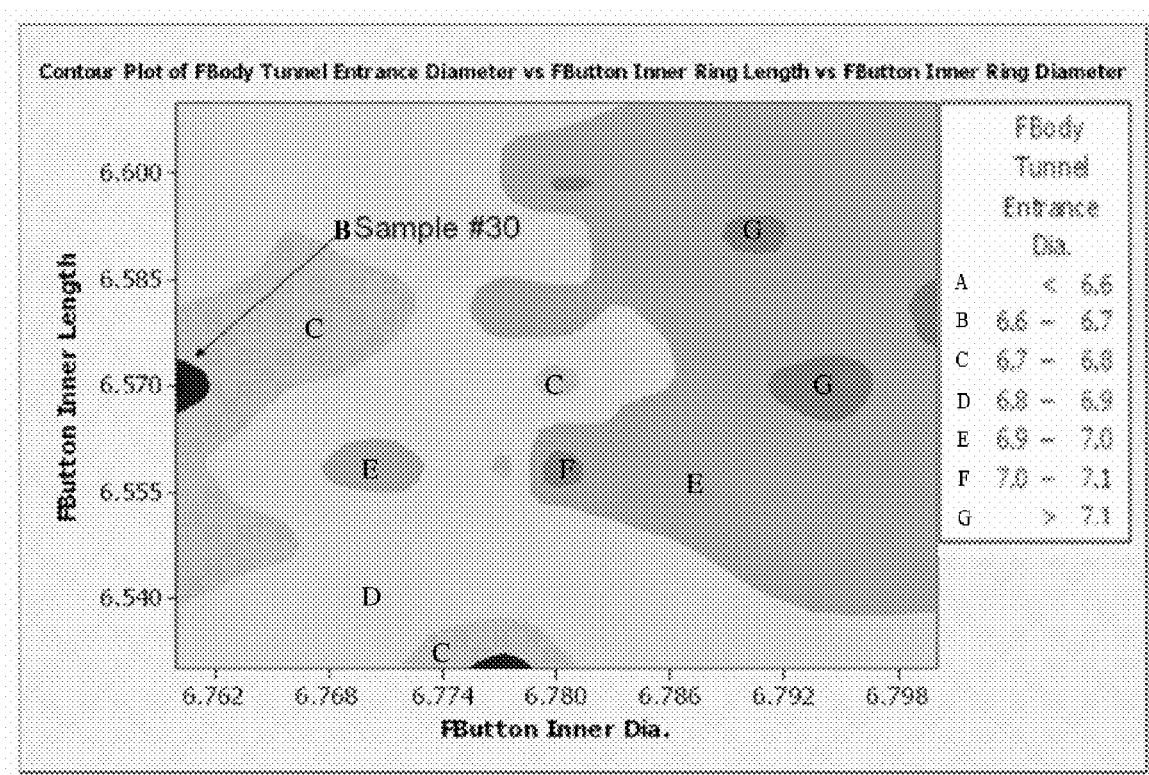
FIG. 56 illustrates a contour plot of firing body tunnel entrance diameters in mm (represented in the legends) against firing button ring lengths in mm (y-axis) and firing button ring inner diameters in mm (x-axis).

FIG. 56 illustrates a contour plot of firing body tunnel entrance inner diameters in mm (represented in the legends) against firing button ring lengths in mm (y-axis) and firing button ring inner diameters in mm (x-axis).

In a first set of tests, all of the seventy five automatic injection devices with different tunnel entrance inner diameters were tested by hand. Of all the devices, only Sample #30 experienced delayed delivery of an injection. As illustrated in FIG. 56, Sample #30 has one of the smallest tunnel entrance inner diameters at about 6.63 mm. This dimension was smaller than the design dimension, and was not within the tolerance limits of between about 6.90 mm and about 7.05 mm.

In a second set of tests, all of the seventy five automatic injection devices with different tunnel entrance inner diameters were tested using a Zwick-Roell Force Tester at a strain of about 2.4 mm. All of the devices fired normally and no delayed delivery of an injection was observed.

In summary, the experimental results showed that, in some exemplary embodiments, the firing body tunnel entrance inner diameter did not significantly affect delayed delivery of an injection, particularly for entrance inner diameters to be above about 6.70 mm. Exemplary embodiments may configure the firing body tunnel entrance inner diameters to be above about 6.70 mm to reduce or eliminate delayed delivery of an injection that may otherwise be caused by the tunnel entrance inner diameter.

H. Relationship Between Tunnel Entrance Inner Diameter and Tunnel Diameter of Firing Body and Delayed Delivery of an Injection Exemplary automatic injection devices were produced by assembling exemplary Rapid Prototype Technology (RPT) firing bodies and firing buttons with exemplary plungers. The assembled automatic injection devices were tested to quantitatively determine the impact of the tunnel entrance inner diameter and the tunnel inner diameter of the firing bodies on the delayed delivery of an injection, if any, of the devices.

Figure 57:
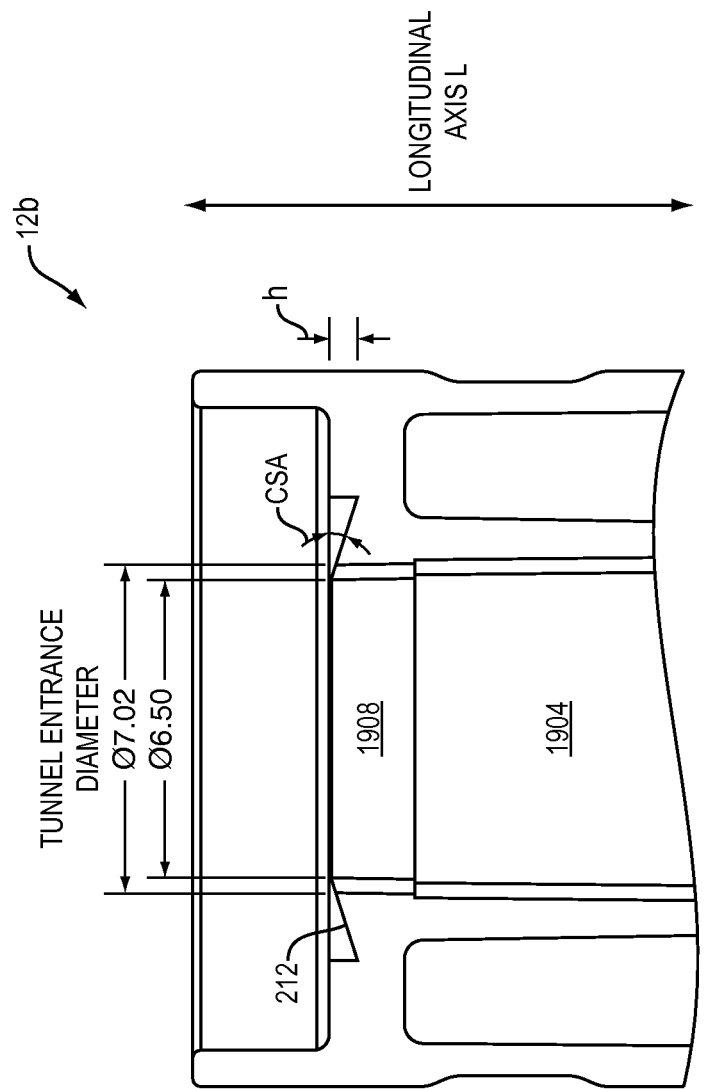
FIG. 57 illustrates a sectional view of a tunnel of a firing body taken along a longitudinal axis, showing the tunnel and the tunnel entrance of the firing body.

FIG. 57 illustrates a sectional view of a tunnel 1904 of a firing body 12b taken along a longitudinal axis, showing the tunnel 1904 and the tunnel entrance 1908 of the firing body 12b. As illustrated in FIG. 57, the entire tunnel geometry (entrance portion and inside portion) was evenly offset about the longitudinal axis with increments corresponding to those shown in Table 9.

The inner diameter of the tunnel entrance of exemplary firing bodies was varied over seventy five automatic injection devices, and the resulting delayed delivery of an injection was measured. Forty automatic injection devices were tested by a Zwick-Roell Force Tester at high strains to ensure that any observed delayed delivery of an injection was not due to insufficient strain. Any devices that were not fired at high strain were removed from the Force Tester and tested by hand.

TABLE 9

Summary of design specifications for different tunnel entrance inner diameter values (in mm) used to test the effect of the CSA on delayed delivery of an injection

| Tunnel Entrance Diameter Design Specification | Designed Tunnel Entrance Diameter (mm) | | | |
|---|---|---|---|---|
| 6.90-7.05 mm | 6.50 | 6.60 | 6.70 | 7.02 |

However, the actual tunnel entrance inner diameters varied to some extent from the design specifications.

Figure 58:
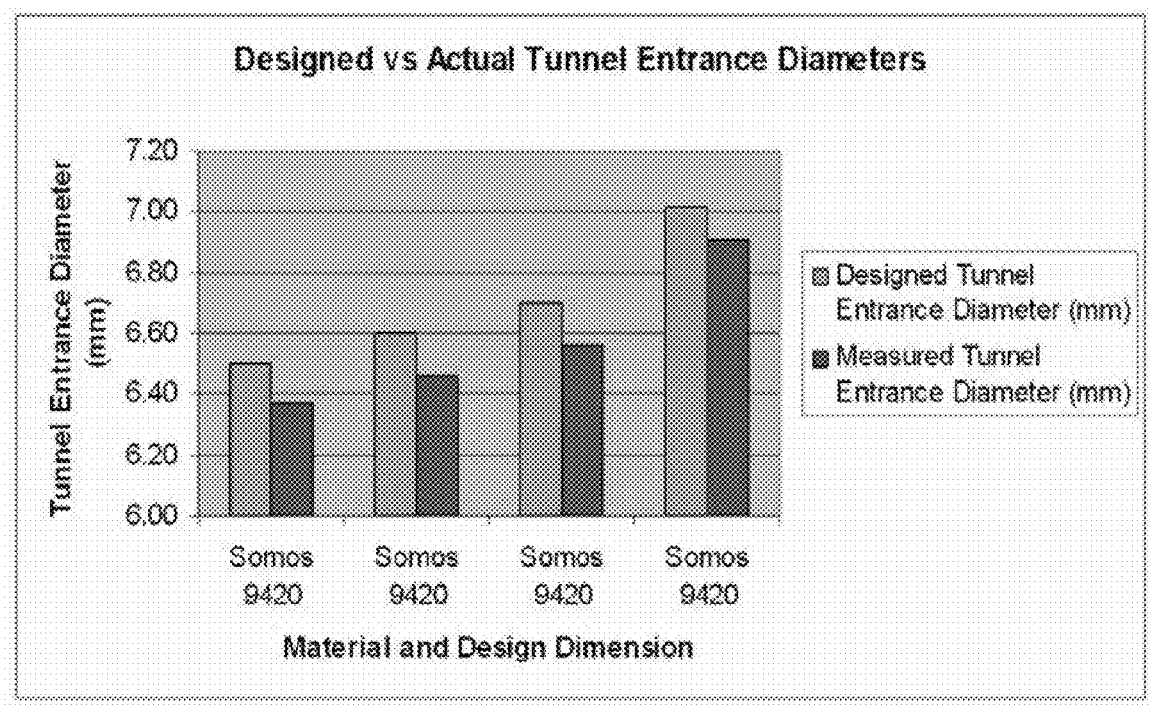
FIG. 58 illustrates a histogram of designed and actual tunnel entrance diameters in mm (y-axis) against different firing body materials (x-axis).

FIG. 58 illustrates a histogram of designed and actual tunnel entrance inner diameters in mm (y-axis) against different firing body materials (x-axis).

Figure 59:
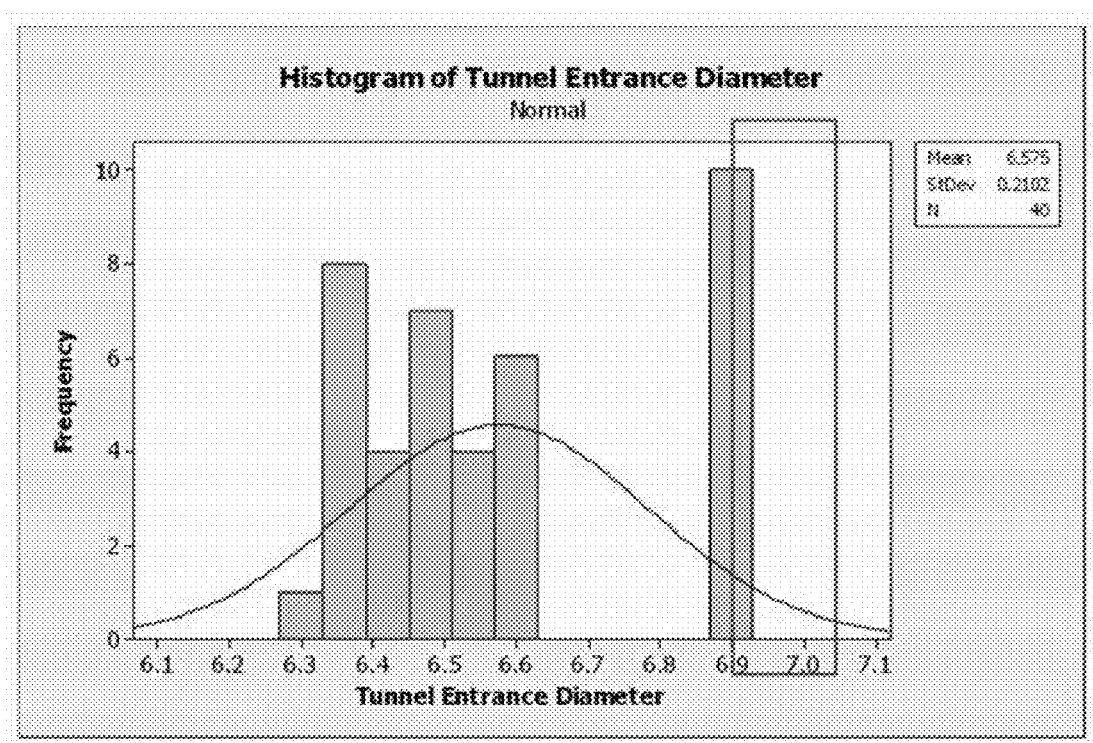
FIG. 59 illustrates a histogram of the number of devices (y-axis) against different actual (measured) tunnel entrance diameters in mm (x-axis) for exemplary firing bodies.

FIG. 59 illustrates a histogram of the number of devices (y-axis) against different actual (measured) tunnel entrance inner diameters in mm (x-axis) for RPT firing bodies.

Figure 60:
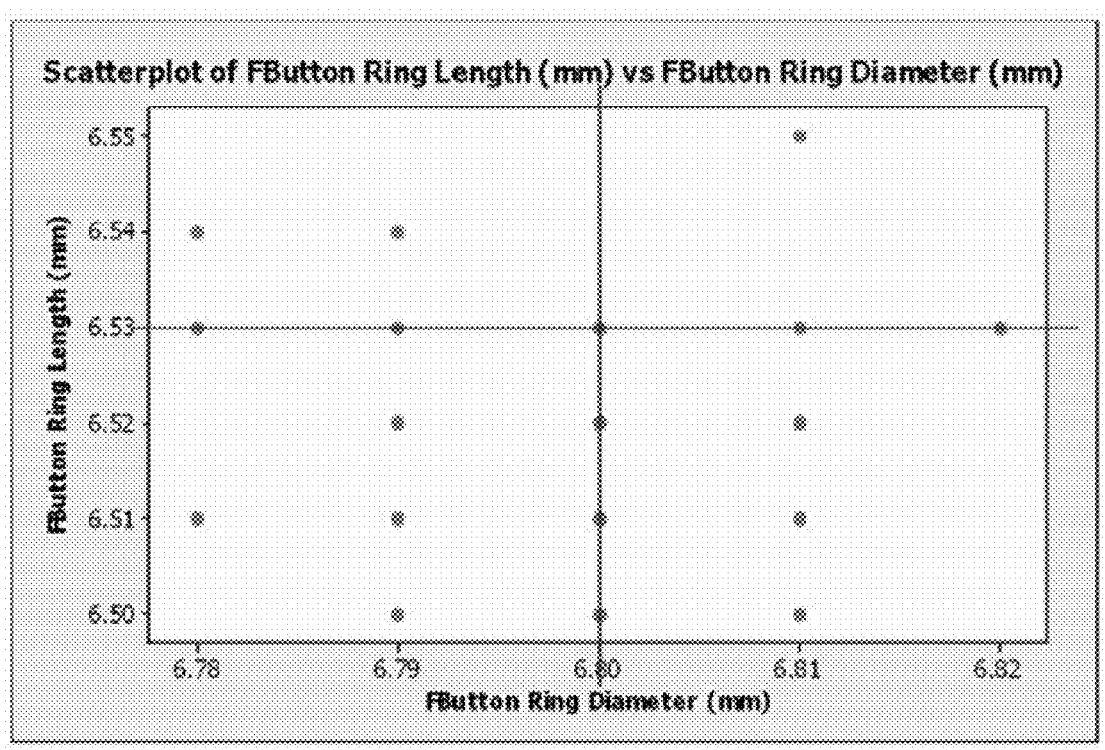
FIG. 60 illustrates a scatterplot of different exemplary firing button ring lengths in mm (y-axis) against different exemplary firing button ring inner diameters in mm (x-axis) for devices tested to determine the effect of the firing body tunnel entrance diameter on delayed delivery.

FIG. 60 illustrates a scatterplot of different exemplary firing button ring lengths in mm (y-axis) against different exemplary firing button ring inner diameters in mm (x-axis) for devices tested to determine the effect of the firing body tunnel entrance inner diameter on delayed delivery of an injection. The dimensions of the firing button ring were within tolerance limits and were configured so that they did not contribute to delayed delivery of an injection, allowing the effect of the firing body tunnel entrance inner diameter to be tested in isolation.

TABLE 10

Summary of experimental results showing the effect of different firing body tunnel entrance inner diameters (at different firing button ring lengths and inner diameters and different strains) on the firing of the devices and on delayed delivery of an injection

| | FIRING BODY | | | FIRING BUTTON | | DIFFERENCE | | RESULTS | | |
|---|---|---|---|---|---|---|---|---|---|---|
| | Designed | Measured | | Ring Inner | Ring | | | | | |
| # | Tunnel Entrance Diameter (mm) | Entrance Tunnel Diameter (mm) | # | Diameter (mm) | Length (mm) | Firing Button – Firing Body | Strain (mm) | Zwick Testing | Hand Testing | NOTES |
| 76 | 6.50 | 6.38 | 1 | 6.79 | 6.51 | −0.41 | 2.6 | Not Fired | Fired | |
| 77 | 6.50 | 6.32 | 2 | 6.80 | 6.51 | −0.48 | 2.8 | Not Fired | Fired | Fired after pushed twice by hand |
| 78 | 6.50 | 6.36 | 3 | 6.80 | 6.53 | −0.44 | 3.0 | Not Fired | Not Fired | Plunger collapsed on Fbody, Fbody touches Fbutton |
| 79 | 6.50 | 6.36 | 4 | 6.81 | 6.52 | −0.45 | 3.1 | Not Fired | Not Fired | Plunger collapsed on Fbody, Fbody touches Fbutton |
| 80 | 6.50 | 6.37 | 5 | 6.78 | 6.54 | −0.41 | 3.1 | Not Fired | Not Fired | Plunger collapsed on Fbody, Fbody touches Fbutton |
| 81 | 6.50 | 6.39 | 6 | 6.80 | 6.51 | −0.41 | 3.1 | Not Fired | Not Fired | Plunger collapsed on Fbody, Fbody touches Fbutton |
| 82 | 6.50 | 6.38 | 7 | 6.81 | 6.52 | −0.43 | 3.1 | Not Fired | Not Fired | Plunger collapsed on Fbody, Fbody touches Fbutton |
| 83 | 6.50 | 6.36 | 8 | 6.81 | 6.55 | −0.45 | 3.1 | Not Fired | Not Fired | Plunger collapsed on Fbody, Fbody touches Fbutton |
| 84 | 6.50 | 6.36 | 9 | 6.79 | 6.51 | −0.43 | 3.1 | Fired | | |
| 85 | 6.50 | 6.37 | 10 | 6.80 | 6.53 | −0.43 | 3.1 | Not Fired | Not Fired | Pushed twice by hand, not fired, then it fired by itself in about 5 sec |
| | | Mean 6.37 StDev 0.02 | | Mean 6.80 StDev 0.01 | Mean 6.52 StDev 0.01 | | | | | |
| 86 | 6.60 | 6.45 | 11 | 6.81 | 6.53 | −0.36 | 3.1 | Fired | | Fired at the end |
| 87 | 6.60 | 6.55 | 12 | 6.81 | 6.51 | −0.26 | 3.1 | Fired | | |
| 88 | 6.60 | 6.47 | 13 | 6.79 | 6.51 | −0.32 | 3.1 | Fired | | |
| 89 | 6.60 | 6.44 | 14 | 6.60 | 6.53 | −0.36 | 3.1 | Fired | | |
| 90 | 6.60 | 6.45 | 15 | 6.60 | 6.51 | −0.35 | 3.1 | Not Fired | | Fired after 5 sec by itself while in the fixture |
| 91 | 6.60 | 6.45 | 16 | 6.78 | 6.54 | −0.33 | 3.1 | Fired | | |
| 92 | 6.60 | 6.46 | 17 | 6.79 | 6.50 | −0.33 | 3.1 | Not Fired | Not Fired | Fired after 25 sec by itself |

TABLE 10-continued

Summary of experimental results showing the effect of different firing body tunnel entrance inner diameters (at different firing button ring lengths and inner diameters and different strains) on the firing of the devices and on delayed delivery of an injection

| | FIRING BODY | | FIRING BUTTON | | | DIFFERENCE | | RESULTS | | |
|---|---|---|---|---|---|---|---|---|---|---|
| | Designed | Measured | | Ring Inner | Ring | | | | | |
| # | Tunnel Entrance Diameter (mm) | Entrance Tunnel Diameter (mm) | # | Diameter (mm) | Length (mm) | Firing Button − Firing Body | Strain (mm) | Zwick Testing | Hand Testing | NOTES |
| 93 | 6.60 | 6.44 | 18 | 6.80 | 6.50 | −0.36 | 3.1 | Not Fired | Not Fired | Fired by itself after 10 min |
| 94 | 6.60 | 6.48 | 19 | 6.81 | 6.51 | −0.33 | 3.1 | Fired | | |
| 95 | 6.60 | 6.44 | 20 | 6.80 | 6.52 | −0.36 | 3.1 | Not Fired | Not Fired | Plunger collapsed on Fbody, Fbody touches Fbutton |
| | | Mean 6.46 StDev 0.03 | | Mean 6.80 StDev 0.01 | Mean 6.52 StDev 0.01 | | | | | |
| 96 | 6.70 | 6.60 | 21 | 6.81 | 6.50 | −0.21 | 3.1 | Fired | | |
| 97 | 6.70 | 6.58 | 22 | 6.80 | 6.51 | −0.22 | 3.1 | Fired | | |
| 98 | 6.70 | 6.57 | 23 | 6.81 | 6.53 | −0.24 | 3.1 | Fired | | |
| 99 | 6.70 | 6.45 | 24 | 6.79 | 6.50 | −0.34 | 3.1 | Not Fired | Not Fired | Fired by itself after 60 sec |
| 100 | 6.70 | 6.59 | 25 | 6.81 | 6.51 | −0.22 | 3.1 | Fired | | |
| 101 | 6.70 | 6.57 | 26 | 6.79 | 6.52 | −0.22 | 3.1 | Fired | | |
| 102 | 6.70 | 6.56 | 27 | 6.79 | 6.53 | −0.23 | 3.1 | Fired | | |
| 103 | 6.70 | 6.55 | 28 | 6.78 | 6.53 | −0.23 | 3.1 | Fired | | |
| 104 | 6.70 | 6.55 | 29 | 6.79 | 6.53 | −0.24 | 3.1 | Fired | | |
| 105 | 6.70 | 6.58 | 30 | 6.82 | 6.53 | −0.24 | 3.1 | Fired | | |
| | | Mean 6.56 StDev 0.01 | | Mean 6.80 StDev 0.01 | Mean 6.52 StDev 0.01 | | | | | |
| 106 | 7.02 | 6.92 | 31 | 6.78 | 6.51 | 0.14 | 3.1 | Fired | | |
| 107 | 7.02 | 6.87 | 32 | 6.79 | 6.51 | 0.08 | 3.1 | Fired | | |
| 108 | 7.02 | 6.89 | 33 | 6.79 | 6.54 | 0.10 | 3.1 | Fired | | |
| 109 | 7.02 | 6.91 | 34 | 6.79 | 6.54 | 0.12 | 3.1 | Fired | | |
| 110 | 7.02 | 6.93 | 35 | 6.79 | 6.52 | 0.14 | 3.1 | Fired | | |
| 111 | 7.02 | 6.92 | 36 | 6.81 | 6.52 | 0.11 | 3.1 | Fired | | |
| 112 | 7.02 | 6.90 | 37 | 6.81 | 6.53 | 0.09 | 3.1 | Fired | | |
| 113 | 7.02 | 6.92 | 38 | 6.79 | 6.52 | 0.13 | 3.1 | Fired | | |
| 114 | 7.02 | 6.92 | 39 | 6.81 | 6.53 | 0.11 | 3.1 | Fired | | |
| 115 | 7.02 | 6.92 | 40 | 6.80 | 6.53 | 0.12 | 3.1 | Fired | | |

At a tunnel entrance inner diameter of about 7.02 mm, all of the devices with fired in the Zwick-Roell Force Tester. At a tunnel entrance inner diameter of about 6.70 mm, only one device was delayed in the Zwick-Roell Force Tester. The same device also did not fire when the firing button was pushed by hand. The device subsequently fired by itself after about a minute. At a tunnel entrance inner diameter of about 6.60 mm, six of the devices fired in the Zwick-Roell Force Tester. One of the devices was delayed for about five seconds, but it fired by itself before the firing button was pushed by hand. Three of the devices did not fire in the Zwick-Roell Force Tester or by hand. Of these three devices that did not fire, two of them fired after about 25 seconds and about 10 minutes, respectively. One of the three devices that did not fire fired by itself overnight. However, in this device, the plunger did not move all the day down the device. At a tunnel entrance inner diameter of about 6.50 mm, one of the devices fired in the Zwick-Roell Force Tester. Two of the devices were not fired in the Zwick-Roell Force Tester, but were fired by hand. Seven of the devices did not fire in the Zwick-Roell Force Tester or by hand. Of these seven devices, one device fired about five seconds after it was pushed by hand, and six devices fired overnight. In the six devices that fired overnight, the plunger did not move all the way down the device in five of the devices.

In some exemplary devices the plunger did not move all the way down because the tunnel was narrow, as the narrow tunnel causes greater dragging of the plunger feet against the tunnel walls as the plunger travels down the tunnel.

TABLE 11

Summary of experimental results showing the effect of different firing body tunnel entrance inner diameters (at different firing button ring inner diameters) on the firing of the devices and on delayed delivery of an injection

| Firing Body Sample No. | Measured Tunnel Entrance Diameter (mm) | Firing Button Sample No. | Measured Ring Diameter (mm) | Firing body - Firing Button | Zwick Testing |
|---|---|---|---|---|---|
| 77 | 6.32 | 2 | 6.80 | −0.48 | Not Fired |
| 79 | 6.36 | 4 | 6.81 | −0.45 | Not Fired |
| 83 | 6.36 | 8 | 6.81 | −0.45 | Not Fired |

TABLE 11-continued

Summary of experimental results showing the effect of different firing body tunnel entrance inner diameters (at different firing button ring inner diameters) on the firing of the devices and on delayed delivery of an injection

| Firing Body Sample No. | Measured Tunnel Entrance Diameter (mm) | Firing Button Sample No. | Measured Ring Diameter (mm) | Firing body - Firing Button | Zwick Testing |
|---|---|---|---|---|---|
| 78 | 6.36 | 3 | 6.80 | −0.44 | Not Fired |
| 82 | 6.38 | 7 | 6.81 | −0.43 | Not Fired |
| 84 | 6.36 | 9 | 6.79 | −0.43 | Fired |
| 85 | 6.37 | 10 | 6.80 | −0.43 | Not Fired |
| 76 | 6.38 | 1 | 6.79 | −0.41 | Not Fired |
| 80 | 6.37 | 5 | 6.78 | −0.41 | Not Fired |
| 81 | 6.39 | 6 | 6.80 | −0.41 | Not Fired |
| 86 | 6.45 | 11 | 6.81 | −0.36 | Fired |
| 89 | 6.44 | 14 | 6.80 | −0.36 | Fired |
| 96 | 6.44 | 18 | 6.80 | −0.36 | Not Fired |
| 95 | 6.44 | 20 | 6.80 | −0.36 | Not Fired |
| 90 | 6.45 | 15 | 6.80 | −0.35 | Not Fired |
| 99 | 6.45 | 24 | 6.79 | −0.34 | Not Fired |
| 91 | 6.45 | 16 | 6.78 | −0.33 | Fired |
| 92 | 6.46 | 17 | 6.79 | −0.33 | Not Fired |
| 94 | 6.48 | 19 | 6.81 | −0.33 | Fired |
| 88 | 6.47 | 13 | 6.79 | −0.32 | Fired |
| 87 | 6.55 | 12 | 6.81 | −0.26 | Fired |
| 104 | 6.55 | 29 | 6.79 | −0.24 | Fired |
| 105 | 6.58 | 30 | 6.82 | −0.24 | Fired |
| 98 | 6.57 | 23 | 6.81 | −0.24 | Fired |
| 102 | 6.56 | 27 | 6.79 | −0.23 | Fired |
| 103 | 6.55 | 28 | 6.78 | −0.23 | Fired |
| 97 | 6.58 | 22 | 6.80 | −0.22 | Fired |
| 100 | 6.59 | 25 | 6.81 | −0.22 | Fired |
| 101 | 6.57 | 26 | 6.79 | −0.22 | Fired |
| 96 | 6.60 | 21 | 6.81 | −0.21 | Fired |
| 107 | 6.87 | 32 | 6.79 | 0.08 | Fired |
| 112 | 6.90 | 37 | 6.81 | 0.09 | Fired |
| 108 | 6.89 | 33 | 6.79 | 0.10 | Fired |
| 111 | 6.92 | 36 | 6.81 | 0.11 | Fired |
| 114 | 6.92 | 39 | 6.81 | 0.11 | Fired |
| 109 | 6.91 | 34 | 6.79 | 0.12 | Fired |
| 115 | 6.92 | 40 | 6.80 | 0.12 | Fired |
| 113 | 6.92 | 38 | 6.79 | 0.13 | Fired |
| 106 | 6.92 | 31 | 6.78 | 0.14 | Fired |
| 110 | 6.93 | 35 | 6.79 | 0.14 | Fired |

Table 11 shows that even when the firing button ring inner diameter is about 0.32 mm larger than the firing body tunnel entrance inner diameter, the devices fire normally.

In summary, the experimental results showed that, in some exemplary embodiments, the firing body tunnel entrance inner diameter did not significantly affect delayed delivery of an injection, particularly for entrance inner diameters above about 6.70 mm. Exemplary embodiments may configure the firing body tunnel entrance inner diameters above about 6.70 mm to reduce or eliminate delayed delivery of an injection that may otherwise be caused by the tunnel entrance inner diameter.

I. Relationship Between Plunger Tip Protrusion and Delayed Delivery of an Injection Exemplary automatic injection devices were produced by assembling exemplary firing bodies and firing buttons with exemplary plungers. The assembled automatic injection devices were tested to quantitatively determine the impact of the protrusion of the tip of the plunger, i.e., the bluntness or sharpness of the tip, on the delayed delivery of an injection, if any, of the devices.

Figures 61A, 61B, 61C:
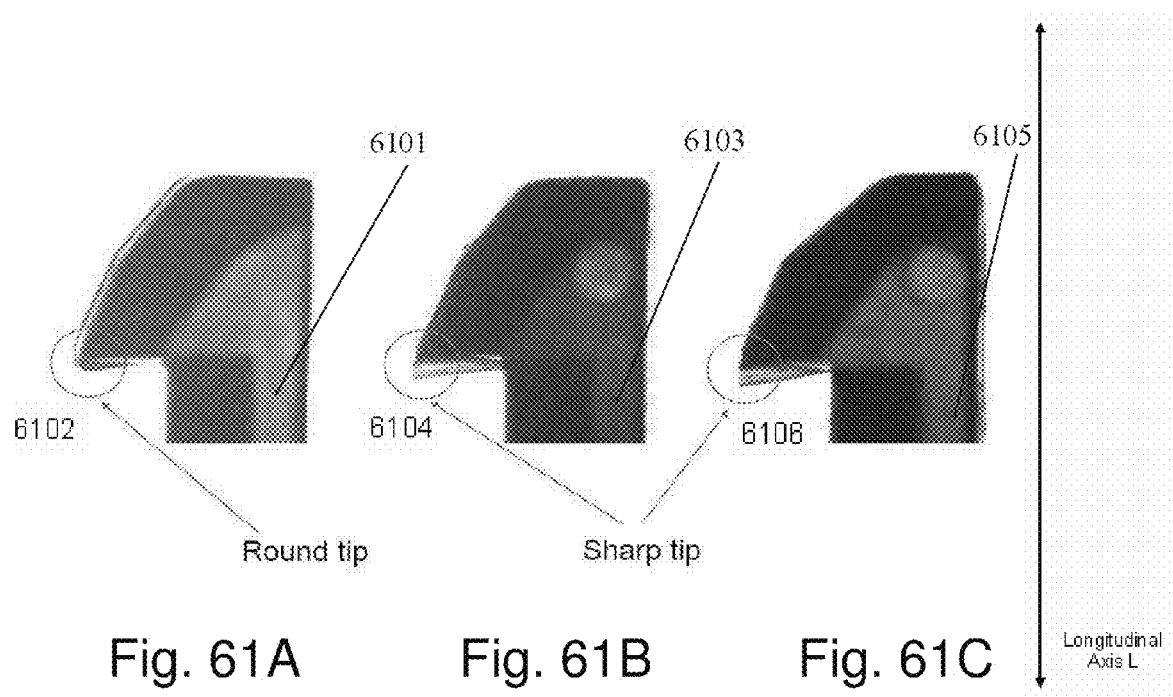
FIG. 61A illustrates a plunger with a rounded or blunt tip.
FIG. 61B illustrates a plunger with an ICS angle of about 38 degrees and a sharp tip.
FIG. 61C illustrates a plunger with an ICS angle of about 48 degrees and a sharp tip.

FIGS. 61A-61C illustrate exemplary tabbed feet of a plunger, in which FIG. 61A illustrates a plunger 6101 with a rounded or blunt tip 6102, FIG. 61B illustrates a plunger 6103 with an ICS angle of about 38 degrees and a sharp tip 6104, and FIG. 61C illustrates a plunger 6105 with an ICS angle of about 48 degrees and a sharp tip 6106.

Figure 62:
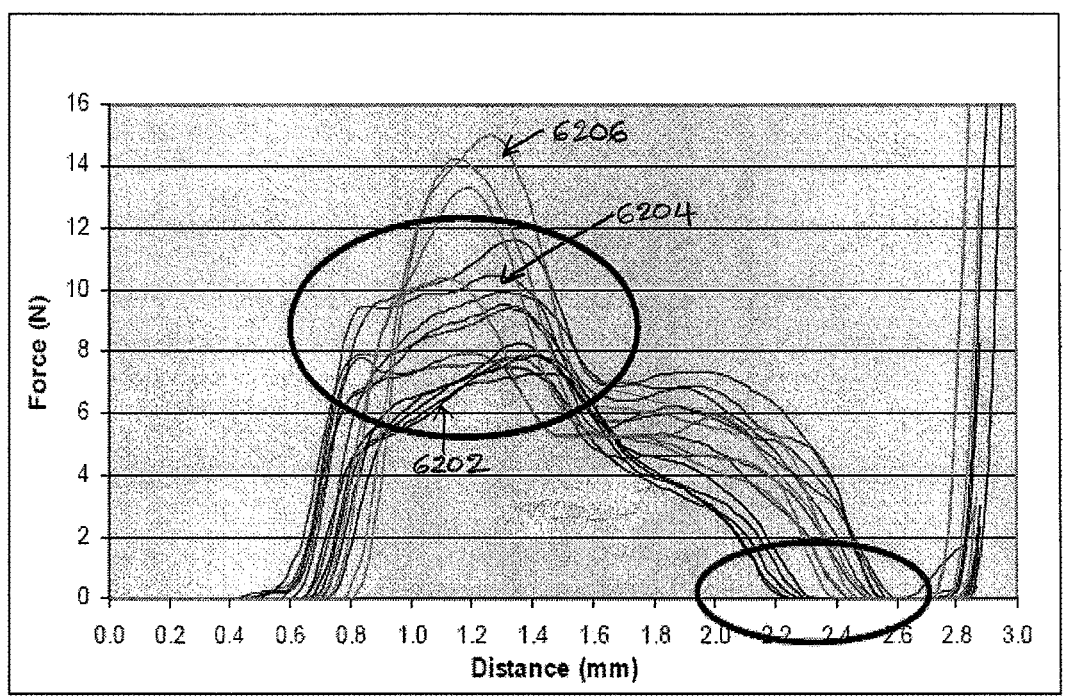
FIG. 62 illustrates force profiles generated by testing the plungers of FIG. 61A-61C.

FIG. 62 illustrates force profiles 6202, 6204 and 6406 (in N) generated by testing the plungers 6102 (FIG. 61A), 6104 (FIG. 61B) and 6106 (FIG. 61C), respectively. The plungers with a rounded or blunt tip showed a larger distance "d" on the x-axis of the force profile (force profile 6202), which minimizes delayed delivery of an injection. The plungers with a rounded or blunt tip showed a lower "fired strain" (force profile 6202), which minimizes the risk of delayed delivery of an injection that may be introduced by insufficient strain.

In summary, the experimental results showed that, in some exemplary embodiments, a rounded or blunt tip of the tabbed feet of the plunger, as compared with a sharp tip, may minimize delayed delivery of an injection. Exemplary embodiments may configure the tabbed feet of the plunger to have a rounded or blunt tip in order to minimize delayed delivery of an injection.

J. Relationship Between Wall Thickness of Firing Button Ring and Delayed Delivery of an Injection The impact of the thickness of the firing button ring on delayed delivery of an injection was tested. Exemplary firing button rings were designed, molded and tested with a substantially constant outer diameter and a varying inner diameter. Since the outer diameter was kept constant, decreasing the inner diameter resulted in a thicker wall of the firing button ring, and increasing the inner diameter resulted in a thinner wall of the firing button ring.

TABLE 12

Summary of exemplary firing button ring inner diameters and lengths used to determine the wall thickness and its effect on delayed delivery of an injection

| SIM Model | Designed Ring Inner Diameter (mm) | Design Ring Length (mm) | Design Change |
|---|---|---|---|
| Control | 6.80 | 6.53 | |
| A | 6.80 | 6.33 | Ring length |
| B | 6.80 | 6.73 | Ring length |
| C | 6.80 | 6.83 | Ring length |
| G | 6.50 | 6.53 | Ring inner diameter |
| H | 6.65 | 6.53 | Ring inner diameter |
| I | 6.95 | 6.53 | Ring inner diameter |
| J | 6.50 | 6.83 | Combination of ring length and inner diameter |
| K | 6.95 | 6.33 | Combination of ring length and inner diameter |

Figure 63:
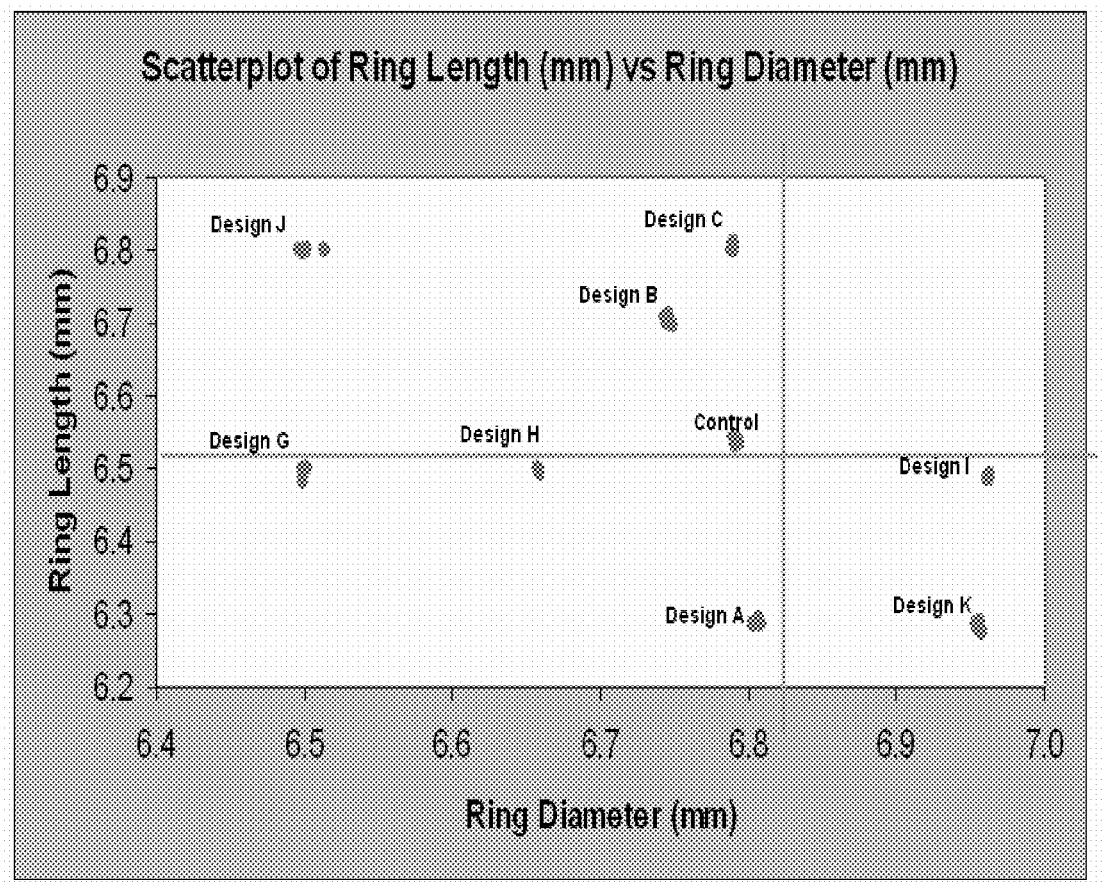
FIG. 63 illustrates a scatterplot of different firing button ring lengths in mm (y-axis) and ring inner diameters in mm (x-axis).

FIG. 63 illustrates a scatterplot of different firing button ring lengths in mm (y-axis) and ring inner diameters in mm (x-axis) used in the tests.

Figure 64:
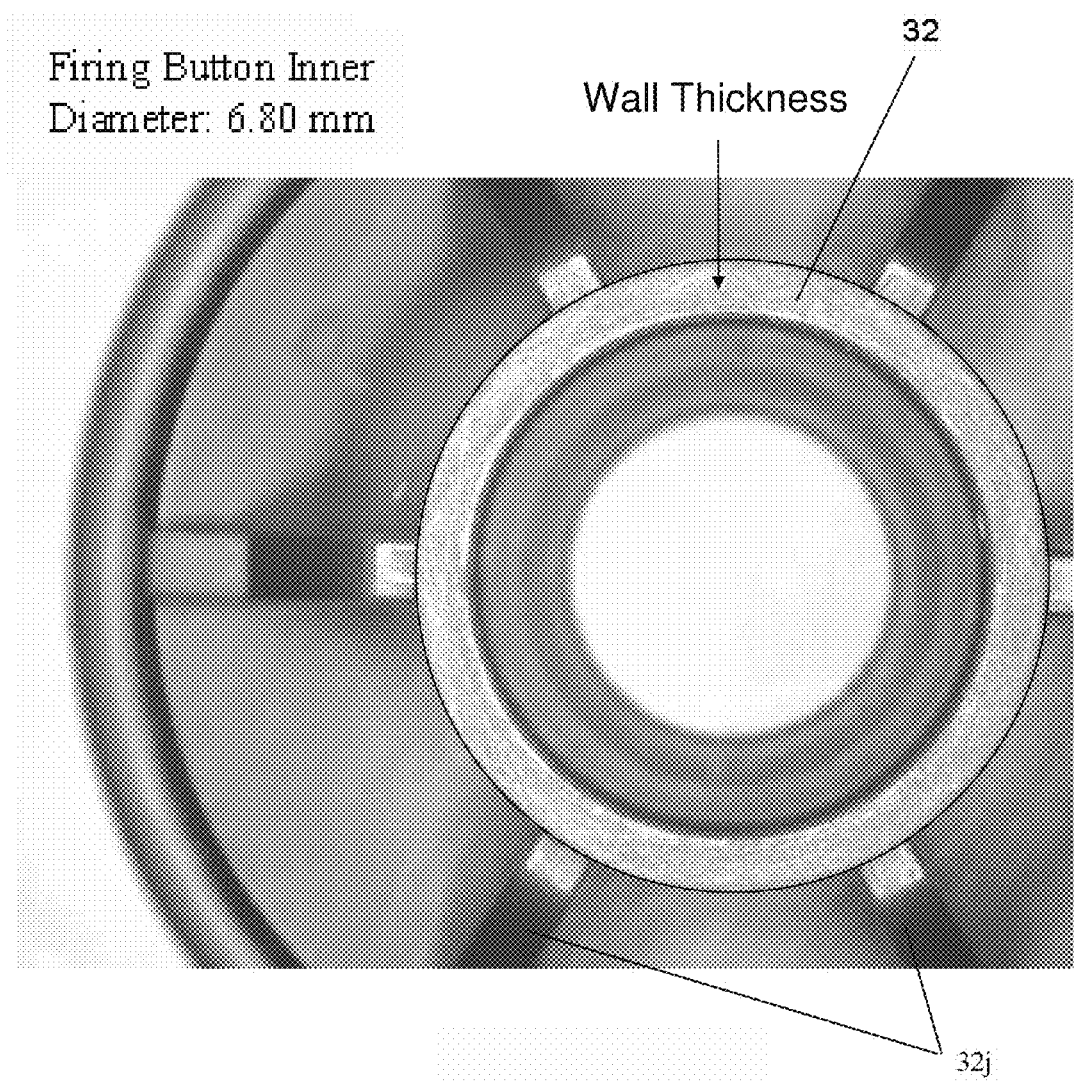
FIG. 64 illustrates a frontal view of a control firing button ring with an inner diameter of about 6.80 mm.

FIG. 64 illustrates a frontal view of the control firing button ring 32 showing the wall thickness of the ring. The control firing button had an exemplary inner diameter of about 6.80 mm, a wall thickness of about 0.75 mm and an exemplary length of about 6.53 mm.

Figure 65:
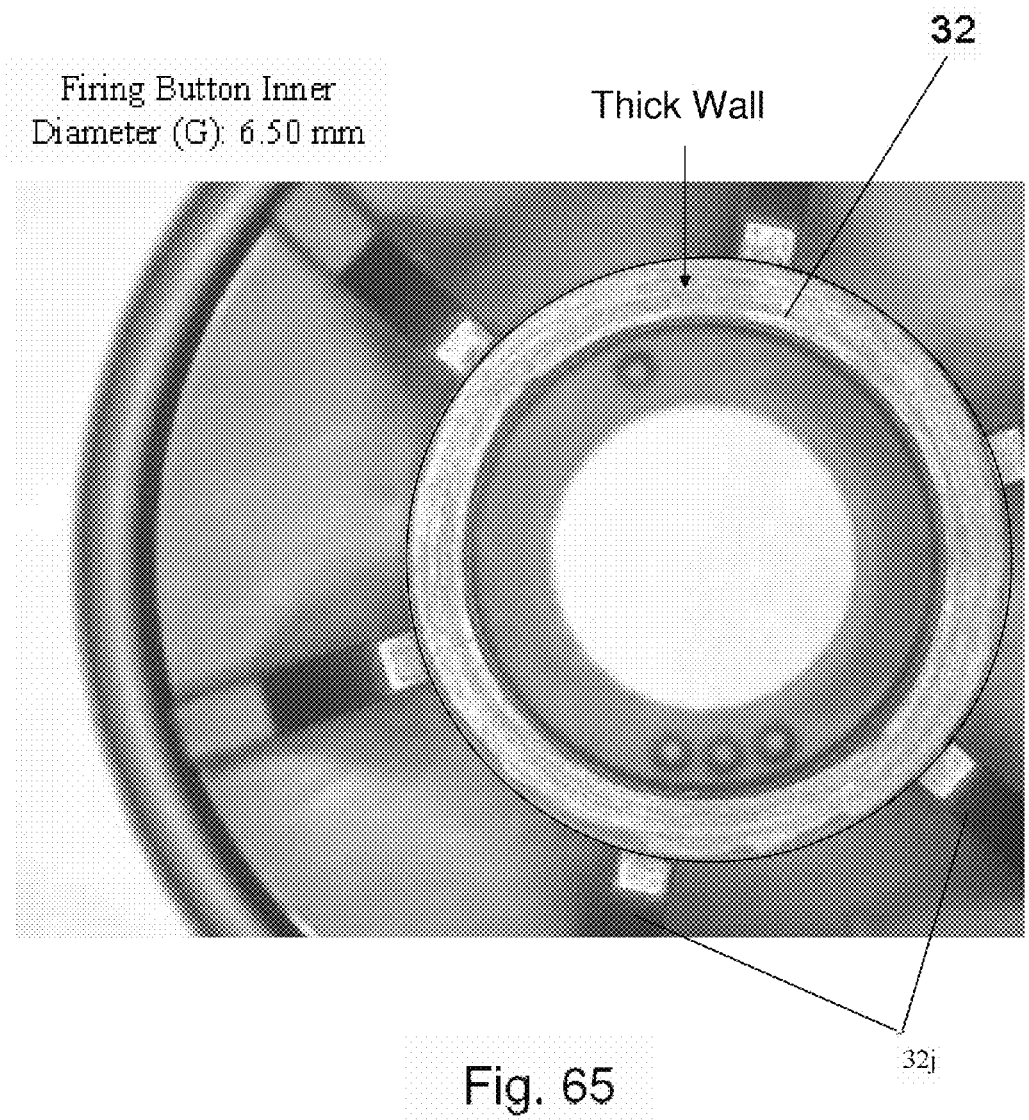
FIG. 65 illustrates a frontal view of the "G" firing button ring with an inner diameter of about 6.50 mm.

FIG. 65 illustrates a frontal view of the "G" firing button ring 32 showing the thick wall of the ring. The inner diameter of the "G" firing button ring was about 6.50 mm, and the wall thickness of the "G" firing button ring was about 0.90 mm which was greater than the wall thickness of the control firing button ring. The increased wall thickness of the "G" firing button ring, compared to the control firing button ring, decreased the extent of deformation of the firing button ring when the firing button was depressed. The reduction in deformation of the "G" firing button ring advantageously minimized delayed delivery of an injection compared to the control firing button ring. In addition, as the inner diameter of the firing button ring was reduced from about 6.80 mm to about 6.50 mm, the force to fire (FtF) required to activate or fire the automatic injection device advantageously increased by about 2 N.

Figure 66:
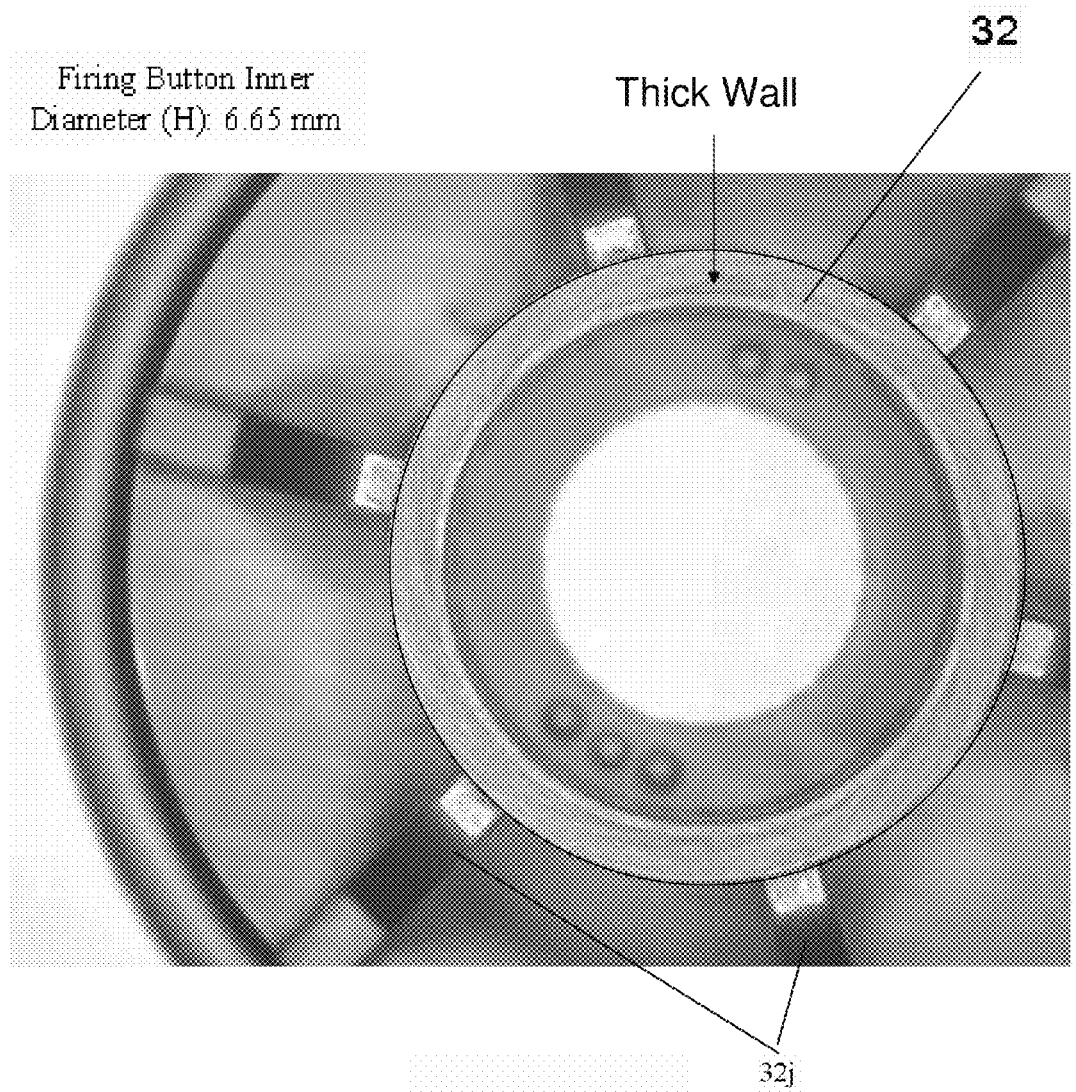
FIG. 66 illustrates a frontal view of the "H" firing button ring with an inner diameter of about 6.65 mm.

FIG. 66 illustrates a frontal view of the "H" firing button ring 32 showing the thick wall of the ring. The inner diameter of the "H" firing button ring was about 6.65 mm, and the wall thickness of the "H" was greater than the control firing button ring but lower than the "G" firing button ring. The increased wall thickness of the "H" firing button ring, compared to the control firing button ring, decreased the extent of deformation of the firing button ring when the firing button was depressed. The reduction in deformation of the firing button ring advantageously minimized delayed delivery of an injection compared to the control firing button ring. However, the decreased wall thickness of the "H" firing button ring, compared to the "G" firing button ring, increased the extent of deformation of the firing button ring when the firing button ring was depressed. The increase in deformation of the "H" firing button ring increased delayed delivery of an injection compared to the "G" firing button ring.

Figure 67:
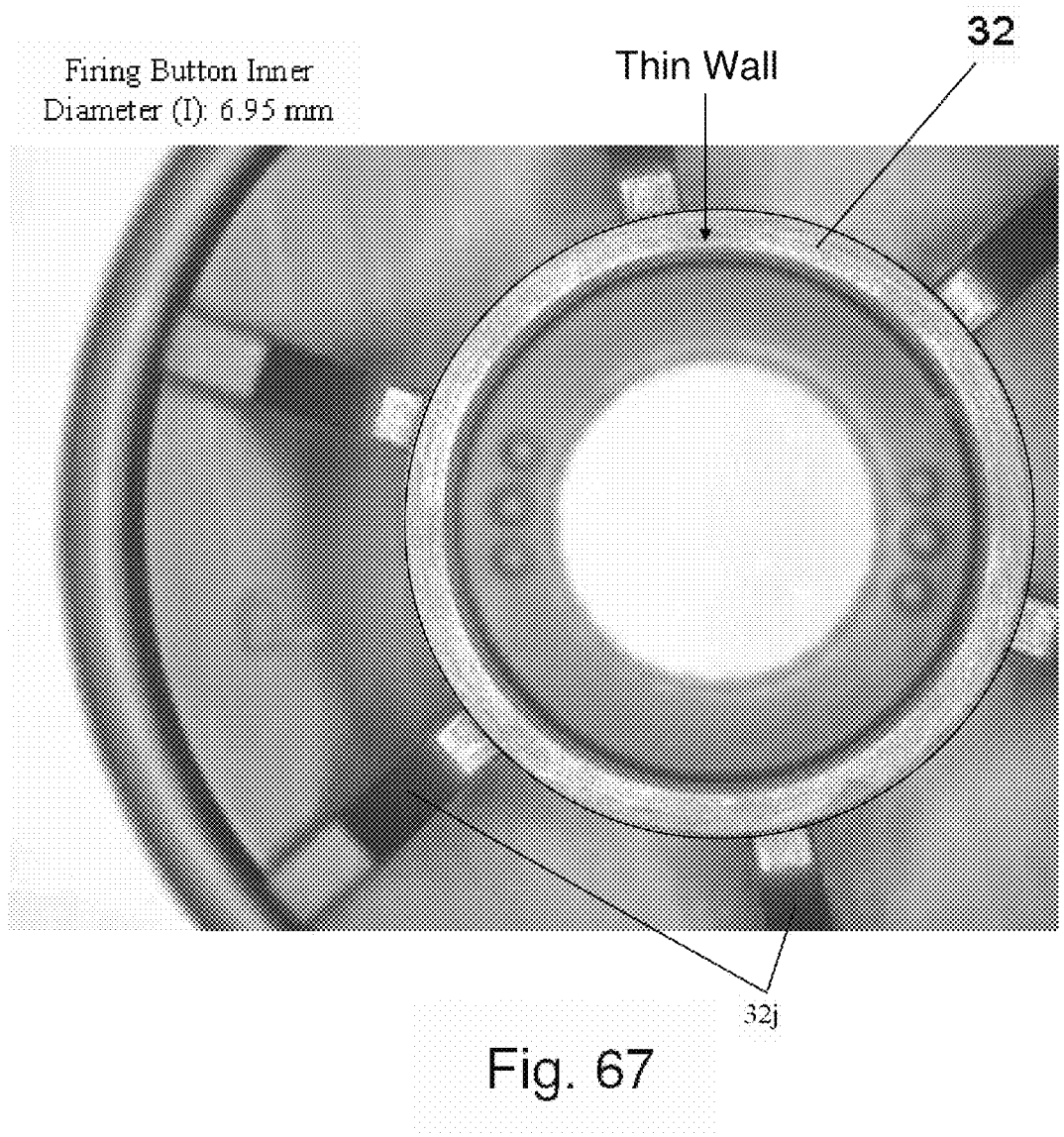
FIG. 67 illustrates a frontal view of the "I" firing button ring with an inner diameter of about 6.95 mm.

FIG. 67 illustrates a frontal view of the "I" firing button ring 32 showing the thick wall of the ring. The inner diameter of the "I" firing button ring was about 6.95 mm, and the wall thickness of the "I" firing button ring was about 0.675 mm which was lower than the wall thickness of the control, "G" and "H" firing button rings. The decreased wall thickness of the "I" firing button ring, compared to the control, "G" and "H" firing button rings, increased the extent of deformation of the firing button ring when the firing button ring was depressed. The increase in deformation of the "I" firing button ring increased delayed delivery of an injection compared to the control, "G" and "H" firing button rings.

Exemplary embodiments may configure exemplary firing button rings to have a smaller inner diameter and a thick wall in order to minimize or eliminate delayed delivery of an injection. In an exemplary embodiment, an exemplary firing button ring is configured based on the specifications of the "G" firing button ring: an exemplary ring inner diameter of about 6.50 mm, an exemplary ring length of about 6.53 mm and an exemplary wall thickness of about 0.90 mm, but exemplary firing button rings are not limited to this configuration.

K. Relationship Between Mold Temperature and Force to Fire (FtF) and Between Cooling Time and FtF Exemplary plungers were molded in a molding process for use in exemplary automatic injection devices. The plungers were formed of the Hostaform™ C 13031 acetal (POM) copolymer plastic material which is an exemplary resin material. The mold temperature and the cooling time used during the molding process were varied, and the resulting effect on the plunger width, i.e., the distance between the plunger arms, and the FtF was determined.

In a first set of tests, the mold temperature was set at about 200 F and the cooling time was set at about 10 seconds. In a second set of tests, the mold temperature was set at about 100 F and the cooling time was set at about 10 seconds. In a third set of tests, the mold temperature was set at about 200 F and the cooling time was set at about 25 seconds. In a fourth set of tests, the mold temperature was set at about 100 F and the cooling time was set at about 25 seconds.

Figure 68:
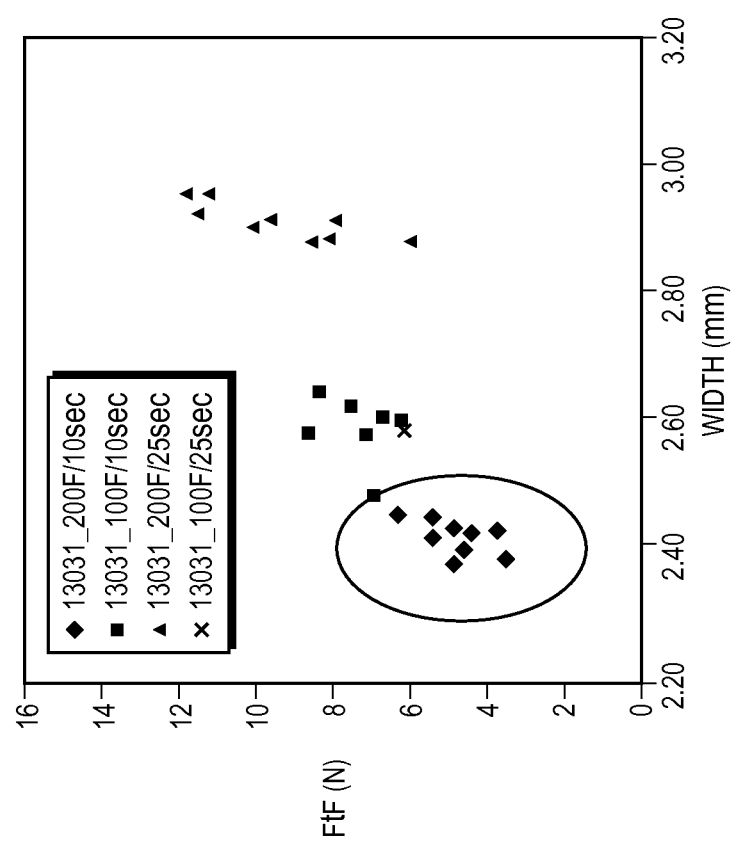
FIG. 68 illustrates a scatterplot of force to fire (FtF) values in N (y-axis) against plunger width values in mm (x-axis) for plungers formed of the Hostaform™ C 13031 acetal (POM) copolymer plastic material at different mold temperatures and different cooling times.

FIG. 68 illustrates a scatterplot of FtF values in N (y-axis) against plunger width values in mm (x-axis) for plungers formed of the Hostaform™ C 13031 acetal (POM) copolymer plastic material at different mold temperatures in F and different cooling times in seconds. FIG. 68 indicates that, in some exemplary embodiments, increasing the cooling time increases the plunger width and, in turn, increases the FtF. FIG. 68 also indicates that, in some exemplary embodiments, decreasing the mold temperature increases the plunger width and, in turn, increases the FtF.

Figure 69:
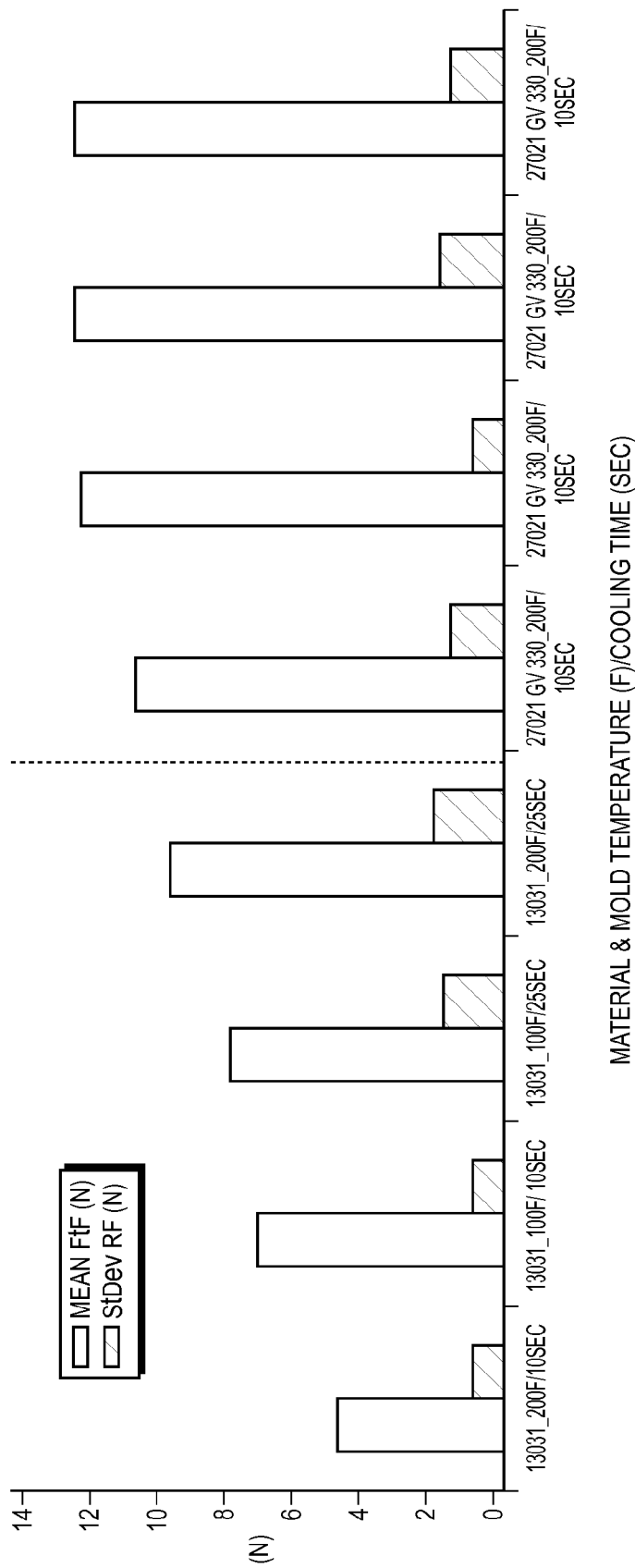
FIG. 69 illustrates a histogram of mean FtF values in N (y-axis) and standard deviation of FtF values in N (y-axis) against combinations of different plunger materials, different mold temperatures in F and different cooling times in seconds (x-axis).

FIG. 69 illustrates a histogram of mean FtF values in N (y-axis) and standard deviation of FtF values in N (y-axis) against combinations of different plunger materials, different mold temperatures in F and different cooling times in seconds (x-axis).

Figure 70:
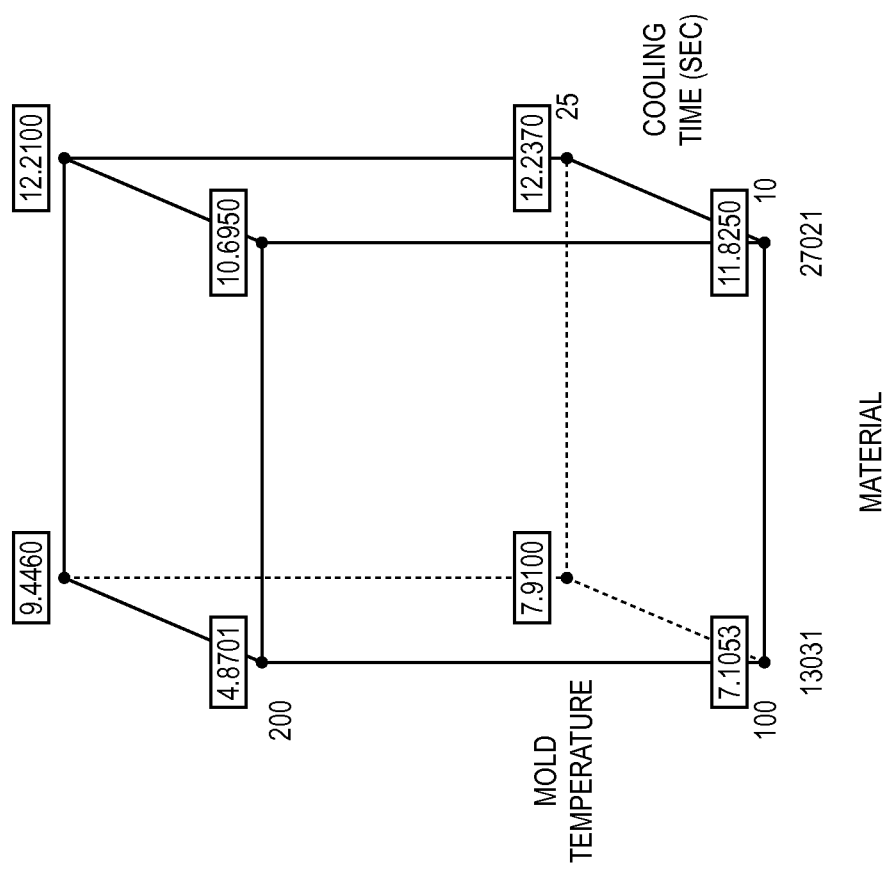
FIG. 70 illustrates a cubic data plot of FtF values in N (provided in boxes) for different plunger materials, different mold temperatures in F and different cooling times in seconds.

FIG. 70 illustrates a cubic data plot of FtF values in N (provided in boxes) for different plunger materials, different mold temperatures in F and different cooling times in seconds. FIGS. 69 and 70 indicate that, in some exemplary embodiments, for the same plunger material, increasing the cooling time increases the plunger width and, in turn, increases the FtF. FIGS. 69 and 70 also indicate that, in some exemplary embodiments, for the same plunger material, decreasing the mold temperature increases the plunger width and, in turn, increases the FtF.

L. Relationship Between Plunger Weight and Force to Fire (FtF)

Exemplary plungers were molded in a molding process for use in exemplary automatic injection devices. The plungers were formed of the Hostaform™ C 13031 acetal (POM) copolymer plastic material which is an exemplary resin material. The plunger weight was varied between about 1.94 grams and about 2.01 grams, and the resulting effect on the FtF was determined.

Figure 71:
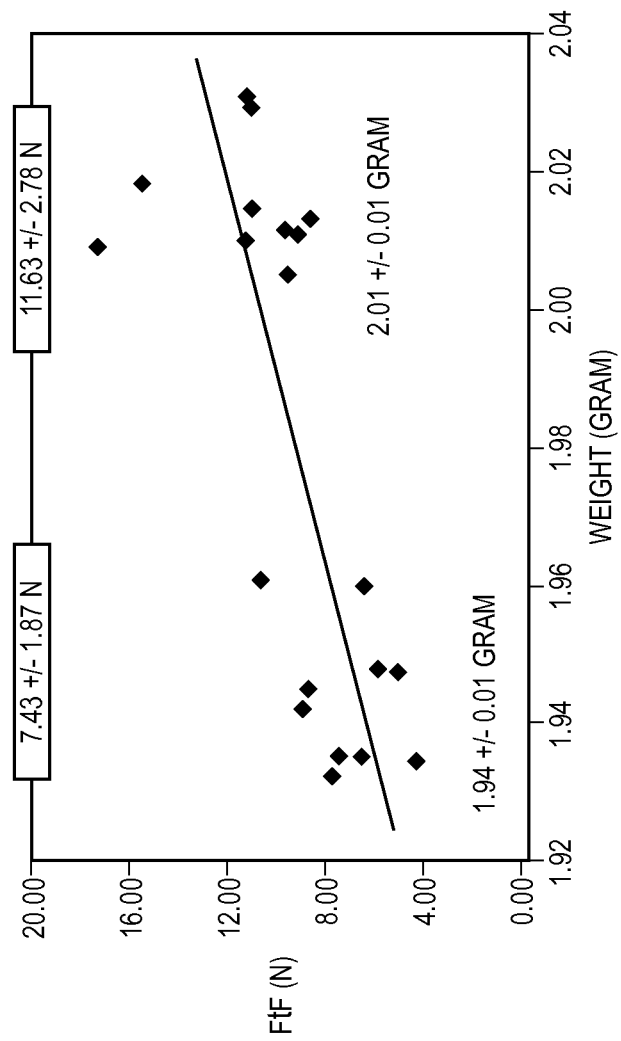
FIG. 71 illustrates a scatterplot of FtF values in N (y-axis) against different plunger weights in grams (x-axis).

FIG. 71 illustrates a scatterplot of FtF values in N (y-axis) against different plunger weights in grams (x-axis). FIG. 71 indicates that increasing the plunger weight increases the FtF. In an exemplary embodiment, a plunger weight of about 1.94 grams corresponds to an exemplary FtF of about 7.43 N. In an exemplary embodiment, a plunger weight of about 2.01 grams corresponds to an exemplary FtF of about 11.63 N.

Figure 72:
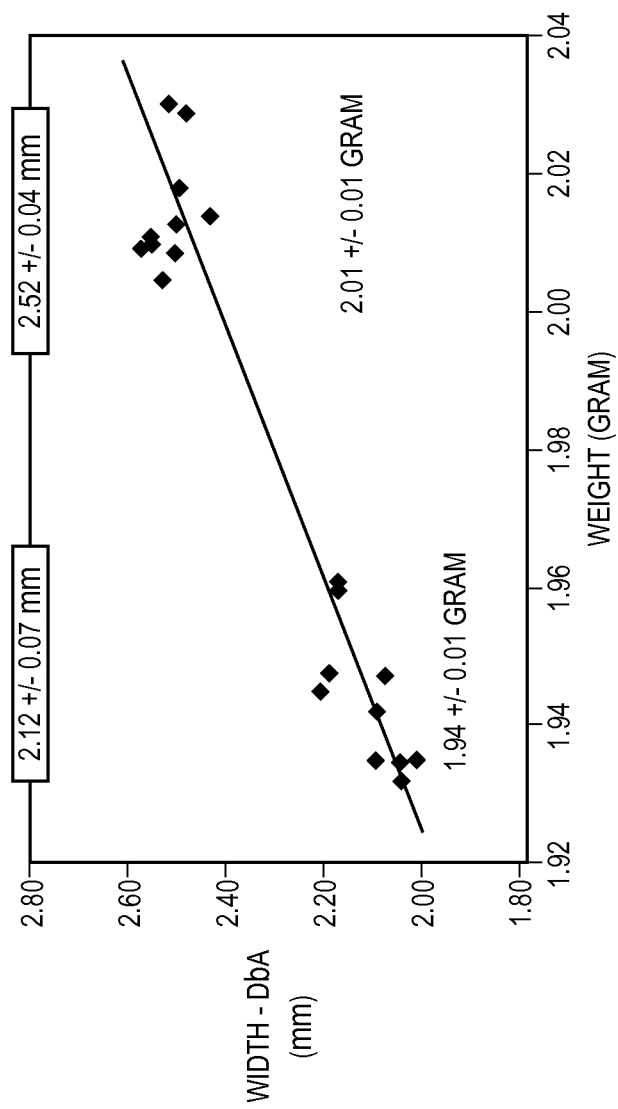
FIG. 72 illustrates a scatterplot of plunger width values in mm (y-axis) against different plunger weights in grams (x-axis).

FIG. 72 illustrates a scatterplot of plunger width values in mm (y-axis) against different plunger weights in grams (x-axis).

Figure 73:
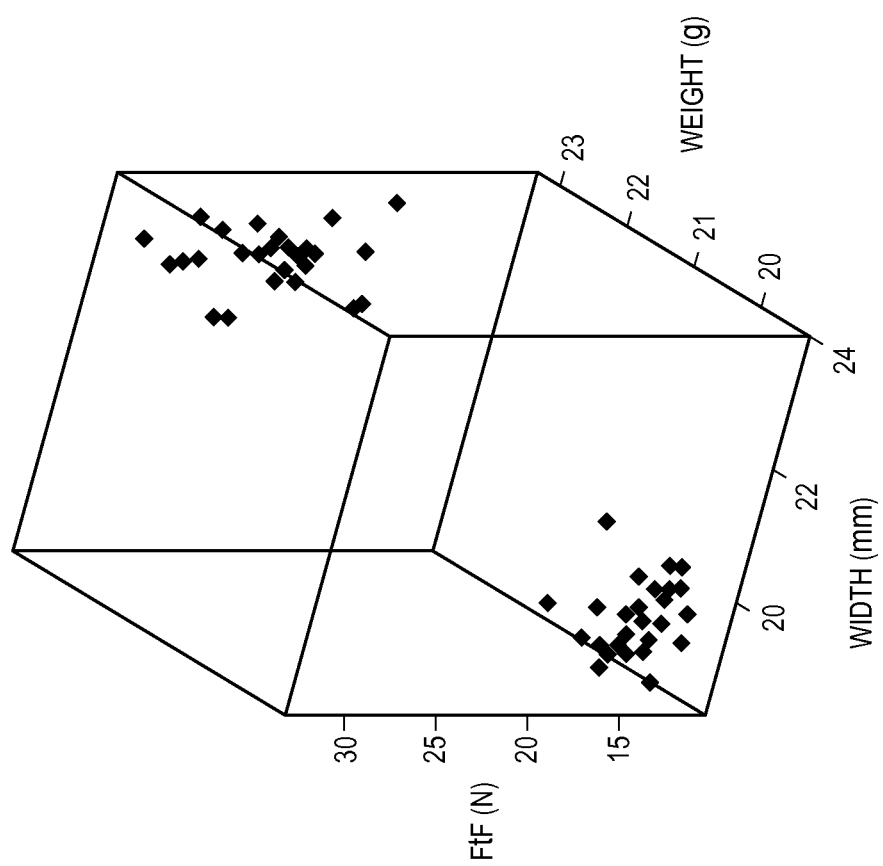
FIG. 73 illustrates a cubic data plot of FtF values in N and plunger width values in mm for different plunger weights in grams.

FIG. 73 illustrates a cubic data plot of FtF values in N and plunger width values in mm for different plunger weights in grams.

FIGS. 72 and 73 indicate that, in some exemplary embodiments, increasing the plunger weight increases the plunger width which, in turn, increases the FtF. In an exemplary embodiment, a plunger weight of about 1.94 grams corresponds to an exemplary plunger width of about 2.12 mm. In an exemplary embodiment, a plunger weight of about 2.01 grams corresponds to an exemplary plunger width of about 2.52 mm.

M. Relationship Between Molding Injection Pressure and Force to Fire (FtF)

Exemplary plungers were molded in an exemplary two-stage molding process for use in exemplary automatic injection devices. The plungers were formed of the Hostaform™ C 13031 acetal (POM) copolymer plastic material which is an exemplary resin material. In the two-stage molding process, the molding injection pressure was varied for the two stages of the process, and the resulting effect on the FtF was determined.

In a first set of tests, the injection pressure was set to be about $750 \times 10^3$ psi during the first stage and was set to be about $500 \times 10^3$ psi during the second stage. The mold temperatures and cooling times were varied for this set of injection pressure values.

Figure 74:
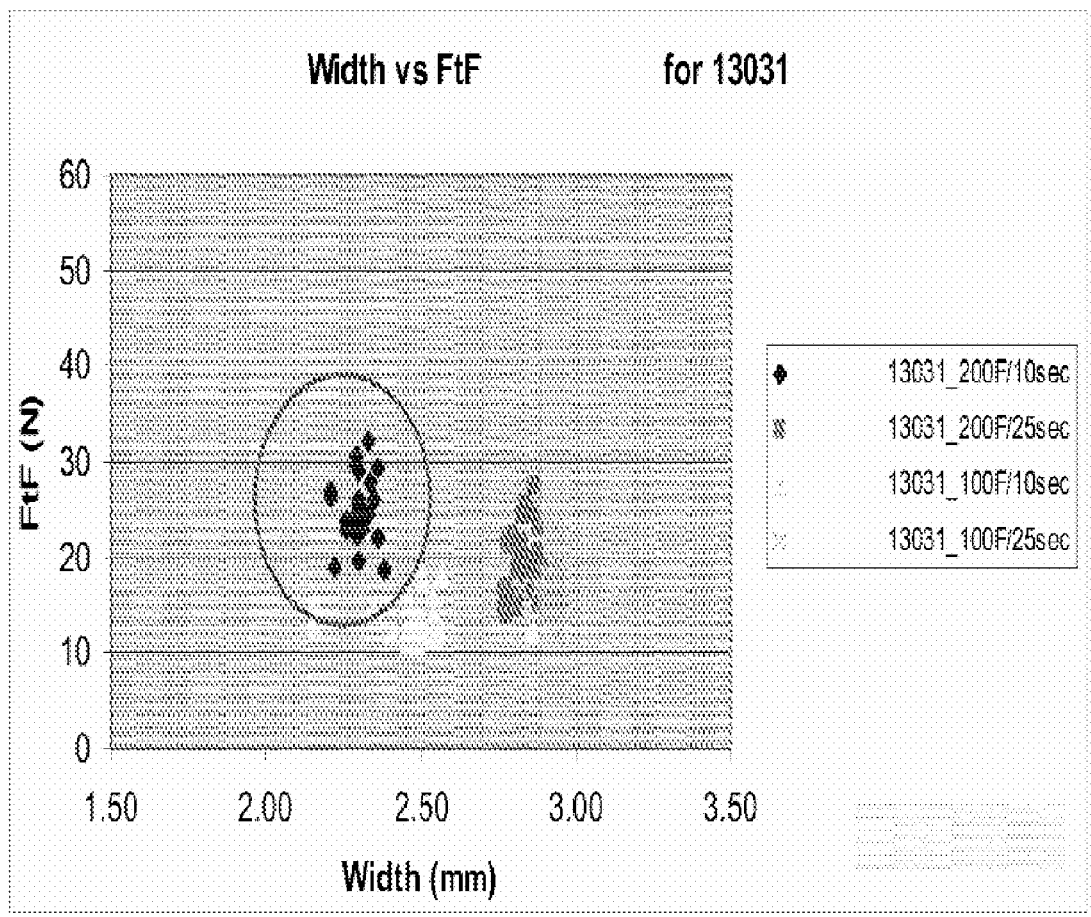
FIG. 74 illustrates a scatterplot of FtF values in N (y-axis) against different plunger widths in mm (x-axis) for different mold temperatures in F and different cooling times in seconds, for a first stage injection pressure of about $750\times10^3$ psi and a second stage injection pressure of about $500\times10^3$ psi.

FIG. 74 illustrates a scatterplot of FtF values in N (y-axis) against different plunger widths in mm (x-axis) for different mold temperatures in F and different cooling times in seconds, for a first stage injection pressure of about $750 \times 10^3$ psi and a second stage injection pressure of about $500 \times 10^3$ psi.

In a second set of tests, the injection pressure was set to be about $1600 \times 10^3$ psi during the first stage and was set to be about $800 \times 10^3$ psi during the second stage. The mold temperatures and cooling times were varied for this set of injection pressure values.

Figure 75:
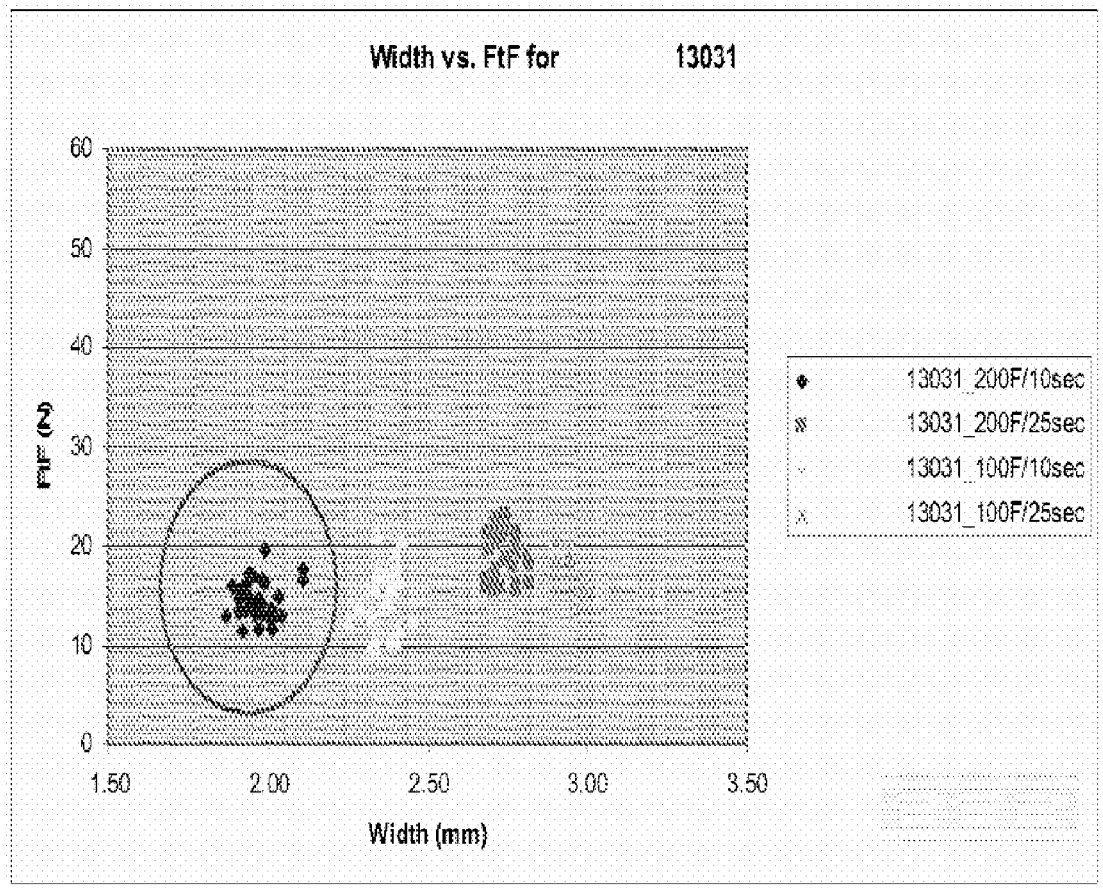
FIG. 75 illustrates a scatterplot of FtF values in N (y-axis) against different plunger widths in mm (x-axis) for different mold temperatures in F and different cooling times in seconds, for a first stage injection pressure of about $1600\times10^3$ psi and a second stage injection pressure of about $800\times10^3$ psi.

FIG. 75 illustrates a scatterplot of FtF values in N (y-axis) against different plunger widths in mm (x-axis) for different mold temperatures in F and different cooling times in seconds, for a first stage injection pressure of about $1600 \times 10^3$ psi and a second stage injection pressure of about $800 \times 10^3$ psi.

In a third set of tests, the injection pressure was set to be about $900 \times 10^3$ psi during the first stage and was set to be about $750 \times 10^3$ psi during the second stage. The mold temperatures and cooling times were varied for this set of injection pressure values.

Figure 76:
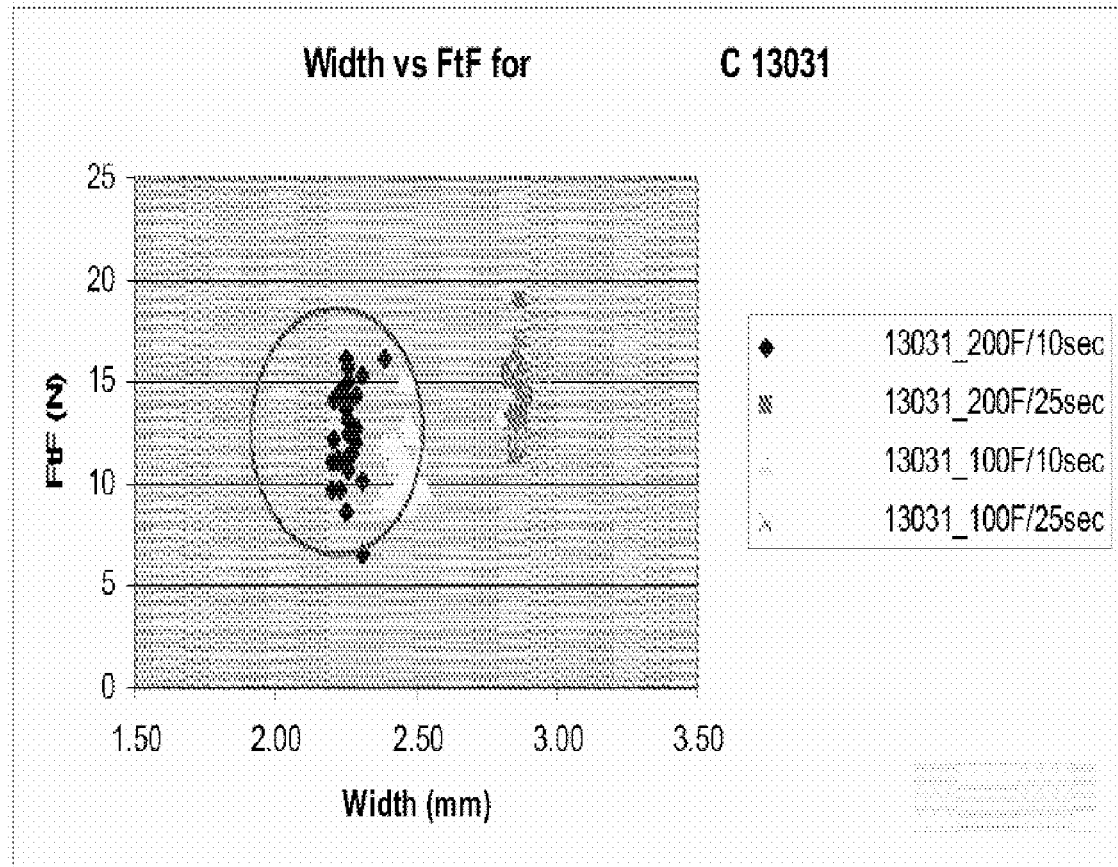
FIG. 76 illustrates a scatterplot of FtF values in N (y-axis) against different plunger widths in mm (x-axis) for different mold temperatures in F and different cooling times in seconds, for a first stage injection pressure of about $900\times10^3$ psi and a second stage injection pressure of about $750\times10^3$ psi.

FIG. 76 illustrates a scatterplot of FtF values in N (y-axis) against different plunger widths in mm (x-axis) for different mold temperatures in F and different cooling times in seconds, for a first stage injection pressure of about $900 \times 10^3$ psi and a second stage injection pressure of about $750 \times 10^3$ psi.

In a fourth set of tests, the injection pressure was set to be about $1600 \times 10^3$ psi during the first stage and was set to be about $900 \times 10^3$ psi during the second stage. The mold temperatures and cooling times were varied for this set of injection pressure values.

Figure 77:
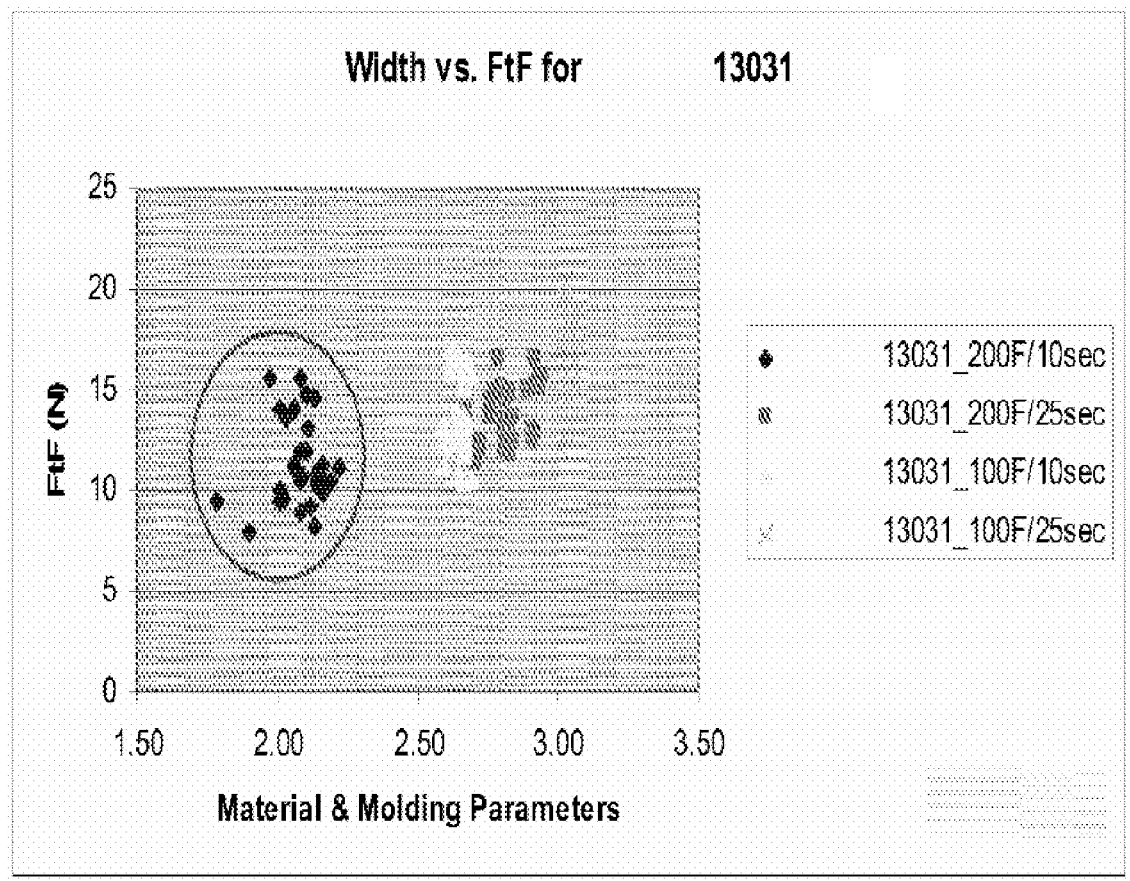
FIG. 77 illustrates a scatterplot of FtF values in N (y-axis) against different plunger widths in mm (x-axis) for different mold temperatures in F and different cooling times in seconds, for a first stage injection pressure of about $1600\times10^3$ psi and a second stage injection pressure of about $900\times10^3$ psi.

FIG. 77 illustrates a scatterplot of FtF values in N (y-axis) against different plunger widths in mm (x-axis) for different mold temperatures in F and different cooling times in seconds, for a first stage injection pressure of about $1600 \times 10^3$ psi and a second stage injection pressure of about $900 \times 10^3$ psi.

VI. MATERIALS FOR USE IN FORMING EXEMPLARY FIRING BUTTONS AND PLUNGERS

Exemplary plungers and firing buttons discussed herein may be formed at least partly of thermosetting and/or thermoplastic materials with a flex modulus ranging from about 300 MPa to about 11,000 MPa. In an exemplary embodiment, the flex modulus of the exemplary material forming the firing button ranges from about 1,500 MPa to about 1,700 MPa. In an exemplary embodiment, the flex modulus of the exemplary material forming the firing button ranges from about 1,600 MPa to about 3,520 MPa.

Exemplary materials that may be used to form an exemplary firing button include, but are not limited to, the WaterShed™ 11120 resin (that may have an exemplary flex modulus of between about 2,865 MPa to about 2,880 MPa in an exemplary embodiment), the ProtoTherm™ 12120 resin (that may have an exemplary flex modulus of about 3,520 MPa in an exemplary embodiment), a polypropylene (PP) thermoplastic polymer (that may have an exemplary flex modulus of about 1,600 MPa in an exemplary embodiment), etc.

Exemplary materials that may be used to form an exemplary plunger include, but are not limited to, acetal polyoxymethylene (POM) copolymers, e.g., from Ticona, the Hostaform™ C 13031 acetal (POM) copolymer plastic material.

Exemplary plungers and firing buttons may also be formed of other thermoplastic and thermosetting materials, examples of which are provided in Table 13 (exemplary thermoplastic materials) and Table 14 (exemplary thermosetting materials).

Table 13 tabulates different thermoplastic materials that may be used to make exemplary plungers and exemplary firing buttons, the vendors of the materials, the material grades, the material densities, the melt volumes, the tensile modulus, and the flex modulus. The tensile modulus is a measure of the stiffness of the material, and the flex modulus is a measure of the tendency of the material to bend.

TABLE 13

Exemplary thermoplastic materials

| Material ID | Vendor | Grade | Density (mg/cm³) | Melt Volume Rate (cm³/10 minutes) | Tensile Modulus (Psi × 10⁵/MPa) (ISO 527-2/1°) | Flex Modulus (Psi × 10⁵/MPa) (ISO 178) |
|---|---|---|---|---|---|---|
| 1 | Ticona | Hostaform C 13031 (copolymer) | 1.41 | 12 | 4.42/3,050 | 4.35/3,000 |
| 2 | Ticona | Hostaform C 27021 GV3/30 (30% glass spheres) | 1.59 | 16 | 5.50/3,800 | 5.07/3,500 |
| 3 | Ticona | Hostaform C 9021 GV3/20 (20% glass spheres) | 1.53 | 8.5 | 4.93/3,400 | 4.64/3,200 |
| 4 | Ticona | Hostaform C 9021 GV3/10 (10% glass spheres) | 1.47 | 9.0 | 4.50/3,100 | 4.35/3,000 |
| 5 | Ticona | Hostaform C 9021 GV1/30 (30% glass fibers) | 1.60 | 4.0 | 13.35/9,200 | |

TABLE 13-continued

Exemplary thermoplastic materials

| Material ID | Vendor | Grade | Density (mg/cm$^3$) | Melt Volume Rate (cm$^3$/10 minutes) | Tensile Modulus (Psi × 10$^5$/MPa) (ISO 527-2/1°) | Flex Modulus (Psi × 10$^5$/MPa) (ISO 178) |
|---|---|---|---|---|---|---|
| 6 | Ticona | Hostaform C 9021 GV1/20 (20% glass fibers) | 1.57 | 4.5 | 10.45/7,200 | |
| 7 | Ticona | Hostaform C 9021 GV1/10 (10% glass fibers) | 1.48 | 6.0 | 6.97/4,800 | |

Additional Hostaform™ C 13031 acetal (POM) copolymer plastic material grades of polyacetal beyond Table 13, sourced from:
http://tools.ticona.com/tools/mcbasei/product-tools.php?sPolymer=POM&sProduct=HOSTAFORM and http://love8ff.diytrade.com/sdp/450410/4/pd-2493053/3735737-1249560.html include, but are not limited to, HOSTAFORM™ AM90S, HOSTAFORM™ AM90S Plus, HOSTAFORM™ C 13021, HOSTAFORM™ C 13021 RM, HOSTAFORM™ C 13031, HOSTAFORM™ C 13031 K, HOSTAFORM™ C 13031 XF, HOSTAFORM™ C 2521, HOSTAFORM™ C 2521 G, HOSTAFORM™ C 2552, HOSTAFORM™ C 27021, HOSTAFORM™ C 27021 AST, HOSTAFORM™ C 27021 GV3/30, HOSTAFORM™ C 52021, HOSTAFORM™ C 9021. HOSTAFORM™ C 9021 10/1570, HOSTAFORM™ C 9021 AW, HOSTAFORM™ C 9021 G, HOSTAFORM™ C 9021 GV1/10, HOSTAFORM™ C 9021 GV1/20, HOSTAFORM™ C 9021 GV1/20 XGM, HOSTAFORM™ C 9021 GV1/30, HOSTAFORM™ C 9021 GV1/30 GT, HOSTAFORM™ C 9021 GV3/10, HOSTAFORM™ C 9021 GV3/20, HOSTAFORM™ C 9021 GV3/30, HOSTAFORM™ C 9021 GV3/30 TF2, HOSTAFORM™ C 9021 K, HOSTAFORM™ C 9021 M, HOSTAFORM™ C 9021 SW, HOSTAFORM™ C 9021 TF, HOSTAFORM™ C 9021 TF5, HOSTAFORM™ C 9021 XAP®, HOSTAFORM™ CP15X, HOSTAFORM™ EC140CF10, HOSTAFORM™ EC140XF (POM), HOSTAFORM™ EC270TX, HOSTAFORM™ FK 1:25, HOSTAFORM™ FK 2:25, HOSTAFORM™ LM140LG, HOSTAFORM™ LM140LGZ, HOSTAFORM™ LM25, HOSTAFORM™ LM90, HOSTAFORM™ LU-02XAP®, HOSTAFORM™ LW15EWX, HOSTAFORM™ LW90BSX, HOSTAFORM™ LW90EWX, HOSTAFORM™ M15HP, HOSTAFORM™ M25AE, HOSTAFORM™ M90XAP®, HOSTAFORM™ MR130ACS, HOSTAFORM™ MT12R01, HOSTAFORM™ MT12U01, HOSTAFORM™ MT12U03, HOSTAFORM™ MT24F01, HOSTAFORM™ MT24U01, HOSTAFORM™ MT8F01, HOSTAFORM™ MT8F02, HOSTAFORM™ MT8R02, HOSTAFORM™ MT8U01, HOSTAFORM™ S 27063, HOSTAFORM™ S 27064, HOSTAFORM™ S 27072 WS10/1570, HOSTAFORM™ S 9063, HOSTAFORM™ S 9064, HOSTAFORM™ S 9243, HOSTAFORM™ S 9244, HOSTAFORM™ S 9364, HOSTAFORM™ TF-10xAP®, and HOSTAFORM™ WR140LG.

Table 14 tabulates different thermosetting materials that may be used to make exemplary plungers, exemplary firing buttons and their flex moduli, as measured, for example, per ASTM D790M (sourced from www.DSMSOMOS.com). The flex modulus is a measure of the tendency of the material to bend. The flex moduli of plungers produced from the resins identified in Table 14 depend, in part, on the type and level of curing, and, therefore, may vary and are reflected in the ranges provided.

TABLE 14

Exemplary thermosetting materials

| Material (derived from DSM Somos which is an epoxy based material) | Flex Modulus (MPa)* by ASTM D790M |
|---|---|
| Somos 9420 | 810 (768-900) |
| ProtoGen O-XT 18420 | 2060 (1990-2130) |
| Watershed 11120 | 2200 (2040-2370) |
| DMX-SL100 | 2290 (2282-2298) |
| ProtoTherm 12120 | 3320 (3060-3320) |
| Nanoform 15120 | 3630 (3630-4450) |
| Somos 8110 Epoxy Photopolymer | 310 |
| Somos 8120 Epoxy Photopolymer | 690 |
| Somos 9110 Epoxy Photopolymer | 1450 |
| Somos 9120 Epoxy Photopolymer | 1310-1455 |
| WaterShed 11110 | 2140 |
| Somos 14120 White | 2250 |
| ProtoTherm 12110 | 3350 |
| ProtoCast AF 19120 | 2430 |
| NanoTool | 10,500 |

VII. SUBSTANCES FOR USE IN EXEMPLARY AUTOMATIC INJECTION DEVICES

The methods and compositions of the invention can be used with automatic injection devices that administer essentially any substance or medication that is suitable for administration by injection. Typically, the substance or medication will be in a fluid, e.g., liquid form, although medications in other forms such as gels or semi-solids, slurries, particulate solutions, etc. also may suitable for use if the automatic injection device is designed to permit the administration of such forms of the medication.

Preferred medications are biological agents, such as antibodies, cytokines, vaccines, fusion proteins and growth factors. Methods of making antibodies are described above.

Non-limiting examples of other biological agents that can be used as the medication in the automatic injection device include but are not limited to antibodies to or antagonists of human cytokines or growth factors, for example, TNF, LT, IL-1, IL-2, IL-3, IL-4, IL-5, IL-6, IL-7, IL-8, IL-15, IL-16, IL-18, IL-21, IL-23, interferons, EMAP-II, GM-CSF, FGF, and PDGF; antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L); TNFα converting enzyme (TACE) inhibitors; IL-1 inhibitors (Interleukin-1-converting enzyme inhibitors, IL-1RA etc.); Interleukin 11;

IL-18 antagonists including IL-18 antibodies or soluble IL-18 receptors, or IL-18 binding proteins; non-depleting anti-CD4 inhibitors; antagonists of the co-stimulatory pathway CD80 (B7.1) or CD86 (B7.2) including antibodies, soluble receptors or antagonistic ligands; agents which interfere with signaling by proinflammatory cytokines such as TNFα or IL-1 (e.g. IRAK, NIK, IKK, p38 or MAP kinase inhibitors); IL-1b converting enzyme (ICE) inhibitors; T-cell signaling inhibitors such as kinase inhibitors; metalloproteinase inhibitors; angiotensin converting enzyme inhibitors; soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R); antiinflammatory cytokines (e.g. IL-4, IL-10, IL-11, IL-13 and TGF-beta); Rituximab; IL-1 TRAP; MRA; CTLA4-Ig; IL-18 BP; anti-IL-18; anti-IL15; IDEC-CE9.1/SB 210396 (non-depleting primatized anti-CD4 antibody; IDEC/Smith-Kline; see e.g., Arthritis & Rheumatism (1995) Vol. 38; S185); DAB 486-IL-2 and/or DAB 389-IL-2 (IL-2 fusion proteins; Seragen; see e.g., Arthritis & Rheumatism (1993) Vol. 36; 1223); Anti-Tac (humanized anti-IL-2Ra; Protein Design Labs/Roche); IL-4 (anti-inflammatory cytokine; DNAX/Schering); IL-10 (SCH 52000; recombinant IL-10, anti-inflammatory cytokine; DNAX/Schering); IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein; see e.g., Arthritis & Rheumatism (1996) 39(9, supplement); 5284; Amer. J. Physiol.—Heart and Circulatory Physiology (1995) 268:37-42); R973401 (phosphodiesterase Type IV inhibitor; see e.g., Arthritis & Rheumatism (1996) 39(9, supplement); S282); MK-966 (COX-2 Inhibitor; see e.g., Arthritis & Rheumatism (1996) 39(9, supplement); S81); Iloprost (see e.g., Arthritis & Rheumatism (1996) 39(9, supplement); S82); zap-70 and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); TNF-convertase inhibitors; anti-IL-12 antibodies; anti-IL-18 antibodies; interleukin-11 (see e.g., Arthritis & Rheumatism (1996) 39(9, supplement), S296); interleukin-13 (see e.g., Arthritis & Rheumatism (1996) 39(9, supplement), S308); interleukin-17 inhibitors (see e.g., Arthritis & Rheumatism (1996) 39(9, supplement), S120); anti-thymocyte globulin; anti-CD4 antibodies; CD5-toxins; ICAM-1 antisense phosphorothioate oligo-deoxynucleotides (ISIS 2302; Isis Pharmaceuticals, Inc.); soluble complement receptor 1 (TP10; T Cell Sciences, Inc.); and anti-IL2R antibodies.

VIII. TNFα INHIBITORS FOR USE IN EXEMPLARY AUTOMATIC INJECTION DEVICES

According to one embodiment of the invention, the illustrative automatic injection device may be used to deliver a dose of a TNF inhibitor used to treat arthritis and other diseases. In one embodiment, the solution contained in the syringe contains 40 or 80 milligrams of drug product (TNFα blocker or inhibitor)/1 mL, for example, 40 or 80 mg adalimumab, 4.93 mg sodium chloride, 0.69 mg monobasic sodium phosphate dehydrate, 1.22 mg dibasic sodium phosphate dehydrate, 0.24 mg sodium citrate, 1.04 mg citric acid monohydrate, 9.6 mg mannitol, 0.8 mg polysorbate 50 and water for injection, with USP sodium hydroxide added as necessary to adjust pH to be about 5.2.

The present invention can be used to administer a dose of a substance, such as a liquid drug, e.g., a TNFα inhibitor, to a patient. In one embodiment, the dose delivered by the automatic injection device of the invention comprises a human TNFα antibody, or antigen-binding portion thereof.

In one embodiment, the TNF inhibitor used in the methods and compositions of the invention includes isolated human antibodies, or antigen-binding portions thereof, that bind to human TNFα with high affinity and a low off rate, and have a high neutralizing capacity. Preferably, the human antibodies of the invention are recombinant, neutralizing human anti-hTNFα antibodies, such as, e.g., the recombinant, neutralizing antibody referred to as D2E7, also referred to as HUMIRA⁰ or adalimumab (Abbott Laboratories; the amino acid sequence of the D2E7 VL region is shown in SEQ ID NO: 1 of U.S. Pat. No. 6,090,382 the amino acid sequence of the D2E7 VH region is shown in SEQ ID NO: 2 of U.S. Pat. No. 6,090,382). Properties of D2E7 have been described in Salfeld et al., U.S. Pat. Nos. 6,090,382, 6,258,562, and 6,509,015. Other examples of TNFα inhibitors include chimeric and humanized murine anti-hTNFα antibodies that have undergone clinical testing for treatment of rheumatoid arthritis (see e.g., Elliott et al. (1994) Lancet 344:1125-1127; Elliot et al. (1994) Lancet 344:1105-1110; and Rankin et al. (1995) Br. J. Rheumatol. 34:334-342).

An anti-TNFα antibody (also referred to herein as a TNFα antibody), or an antigen-binding fragment thereof, includes chimeric, humanized, and human antibodies. Examples of TNFα antibodies that may be used in the invention include, but not limited to, infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), and CNTO 148 (golimumab; Medarex and Centocor, see WO 02/12502). Additional TNF antibodies that may be used in the invention are described in U.S. Pat. Nos. 6,593,458; 6,498,237; 6,451,983; and 6,448,380.

Other examples of TNFα inhibitors which may be used in the methods and compositions of the invention include etanercept (Enbrel, described in WO 91/03553 and WO 09/406, 476), soluble TNF receptor Type I, a pegylated soluble TNF receptor Type I (PEGs TNF-R1), p55TNFR1gG (Lenercept), and recombinant TNF binding protein (r-TBP-I) (Serono).

In one embodiment, exemplary embodiments provide improved uses and compositions for treating a disorder in which TNFα is detrimental, e.g., rheumatoid arthritis, with a TNFα inhibitor, e.g., a human TNFα antibody, or an antigen-binding portion thereof, through an automatic injection device.

A TNFα inhibitor includes any agent (or substance) that interferes with TNFα activity. In a preferred embodiment, the TNFα inhibitor can neutralize TNFα activity, particularly detrimental TNFα activity which is associated with disorders in which TNFα activity is detrimental, including, but not limited to, rheumatoid arthritis, juvenile rheumatoid arthritis, ankylosing spondylitis, Crohn's disease, psoriasis, and psoriatic arthritis.

IX. PHARMACEUTICAL COMPOSITIONS FOR USE IN EXEMPLARY AUTOMATIC INJECTION DEVICES

Pharmaceutical compositions may be loaded into the automatic injection device of the invention for delivery to a patient. In one embodiment, antibodies, antibody-portions, as well as other TNFα inhibitors, can be incorporated into pharmaceutical compositions suitable for administration to a patient using the device of the invention. Typically, the pharmaceutical composition comprises an antibody, antibody portion, or other TNFα inhibitor, and a pharmaceutically acceptable carrier. "Pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions for use in the methods and compositions of the invention may be in a variety of forms in accordance with administration via the device of the invention, including, for example, liquid solutions (e.g., injectable and infusible solutions), dispersions or suspensions. In a preferred embodiment, the antibody or other TNFα inhibitor is administered by subcutaneous injection using the device of the invention. In one embodiment, the patient administers the TNFα inhibitor, including, but not limited to, TNFα antibody, or antigen-binding portion thereof, to himself/herself using the device of the invention Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In one embodiment, exemplary embodiments provide an automatic injection device, e.g., autoinjector pen, comprising an effective TNFα inhibitor and a pharmaceutically acceptable carrier. Thus, the invention provides a pre-filled automatic injection device comprising a TNFα inhibitor.

In one embodiment, the antibody or antibody portion for use in the methods of the invention is incorporated into a pharmaceutical formulation as described in PCT/IB03/04502 and U.S. Patent Publication No. 2004/0033228. This formulation includes a concentration 50 mg/ml of the antibody D2E7 (adalimumab), wherein an automatic injection device contains 40 mg of antibody for subcutaneous injection. In one embodiment, the automatic injection device of the invention (or more specifically the syringe of the device) comprises a formulation of adalimumab having the following formula: adalimumab, sodium chloride, monobasic sodium phosphate dihydrate, dibasic sodium phosphate dihydrate, sodium citrate, citric acid monohydrate, mannitol, polysorbate 80 and water, e.g., water for injection. In another embodiment, the automatic injection device comprises a volume of adalimumab including 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80 and water, e.g., water for injection. In one embodiment, sodium hydroxide is added as necessary to adjust pH.

The dose amount of TNFα inhibitor in the automatic injection device may vary according to the disorder for which the TNFα inhibitor is being used to treat. In one embodiment, the invention includes an automatic injection device comprising a dose of adalimumab of about 20 mg of adalimumab; 40 mg of adalimumab; 80 mg of adalimumab; and 160 mg of adalimumab. It should be noted that for all ranges described herein, including the dose ranges, all numbers intermediary to the recited values are included in the invention, e.g., 36 mg of adalimumab, 48 mg of adalimumab, etc. In addition, ranges recited using said numbers are also included, e.g. 40 to 80 mg of adalimumab. The numbers recited herein are not intended to limit the scope of the invention.

The TNFα antibodies and inhibitors used in the invention may also be administered in the form of protein crystal formulations that include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a patient with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in International Patent Application No. PCT/IB03/04502 and U.S. Patent Publication No. 2004/0033228 is used to treat rheumatoid arthritis using the methods of the invention.

Supplementary active compounds can also be incorporated into the compositions. In certain embodiments, an antibody or antibody portion for use in the methods of the invention is co-formulated with and/or co-administered with one or more additional therapeutic agents, including a rheumatoid arthritis inhibitor or antagonist. For example, an anti-hTNFα antibody or antibody portion may be co-formulated and/or co-administered with one or more additional antibodies that bind other targets associated with TNFα related disorders (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies. Additional agents that may be used in combination with a TNFα antibody or antibody portion are described in U.S. patent application Ser. No. 11/800,531, which is expressly incorporated herein by reference in its entirety.

X. INCORPORATION BY REFERENCE

The contents of all references, including patents and patent applications, cited throughout this application are hereby incorporated herein by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

XI. EQUIVALENTS

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2, etc., or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

What is claimed is:

1. An automatic injection device having a proximal end configured to deliver a dose of a therapeutic agent and a distal end configured to be controllable by a user, the automatic injection device comprising:

a firing body provided at the distal end of the automatic injection device, the firing body comprising:

a hollow tubular member having a bore, and a radial surface extending inwardly from a distal portion of the hollow tubular member;

a plunger having a first and second longitudinally extending plunger arm, each plunger arm terminating in a respective, first radially extending plunger foot and a second radially extending plunger foot, the plunger arms extending through the bore of the hollow tubular member of the firing body, and the first and second plunger foot seated on the radial surface of the firing body, the first plunger foot of the first plunger arm has a first conical surface and a second conical surface, and the second plunger foot of the second plunger arm has a first conical surface and a second conical surface, wherein a first contact surface of the plunger is defined by the first conical surface of the first plunger foot and the first conical surface of the second plunger foot, and wherein a second contact surface of the plunger is defined by the second conical surface of the first plunger foot and the second conical surface of the second plunger foot; and a firing button provided at the distal end of the automatic injection device, the firing button comprising:
an inner ring having an inner diameter of between 6.0 mm and 6.7 mm provided in proximity to the plunger foot, the inner ring configured to contact the plunger foot and to disengage the plunger foot from the radial surface of the firing body to allow the plunger to move through the bore of the hollow tubular member of the firing body, when the firing button is activated by the user.

2. The automatic injection device of claim 1, further comprising:
a housing;
a syringe slideably mounted within the housing; and
a bung slideably mounted in the syringe and moveable to expel a dose through a needle provided at the proximal end of the syringe;
wherein the plunger is configured to contact the bung and to transmit an expulsion force thereto.

3. The automatic injection device of claim 1, further comprising:
an actuating bias member operable to move the plunger when released.

4. The automatic injection device of claim 1, further comprising:
a return bias member acting between the housing and a distal end of the syringe to hold the syringe retracted within the housing until the actuating bias member is released.

5. The automatic injection device of claim 1, wherein the inner diameter of the inner ring is 6.4 mm.

6. The automatic injection device of claim 1, wherein the inner diameter of the inner ring is 6.5 mm.

7. The automatic injection device of claim 1, wherein the inner diameter of the inner ring is 6.6 mm.

8. The automatic injection device of claim 1, wherein the inner diameter of the inner ring is 6.7 mm.

9. The automatic injection device of claim 1, wherein a length of the inner ring is 6.73 mm.

10. The automatic injection device of claim 1, wherein a length of the inner ring is greater than 6.73 mm.

11. The automatic injection device of claim 1, wherein a length of the 5 inner ring is 6.75 mm.

12. The automatic injection device of claim 1, wherein a length of the inner ring is between 6.73 mm and 6.83 mm.

13. The automatic injection device of claim 1, wherein a length of the inner ring is 6.80 mm.

14. The automatic injection device of claim 1, wherein a length of the inner ring ranges 15 from 6.73 mm to 6.83 mm.

15. The automatic injection device of claim 1, wherein the inner ring is formed of a thermoplastic material or a thermosetting material.

16. The automatic injection device of claim 1, wherein the firing button further comprises:
an outer portion configured for contact by the user of the automatic injection device to allow the user to depress the outer portion toward the proximal end of the automatic injection device.

17. The automatic injection device of claim 16, wherein the outer portion protrudes from the distal end of the automatic injection device.

18. The automatic injection device of claim 16, wherein the outer portion covers all or part of the distal end of the automatic injection device.

19. The automatic injection device of claim 16, wherein the outer portion of the firing button further comprises:
an outer tubular wall; and
an end wall coupled to a terminal end of the outer tubular wall, the end wall configured for contact by the user.

20. The automatic injection device of claim 1, wherein the inner ring comprises:
a tubular wall with a circular cross-section.

21. The automatic injection device of claim 1, wherein the inner ring has a minimum wall thickness configured to minimize deformation of the inner ring during engagement of the inner ring with the first and the second plunger foot.

22. The automatic injection device of claim 21, wherein the minimum wall thickness of the inner ring ranges between 0.6 mm and 2.0 mm.

23. The automatic injection device of claim 21, wherein the minimum wall thickness of the inner ring ranges between 0.8 and 2.0 mm.

24. The automatic injection device of claim 21, wherein the minimum wall thickness of the inner ring is 0.9 mm.

25. The automatic injection device of claim 1, wherein the firing button avoids a misfiring of the automatic injection device, the misfiring causing a delayed 5 delivery of an injection.

26. The automatic injection device of claim 25, wherein a measure of the delay in the delivery of the injection caused by the misfiring is greater than three seconds.

27. The automatic injection device of claim 1, further comprising a dose of a TNFα inhibitor.

28. The automatic injection device of claim 27, wherein the TNFα inhibitor is a human TNFα antibody, or antigen-binding portion thereof.

29. The automatic injection device of claim 28, wherein the human TNFα antibody, or antigen-binding portion thereof, is adalimumab or golimumab.

30. The automatic injection device of claim 1, wherein the first plunger foot of the first plunger arm further includes a third conical surface, the second plunger foot of the second plunger arm further includes a third conical surface, and the plunger further includes a third contact surface defined by the third conical surface of the first plunger foot of the first plunger arm and the third conical surface of the second plunger foot of the second plunger arm.

31. The automatic injection device of claim 1, wherein the inner ring of the firing button is configured so that, when the firing button is activated by the user, the initial contact of the inner ring with the plunger is at a distal portion of the first conical surface.

32. The automatic injection device of claim 1, wherein the firing button is displaced toward the plunger when activated by the user.

33. The automatic injection device of claim 1, wherein the radial surface of the firing body is an inclined surface.

34. The automatic injection device of claim 1, wherein the inner ring of the firing button is configured to initially contact a distal portion of the plunger foot during an injection.

35. The automatic injection device of claim 1, wherein the inner ring of the firing button initially contacts the plunger foot after the firing button is depressed over a first distance relative to the firing body.

* * * * *

UNITED STATES PATENT AND TRADEMARK OFFICE
CERTIFICATE OF CORRECTION

PATENT NO.          : 8,758,301 B2                                   Page 1 of 1
APPLICATION NO.     : 12/968744
DATED               : June 24, 2014
INVENTOR(S)         : Shang et al.

It is certified that error appears in the above-identified patent and that said Letters Patent is hereby corrected as shown below:

In the Claims

Column 87, line 49, claim 11: "length of the 5 inner ring" to read as --length of the inner ring--

Column 87, line 55, claim 14: "ranges 15 from" to read as --ranges from--

Column 88, line 27, claim 25: "causing a delayed 5 delivery" to read as --causing a delayed delivery--

Signed and Sealed this
Third Day of March, 2015

Michelle K. Lee
*Deputy Director of the United States Patent and Trademark Office*

```
                          SEQUENCE LISTING

<160> NUMBER OF SEQ ID NOS: 37

<210> SEQ ID NO 1
<211> LENGTH: 107
<212> TYPE: PRT
<213> ORGANISM: Artificial
<220> FEATURE:
<223> OTHER INFORMATION: D2E7 light chain variable region

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
                100                 105

<210> SEQ ID NO 2
<211> LENGTH: 121
<212> TYPE: PRT
<213> ORGANISM: Artificial
<220> FEATURE:
<223> OTHER INFORMATION: D2E7 heavy chain variable region

<400> SEQUENCE: 2

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
```

```
                35                  40                  45
Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial
<220> FEATURE:
<223> OTHER INFORMATION: D2E7 light chain variable region CDR3
<221> NAME/KEY: VARIANT
<222> LOCATION: 9
<223> OTHER INFORMATION: Xaa = Any Amino Acid

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial
<220> FEATURE:
<223> OTHER INFORMATION: D2E7 heavy chain variable region CDR3
<221> NAME/KEY: VARIANT
<222> LOCATION: 12
<223> OTHER INFORMATION: Xaa = Any Amino Acid

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial
<220> FEATURE:
<223> OTHER INFORMATION: D2E7 light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial
<220> FEATURE:
<223> OTHER INFORMATION: D2E7 heavy chain variable region CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
```

```
<211> LENGTH: 11
<212> TYPE: PRT
<213> ORGANISM: Artificial
<220> FEATURE:
<223> OTHER INFORMATION: D2E7 light chain variable region CDR1

<400> SEQUENCE: 7

Arg Ala Ser Gln Gly Ile Arg Asn Tyr Leu Ala
 1               5                  10

<210> SEQ ID NO 8
<211> LENGTH: 5
<212> TYPE: PRT
<213> ORGANISM: Artificial
<220> FEATURE:
<223> OTHER INFORMATION: D2E7 heavy chain variable region CDR1

<400> SEQUENCE: 8

Asp Tyr Ala Met His
 1               5

<210> SEQ ID NO 9
<211> LENGTH: 107
<212> TYPE: PRT
<213> ORGANISM: Artificial
<220> FEATURE:
<223> OTHER INFORMATION: 2SD4 light chain variable region

<400> SEQUENCE: 9

Asp Ile Gln Met Thr Gln Ser Pro Ser Ser Leu Ser Ala Ser Ile Gly
 1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Tyr
                 85                  90                  95

Ala Phe Gly Gln Gly Thr Lys Val Glu Ile Lys
             100                 105

<210> SEQ ID NO 10
<211> LENGTH: 121
<212> TYPE: PRT
<213> ORGANISM: Artificial
<220> FEATURE:
<223> OTHER INFORMATION: 2SD4 heavy chain variable region

<400> SEQUENCE: 10

Gln Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Asp Trp Val
         35                  40                  45

Ser Ala Ile Thr Trp Asn Ser Gly His Ile Asp Tyr Ala Asp Ser Val
 50                  55                  60

Glu Gly Arg Phe Ala Val Ser Arg Asp Asn Ala Lys Asn Ala Leu Tyr
 65                  70                  75                  80
```

```
Leu Gln Met Asn Ser Leu Arg Pro Glu Asp Thr Ala Val Tyr Tyr Cys
                 85                  90                  95

Thr Lys Ala Ser Tyr Leu Ser Thr Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial
<220> FEATURE:
<223> OTHER INFORMATION: 2SD4 light chain variable region CDR3

<400> SEQUENCE: 11

Gln Lys Tyr Asn Ser Ala Pro Tyr Ala
1               5

<210> SEQ ID NO 12
<211> LENGTH: 9
<212> TYPE: PRT
<213> ORGANISM: Artificial
<220> FEATURE:
<223> OTHER INFORMATION: EP B12  light chain variable region CDR3

<400> SEQUENCE: 12

Gln Lys Tyr Asn Arg Ala Pro Tyr Ala
1               5

<210> SEQ ID NO 13
<211> LENGTH: 9
<212> TYPE: PRT
<213> ORGANISM: Artificial
<220> FEATURE:
<223> OTHER INFORMATION: VL10E4 light chain variable region CDR3

<400> SEQUENCE: 13

Gln Lys Tyr Gln Arg Ala Pro Tyr Thr
1               5

<210> SEQ ID NO 14
<211> LENGTH: 9
<212> TYPE: PRT
<213> ORGANISM: Artificial
<220> FEATURE:
<223> OTHER INFORMATION: VL100A9 light chain variable region CDR3

<400> SEQUENCE: 14

Gln Lys Tyr Ser Ser Ala Pro Tyr Thr
1               5

<210> SEQ ID NO 15
<211> LENGTH: 9
<212> TYPE: PRT
<213> ORGANISM: Artificial
<220> FEATURE:
<223> OTHER INFORMATION: VLL100D2 light chain variable region CDR3

<400> SEQUENCE: 15

Gln Lys Tyr Asn Ser Ala Pro Tyr Thr
1               5

<210> SEQ ID NO 16
<211> LENGTH: 9
<212> TYPE: PRT
```

```
<213> ORGANISM: Artificial
<220> FEATURE:
<223> OTHER INFORMATION: VLL0F4 light chain variable region CDR3

<400> SEQUENCE: 16

Gln Lys Tyr Asn Arg Ala Pro Tyr Thr
1               5

<210> SEQ ID NO 17
<211> LENGTH: 9
<212> TYPE: PRT
<213> ORGANISM: Artificial
<220> FEATURE:
<223> OTHER INFORMATION: LOE5 light chain variable region CDR3

<400> SEQUENCE: 17

Gln Lys Tyr Asn Ser Ala Pro Tyr Tyr
1               5

<210> SEQ ID NO 18
<211> LENGTH: 9
<212> TYPE: PRT
<213> ORGANISM: Artificial
<220> FEATURE:
<223> OTHER INFORMATION: VLL0G7 light chain variable region CDR3

<400> SEQUENCE: 18

Gln Lys Tyr Asn Ser Ala Pro Tyr Asn
1               5

<210> SEQ ID NO 19
<211> LENGTH: 9
<212> TYPE: PRT
<213> ORGANISM: Artificial
<220> FEATURE:
<223> OTHER INFORMATION: VLL0G9 light chain variable region CDR3

<400> SEQUENCE: 19

Gln Lys Tyr Thr Ser Ala Pro Tyr Thr
1               5

<210> SEQ ID NO 20
<211> LENGTH: 9
<212> TYPE: PRT
<213> ORGANISM: Artificial
<220> FEATURE:
<223> OTHER INFORMATION: VLL0H1 light chain variable region CDR3

<400> SEQUENCE: 20

Gln Lys Tyr Asn Arg Ala Pro Tyr Asn
1               5

<210> SEQ ID NO 21
<211> LENGTH: 9
<212> TYPE: PRT
<213> ORGANISM: Artificial
<220> FEATURE:
<223> OTHER INFORMATION: VLL0H10 light chain variable region CDR3

<400> SEQUENCE: 21

Gln Lys Tyr Asn Ser Ala Ala Tyr Ser
1               5

<210> SEQ ID NO 22
<211> LENGTH: 9
<212> TYPE: PRT
<213> ORGANISM: Artificial
```

```
<220> FEATURE:
<223> OTHER INFORMATION: VL1B7 light chain variable region CDR3

<400> SEQUENCE: 22

Gln Gln Tyr Asn Ser Ala Pro Asp Thr
 1               5

<210> SEQ ID NO 23
<211> LENGTH: 9
<212> TYPE: PRT
<213> ORGANISM: Artificial
<220> FEATURE:
<223> OTHER INFORMATION: VL1C1 light chain variable region CDR3

<400> SEQUENCE: 23

Gln Lys Tyr Asn Ser Asp Pro Tyr Thr
 1               5

<210> SEQ ID NO 24
<211> LENGTH: 9
<212> TYPE: PRT
<213> ORGANISM: Artificial
<220> FEATURE:
<223> OTHER INFORMATION: VL0.1F4 light chain variable region CDR3

<400> SEQUENCE: 24

Gln Lys Tyr Ile Ser Ala Pro Tyr Thr
 1               5

<210> SEQ ID NO 25
<211> LENGTH: 9
<212> TYPE: PRT
<213> ORGANISM: Artificial
<220> FEATURE:
<223> OTHER INFORMATION: VL0.1H8 light chain variable region CDR3

<400> SEQUENCE: 25

Gln Lys Tyr Asn Arg Pro Pro Tyr Thr
 1               5

<210> SEQ ID NO 26
<211> LENGTH: 9
<212> TYPE: PRT
<213> ORGANISM: Artificial
<220> FEATURE:
<223> OTHER INFORMATION: LOE7.A light chain variable region CDR3

<400> SEQUENCE: 26

Gln Arg Tyr Asn Arg Ala Pro Tyr Ala
 1               5

<210> SEQ ID NO 27
<211> LENGTH: 12
<212> TYPE: PRT
<213> ORGANISM: Artificial
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
 1               5                  10

<210> SEQ ID NO 28
<211> LENGTH: 12
<212> TYPE: PRT
<213> ORGANISM: Artificial
<220> FEATURE:
```

```
<223> OTHER INFORMATION: VH1B11 heavy chain variable region CDR3

<400> SEQUENCE: 28

Ala Ser Tyr Leu Ser Thr Ser Ser Ser Leu Asp Lys
1               5                   10

<210> SEQ ID NO 29
<211> LENGTH: 12
<212> TYPE: PRT
<213> ORGANISM: Artificial
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
1               5                   10

<210> SEQ ID NO 30
<211> LENGTH: 12
<212> TYPE: PRT
<213> ORGANISM: Artificial
<220> FEATURE:
<223> OTHER INFORMATION: VH1A11 heavy chain variable region CDR3

<400> SEQUENCE: 30

Ala Ser Tyr Leu Ser Thr Ser Ser Ser Leu Asp Asp
1               5                   10

<210> SEQ ID NO 31
<211> LENGTH: 12
<212> TYPE: PRT
<213> ORGANISM: Artificial
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
1               5                   10

<210> SEQ ID NO 32
<211> LENGTH: 12
<212> TYPE: PRT
<213> ORGANISM: Artificial
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
1               5                   10

<210> SEQ ID NO 33
<211> LENGTH: 12
<212> TYPE: PRT
<213> ORGANISM: Artificial
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
1               5                   10

<210> SEQ ID NO 34
<211> LENGTH: 12
<212> TYPE: PRT
<213> ORGANISM: Artificial
<220> FEATURE:
<223> OTHER INFORMATION: 3C-H2 heavy chain variable region CDR3
```

-continued

```
<400> SEQUENCE: 34

Ala Ser Tyr Leu Ser Thr Ala Ser Ser Leu Glu Tyr
 1               5                  10

<210> SEQ ID NO 35
<211> LENGTH: 12
<212> TYPE: PRT
<213> ORGANISM: Artificial
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
 1               5                  10

<210> SEQ ID NO 36
<211> LENGTH: 321
<212> TYPE: DNA
<213> ORGANISM: Artificial
<220> FEATURE:
<223> OTHER INFORMATION: D2E7 light chain variable region

<400> SEQUENCE: 36
gacatccaga tgacccagtc tccatcctcc ctgtctgcat ctgtagggga cagagtcacc      60
atcacttgtc gggcaagtca gggcatcaga aattacttag cctggtatca gcaaaaacca     120
gggaaagccc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttatta ctgtcaaagg tataaccgtg caccgtatac ttttggccag     300
gggaccaagg tggaaatcaa a                                                321

<210> SEQ ID NO 37
<211> LENGTH: 363
<212> TYPE: DNA
<213> ORGANISM: Artificial
<220> FEATURE:
<223> OTHER INFORMATION: D2E7 heavy chain variable region

<400> SEQUENCE: 37
gaggtgcagc tggtggagtc tgggggaggc ttggtacagc ccggcaggtc cctgagactc      60
tcctgtgcgg cctctggatt cacctttgat gattatgcca tgcactgggt ccggcaagct     120
ccagggaagg gcctggaatg ggtctcagct atcacttgga atagtggtca catagactat     180
gcggactctg tggagggccg attcaccatc tccagagaca cgccaagaa ctccctgtat      240 ctgcaaatga acagtctgag agctgaggat acggccgtat attactgtgc gaaagtctcg     300
taccttagca ccgcgtcctc ccttgactat tggggccaag gtaccctggt caccgtctcg     360
agt                                                                    363
```